(12) United States Patent
Sachdeva et al.

(10) Patent No.: US 8,469,705 B2
(45) Date of Patent: Jun. 25, 2013

(54) METHOD AND SYSTEM FOR INTEGRATED ORTHODONTIC TREATMENT PLANNING USING UNIFIED WORKSTATION

(75) Inventors: Rohit Sachdeva, Plano, TX (US); Peer Sporbert, Berlin (DE); Stephan Maetzel, Berlin (DE); Hans Imgrund, Berlin (DE); Claudia Strauss, Berlin (DE); Phillip Getto, Plano, TX (US); Sanjeev Taneja, Plano, TX (US); Matthew Johnson, Dallas, TX (US); John Penman, Plano, TX (US); Justyna Badura, Berlin (DE); Danesh De Silva, Plano, TX (US)

(73) Assignee: Orametrix, Inc., Richardson, TX (US)

( * ) Notice: Subject to any disclaimer, the term of this patent is extended or adjusted under 35 U.S.C. 154(b) by 125 days.

(21) Appl. No.: 12/728,972

(22) Filed: Mar. 22, 2010

(65) Prior Publication Data
US 2010/0179789 A1    Jul. 15, 2010

Related U.S. Application Data

(62) Division of application No. 10/428,461, filed on May 2, 2003, now Pat. No. 7,717,708.

(51) Int. Cl.
*A61C 3/00*    (2006.01)

(52) U.S. Cl.
USPC ............................................. 433/24

(58) Field of Classification Search
USPC ................................... 433/24, 214; 703/1, 11
See application file for complete search history.

(56) References Cited

U.S. PATENT DOCUMENTS
2005/0019721 A1*    1/2005    Chishti ........................ 433/24

* cited by examiner

*Primary Examiner* — Sunil K Singh
(74) *Attorney, Agent, or Firm* — McDonnell Boehnen Hulbert & Berghoff LLP

(57) ABSTRACT

A method and workstation for orthodontic treatment planning of a patient. The workstation is based on a computing platform having a graphical user interface, a processor and a computer storage medium containing digitized records pertaining to a patient including image data (3D image data and/or 2D image data). The workstation further includes a set of software instructions providing graphical user interface tools which the user marks a midline and an aesthetic occlusal plane in a two- or three-dimensional virtual model of the patient, marks an occlusal plane in the virtual model; selects a reference tooth in the virtual model; aligns virtual teeth in the virtual model in a proposed arrangement to treat the patient; manages space between the virtual teeth in the proposed arrangement; and repeats one or more of these steps in an iterative fashion to make any further adjustments in the proposed arrangement. When the adjustments are complete, the user selects or identifies a finalized proposed treatment plan for treating the patient.

5 Claims, 86 Drawing Sheets

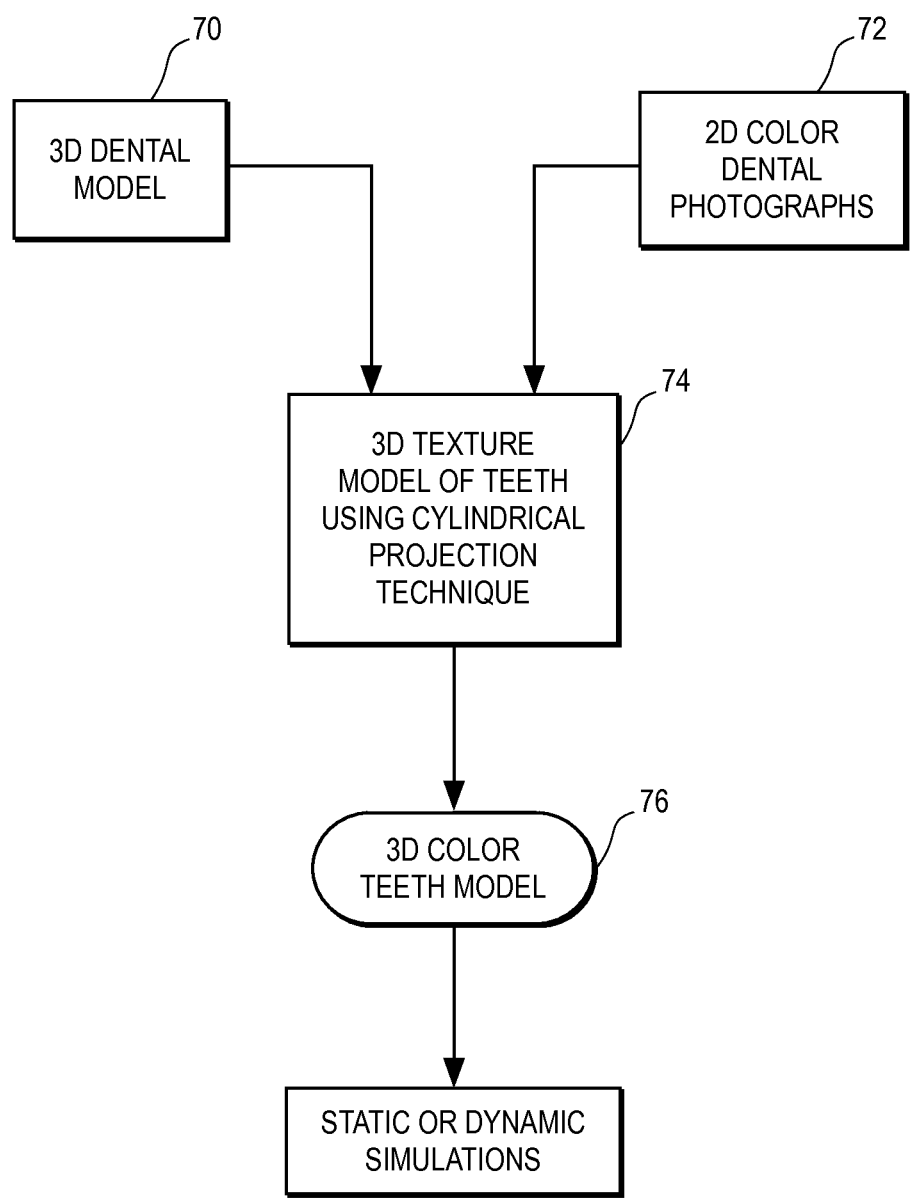

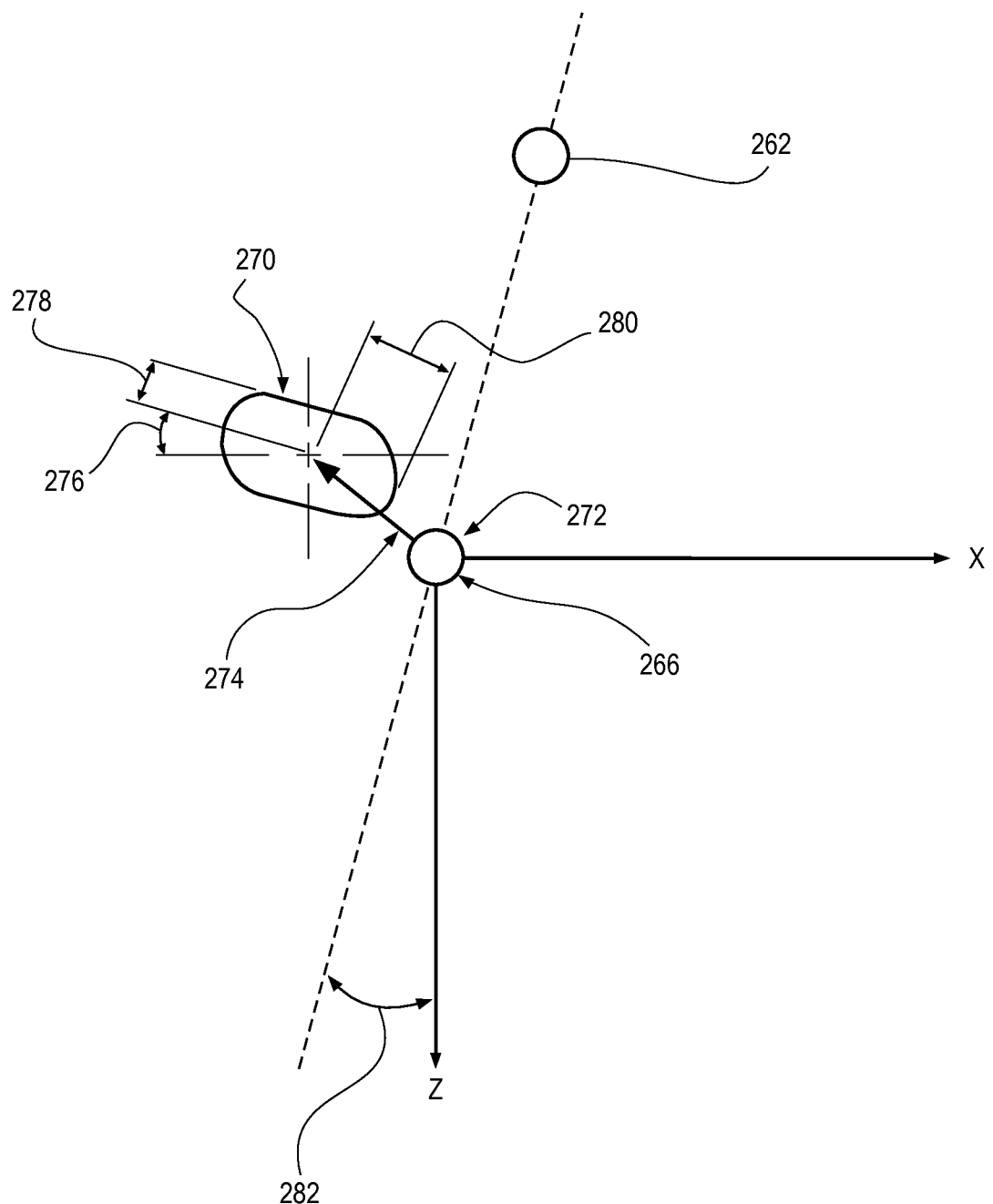

FIG. 21A

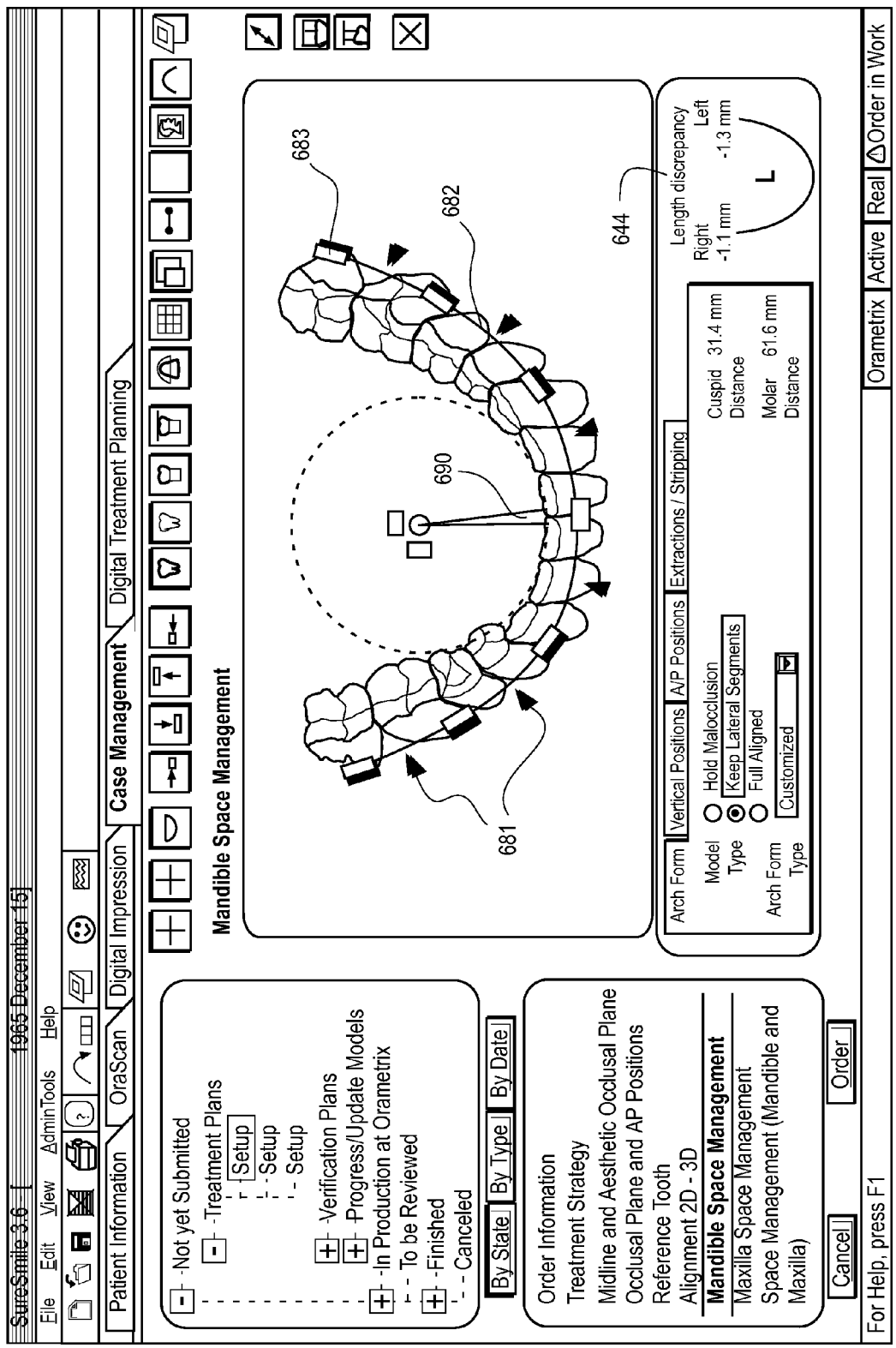

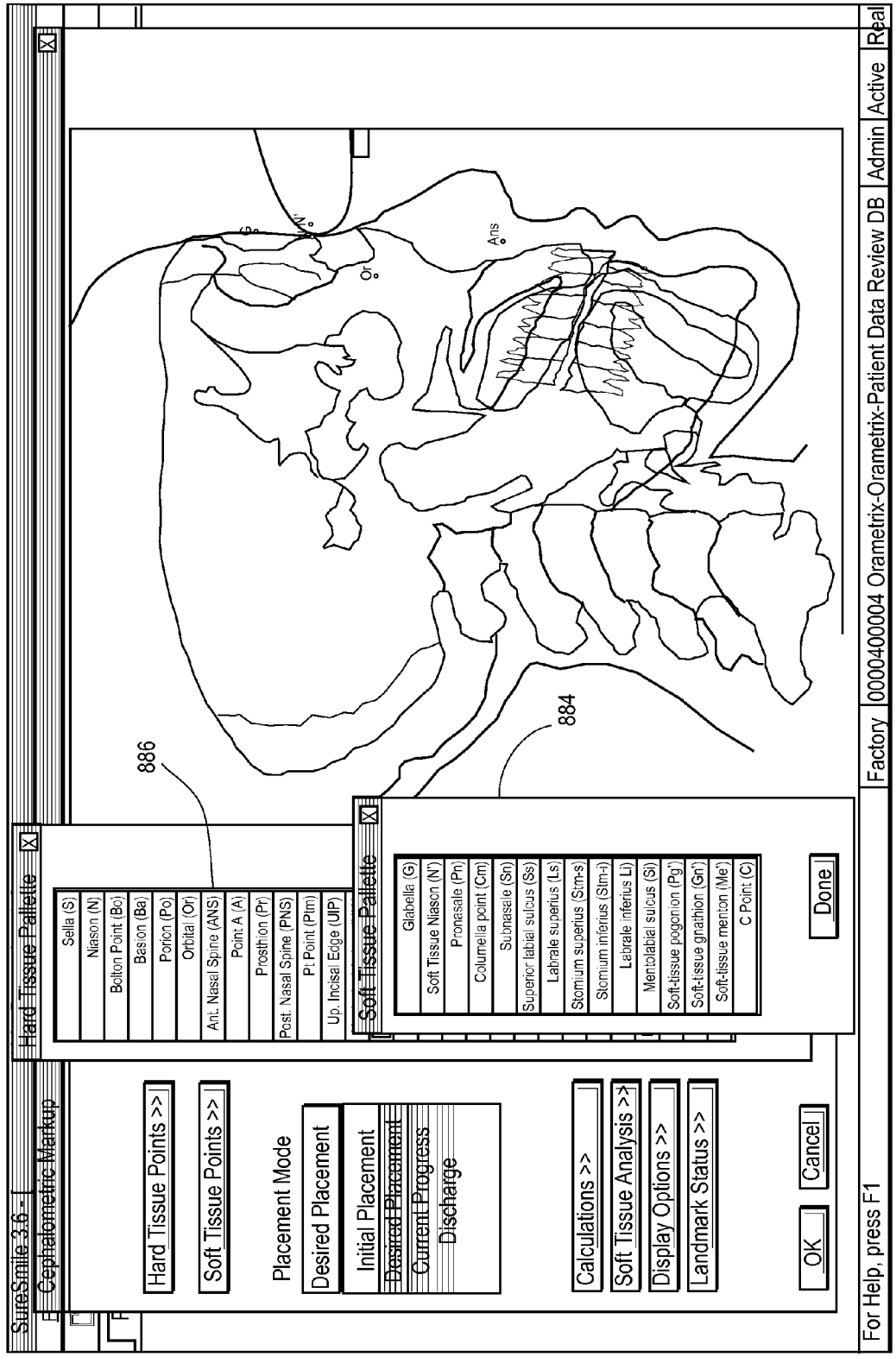

METHOD AND SYSTEM FOR INTEGRATED ORTHODONTIC TREATMENT PLANNING USING UNIFIED WORKSTATION

RELATED APPLICATIONS

This is divisional application of Ser. No. 10/428,461, filed May 2, 2003, now issued as US Pat. No.7,717,708, the entire contents of which are incorporated by reference herein. This application is related to application Ser. No. 12/110,253, filed Apr. 25, 2008, pending, which is also a divisional application of Ser. No. 10/428,461.

This application in turn is related to patent applications filed on the same date as application Ser. No. 10/428,461, entitled "UNIFIED WORKSTATION FOR VIRTUAL CRANIOFACIAL DIAGNOSIS, TREATMENT PLANNING AND THERAPEUTICS", Rohit Sachdeva et al, inventors, Ser. No. 10/429,123, now issued as U.S. Pat. No. 7,234,937, the entire contents of which are incorporated by reference herein, and entitled "INTERACTIVE UNIFIED WORKSTATION FOR BENCHMARKING AND CARE PLANNING", Rohit Sachdeva et al, inventors, Ser. No. 10/429,074, pending, the entire contents of which are incorporated by reference herein.

BACKGROUND OF THE INVENTION

A. Field of the Invention

This invention relates to the field of computerized techniques for orthodontic treatment planning for human patients. More particularly, the invention is directed to an interactive workstation and associated computerized techniques for facilitating integration of various tasks performed in planning treatment for orthodontic patients.

B. Description of Related Art

The traditional process of diagnosis and treatment planning for a patient with orthodontic problems or disease typically consists of the practitioner obtaining clinical history, medical history, dental history, and orthodontic history of the patient supplemented by 2D photographs, 2D radio graphic images, CT scans, 2D and 3D scanned images, ultrasonic scanned images, and in general non-invasive and sometimes invasive images, plus video, audio, and a variety of communication records. Additionally, physical models, such as made from plaster of paris, of the patient's teeth are created from the impressions taken of the patient's upper and lower jaws. Such models are manually converted into teeth drawings by projecting teeth on drawing paper. Thus, there is a large volume of images and data involved in the diagnosis and treatment planning process. Furthermore, the information may require conversion from one form to another and selective reduction before it could become useful. There are some computerized tools available to aid the practitioner in these data conversion and reduction steps, for example to convert cephalometric x-rays (i.e., 2 dimensional x-ray photographs showing a lateral view of the head and jaws, including teeth) into points of interest with respect to soft tissue, hard tissue, etc., but they are limited in their functionalities and scope. Even then, there is a fairly substantial amount of manual work involved in these steps.

Additionally, a number of measurements, e.g., available space between teeth, are also often done manually. Generally, these steps are time consuming and prone to inherent inaccuracies. Furthermore, the practitioner has to contend with the biological interdependencies within the patient, which introduces constraints eliminating certain treatment options that would otherwise be acceptable, between the soft tissue, the hard tissue, and the teeth. There is lack of an integrated platform which a practitioner could utilize to filter-out non-practicable treatment options.

Consequently, the practitioner is left to mental visualization, chance process to select the treatment course that would supposedly work. Furthermore, the diagnosis process is some-what ad-hoc and the effectiveness of the treatment depends heavily upon the practitioner's level of experience. Often, due to the complexities of the detailed steps and the time consuming nature of them, some practitioners take a short-cut, relying predominantly on their intuition to select a treatment plan. For example, the diagnosis and treatment planning is often done by the practitioner on a sheet of acetate over the X-rays. All of these factors frequently contribute towards trial and error, hit-and-miss, lengthy and inefficient treatment plans that require numerous mid-course adjustments. While at the beginning of treatment things generally run well as all teeth start to move at least into the right direction, at the end of treatment a lot of time is lost by adaptations and corrections required due to the fact that the end result has not been properly planned at any point of time. By and large, this approach lacks reliability, reproducibility and precision. More over, there is no comprehensive way available to a practitioner to stage and simulate the treatment process in advance of the actual implementation to avoid the often hidden pitfalls. And the patient has no choice and does not know that treatment time could be significantly reduced if proper planning was done.

In recent years, computer-based approaches have been proposed for aiding orthodontists in their practice. However, these approaches are limited to diagnosis and treatment planning of craniofacial structures, including the straightening of teeth. See Andreiko, U.S. Pat. No. 6,015,289; Snow, U.S. Pat. No. 6,068,482; Kopelmann et al., U.S. Pat. No. 6,099,314; Doyle, et al., U.S. Pat. No. 5,879,158; Wu et al., U.S. Pat. No. 5,338,198, and Chisti et al., U.S. Pat. Nos. 5,975,893 and 6,227,850, the contents of each of which is incorporated by reference herein. Also see imaging and diagnostic software and other related products marketed by Dolphin Imaging, 6641 Independence Avenue, Canoga Park, Calif.

A method for generation of a 3D model of the dentition from an in-vivo scan of the patient, and interactive computer-based treatment planning for orthodontic patients, is described in published PCT patent application of OraMetrix, Inc., the assignee of this invention, publication no. WO 01/80761, the contents of which are incorporated by reference herein.

Other background references related to capturing three dimensional models of dentition and associated craniofacial structures include S. M. Yamany and A. A. Farag, "A System for Human Jaw Modeling Using Intra-Oral Images" in *Proc. IEEE Eng. Med. Biol. Soc. (EMBS) Conf,* Vol. 20, Hong Kong, October 1998, pp. 563-566; and M. Yamany, A. A. Farag, David Tasman, A. G. Farman, "A 3-D Reconstruction System for the Human Jaw Using a Sequence of Optical Images," *IEEE Transactions on Medical Imaging,* Vol. 19, No. 5, May 2000, pp. 538-547. The contents of these references are incorporated by reference herein.

The technical literature further includes a body of literature describing the creation of 3D models of faces from photographs, and computerized facial animation and morphable modeling of faces. See, e.g., Pighin et al., *Synthesizing Realistic Facial Expression from Photographs,* Computer Graphics Proceedings SIGGRAPH '98, pp. 78-94 (1998); Pighin et al., *Realistic Facial Animation Using Image-based 3D Morphing,* Technical Report no. UW-CSE-97-01-03, University of Washington (May 9, 1997); and Blantz et al., *A Morphable*

*Model for The Synthesis of 3D Faces, Computer Graphics Proceedings SIGGRAPH '99* (August, 1999). The contents of these references are incorporated by reference herein.

The present invention is directed to an effective, computer-based, integrated and interactive orthodontic treatment planning system that provides the necessary tools to allow the orthodontist to quickly and efficiently design a treatment plan for a patient. The present invention also provides a treatment planning system in which the orthodontist-derived parameters for the treatment can be translated into a design of the treatment. The preferred embodiment integrates 2D and 3D images to drive effective treatment planning Intelligence is built into the system whereby predefined therapeutic strategies, such as extraction, interproximal reduction, distal movement of molars, can have associated value sets predefined by the clinician that are used to drive the appropriate set-up automatically. Such predefined therapeutic strategies could be entered via convenient user interface tools, such as by templates.

The treatment design as described herein also allows for real-time communication of the treatment plan to occur with the patient, or transmitted over a communications link and shared with a colleague or remote appliance manufacturing facility. Alternatively, the treatment planning can be performed remotely and a digital treatment plan sent to the orthodontist for review, interactive modification, or approval.

SUMMARY OF THE INVENTION

In a preferred embodiment of the invention, the unified workstation is provided with software features that facilitate diagnosis and treatment planning through a process flow that guides and assists the practitioner in making decisions at various stages of the process in a systematic and coordinated manner. The workstation includes a computer that stores, and makes available to the practitioner, records in the form of digital data pertaining to some or all of the following: the patient's clinical history, medical history, dental history, and orthodontic history as well as 2D photographs, 2D radiographic images, CT scans, 2D and 3D scanned images, ultrasonic scanned images, and in general, non-invasive and optionally invasive images, plus video, audio, and a variety of communication records, such notes, records of office visits, patient letters or communications, etc. All records and images are digitized. The records and images are made available through suitable user interface icons and graphical displays, which cause display of the images on the user interface. The images can be combined or superimposed to create a virtual patient model that includes surface features (soft tissue) of the patient in one possible embodiment.

The workstation further maintains a comprehensive set of computer instructions providing tools in the form of icons, screen displays, windows, menus and similar functions and features, accessible through the user interface of the workstation to assist the practitioner in planning the treatment. Various types of tools are contemplated; numerous examples are set forth herein.

From the information gathered, the workstation assists the practitioner in identifying the constraints driven by the practitioner pertinent to the treatment planning. The treatment planning process flow for a patient typically includes the following steps. To begin with, the general approach to the treatment is postulated or proposed by the practitioner, based upon attending to the patient's complaints by clinical examination and radiographic images, listening and examination and, in light of that, assessment of the real problem or problems. In one possible embodiment, patient information regarding diagnosis and practitioner-derived constraints are entered into the computer memory via the user interface. The supplying of this information could take a variety of forms, including the form of filling in fields of a problem-oriented matrix, the matrix recording the conditions relevant to the patient's soft tissue, skeletal, and dental anatomy, each with respect to vertical, sagittal, and transverse positions.

Next, the workstation provides software tools which enable the practitioner to mark the facial, dental, maxilla and mandibular midlines and levels and cant of the upper and lower aesthetic occlusal planes. The designation or marking could be performed on 2D photographs of the patient displayed on the user interface. In particular, the 2D photographs of the patient are recalled from computer memory and displayed on the screen display, and the user identifies with the user interface devices (mouse) these locations, with the assistance of suitable user interface tools described herein.

The workstation further is provided with tools for marking the occlusal plane and occlusal plane positions such as upper and lower positions with respect to posterior, functional, and aesthetic locations on a 2D lateral X-ray view of the head, jaw and associated anatomical structures.

The software provides a feature by which a reference tooth or teeth is identified. The reference tooth or teeth are a tooth or teeth in which the movement of the tooth or teeth is expected to be a minimum over the course of treatment. The reference tooth is indicated or marked in any convenient fashion, such as by using suitable icons displayed simultaneously with a x-ray layout of the patient's teeth displayed on the user interface. Information as to roots of the reference teeth is available through X-ray, CT scans, with respect to the crowns of the teeth (2D or 3D).

The workstation further provides software tools for aligning two dimensional image data, such as X-ray data, with a virtual three-dimensional models of the teeth.

The method and workstation further involves using the graphical user interface to a) evaluate space between the virtual teeth and arch length requirements, b) evaluate the effect of various constraints on the arch length, and design a desired arch form for the patient, and c) move virtual teeth in a three-dimensional model of the patient from an initial orientation relative to the desired arch form, occlusal plane, midline, tooth position, reference tooth so as to arrive at a proposed tooth arrangement for treatment of the patient. Furthermore, the interdependency of the constraints can be evaluated. Preferably, the user interface provides tools that enable the practitioner to perform the task of space management between teeth in each arch to assure that there would be adequate space to accommodate the contemplated teeth alignment. Space management is done with respect to mandible and maxilla, both at the intra arch and inter arch level.

One important aspect of the invention is that throughout the process, the adjustments made are evaluated against the constraints identified by the practitioner in the matrix of patient parameters). Potential violations between the proposed treatment and the constraints are preferably pointed out so that only the feasible adjustments can be selected for inclusion in the treatment plan. The constrains are identified in the marking of midline, occlusal planes, etc. or identification of the constraints in terms of the shape of the maxilla and mandible, the shape and location of the patient's soft tissue, functional relationships or by other means.

The preferred sequence for these steps is as discussed above; however, the steps can be performed in any order, and repeated as many times as necessary. The preferred sequence can be driven by the patient's needs or the practitioner's preference. The workstation keeps a record of the latest changes made at each step. If at any step, the results are not satisfactory, then one or more of the previous steps might be revisited and appropriate adjustments made. In this manner the entire process is iterative and closed-loop. These steps described herein can be a precursor to additional treatment planning and appliance design steps in the situation where such planning is called for, e.g., in an orthodontic application, surgical application, prosthodontic application and restorative application. When no further adjustments are necessary in any area the treatment plan is considered finalized. This process can be utilized for initial treatment planning or to make treatment adjustments based upon periodic to monitoring of patient response to the treatment.

In another embodiment of the invention, assignment of values to variables, such as markings, tooth alignment, and space allocation, is integrated in a manner such that the most current selection or value for each such variable is retained by the workstation and made available at any other step in the treatment planning process besides the one where the specific value was originally assigned. For example, the midline marking done first on the 2D photos of the patient will be shown in the same position on appropriate 3D model of the patient's teeth used in teeth alignment and space management. The converse is also true, i.e., markings on a 3D virtual patient model will be available in 2D images of the same patient. An aspect of this invention is that a variable (such as the location of the midline in a 2D photograph) may be assigned a certain value at one step, and be modified at another step.

Such integration is realized through proper scaling and synchronization of patient's characteristics and features prevalent through 2D photographs and 2D and 3D images and models. A major benefit of this invention is that throughout the treatment planning process patient's biological interdependence between soft tissue, skeletal, and dental disposition is maintained and resulting constraints applied in a consistent manner such that unfeasible treatment options are filtered out. In turn, the benefit results in producing efficient and cost effective treatment plans. Additionally it is possible to stage treatment and compare progress against the staged treatment. The treatment plan can be actuated or initiated at any point in treatment to respond to any change that may occur.

In yet another aspect of the invention, the unified workstation facilitates simulation of realizing the target treatment objective through a number of staged incremental or step-wise treatment plans. The treatment increments can be varied and its impact seen on associated teeth disposition and space management. A practitioner can use this process in an interactive and dynamic manner to evaluate several treatment scenarios. A major benefit of this invention is that it enables the practitioner and the patient to tailor the treatment plan that best suits the patient needs.

In yet another embodiment of the invention, the unified work station facilitates rapid selection of treatment plan driven by templates. The practitioner provides specific values or ranges of values for the treatment parameters, such as for midline, maxilla and mandible levels and cant for aesthetic occlusal plane, various positions for upper and lower occlusal planes, reference tooth, arch form and alignment parameters for teeth, and space requirements, etc. for patient. The unified workstation, using computer instructions based tools, searches a clinical benchmarking knowledge base consisting of reference treatment plans for a large number of individual patients for a reference treatment plan. The search essentially cross-references using parameter values (e.g., archform shape, diagnosis, appliance type, etc.) and successful treatments and finds the most suitable reference treatment, if one is available in the knowledge base. In one possible embodiment, the workstation enables the practitioner to create and update such knowledge base through a self-learning process aided by computer instruction tools resident in the unified workstation.

In yet another embodiment of the invention, the unified workstation can be implemented in a manner such that consultation services from one or more specialists located remotely from the practitioner can be utilized on-line by providing capabilities whereby the practitioner and one or more specialists can all view the same images and charts or other information at the same time and exchange information as appropriate. Thus, the unified workstation can be implemented at a single site or at multiple sites all working together.

In yet another embodiment of the invention, the unified workstation provides computer software instruction in the form of user interface tools that aid in treatment to planning in a number of ways. For example, original teeth models can be superimposed on the aligned teeth model, where original teeth positions are shown in one color and the aligned teeth in another color, to visualize the effect of teeth disposition. Constraints (e.g., midline, occlusal plane, etc.) can be defined both in 2D and 3D images. They are interchangeable and changes made in 3D are applied automatically in 2D and vice versa. Occlusal planes can be superimposed on 3D teeth model to display malocclusion of the original teeth, and the combination further superimposed on the model of the properly aligned teeth to see the improvement. The midline can be superimposed on 3D teeth models. Three-dimensional gingival tissue, obtained from an intra-oral scan, can be superimposed on 3D teeth model at any stage in the treatment planning process. In a representative embodiment, color coding is invoked to show different aspects of the display. A grid can be superimposed on 3D teeth model to aid in visualizing certain measurements. Animation light can be thrown on 3D teeth model, and teeth can be shaded based upon their location with respect to the animated light source so as to aid in viewing otherwise difficult to see detailed teeth features. This can also be done while 3D teeth model is rotated to give views from different angles.

BRIEF DESCRIPTION OF THE DRAWINGS

Presently preferred embodiments of the invention are described below in reference to the appended drawings, wherein like reference numerals refer to like elements in the various views, and in which:

FIG. 4 is a flow chart showing a method of creating a complete textured three-dimensional model of teeth.

FIG. 5 also shows a plurality of icons, which, when activated, provide tools for manipulating the models shown in the Figure.

FIG. 17 is an illustration of a method of mapping the orientation reference points of FIGS. 16A-16C to a three-dimensional coordinate system.

FIGS. 21-60 illustrate screen shots from the workstation of FIG. 1, showing various treatment planning features that are provided by the treatment planning software of FIG. 19 in a presently preferred embodiment.

DETAILED DESCRIPTION OF PREFERRED EMBODIMENTS

Before describing the treatment planning features of this invention in detail, an overview of a unified workstation will be set forth initially. The workstation, in a preferred embodiment, provides software features that create two dimensional and/or three-dimensional virtual patient model on a computer, which can be used for purposes of treatment planning in accordance with a presently preferred embodiment.

Many of the details and computer user interface tools which a practitioner may use in adjusting tooth position, designing appliance shape and location, managing space between to teeth, and arriving at a finish tooth position using interaction with a computer storing and displaying a virtual model of teeth are set forth in the prior application Ser. No. 09/834,412 filed Apr. 13, 2001, and in published OraMetrix patent application WO 01/80761, the contents of which are incorporated by reference herein. Other suites of tools and functions are possible and within the scope of the invention. Such details will therefore be omitted from the present discussion.

General Description

A unified workstation environment and computer system for diagnosis, treatment planning and delivery of therapeutics, especially adapted for treatment of craniofacial structures, is described below. In one possible example, the system is particularly useful in diagnosis and planning treatment of an orthodontic patient. Persons skilled in the art will understand that the invention, in its broader aspects, is applicable to other craniofacial disorders or conditions requiring surgery, prosthodontic treatment, restorative treatment, etc.

Figure 1:
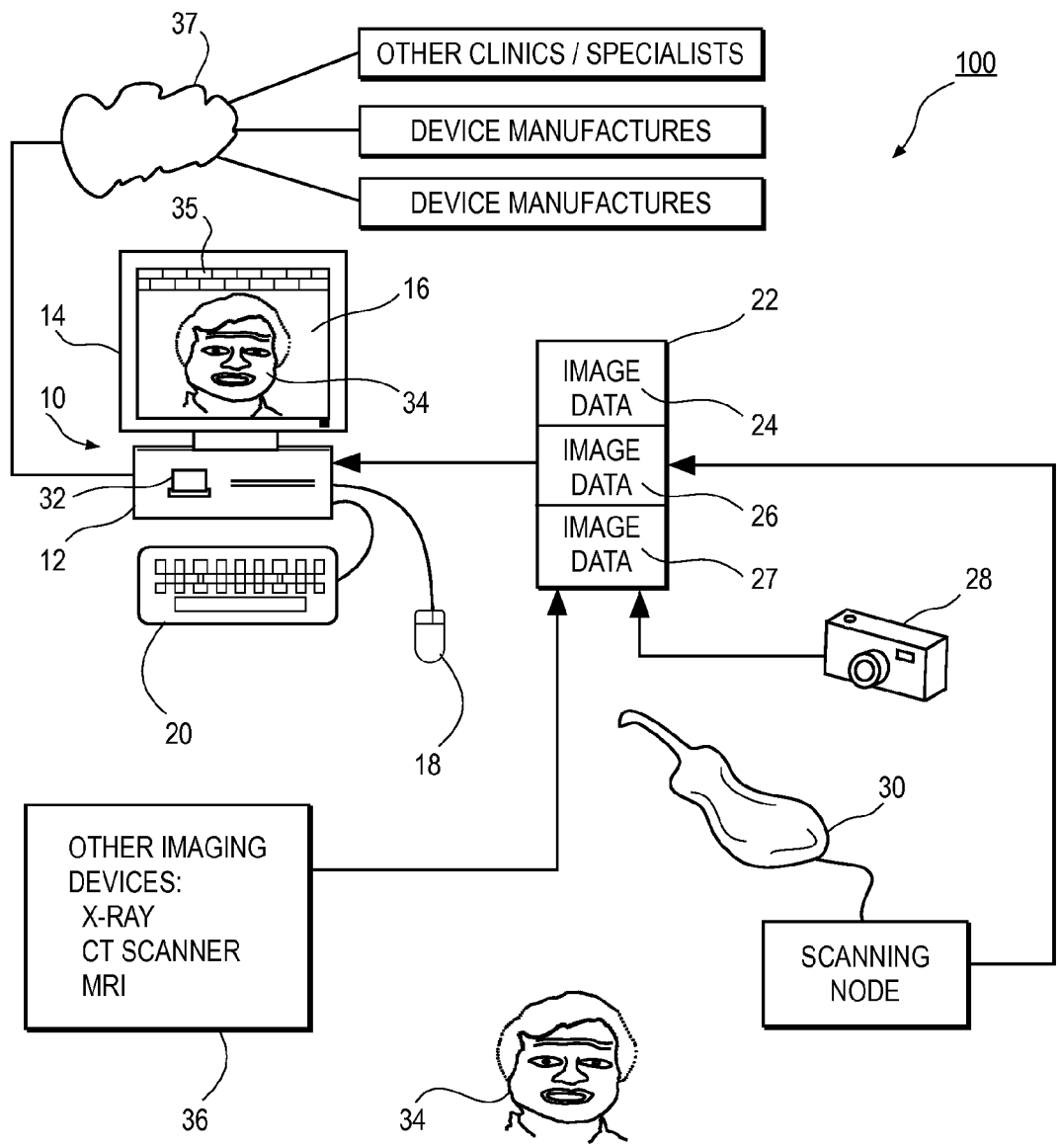
FIG. 1 is block diagram of a system for creating a three-dimensional virtual patient model and for diagnosis and planning treatment of the patient.

A presently preferred embodiment is depicted in FIG. 1. The overall system 100 includes a general-purpose computer system 10 having a processor (CPU 12) and a user interface 14, including screen display 16, mouse 18 and keyboard 20. The system is useful for planning treatment for a patient 34.

The system 100 includes a computer storage medium or memory 22 accessible to the general-purpose computer system 10. The memory 22, such as a hard disk memory or attached peripheral devices, stores two or more sets of digital data representing patient craniofacial image information. These sets include at least a first set of digital data 24 representing patient craniofacial image information obtained from a first imaging device and a second set of digital data 26 representing patient craniofacial image information obtained from a second image device different from the first image device. The first and second sets of data represent, at least in part, common craniofacial anatomical structures of the patient. At least one of the first and second sets of digital data normally would include data representing the external visual appearance or surface configuration of the face of the patient.

In a representative and non-limiting example of the data sets, the first data set 24 could be a set of two dimensional color photographs of the face and head of the patient obtained via a color digital camera 28, and the second data set is three-dimensional image information of the patient's teeth, acquired via a suitable scanner 30, such as a hand-held optical 3D scanner, or other type of scanner. The memory 22 may also store other sets 27 of digital image data, including digitized X-rays, MRI or ultrasound images, CT scanner etc., from other imaging devices 36. The other imaging devices need not be located at the location or site of the workstation system 100. Rather, the imaging of the patient 34 with one or other imaging devices 36 could be performed in a remotely located clinic or hospital, in which case the image data is obtained by the workstation 100 over the Internet 37 or some other communications medium, and stored in the memory 22.

The system 100 further includes a set of computer instructions stored on a machine-readable storage medium. The instructions may be stored in the memory 22 accessible to the general-purpose computer system 10. The machine-readable medium storing the instructions may alternatively be a hard disk memory 32 for the computer system 10, external memory devices, or may be resident on a file server on a network connected to the computer system, the details of which are not important. The set of instructions, described in more detail below, comprise instructions for causing the general computer system 10 to perform several functions related to the generation and use of the virtual patient model in diagnostics, therapeutics and treatment planning.

These functions include a function of automatically, and/or with the aid of operator interaction via the user interface 14, superimposing the first set 24 of digital data and the second set 26 of digital data so as to provide a composite, combined digital representation of the craniofacial anatomical structures in a common coordinate system. This composite, combined digital representation is referred to herein occasionally as the "virtual patient model," shown on the display 16 of FIG. 1 as a digital model of the patient 34. Preferably, one of the sets 24, 26 of data includes photographic image data of the patient's face, teeth and head, obtained with the color digital camera 28. The other set of data could be intra-oral 3D scan data obtained from the hand-held scanner 30, CT scan data, X-Ray data, MRI, etc. In the example of FIG. 1, the hand-held scanner 30 acquires a series of images containing 3D information and this information is used to generate a 3D model in the scanning node 31, in accordance with the teachings of the published PCT application of OraMetrix, PCT publication no. WO 01/80761, the content of which is incorporated by reference herein. Additional data sets are possible, and may be preferred in most embodiments. For example the virtual patient model could be created by a superposition of the following data sets: intra-oral scan of the patient's teeth, gums, and associated tissues, X-Ray, CT scan, intra-oral color photographs of the teeth to add true color (texture) to the 3D teeth models, and color photographs of the face, that are combined in the computer to form a 3D morphable face model. These data sets are superimposed with each other, with appropriate scaling as necessary to place them in registry with each other and at the same scale. The resulting representation can be stored as a 3D point cloud representing not only the surface on the patient but also interior structures, such as tooth roots, bone, and other structures. In one possible embodiment, the hand-held in-vivo scanning device is used which also incorporates a color CCD camera to capture either individual images or video.

The software instructions further includes a set of functions or routines that cause the user interface 16 to display the composite, combined digital three-dimensional representation of craniofacial anatomical structures to a user of the system. In a representative embodiment, computer-aided design (CAD)-type software tools are used to display the model to the user and provide the user with tools for viewing and studying the model. Preferably, the model is cable of being viewed in any orientation. Tools are provided for showing slices or sections through the model at arbitrary, user defined planes. Alternatively, the composite digital representation may be printed out on a printer or otherwise provided to the user in a visual form.

The software instructions further include instructions that, when executed, provide the user with tools on the user interface 14 for visually studying, on the user interface, the interaction of the craniofacial anatomical structures and their relationship to the external, visual appearance of the patient. For example, the tools include tools for simulating changes in the anatomical position or shape of the craniofacial anatomical structures, e.g., teeth, jaw, bone or soft tissue structure, and their effect on the external, visual appearance of the patient. The preferred aspects of the software tools include tools for manipulating various parameters such as the age of the patient; the position, orientation, color and texture of the teeth; reflectivity and ambient conditions of light and its effect on visual appearance. The elements of the craniofacial and dental complex can be analyzed quickly in either static format (i.e., no movement of the anatomical structures relative to each other) or in an dynamic format (i.e., during movement of anatomical structures relative to each other, such as chewing, occlusion, growth, etc.). To facilitate such modeling and simulations, teeth may be modeled as independent, individually moveable 3 dimensional virtual objects, using the techniques described in the above-referenced OraMetrix published PCT application, WO 01/80761.

The workstation environment provided by this invention provides a powerful system and for purposes of diagnosis, treatment planning and delivery of therapeutics. For example, the effect of jaw and skull movement on the patient's face and smile can be studied. Similarly, the model can be manipulated to arrive at the patient's desired feature and smile. From this model, and more particularly, from the location and position of individual anatomical structures (e.g., individual tooth positions and orientation, shape of arch and position of upper and lower arches relative to each other), it is possible to automatically back solve for or derive the jaw, tooth, bone and/or soft tissue corrections that must be applied to the patient's initial, pre-treatment position to provide the desired result. This leads directly to a patient treatment plan.

These simulation tools, in a preferred embodiment, comprise user-friendly and intuitive icons 35 that are activated by a mouse or keyboard on the user interface of the computer system 10. When these icons are activated, the software instruction provide pop-up, menu, or other types screens that enable a user to navigate through particular tasks to highlight and select individual anatomical features, change their positions relative to other structures, and simulate movement of the jaws (chewing or occlusion). Examples of the types of navigational tools, icons and treatment planning tools for a computer user interface that may be useful in this process and provide a point of departure for further types of displays useful in this invention are described in the patent application of Rudger Rubbert et al., Ser. No. 09/835,039 filed Apr. 13, 2001, the contents of which are incorporated by reference herein.

The virtual patient model, or some portion thereof, such as data describing a three-dimensional model of the teeth in initial and target or treatment positions, is useful information for generating customized orthodontic appliances for treatment of the patient. The position of the teeth in the initial and desired positions can be used to generate a set of customized brackets, and customized flat planar archwire, and customized bracket placement jigs, as described in the above-referenced Andreiko et al. patents. Alternatively, the initial and final tooth positions can be used to derive data sets representing intermediate tooth positions, which are used to fabricate transparent aligning shells for moving teeth to the final position, as described in the above-referenced Chisti et al. patents. The data can also be used to place brackets and design a customized archwire as described in the previously cited application Ser. No. 09/835,039.

To facilitate sharing of the virtual patient model among specialists and device manufacturers, the system 100 includes software routines and appropriate hardware devices for transmitting the virtual patient model or some subset thereof over a computer network. The system's software instructions are preferably integrated with a patient management program having a scheduling feature for scheduling appointments for the patient. The patient management program provides a flexible scheduling of patient appointments based on progress of treatment of the craniofacial anatomical structures. The progress of treatment can be quantified. The progress of treatment can be monitored by periodically obtaining updated three-dimensional information regarding the progress of treatment of the craniofacial features of the patient, such as by obtaining updated scans of the patient and comparison of the resulting 3D model with the original 3D model of the patient prior to initiation of treatment.

Thus, it is contemplated that system described herein provides a set of tools and data acquisition and processing sub-systems that together provides a flexible, open platform or portal to a variety of possible therapies and treatment modalities, depending on the preference of the patient and the practitioner. For example, a practitioner viewing the model and using the treatment planning tools may determine that a patient may benefit from a combination of customized orthodontic brackets and wires and removable aligning devices. Data from the virtual patient models is provided to diverse manufacturers for coordinated preparation of customized appliances. Moreover, the virtual patient model and powerful tools described herein provide a means by which the complete picture of the patient can be shared with other specialists (e.g., dentists, maxilla-facial or oral surgeons, cosmetic surgeons, other orthodontists) greatly enhancing the ability of diverse specialists to coordinate and apply a diverse range of treatments to achieve a desired outcome for the patient. In particular, the overlay or superposition of a variety of image information, including 2D X-Ray, 3D teeth image data, photographic data, CT scan data, and other data, and the ability to toggle back and forth between these views and simulate changes in position or shape of craniofacial structures, and the ability to share this virtual patient model across existing computer networks to other specialists and device manufacturers, allows the entire treatment of the patient to be simulated and modeled in a computer. Furthermore, the expected results can be displayed before hand to the patient and changes made depending on the patient input.

With the above general description in mind, additional details of presently preferred components and aspects of the inventive system and the software modules providing the functions referenced above will be described next.

Capture of Image Information

The creation of the virtual patient model uses the capture and storage of at least two different digital sets of image data of the patient. The image sets will typically represent, at least in part, overlapping craniofacial anatomical structures so that a superposition of them in a common three-dimensional coordinate system may occur.

The type of image data that will be obtained will vary depending on the available image acquisition devices available to the practitioner. Preferably, the system employs software simulation of changes in shape or position of craniofacial structures (e.g., teeth or jaw) on the visual appearance, e.g., smile, of the patient. Accordingly, at least one of the data sets will include normally include data regarding the surface configuration of the face and head. A commercially available digital CCD camera 28 (FIG. 1), e.g., camera available from Sony or Canon, can be used to obtain this information. Preferably, the image data is color image data. The data sets are obtained by photographing the patient's head and face at various viewing angles with the camera and storing the resulting image files in the memory of the computer. These images can provide a basis for creating a morphable face model.

The image data regarding the patient's exterior appearance can be obtained through other means including via scanning of the head and face of the patient via the hand-held 3D-scanner 30 described in the published OraMetrix PCT application, referenced previously. If this approach is used, it may be beneficial to apply a thin layer of non-toxic, opaque and reflective substance to the skin prior to scanning to insure adequate data capture by the hand-held scanner. A suitable opaquing substance is described in the patent application of Nancy Butcher et al. Ser. No. 10/099,042 filed Mar. 14, 2002, entitled "Method for Wet-Field Scanning," the contents of which are incorporated by reference herein. In operation, the scanner captures a sequence of overlapping images of the surface of the patient as the scanner is held by the hand and moved about the face. The set of images can be obtained in only a few minutes. Each image is converted to a set of X, Y and Z coordinate positions comprising a cloud of points representing the surface of the face. The point clouds from each image are registered to each other to find a best fit to the data. The resulting registered point cloud is then stored in the memory as a virtual three-dimensional object. The construction, calibration and operation of the scanner, and the manner of converting scanned data to point clouds and registering three-dimensional point clouds to form a three-dimensional object is described at length in the published PCT application of OraMetrix and therefore omitted from the present discussion for the sake of brevity. Other types of scanners or coordinate measuring instruments could be used in less preferred embodiments, such as the scanning devices in the Yamany et al. articles referenced previously.

Aside from surface data of the patient obtained by the camera 28 or 3D scanner 30, the system typically will include the capture of additional data representing the teeth of the patient, and also capture of additional data representing craniofacial structures not visible to the naked eye using other imaging devices 36 (FIG. 1). For example, the system will acquire digitized images from an X-ray machine capturing X-ray photographs of the patient's head, jaw, teeth, roots of teeth, and other craniofacial structures. These photographs are digitized and stored in the memory of the computer system.

As other possible examples, three-dimensional magnetic resonance images of the patient's head or jaws are obtained and stored in the memory. Other examples include images acquired from a computed tomography (CT) scanner, ultrasound imager, or other type of imaging device.

While the above discussion has described how 3D image of the face can be obtained from a three-dimensional scanner, there are other possibilities that may be used in the practice of alternative embodiments. One such alternative is creating a 3D virtual face from a series of 2-D color photographs. This technique is known and described in Pighin et al., *Synthesizing Realistic Facial Expression from Photographs*, Computer Graphics Proceedings SIGGRAPH '98, pp. 78-94 (1998); Pighin et al., *Realistic Facial Animation Using Image-based 3D Morphing*, Technical Report no. UW-CSE-97-01-03, University of Washington (May 9, 1997); and Blantz et al., *A Morphable Model for The Synthesis of 3D Faces*, Computer Graphics Proceedings SIGGRAPH '99 (August, 1999), the contents of which are incorporated by reference herein. Basically, in this alternative, two-dimensional color pictures of the face are taken which are converted automatically to a textured 3 dimensional model using a 'morphable model' technique. Here, the phrase "textured 3 dimensional model" is used in the particular sense of a colorized three-dimensional object, with the word "texture" synonymous with color data, as that term is used in this particular art. Morphable models can be built based on various known approaches such as optic flow algorithms or active model matching strategy, or a combination of both. One approach is to scan a set of 2D faces. A shape vector containing 3D vertices and texture vector containing RGB color values of each vertex represents the geometry of the face. Each face is divided into sub regions such as eyes, nose, mouth etc. Blending the sub-regions at the borders generates the complete 3D face. Automatic matching and estimating 3D face of a 2D color image from morphable model is carried out as follows:

New Shape (Sn) and texture (Tn) are computed as follows:

$$Sn = Sa + \Sigma \alpha s; \quad (1)$$

$$Tn = Ta + \Sigma \beta t, \quad (2)$$

where Sa and Ta are the averages of Shape S and Texture T over all the 3D face datasets; s & t are the eigenvectors of the covariance matrices; α and β are the coefficients of the facial shape and texture for all the faces, and n is a sub-region index.

Rendering parameters ρ contain camera position, object scale, image plane rotation and translation and light intensity. From Bayes decision theory, the set of parameters, (α,β, ρ) are determined with maximum posterior probability for getting a corresponding 3D face from a 2D image.

Three-dimensional image data sets of the upper and lower arches including upper and lower teeth are preferably created with a 3D optical scanner 30, such as the OraMetrix hand-held in-vivo scanner. If the 3D jaw model has no texture model, i.e., no color data, the texture data can be extracted from the 2 dimensional colored picture of the upper and lower jaw and mapped to the 3D coordinates on the jaw model using a cylindrical projection technique. In this technique, a map is constructed in texture space, that for each point (u, v), specifies a triangle whose cylindrical projection covers that point. The 3D point p corresponding to point (u, v) in texture space is computed by intersecting a ray with the surface of the corresponding point in the 2D colored image.

Superposition or Registration of the Data Sets

After the images of the face, craniofacial structures, X-rays, teeth etc. are obtained and stored in memory in digital form they are superimposed on each other (i.e., registered to each other via software in the workstation) to create a complete virtual patient model on the workstation. The superposition of the sets of image data may be developed as an automatic software process, or one in which there is user involvement to aid in the process. In one possible example, the three-dimensional textured model of the face is properly aligned with the 3D jaw model obtained from the intra-oral scan, 3D skull data from CT scan, and 2 dimensional X-rays to create a virtual patient model. For correct alignment of the data sets to each other, a preferred method executed by the software selects three or more corresponding points on the 3D jaw and the 3D face, and then computes a transformation matrix to re-orient the 3D face relative to the 3D jaw. This transformation matrix will contain the information needed to rotate and translate the 3D face relative to the 3D jaw in a best-fit manner to align the two to each other. Methods of calculation of transformation matrices to achieve registration are taught in the published PCT patent application of OraMetrix, Inc., cited previously. Similar methods are used for registering the CT scan data and X-ray data to the combined 3D face and jaw model. Once the superposition is achieved, the resulting model is displayed on the workstation user interface. The user is provided with tools for simulating movement or repositioning of craniofacial structures of the virtual patient, and the computer animates such movement or repositioning and shows the effect of such movement or repositioning on the external visual appearance of the patient.

Figure 2:
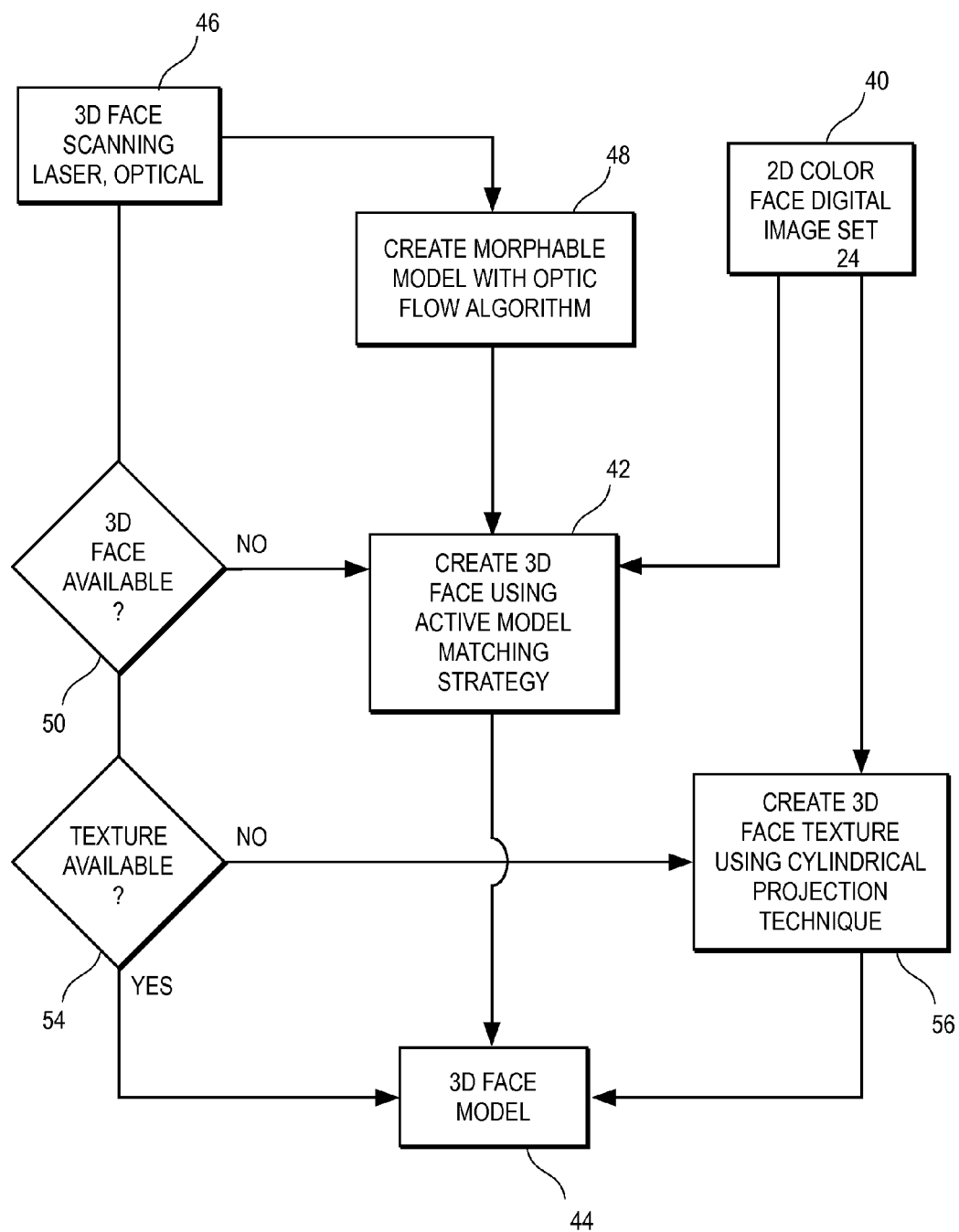
FIG. 2 is a flow chart showing a method of three-dimensional face creation from scanning systems, which may be executed in software in the computer system of FIG. 1.

An example of registering scan data of a jaw from an intra-oral scan to a 3D face model using human interaction is shown in FIGS. 2-7. FIG. 2 is a flow chart showing a software method of three-dimensional face creation from scanning systems, which may be executed in software in the computer system 10 of FIG. 1. There are two possible approaches for creating the 3D face, one using a color digital camera 28 (FIG. 1) and another using scanning of the face using the hand held scanner 30 and scanning node 31 (FIG. 1). In the situation in which a color digital camera is used, at step 40 a set 24 of 2D digital color photographic images of the face and head are obtained and stored in the memory 22 of FIG. 1. The set 24 of images is supplied to a module 42 which creates a virtual 3D face using an active model matching strategy, using the techniques known in the art and described in Pighin et al., *Synthesizing Realistic Facial Expression from Photographs*, Computer Graphics Proceedings SIGGRAPH '98, pp. 78-94 (1998); Pighin et al., *Realistic Facial Animation Using Image-based 3D Morphing*, Technical Report no. UW-CSE-97-01-03, University of Washington (May 9, 1997); and Blantz et al., *A Morphable Model for The Synthesis of 3D Faces*, Computer Graphics Proceedings SIGGRAPH '99 (August, 1999). This 3D face model is then stored in the hard disk memory of the computer 10, as indicated at process module 44.

In alternative embodiments, a 3D scanning of the face using a laser or 3D optical scanner is performed, as indicated at 44. The 3D model is provided to a module 46 which creates a morphable model of the face and head with an optic flow algorithm. This morphable model is provided to the module 42 for creating a 3D face. At step 50, the software inquires as to whether a morphable 3D face is available, and if not the processing of module 42 executes, in which a 3D morphable model of the face is created. If a morphable 3D face is already available, the software inquires at step 54 as to whether texture (color) information is available to add to the 3D face. (Note that in many 3D scanner systems there is no acquisition of color information, only spatial information). If color information is not available, the processing proceeds to module 56. In module 56, the color data is provided to the 3D model to create a 3D color morphable virtual model. The color data is supplied from the digital photographs of the patient, obtained at step 40. The texture information is supplied to the 3D model from the scanner using a cylindrical projection technique in module 56 (or by using any other known technique). The textured, morphable 3D model of the face and head is stored as indicated at module 44.

Figure 3:
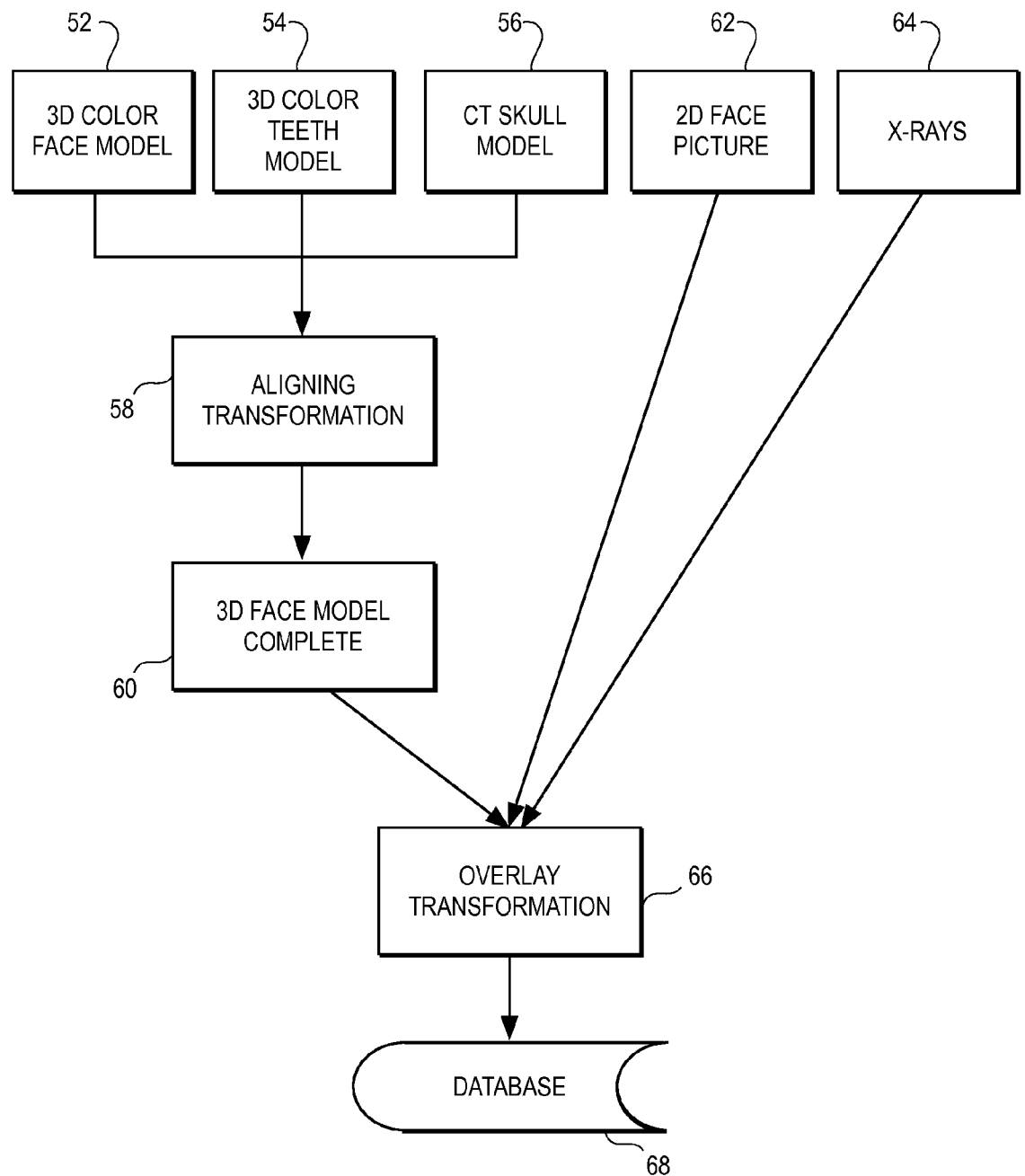
FIG. 3 is a flow chart showing an alternative method of three-dimensional face model face creation using a plurality of possible input image or data formats, which may be executed in software in the computer system of FIG. 1.

An alternative software method or process for creating a 3D model of the face is shown in FIG. 3. The method involves the acquisition of a 3D color face model 52 (using for example the techniques of FIG. 2), the acquisition of 3D color model of the teeth 54, and the acquisition of a model 56 of the skull using a CT scanner. These three models are supplied to a module 58 which performs an aligning transformation on the data sets from each of these modules. The aligning transformation process 58 basically scales and provides the necessary X, Y and Z translations and rotations to place the data sets into a common coordinate system such that common anatomical structures overlap each other. The complete 3D face model is stored as indicated at step 60 and then supplied to an overlay transformation module 66. The overlay transformation module 66 obtains a set of 2D color face photographs 62 and X-Rays 64, and overlays them to the complete 3D face model to result in a combined, composite model of the face, skull, teeth, and associated tooth roots, bone and other anatomical data. This composite representation of the patient is stored in a database 68 for the system 100.

FIG. 4 shows a process that can be used to combine 3D scan data with 2D color photographs to create a 3D color model of the teeth. In step 70, the teeth are scanned with the hand-held intra-oral scanner 30 of FIG. 1. The resulting data represent a 3D model of the dentition, which is stored in the computer 10. This process is described in the published PCT application of OraMetrix, Inc. cited previously. At step 72, 2D color photographs of the teeth are obtained with a color digital camera. In one possible embodiment, the hand-held scanner 30 includes a video camera that obtains a continuous stream of color video frames separate and apart from the acquisition of 3D image data. The color photographs of the dentition at step 72 could be obtained in this manner.

At step 74, a 3D textured model of the teeth is created using a cylindrical projection technique. Basically, in this technique, the color data from the color photographs is projected onto the tooth data. The tooth data can be represented as triangular surfaces, with the vertices of each triangle being adjacent points in a point cloud defining the surface of the tooth. The color is projected on the surfaces, and each surface is assigned a value associated with a particular color. The result is a 3D color model of the teeth.

Figure 4A:
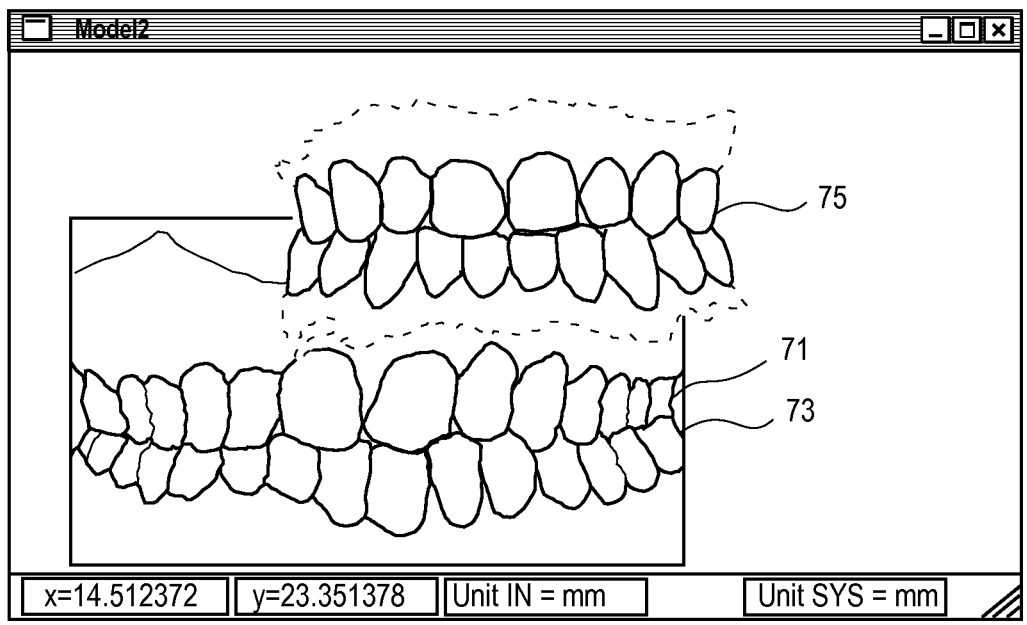
FIGS. 4A-4E show a technique for combining 2D color photographs with 3D tooth data to created textured (colored) 3D tooth models.
Figure 4B:
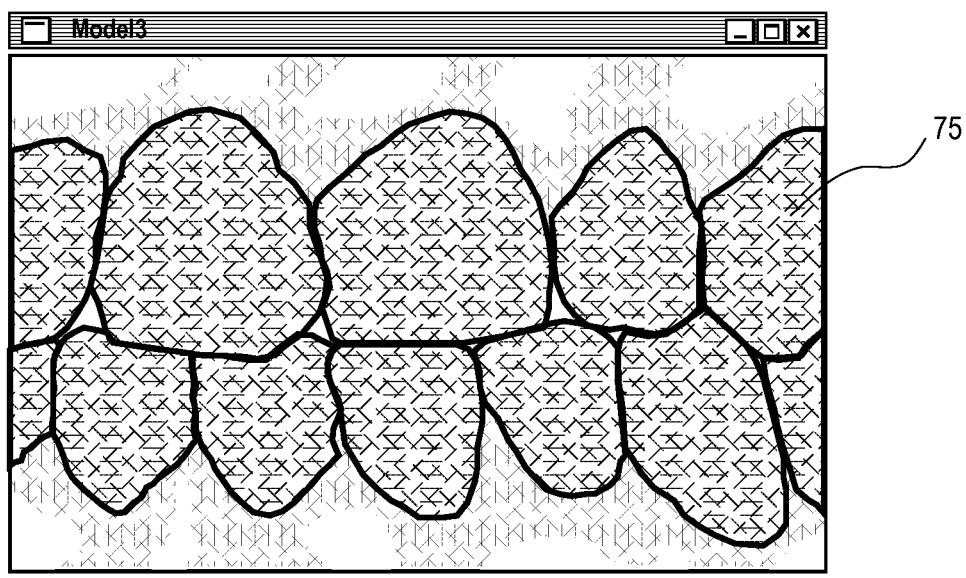

FIGS. 4A-4E show several screen displays from a user interface of the unified workstation that illustrate the process of texture mapping a 3D object (here, teeth) by projection of color data from a 2D photograph. After a patient's dentition is scanned, the virtual teeth and gingiva for both upper and lower arches are represented as a single surface, in the present example a triangle mesh surface. FIG. 4A shows a 2D digital photograph of teeth/gingivae 71 displayed in a graphical window 73 along with a 3D virtual model of the teeth 75 to one side. The 2D digital photograph 71 is scaled up or down in size as necessary to as to be approximately the same in scale (size) as the 3D model of the teeth 75. This is accomplished using any suitable icons or mouse action, such as clicking on the 2D photograph and scrolling up or down with the mouse to change the size of the 2D image so that it matches the size of the 3D model. FIG. 4B shows the surface of the teeth and gingivae of the 3D virtual model 75 in greater detail. The surface of the model 75 comprises a set of minute interconnecting triangle surfaces, with the vertices of the triangle surfaces being points that represent the surface. This is only one possible format for representing the surface of a 3D object.

Figure 4C:
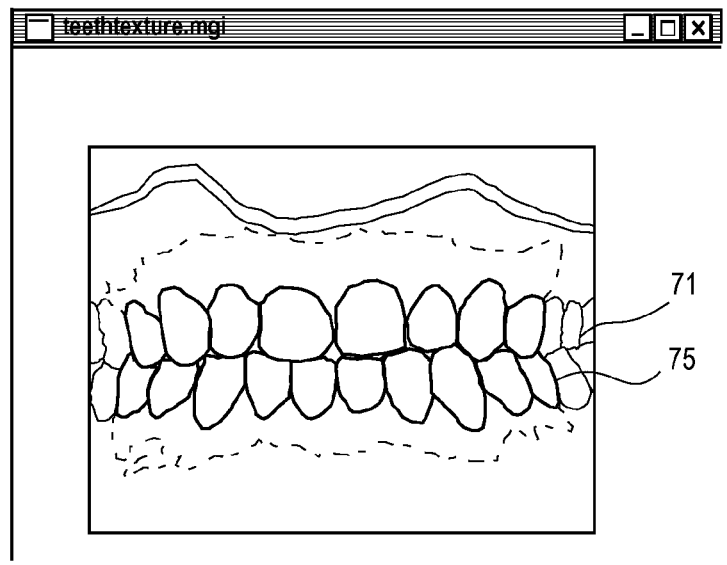
Figure 4D:
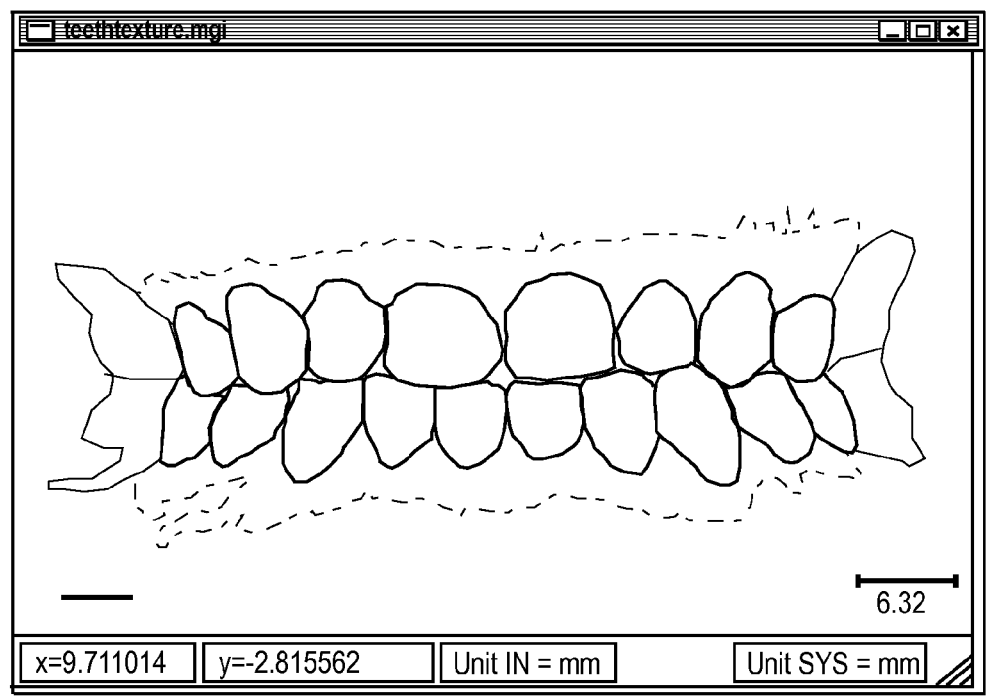
Figure 4E:
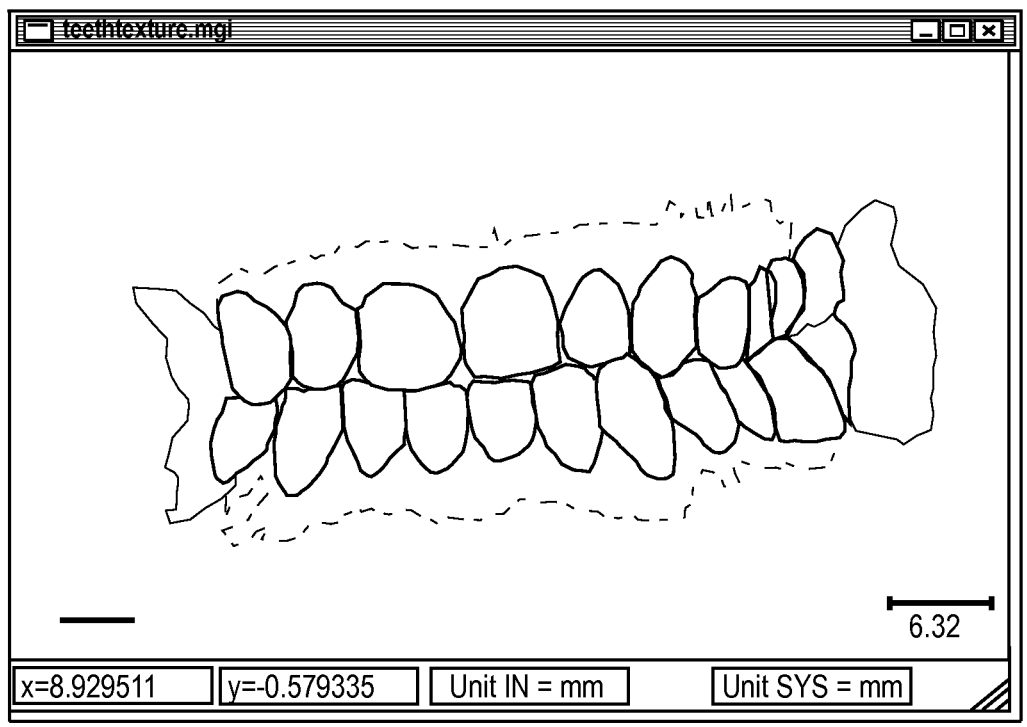

After the 2D photograph and 3D model have been scaled, a translation is performed to as to overlap the 3D model and the 2D photograph. FIG. 4C shows the 2D picture 71 transformed by scaling and translation such that it is superimposed on the 3D model 75. This superposition could be performed manually or automatically. For example, the user can click and drag the 2D digital photograph 71 and manually move it using the mouse so that it overlaps exactly the 3D model 75. The color information in the 2D photograph 71 is projected and mapped to the individual triangle surfaces forming the lower jaw and upper jaw of the 3D model 75 using, for example, a projection algorithm. The result, a textured 3D model, is shown in FIG. 4D. FIG. 4E shows textured 3D model after rotation on the user interface.

Occlusal and lingual 2-D color photographs of each jaw are also obtained and texture data is mapped to the surface data. The result is a complete true color 3D model of the teeth of both arches.

Figure 5:
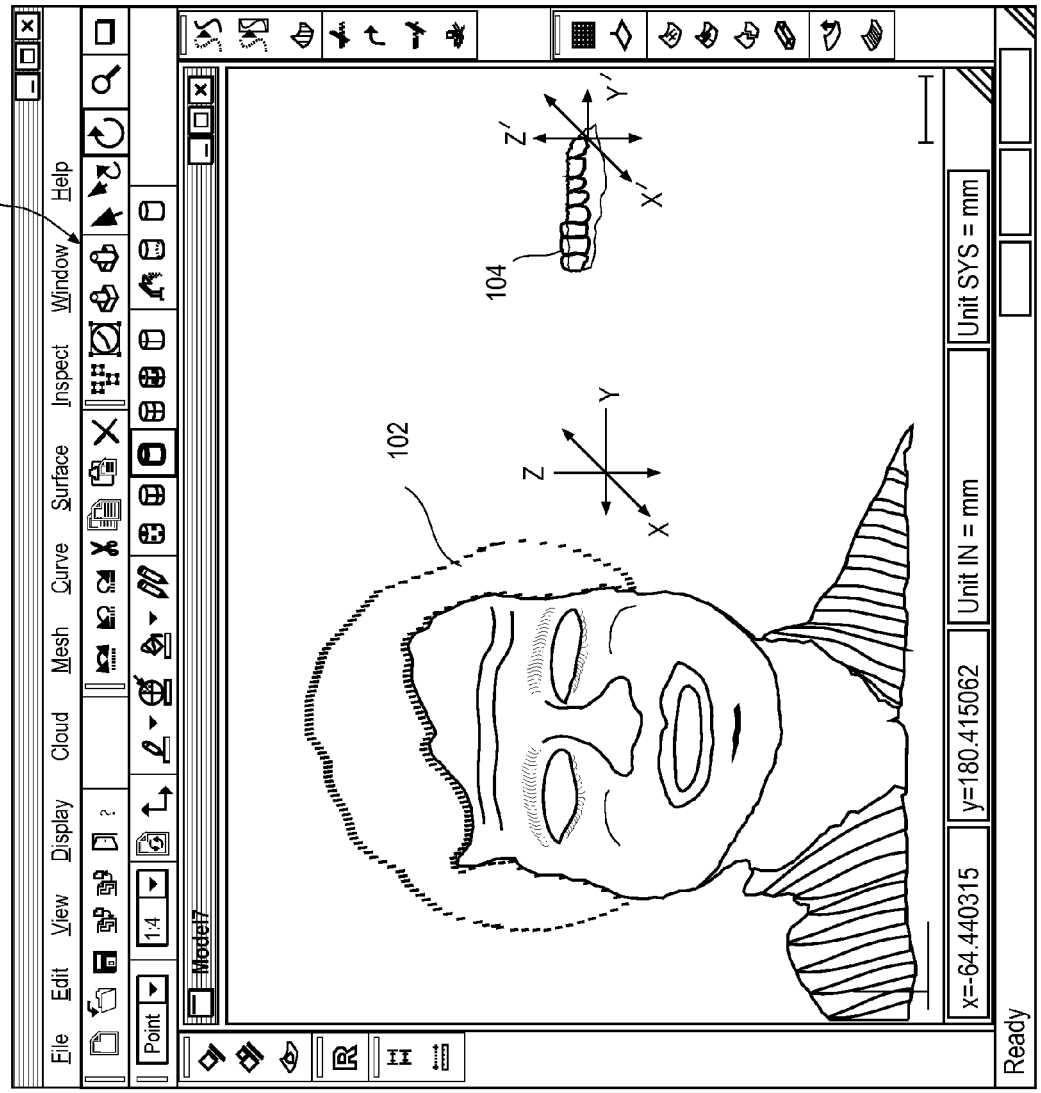
FIG. 5 is a screen shot of the user interface of FIG. 1 showing a three-dimensional face model and a three-dimensional tooth model, in separate coordinate systems (i.e., prior to registration or superposition of the two relative to each other).

FIG. 5 is an illustration of a screen display on the user interface of the computer 10. The display shows a 3D morphable model 102 of patient on the left hand side of the display, in a given arbitrary coordinate system X, Y, Z. The morphable model 102 is obtained, for example, from color photographs using the techniques described previously. A three-dimensional model 104 of teeth of the patient is shown on the right hand side of the screen.

The 3D model of the teeth 104 can be obtained from intra-oral scanning using the scanner 30 of FIG. 1, from a laser scan of a physical model of the dentition obtained from an impression, from a coordinate measuring device or some other source. The source is not particularly important. The 3D model of the teeth 104 is shown in a separate coordinate system X', Y', Z'. Screen display includes various icons 35 the allow the user to position the tooth model 104 relative to the morphable model 102 in order to combine the two in a common coordinate system and construct a composite model.

Figure 6:
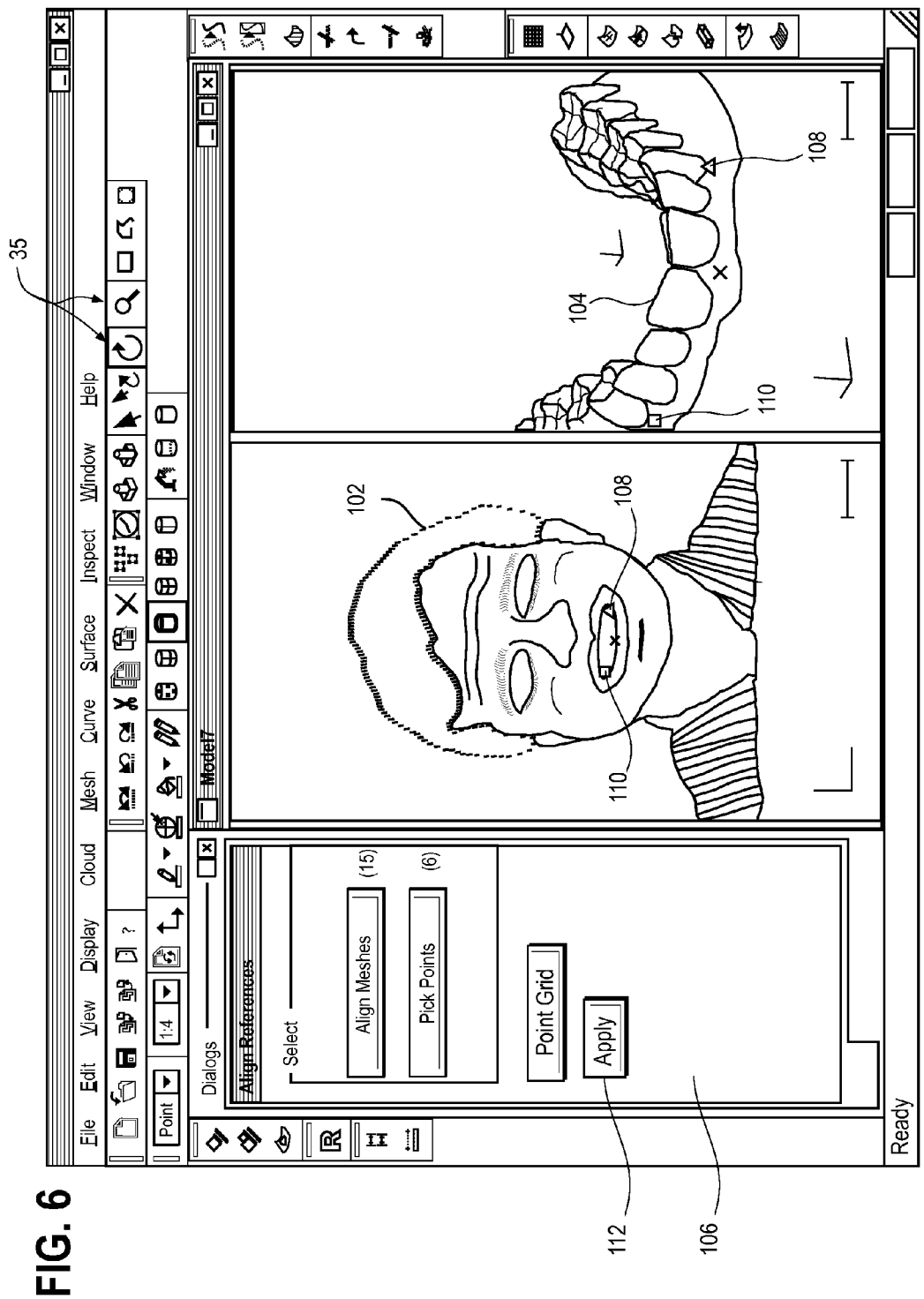
FIG. 6 is a screen shot showing one possible method of placement of the lower jaw 3D data into the face data coordinate system using corresponding points that are common to each data set.

In FIG. 6, the user has activated an "Align References" icon, which causes the screen display to show the box 106 on the left hand side of the screen. The user is provided with the option to pick points that represent anatomical structures that are common to both the morphable model 102 and the 3D tooth model 104. In this particular situation, the user has selected with the mouse two points on the lower arches which lie at the intersection of the teeth and the gums. These two points are shown as a triangle 108 and a square 110. Obviously, other points could be chosen. The user then clicks on the "Apply" tab 112. The result is shown in FIG. 7, in which the 3D tooth model 104 is combined with the morphable face 102 model to produce a combined virtual patient model 34.

Figure 7:
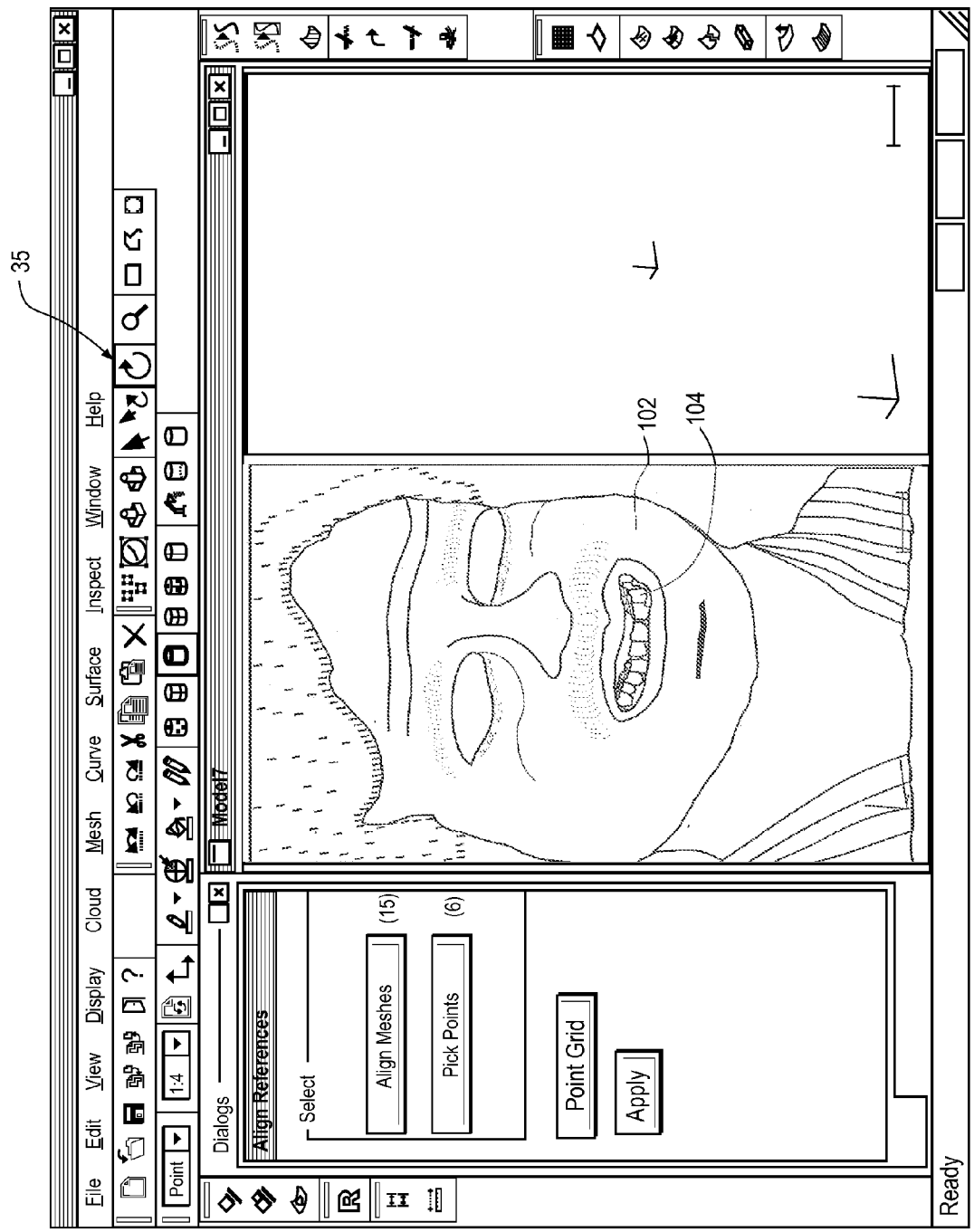
FIG. 7 is a screen shot showing the face data and the lower jaw 3D data in a common coordinate system (the face coordinate system of FIGS. 5 and 6).

In the example of FIGS. 5-7, the morphable model 102 was already scaled to the same scale as the tooth model 104. In other words, the data representing the morphable face model indicates that the spatial dimensions of the teeth in the morphable face model is substantially the same as the spatial dimensions of the virtual tooth model 104. Methods of performing scaling are described below.

Figure 8:
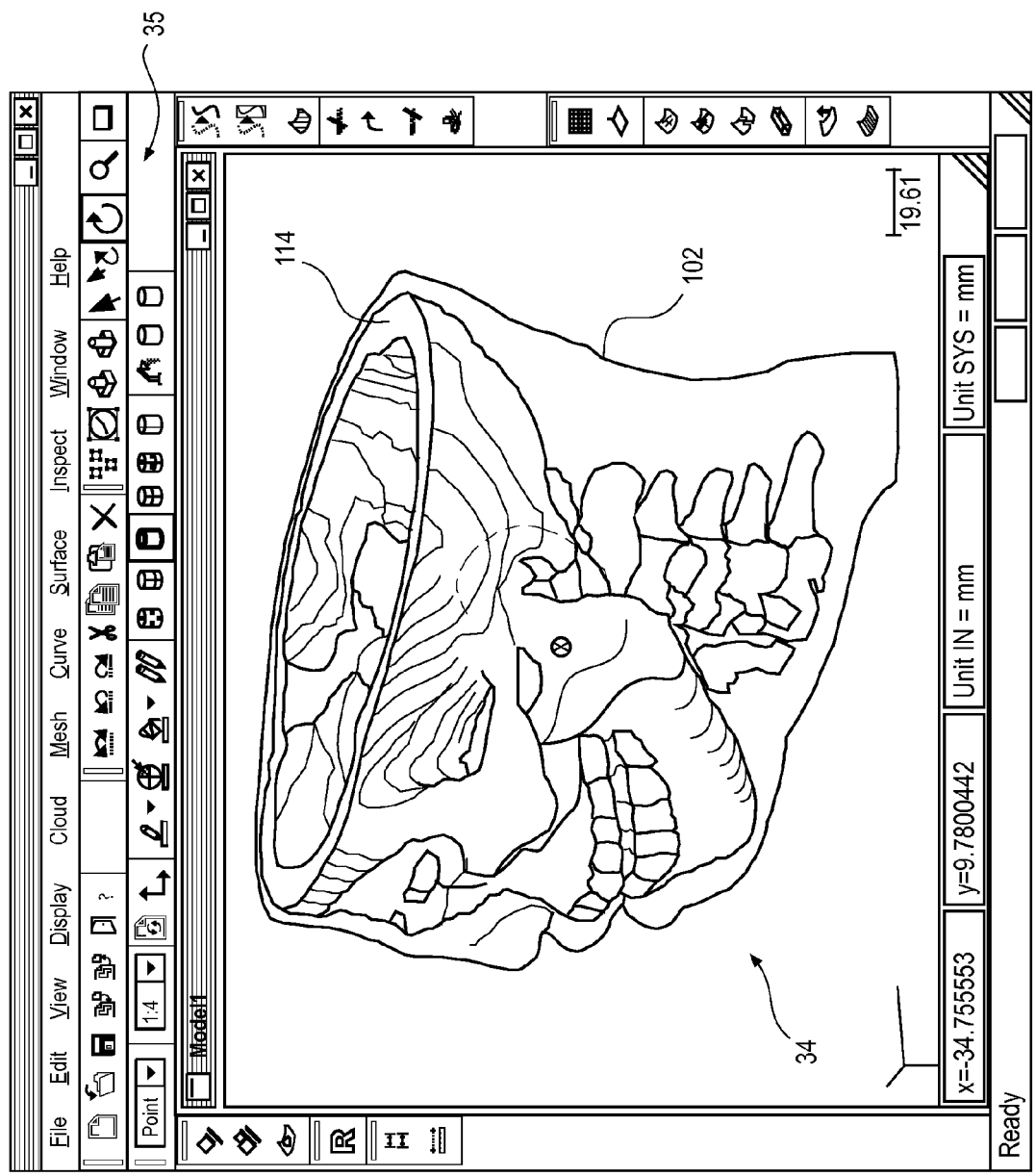
FIG. 8 is a screen shot showing the face data and skull data obtained from a CT scan in a common coordinate system.

FIG. 8 is an illustration of an alternative embodiment of a virtual patient model 34. In this embodiment, the model 34 is a combination of data 102 representing a morphable face, obtained from a plurality of 2D color photographs, and skull data 114 obtained from a CT scan. The two sets of data are shown in a common coordinate system, appropriately scaled. The manner of combining the two data sets can be using the approach described in FIGS. 6 and 7. Alternatively, the user could click and drag using a mouse one or the other of the data sets and manually position it until it is in the correct position. As yet another alternative, the software could be programmed to find common overlapping features (such as for example teeth) using surface matching algorithms, and then position the CT scan model relative to the face model such that the common features overlap exactly.

Figure 9:
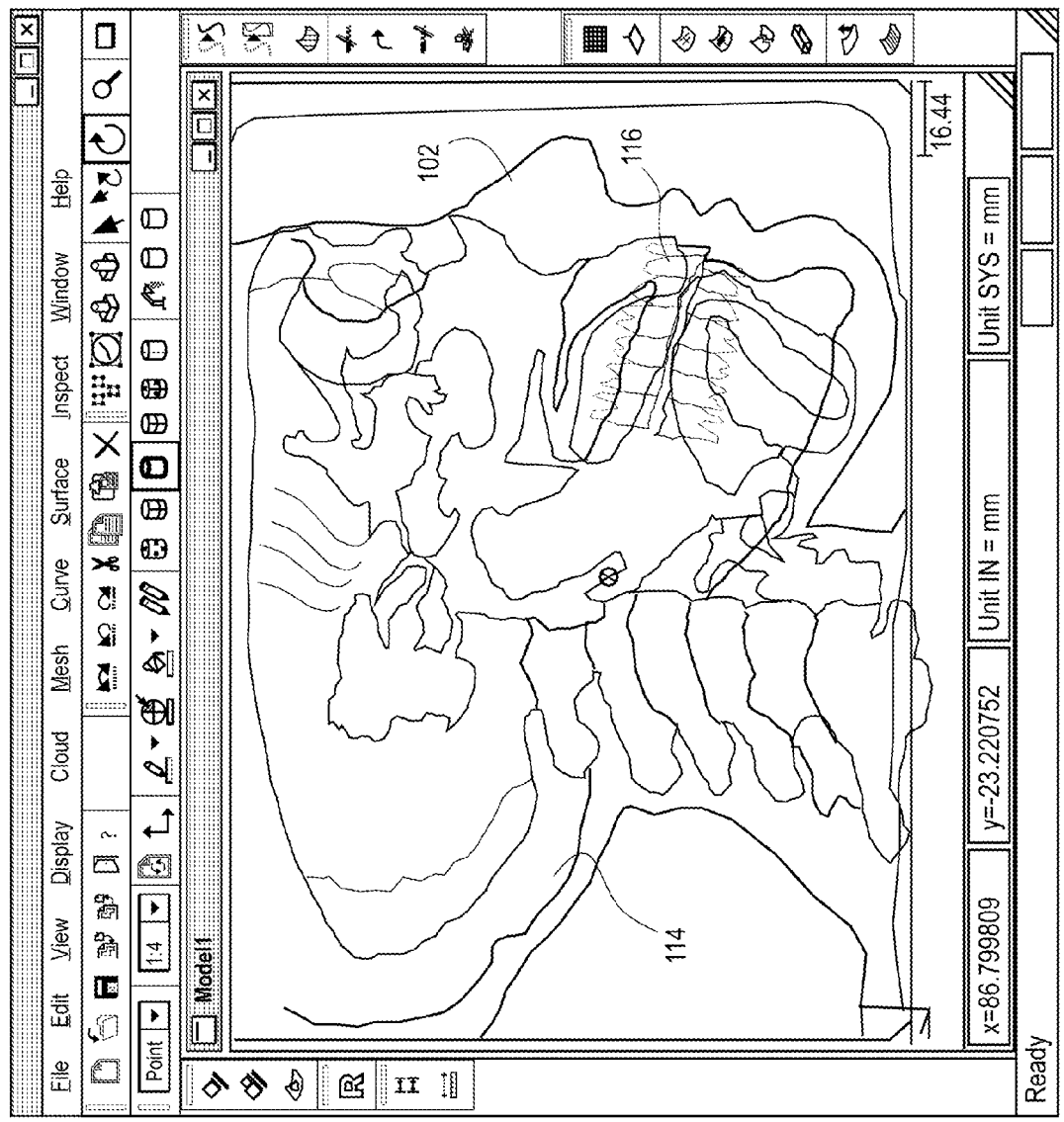
FIG. 9 is a screen shot showing face data and skull data superimposed on X-ray data obtained from the patient.

FIG. 9 is a screen shot of yet another possible embodiment of a virtual patient model. This model combines face data 102 from a morphable face model (obtained from 2D color photographs), skull data 114 from a CT scan, and X-ray data 116 obtained from a set of digital X-Rays of the patient. The manner of creating the virtual patient model can be for example using the procedure of FIG. 3 and FIG. 6-7. The morphable face model is aligned relative to the CT scan data either automatically or using some human interaction. The 2D X-Ray data can be morphed into 3D digital data using the morphable model algorithms cited previously. Alternatively, the 2D X-Ray data can be combined with 3D optical scan data of crowns of the teeth to create a combined X-Ray/3D tooth model, which is then combined with the CT/morphable face model. This process may be optimized by using virtual template tooth roots, which are modified to fit the X-ray data, and then this combined 3D root model is combined with crown data to produce a complete set of 3D teeth, including roots. This combined model is merged into the CT scan/morphable face model using the techniques of FIGS. 6 and 7 (selecting common points then using the "Apply Points" icon, FIG. 7, item 112), using click and drag techniques, or any other appropriate registration or transformation technique.

Figure 10:
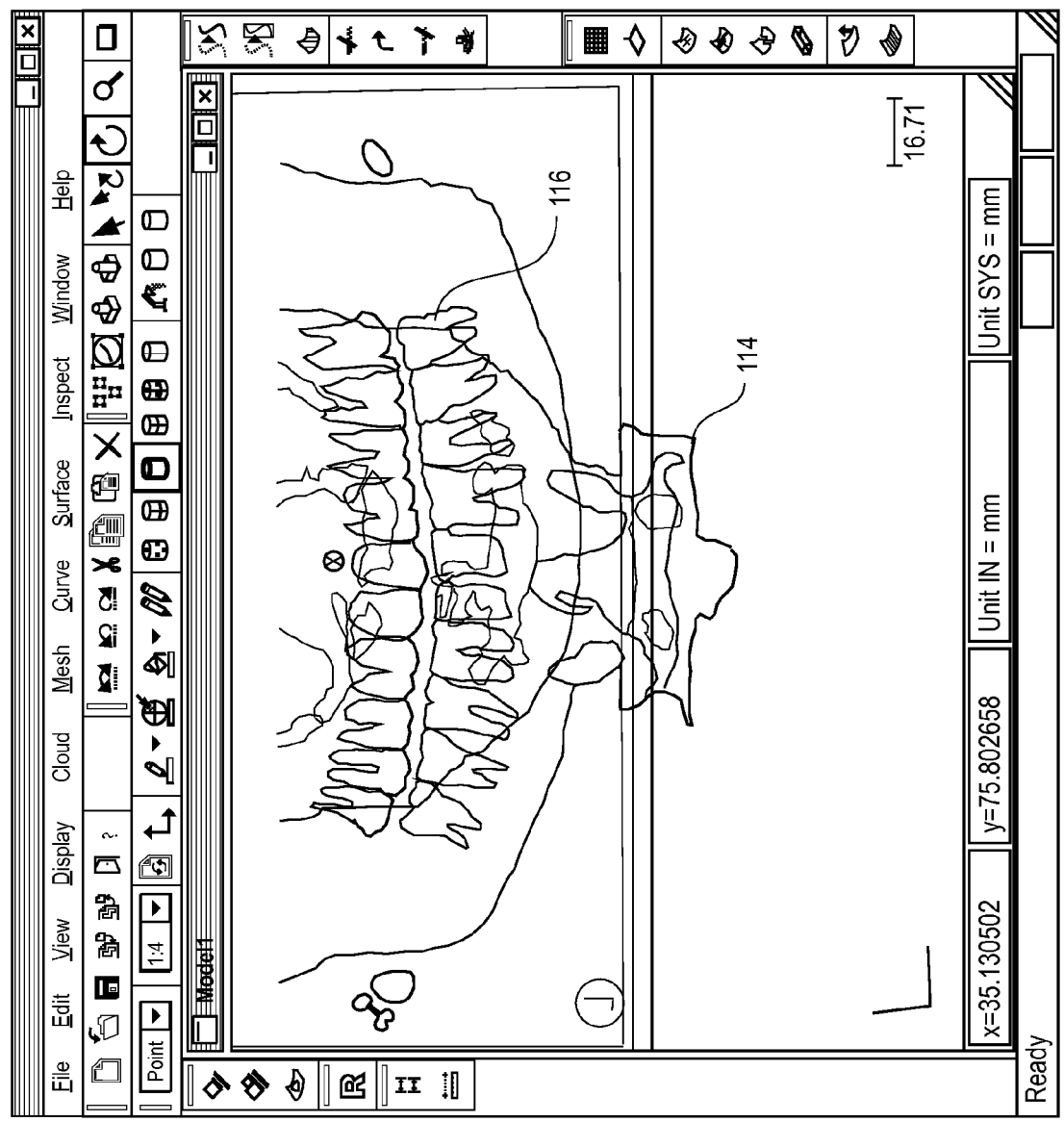
FIG. 10 is a screen shot showing the superposition of skull and face data with X-Ray data.
Figure 11A:
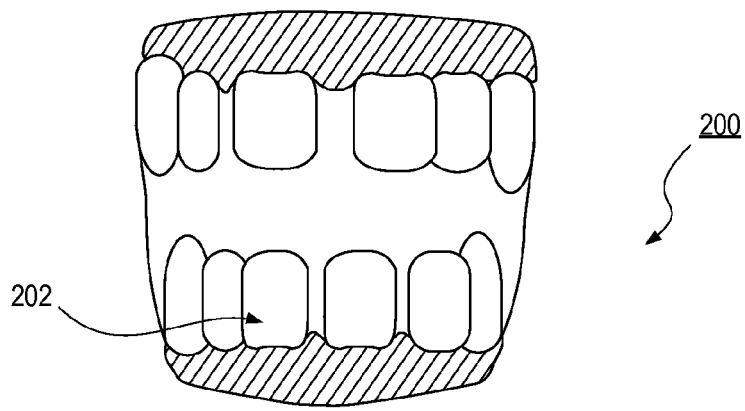
FIGS. 11A-11E are a series of views of a digital model of an orthodontic patient obtained, for example from CT scan, photographs, or intra-oral scanning with a hand-held 3D scanner.
Figure 11B:
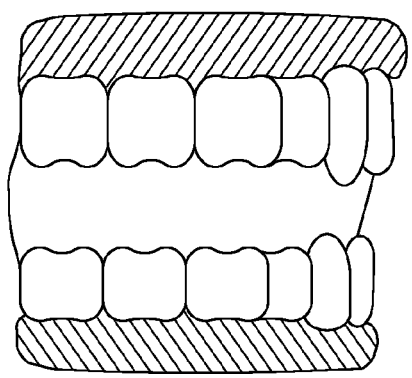
Figure 11C:
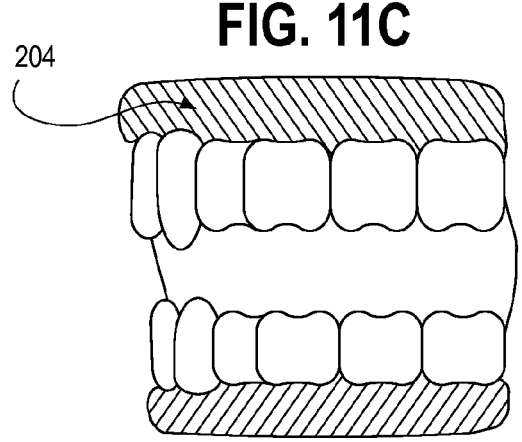
Figure 11D:
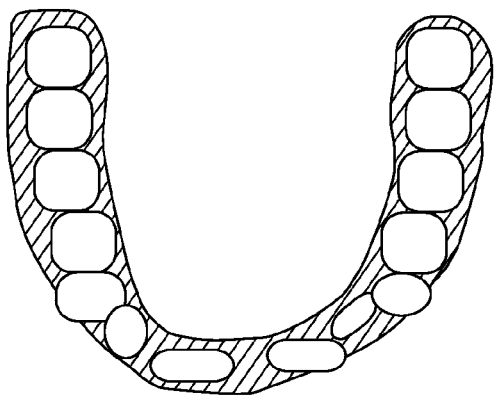
Figure 11E:
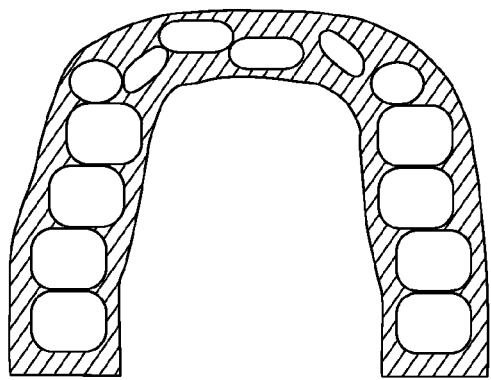

Once the virtual model is created, the user is provided with tools that allow the user to hide one or more image data in order to study certain features. Furthermore, the user is provided with navigation tools with the ability to manipulate the model so as to view it from any user-specified perspective. For example, in FIG. 10 a screen shot is shown of the superposition of skull data 114 with X-Ray data 116. In this example, complete 3D models of the teeth 116 are created from X-ray data using the algorithms described previously.

Alternatively, the complete 3D tooth models 116 are created from combining X-Ray data with 3D models of teeth obtained by a scan of the crowns of the teeth (using the scanner 30 of FIG. 1 or from a laser scan of a physical model of the dentition), and/or with the use of template tooth roots that are modified to match the X-ray data.

Scaling of Data

When digital image data from multiple sources are combined or superimposed relative to each other to create a composite model, it may be necessary to scale data from one set to the other in order to create a single composite model in a single coordinate system in which the anatomical data from both sets have the same dimensions in three-dimensional space. Hence, some scaling may be required. This section describes some approaches to scaling that may be performed in one possible embodiment of the invention.

FIG. 11A-11E are views of scan data 200 representing the front, right side, left side, lower and upper arches of a patient. The data includes the teeth 202 and the gingiva 204.

Figure 12:
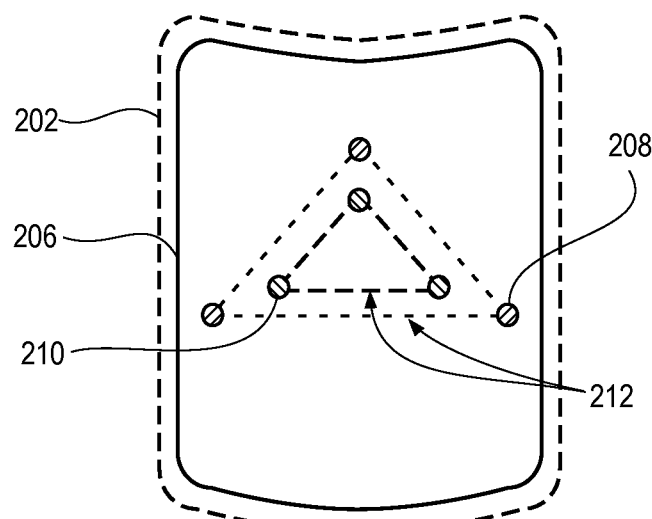
FIG. 12 is a diagram illustrating a technique for scaling orthodontic data obtained from an imaging device, such as a camera, to the actual anatomy of the patient.

FIG. 12 illustrates a technique of scaling the orthodontic data to match the actual orthodontic size. Depending on of the scanning technique, the orthodontic data will not completely reproduce the exact size of the teeth and other portions of the orthodontic structure. To facilitate the accuracy of the three-dimensional digital model, at least one tooth 206 can be marked utilizing one or more markings 208. The marking is done prior to obtaining the orthodontic data. Once the orthodontic data for the tooth 206 is obtained, scaling reference points 210 are also obtained. The scaling reference points are the points in the scan data that represent the image of the markings 208. A determination between the differences between the scaling reference points 210 and the actual markings 208 determine a scaling factor 212. As one of average skill in the art will readily appreciate, having the actual markings 208 and the scaling reference points 210, a variety of mathematical operations may be used to determine the scaling factor 212. For example, the coordinate differences (distance) between each of the vertices of the triangle may be utilized. As one of average skill in the art will further appreciate, a different number of markings 208 may be utilized. For example, two markings may be used or four markings may be used, etc. In addition, more than one tooth may be marked with similar markings 208. Note that the markings may be on the exterior of the patient, and a local triangulation technique may be used to obtain the scaling factor. Further note that the scaling factor 212 determination is based on an assumption that the scan data will have a linear error term in each of the x, y and z axis, such that a single scaling factor is determined and used to scale each of the teeth as well as the other aspects of the orthodontic structure of the patient.

Figure 13:
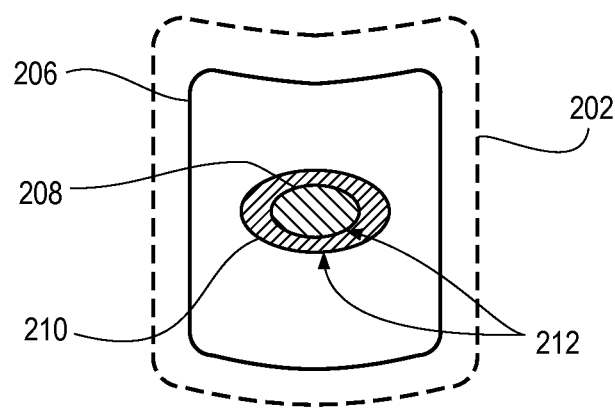
FIG. 13 is a diagram showing an alternative scaling method similar to that shown in FIG. 12.

FIG. 13 illustrates an alternate marking technique for determining a scaling factor for the orthodontic data. As shown, an actual tooth 206 is marked with a marking 208. The marking 34 is of a substantial size so as to be adequately measured. Once the orthodontic data is obtained, the orthodontic data of the tooth 202 and a corresponding scaling reference point (area) 210 are used to determine the scaling factor 212. As one of average skill in the art will readily appreciate, a simple mathematical function may be used to determine the scaling factor 212 based on the size (diameter) difference between the actual marking 34 and the scaling reference point 36. As an alternative to marking as described with reference to FIGS. 12 and 13, the actual tooth size, and the size of the model of the tooth, may be measured and used to determine the scaling factor. Accordingly, the difference between the actual tooth size the size of the tooth in the scan data will constitute the scaling factor.

When three-dimensional scanning of the type described in the published PCT application or OraMetrix is used, scaling of the three-dimensional data is not needed as a true, accurate and to scale three-dimensional image is obtained through the use of triangulation. Likewise, a true three-dimensional image can be obtained techniques such as computed tomography. However, for video or photographic data, and for X-ray data, scaling such as shown in FIGS. 12 and 13 may be needed in order to merge that data to other data such as 3D scan data.

Figure 14:
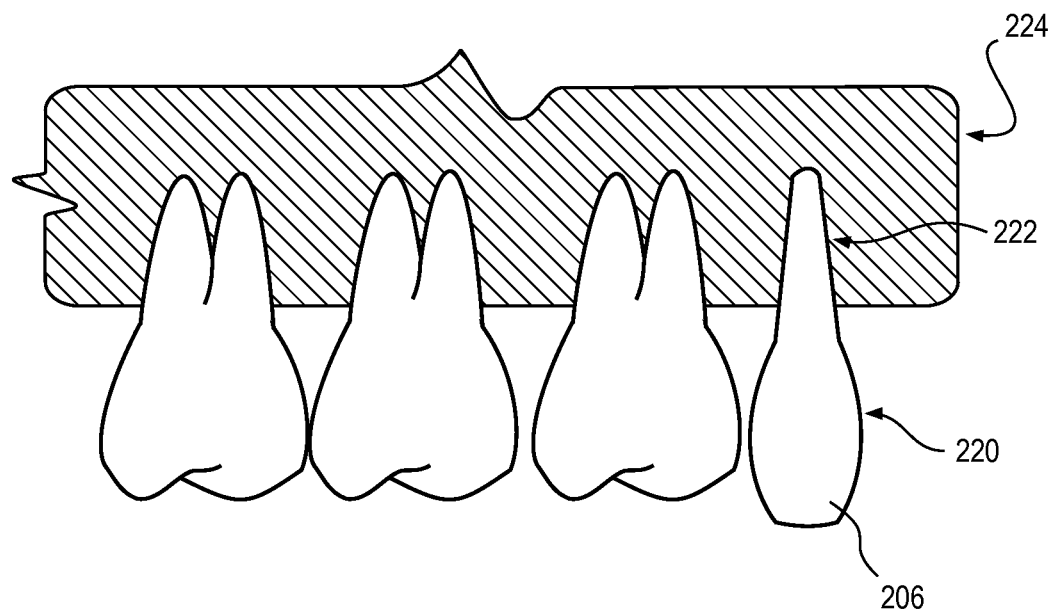
FIG. 14 is an illustration of an X-ray of a set of teeth and adjacent bone.

FIG. 14 illustrates a two-dimensional representation of image data, such as a graphical diagram of a radiographic image, such as an x-ray of a few teeth. In another embodiment, the radiographic image can be a computed tomographic image volume. As previously mentioned, the orthodontic data contains three-dimensional images of the surface of the orthodontic structure. X-rays provide a more detailed view of the teeth and surrounding hard and soft tissue as two dimensional image data. As shown in FIG. 14, each tooth 206 includes a crown 220, and a root 222 and is embedded in bone 224. Accordingly, the orthodontic data 200 of FIG. 11 only illustrates the crown 206 of the teeth. As such, a complete three-dimensional model of the orthodontic patient requires the roots and bone to be included.

Figure 15:
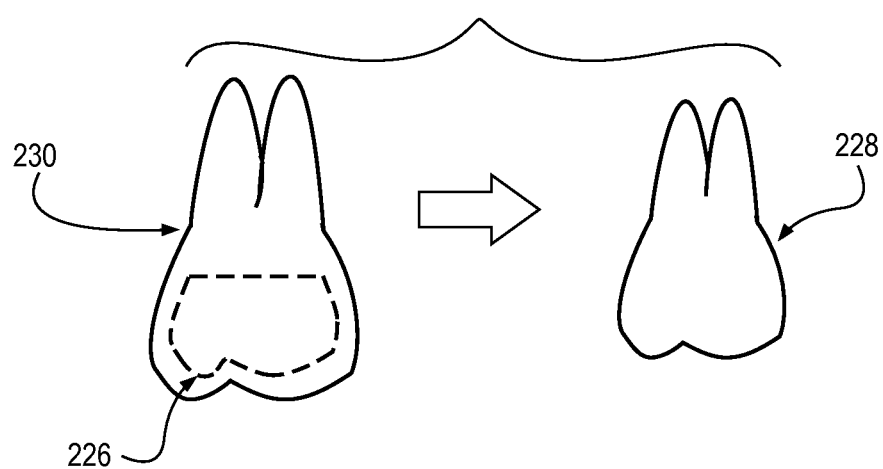
FIG. 15 is an illustration of scaling the X-ray data of the tooth to the actual size of the tooth to produce a scaled digital model of the tooth.

FIG. 15 illustrates a technique of using the scaled digital model 226 of the tooth's crown to produce an integrated or composite digital model 228 of the tooth. In this embodiment, the x-rayed data 230 of the tooth is used in comparison with the scaled digital model 226 to determine a per tooth scaling factor. The scaled digital model 226 of the tooth is positioned to be planar with the x-ray of the tooth 230. Having obtained the proper orientation between the two objects, the per tooth scaling factor is determined and subsequently used to generate the composite scaled digital model 228 of the tooth. In a specific embodiment, the per tooth scaling factor is required for current x-ray technologies, since x-rays produce a varying amount of distortion from tooth to tooth depending on the distance of the tooth from the film, the angle of x-ray transmission, etc.

To more accurately map the two-dimensional images of a tooth onto the three-dimensional model, multiple angles of the tooth should be used. Accordingly, a side, a front, and a bottom view of the tooth should be taken and mapped to the scaled digital model of the tooth. Note that the bone and other portions of the orthodontic structure are scaled in a similar manner. Further note that MRI images, and any other images obtained of the orthodontic patient, may also be scaled in a similar manner. A more complete representation of the tooth roots may be obtained using standardized, template 3D virtual tooth roots, applying the X-Ray data to the template tooth roots and modifying their shape accordingly, and them applying the modified template tooth root to the scan data of the crown to create a scaled, complete virtual tooth object including tooth roots.

Figure 16A:
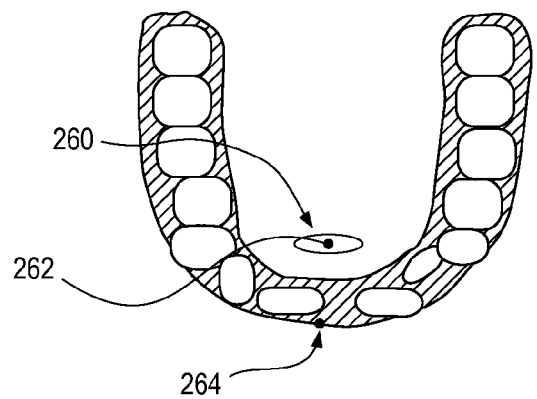
FIGS. 16A-16C are an illustration of a method of determining orientation reference points in a digital model of a patient.
Figure 16B:
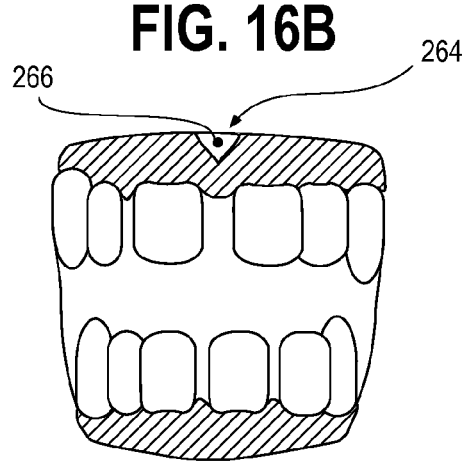
Figure 16C:
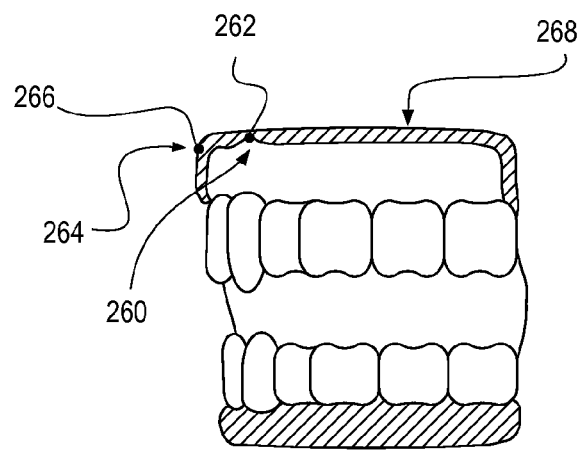

FIGS. 16A-16C illustrate a graphical diagram of selecting orientation reference points based on physical attributes of the orthodontic structure. The orientation reference points 262 and 266 will be subsequently used to map the digital image of the orthodontic structure into a three-dimensional coordinate system that will not change during the course of treatment. In this example, the frenum 264 has been selected to be one of the orientation reference points 266 and the rugae 260 has been selected as the other reference point 262. The frenum 264 is a fixed point in the orthodontic patient that will not change, or change minimally, during the course of treatment. As shown, the frenum 264 is a triangular shaped tissue in the upper-portion of the gum of the upper-arch. The rugae 260 is a cavity in the roof of the mouth 268 in the upper-arch.

The rugae will also not change its physical position through treatment. As such, the frenum 264 and the rugae 260 are fixed physical points in the orthodontic patient that will not change during treatment. As such, by utilizing these as the orientation reference points 262 and 266, a three-dimensional coordinate system may be mapped thereto. Note that other physical attributes of the orthodontic patient may be used as the orientation reference points 262 and 266. However, such physical points need to remain constant throughout treatment. Accordingly, alternate physical points include the incisive papilla, cupid's bow, the inter-pupillar midpoint, inter-comissural midpoint (e.g., between the lips), inter-alar midpoint (e.g., between the sides of the nose), the prone nasale (e.g., the tip of the nose), sub-nasale (e.g., junction of the nose and the lip), a dental mid-line point, a point on the bone, a fixed bone marker such as an implant (e.g., a screw from a root canal, oral surgery).

The x, y, z coordinate system may be mapped to the physical points on the digital model of the orthodontic structure in a variety of ways. In one example, the origin of the x, y, z coordinate system may be placed at the frenum 264, the z-axis aligned with reference to the frenum and the rugae 260, and the x-axis is aligned with the midline of the upper and/or lower arch. This is further illustrated in FIGS. 17 and 18. Note that an external positioning system may be used to obtain the orientation reference points. For example, the patient may sit in a chair at a specific location of an examination room that includes a triangulation positioning system therein. As such, when the patient is scanned, the scanned images may be referenced with respect to the room's triangulation positioning system.

FIG. 17 illustrates a graphical representation of mapping the orientation reference points 262 and 266 to the x-z plane of the three-dimensional x, y, z coordinate system. In this illustration, orientation point 266, which corresponds to the frenum 264, is selected as the origin of the x, y, z coordinate system. Note that any location may be selected as the origin 72. The orientation points 262 and 266 are used to determine an x, z plane orientation angle 262. Typically, the x, y, z coordinate system will be selected such that when looking at the patient from a frontal view, the x direction will be to right of the patient, the y direction towards the top of the patient's head and the z direction will be out away from the patient.

As one of average skill in the art will appreciate, the orientation of the x, y, z plane may be in any orientation with respect to the reference points 262 and 266.

Figure 18:
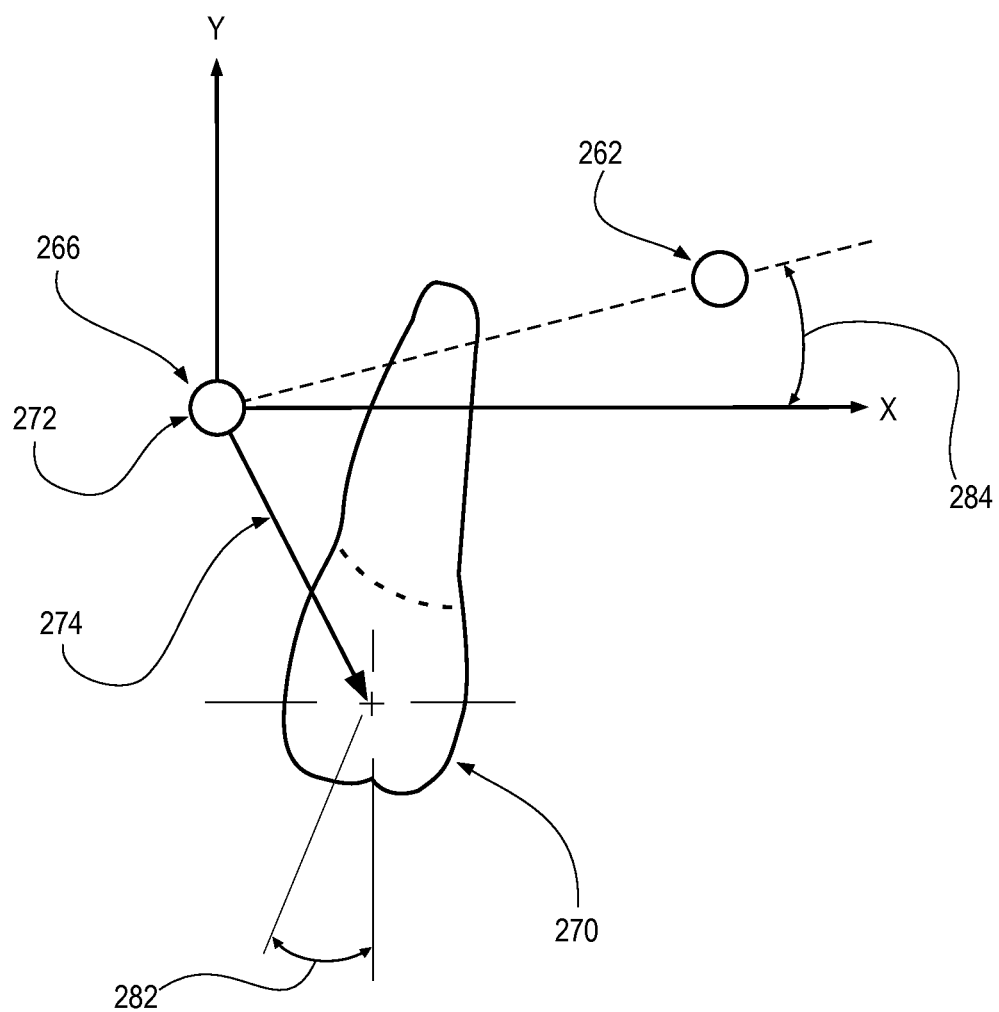
FIG. 18 is an illustration of a method of mapping the orientation reference points of FIGS. 16A-16C to a three-dimensional coordinate system.

The x-y plane is mapped to the orientation reference point 262 and 266 as shown in FIG. 18. The orientation reference point 262 and 266 are used to generate an x-y plane orientation angle 284. Based on the x-y plane orientation angle 284 and the x-z plane orientation angle 262, a digital model of a tooth 270 may be positioned in three-dimensional space with respect to the x, y, z coordinate system. As shown in FIGS. 17 and 18, the digital model of the tooth 270 includes a tooth depth 278, an angle of rotation 276 with respect to the x-z axis, an angle of rotation 282 with respect to the x-y plane, a positioning vector 274 which is in a three-dimensional space, the length of the tooth including the crown dimension, and the root dimension. Accordingly, each tooth is then mapped into the x, y, z coordinate system based on the tooth's center, or any other point of the tooth, and the dimensions of the digital model of the corresponding tooth. Once each tooth has been placed into the x, y, z coordinate system, the digital model of the tooth is complete. Note that the lower-arch is also referenced to the x, y, z coordinate system wherein the determination is made based on the occlusal plane of the patient's orthodontic structure. Alternatively, the lower-arch may include a separate three-dimensional coordinate system that is mapped to the coordinate system of the upper-arch. In this latter example, fixed points within the lower-arch would need to be determined to produce the lower arch's three-dimensional coordinate system.

Treatment Planning

The computer or workstation 10 (FIG. 1) that includes the software for generating the patient model preferably includes interactive treatment planning software that allows the user to simulate various possible treatments for the patient on the workstation and visualize the results of proposed treatments on the user interface by seeing their effect on the visual appearance of the patient, especially their smile. The interactive treatment planning preferably provides suitable tools and icons that allow the user to vary parameters affecting the patient. Such parameters would include parameters that can be changed so as to simulate change in the age of the patient, and parameters that allow the user to adjust the color, texture, position and orientation of the teeth, individually and as a group. The user manipulates the tools for these parameters and thereby generates various virtual patient models with different features and smiles. The patient models are displayed on the user interface of the workstation where they can be shared with the patient directly. Alternatively, the workstation can be coupled to a color printer. The user would simply print out hard copies of the screen shots showing the virtual patient model.

The manner in which the software is written to provide tools allowing for simulation of various parameters can vary widely and is not considered especially critical. One possibility is a Windows-based system in which a series of icons are displayed, each icon associated with a parameter. The user clicks on the icon, and a set of windows are displayed allowing the user to enter new information directing a change in some aspect of the model. The tools could also include slide bars, or other features that are displayed to the user and tied to specific features of the patient's anatomy. Treatment planning icons for moving teeth are disclosed in the published PCT application of OraMetrix, Inc., WO 01/80761, which gives some idea of the types of icons and graphical user interface tools that could be used directly or adapted to simulate various parameters.

Once the user has modified the virtual patient model to achieve the patient's desired feature and smile, it is possible to automatically back-solve for the teeth, jaw and skull movement or correction necessary to achieve this result. In particular, the tooth movement necessary can be determined by isolating the teeth in the virtual patient model, treating this tooth finish position as the final position in the interactive treatment planning described in the published OraMetrix PCT application, WO 01/80761, designing the bracket placement and virtual arch wire necessary to move teeth to that position, and then fabricating the wire and bracket placement trays, templates or jigs to correctly place the brackets at the desired location. The desired jaw movement can be determined by comparing the jaw position in the virtual patient model's finish position with the jaw position in the virtual patient model in the original condition, and using various implant devices or surgical techniques to change the shape or position of the jaw to achieve the desired position.

The virtual patient model as described herein provides a common set of data that is useable in a variety of orthodontic or other treatment regimes. For example, the initial and final (target) digital data sets of the patient's tooth positions can be relayed to a manufacturer of customized transparent removable aligning shells for manufacture of a series of aligning devices, as taught in the Chisti et al. patents cited previously.

Alternatively, the tooth positions may be used to derive customized bracket prescriptions for use with a flat planar archwire.

The choice of which treatment modality, and whether to use any additional treatment or therapeutic approaches (including surgery) will depend on the patient in consultation with the treating physician. The integrated environment proposed herein provides essentially a platform for a variety of possible treatment regimes. Further, the creation and display of the virtual patient model provides for new opportunities in patient diagnosis and sharing of patient information across multiple specialties in real time over communications networks.

Figure 19:
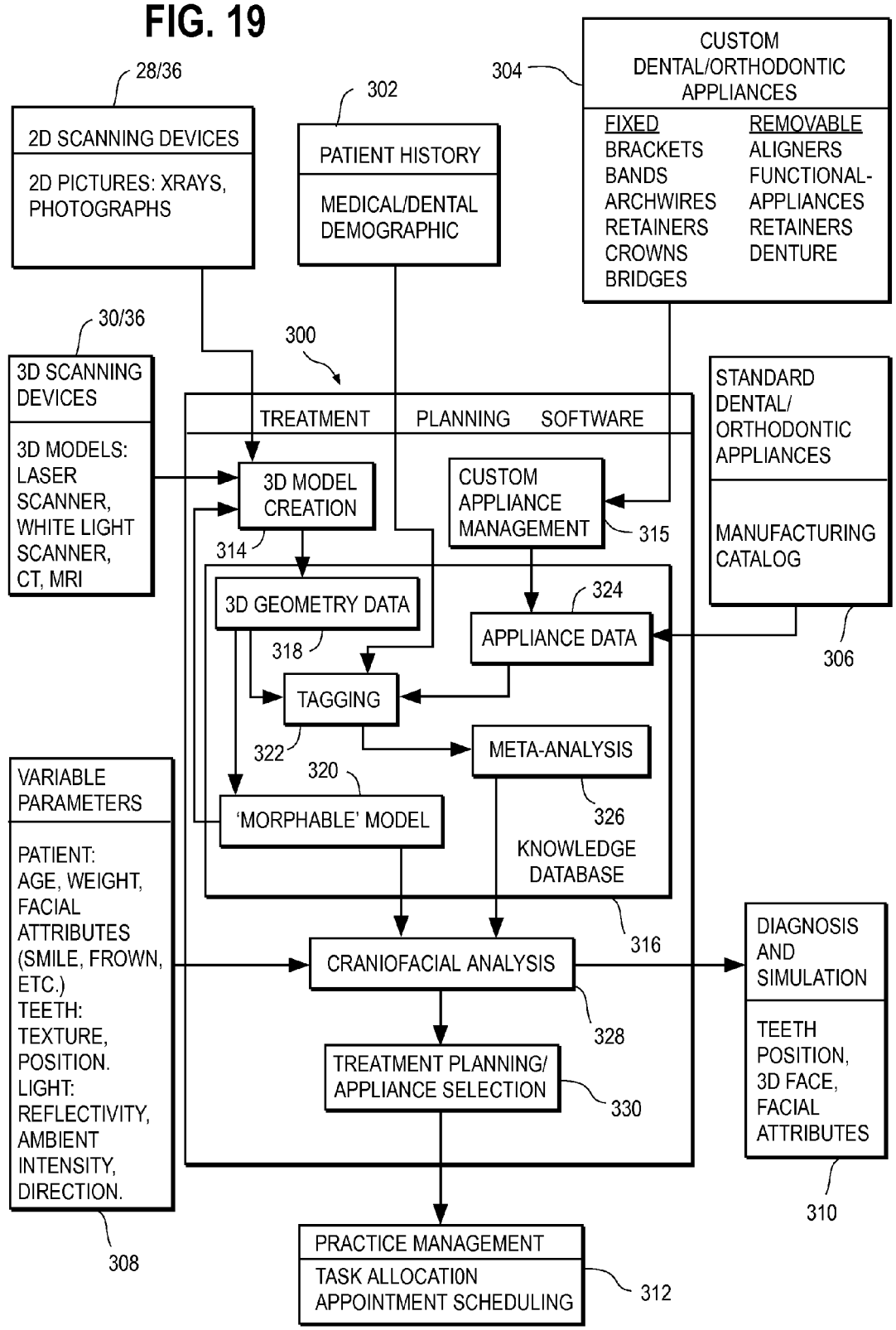
FIG. 19 is a more detailed block diagram of the treatment planning software executed by the workstation of FIG. 1.

FIG. 19 is a block diagram of an integrated workstation environment for creation of the virtual patient model and diagnosis, treatment planning and delivery of therapeutics. The workstation environment shown in block diagram form in FIG. 19 may incorporate many of the hardware aspects shown in FIG. 1, including scanning or imaging devices 28/36 for capturing two dimensional images, such as a color digital camera or X-Ray machine. The workstation environment will preferably include scanning or imaging devices 30/36 for capturing three dimensional images and creating 3D models of the patient, including one or more of the following: laser scanners for scanning a plaster model of the teeth, optical scanner such as the OraMetrix hand-held scanner 30 referenced in FIG. 1, CT scanner or MRI. In some instances, the scanning devices may be located at other facilities, in which case the 3D scans are obtained at another location and the 3D data is supplied to the workstation 10 (FIG. 1) over a suitable communications channel (Internet) or via a disk sent in the mail.

The workstation includes a memory storing machine readable instructions comprising an integrated treatment planning and model manipulation software program indicated generally at 300. The treatment planning instructions 300 will be described in further detail below. The treatment planning software uses additional software modules. A patient history module 302 contains user interface screens and appropriate prompts to obtain and record a complete patient medical and dental history, along with pertinent demographic data for the patient.

A module 304 contains instructions for designing custom dental and orthodontic appliances. These appliances could include both fixed appliances, e.g., brackets, bands, archwires, crowns and bridges, surgical splints, surgical archwires, surgical fixation plates, laminates, implants, as well as removable appliances including aligning shells, retainers and partial or full dentures. In one possible embodiment, the module 304 may be located and executed at the site of a vendor of custom orthodontic applicants. The vendor would receive an order for a custom appliance specifically to fit an individual patient. Module 34 would process this order and containing instruction for designing the appliance to fit the individual morphology and condition of the patient. The vendor would take the appliance design, manufacture the appliance in accordance with the design, and then ship the custom appliance to the practitioner. Examples of how the appliance design module 304 might be implemented include the appliance design software developed by OraMetrix and described in the published PCT patent application cited previously, the customized bracket, jig and wire appliance design software of Ormco described in the issued Andreiko patents (see, e.g., U.S. Pat. No. 5,431,562) and in the published patent application of Chapoulaud, US patent publication no. 2002/002841, the techniques of Chisti et al., U.S. Pat. Nos. 6,227,850 and 6,217,325, all incorporated by reference herein.

The treatment planning software 300 also obtains information on standard ("off the shelf") dental or appliances from a module 306, which stores manufacturer catalogs of such appliances, including 3D virtual models of the individual appliances.

The treatment planning software includes a module 308 that allows the user to input selections as to variable parameters that affect the visual appearance of the patient, as input to a craniofacial analysis module 328 described below. The variable parameters include patient factors: age, weight, sex, facial attributes (smile, frown, etc.). The variable parameters also include parameters affecting the teeth, including texture (color), position, spacing, occlusion, etc. The variable parameters further include various illumination parameters, including reflectivity of the skin, ambient light intensity, and light direction. These parameters are accessed though appropriate icons on the screen display, such as the icons shown in FIGS. 4-7, and pop-up displays that appear that prompt the user to enter or vary the selected variable parameter.

The treatment planning software further uses a diagnosis and simulation module 310 that displays diagnosis data graphically and/or in report format. This diagnosis data includes teeth position, 3D face and smile appearance, and various facial attributes.

The software further includes third party practice management software 312. Information about treatment planes generated by the craniofacial analysis module 328 is input to the practice management software 312. Based on the treatment plan, this software generates the most productive scheduling of appointments for the patient. The practice management software 312 also generates reports, provides insurance and benefit tracking, and supports electronic claims filing with the patient's insurance company. Preferably, the practice management software provides a flexible scheduling of patient appointments based on progress of treatment of the patient's craniofacial anatomical structures. The progress of treatment is obtained from periodically obtaining updated three-dimensional information regarding the progress of treatment of the craniofacial features of the patient. For example, the patient is periodically rescanned during the course of treatment. A new virtual patient model is created. Depending on the progress of treatment (e.g., movement of the teeth to target positions) the patient may be scheduled for more or less frequent visits depending on their progress.

Referring again generally to the treatment planning software 300, the software includes a 3D model generation module 314 that uses as input the 2D and 3D scanning devices. A 3D virtual model of the patient is created by module 314, for example, in the manner described previously in FIGS. 2 and 3.

The system further includes a custom appliance management module 315. This module provides appliance specifications and 3D geometry data to the vendor site for the purpose of providing necessary input for the design and manufacture of custom appliances, such as custom orthodontic appliances, for the patient. This module also provides updates to an appliance data module 324 for storing custom appliance data within the database. The module 324 is responsible for managing the database of all the appliances, including custom appliances.

The 3D virtual patient model is supplied to a knowledge database 316. The knowledge database includes a 3D Geometry data file 316 that stores the 3D geometry data of the virtual patient model. This data is supplied to a tagging module 322 and a morphable model module 320. The morphable model module 320 includes instructions for creating a morphable model from various 3D model samples, using the techniques for example set forth in the article of Blantz et al., *A Morphable Model for The Synthesis of 3D Faces*, Computer Graphics Proceedings SIGGRAPH '99 (August, 1999). The tagging module 322 includes instructions for tagging or placing pieces of information regarding the virtual patient model into each patient record, which is used for statistical procedures. In particular, the tagged information is supplied to a meta-analysis module 326. The meta-analysis module implements a set of statistical procedures designed to accumulate experimental and correlational results across independent studies that address a related set of research questions. Meta-analysis uses the summary statistics from individual studies as the data points. A key assumption of this analysis is that each study provides a different estimate of the underlying relationship. By accumulating results across studies, one can gain a more accurate representation of the relation than is provided by the individual study estimators. In one example, the software will use previous patient cases/studies to help in the craniofacial analysis module 328. For example, surgery cases for "lip and chin" will be one set of independent studies, whereas jaw surgery to correctly position the upper and lower jaw will be another. An orthodontist trying to align the upper and lower jaw will do a meta-analysis with the module 326 in order to see how this treatment will affect the patient's lip and chin.

The output of the morphable model from module 320 and the meta-analysis from module 326 is provided to a craniofacial analysis module 328. This module takes as input, patient information and the patient 3D virtual model to generate diagnosis and simulation data. Based on one or more simulation results, this module 328, and/or module 330 generates a treatment plan and appliance selection. User involvement is contemplated in modules 328 and 330. In particular, the user may interact with the patient information and the morphable model, and vary the parameters 308, to simulate different possible treatments and outcomes to arrive at a final or target treatment objective for the patient. The craniofacial analysis module 328 may include some or all of the treatment planning features described at length in the published PCT application of OraMetrix, Inc. cited previously.

The software instructions included in the craniofacial analysis module 326 preferably includes a set of instructions providing the user with user interface tools (e.g., icons), for visually studying on the user interface 16 the interaction of the craniofacial anatomical structures and their relationship to the external, visual appearance of the patient. For example, tools may provide a chewing simulation. Alternatively, the tools may provide a smile function in which the face is morphed to smile, showing the position of the teeth, gums, lips and other structures. These tools simulate changes in the anatomical position or shape of craniofacial anatomical structures (teeth, lips, skin, etc.) and show the effect of such changes on the visual appearance of the patient. As another example, the tools may include tools for modifying the shape or position of one or more bones of the upper and lower jaws, and show how those modifications affect the patient's appearance and smile.

With reference to FIG. 7, the user would activate one of the icons 35 at the top of the screen display. The icon may be associated with a function that would allow the user to reposition the location of the upper and lower teeth. After the user changes the position of the teeth, the user would activate another icon, "smile", and the face would morph to a smile with the teeth in the new position.

After the patient simulations have been completed and the patient and physician are satisfied, the resulting data set of teeth position, jaw position, etc. are stored by the diagnosis and simulation module 310 of FIG. 19. This module 310 preferably includes a routine for storing a three-dimensional representation of said patient's craniofacial structures (e.g., teeth) in a format suitable for use by a manufacturer of orthodontic appliances. Each manufacturer may have a unique format needed for use by the manufacturer, and the routine takes that into consideration in storing the data. For example, a manufacturer may require 3D digital models of the teeth in initial and final positions in the form of triangle surfaces, along with archwire and bracket prescription data.

It is contemplated that the creation and usage of the virtual model may occur at the patient care site. In particular, the treating physician or orthodontist will access the scan and photographic data, create the virtual model therefrom, and perform the treatment planning and simulation described herein in their own office. Once the treatment plan is arrived at, the treating physician can export the virtual patient model or some subset of data to appliance manufacturers or specialists, as indicated in FIG. 1.

Alternatively, the virtual patient model may be created at a remote location. In this latter example, a third party, such as an appliance manufacturer, may be the entity that creates the virtual patient model and makes it available to the treating physician. In this example, the treating physician will have access to the scanners, X-Ray, digital camera, or other imaging device, obtain the required data from the patient, and forward such data to the third party. The third party executes the instructions to create, visualize and manipulate the virtual patient model. This model can be transmitted to the treating physician for their review and usage. Then, either the third party could create a proposed treatment for review and approval by the treating physician, or the treating physician could create the treatment plan. The plan is then transmitted to one or more appliance manufacturers for fabrication of therapeutic devices (e.g., brackets and wires, aligning shells, maxillary expansion devices, etc.) A treatment plan created from the virtual patient model described herein may be one in which only one type of appliances, e.g. fixed of removable, is used during the entire course of the treatment. For example, the treatment plan may be one in which brackets and wires are the type of appliance that is used. Or, alternatively, the treatment plan may be one in which removable aligning shells are the type of appliance that is used. On the other hand, the treatment plan might be such that it is a hybrid plan requiring the use of different types of appliances during the course of the treatment. In the hybrid orthodontic treatment plan, a variety of scenarios are possible. In one type of hybrid treatment plan, different types of appliances might be used at different times during the course of the treatment. For example, patient may start out with brackets and wires and shift at some point during treatment to an approach based on removable aligning shells. In another type of hybrid treatment plan, different types of appliances might be used simultaneously, for example in different portions of the mouth, for example brackets and wires could be used for certain teeth and transparent aligning shells uses for a different set of teeth. A hybrid treatment plan may be chosen right from the beginning, or it may be introduced dynamically at any stage during the treatment course.

To develop a hybrid treatment plan, the treatment planning software will preferably include features of the appliance design and treatment planning software of the manufacturers of the appliances that are used in the hybrid treatment. As one example, the treatment planning software may include the wire and bracket features of the OraMetrix treatment planning software described in the published application WO 01/80761, as well as the treatment planning software described in the Align Technologies patents to Chisti et al., U.S. Pat. Nos. 5,975,893 and 6,227,850. The software would thus allow the user to simulate treatment with brackets and wires for part of the tooth movement to reach a particular milestone, and also design the configuration of intermediate tooth positions and configuration of removable aligning shells for the remainder of tooth movement. Alternatively, the shape of the aligning shells could be determined automatically via the treatment planning software from the tooth configuration at which the shells are first introduced to the patient and the final tooth position in accordance with the teachings of the Chisti et al. patents.

Figure 20:
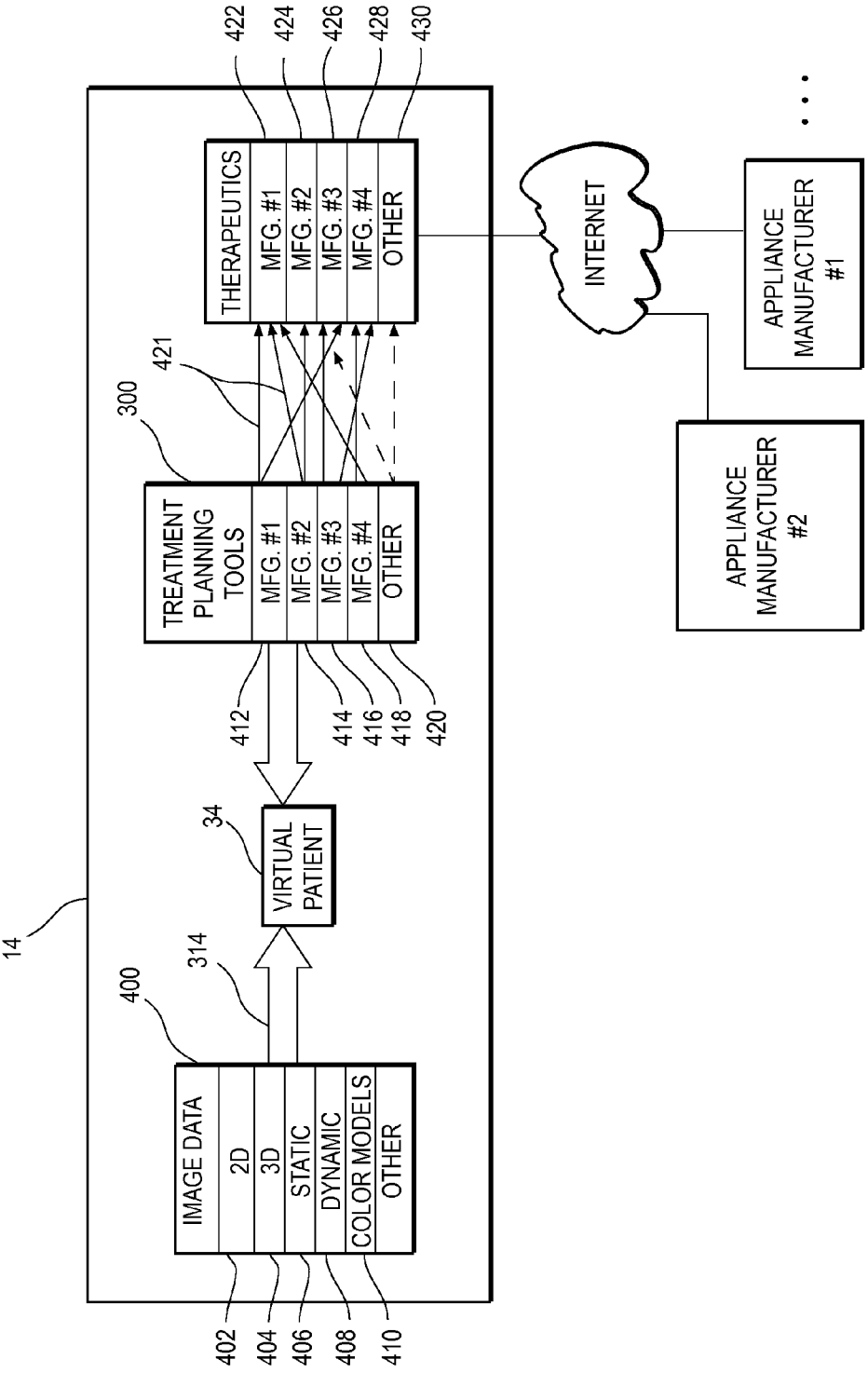
FIG. 20 is an illustration of the integration of the patient data acquisition, treatment planning and appliance design functions that are facilitated by a preferred embodiment of the unified workstation.

FIG. 20 is an illustration of the integration of the patient data acquisition, treatment planning and appliance design functions that are facilitated by a preferred embodiment of the unified workstation 14. The workstation is provided with a plurality of image data sets 400, which can include 2D data (e.g., photographs) 402, 3D image data 404 from various 3D image sources, static models 406 of all or part of the patient's craniofacial anatomy, dynamic models 408 of all or part of the patient's craniofacial anatomy, color models 410, and possibly other types of image data. The workstation 14 includes software 314 (such as described above in conjunction with FIG. 19) that takes any possible combination of this image data to produce a virtual patient model 34. From this virtual patient model, the workstation in one possible embodiment includes one or more treatment planning tools or software 300 for planning treatment for the patient. These treatment planning tools could include specific software provided by vendors of treatment planning software or appliances, such as manufacturer #1 software 412, manufacturer #2 software 414, software for manufacturers #3, 4, 5, . . . at 416, 418, 420, as shown. Such software would be operable on the virtual patient model 34 and associated data sets representing the teeth as described at length herein. To provide interoperability of the software on the virtual patient model, the virtual patient model may have to have representations of the data that is compatible with the software of various vendors, which is within the ability of persons skilled in this art. Moreover, once appliance designs have been created by the various species of treatment planning software, the preferred embodiment of the workstation allows export of appliance design, tooth position data or other required outputs to any appliance manufacturer so as to allow the manufacture of a customized orthodontic appliance. In other words, if the workstation is equipped with OraMetrix treatment planning software, such software could output tooth position data, appliance design data and any other required data into a format compatible with the manufacturing requirements of any appliance manufacture. This interoperability of data formats for appliance design is shown by arrows 421. Thus, the workstation provides a conversion or formatting of appliance design data into a data set or output format specified by any one of a variety of particular appliance manufacturers. In the illustrated embodiment, the available therapeutics data sets are shown as manufacturer no. 1 data set 422 (brackets and customized wires), manufacturer no. 2 data set 426 (brackets and wires), manufacturer no. 3 data set 426 (removable aligning shells), manufacturer no. 4 data set 428 (brackets and wires), or still other sets 430. The appliance design data set is then furnished over the Internet to the vendor of such appliances for manufacture of a custom appliance. Hybrid treatment plans, as described above, are one possibility of a treatment plan that may be developed using the workstation and virtual patient model described herein.

In one possible variant of the invention, the treatment planning software tools 300 are also provided at a remote location and some of the tasks of appliance design may be performed as a service by a separate workstation, such as a workstation of an appliance manufacturer. In this situation, the virtual patient model 34 could be provided to the appliance manufacturer, a proposed treatment plan is prepared and furnished to the practitioner, and after the plan is approved, the appliance manufacturer coordinates the furnishing of appliance design data to any designated appliance manufacturers that are used to furnish the custom appliance.

In one possible embodiment, the treatment planning software includes a set of instructions that perform a measurement function to measure distances in two or three dimensions in the virtual patient model, e.g., arch form shape measurements, and compare the measurements with reference dimensions for an "average" patient of similar age, sex, and race. These measurements could be obtained in any convenient manner, for example from textbooks, organizations, practitioners, etc. These measurement tools would be invoked during the course of treatment to compare tooth movement and current tooth position with expected positions and if deviations occur, the variances could be used as information to modify one or more aspects of the treatment plan, such as change the appliance design.

A specific example of interactive treatment planning with a unified workstation will now be now described in conjunction with FIGS. 21-60. In order to provide the functions and features described in the features, the workstation includes a computing platform (general purpose computer) having a graphical user interface, a processor and a computer storage medium containing digitized records pertaining to a patient. The digitized records include image data, such as photographs, x-rays, and scan data of the teeth. The workstation further includes a set of software instructions providing graphical user interface tools for providing access to the digitized records, such as display and manipulation of the images or scan data in the form of 3D models. The workstation further includes software instructions for execution by the processor for facilitating treatment planning for a patient.

While there are various ways in which practitioner may go about the process of designing a treatment plan for a patient, in a preferred embodiment of the invention certain specified tools are provided which allow a treatment plan to be developed in which constraints can be identified and the treatment plan can be developed without violation of such constraints.

Figure 21:
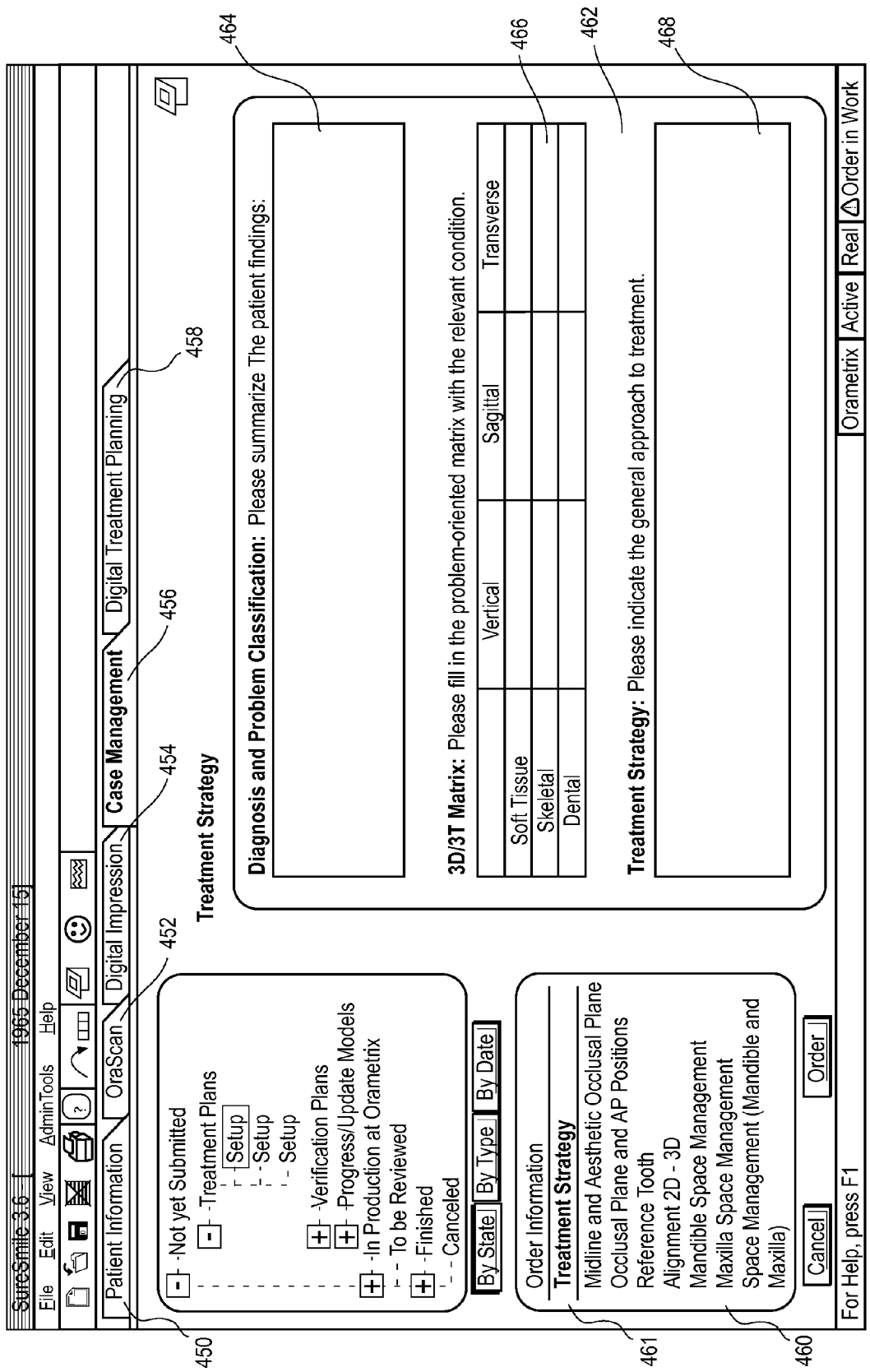

Referring now to FIG. 21, a screen shot from the graphical user interface of the workstation of FIG. 1 is shown. The workstation includes a computer memory that stores, and makes available to the practitioner, records in the form of digital data pertaining to some or all of the following: the patient's clinical history, medical history, dental history, and orthodontic history as well as 2D photographs, 2D radio graphic images, CT scans, 2D and 3D scanned images, ultrasonic scanned images, and in general, non-invasive and sometimes invasive images, plus video, audio, and a variety of communication records, such notes, records of office visits, patient letters or communications, etc. All records and images are digitized. The records and images are made available through suitable user interface icons which cause display of the images and records on the user interface. The images can be combined or superimposed to create a virtual patient model that includes surface features (soft tissue) of the patient in one possible embodiment.

The workstation also further maintains a comprehensive set of computer instructions providing tools in the form of icons, screen displays, windows, functions and features, accessible through the user interface of the workstation to assist the practitioner in planning the treatment. Various types of tools are contemplated; numerous examples are set forth herein.

In FIG. 21, a set of tabs 450, 452, 454, 456 and 458 are provided. The tab 450 is a patient information tab which provides suitable screen displays for entering a variety of patient information, such as their name and address, dental and clinical history, insurance information, diagnostic information, names of other treating or consulting practitioners, etc. Tab 450 will be discussed in further detail below in conjunction with FIGS. 21A and 21B and FIGS. 54-58. The tab 452 is a tab whereby the user accesses scan or other image data and accesses instructions and menus for scanning the patient with an in-vivo intra-oral scanner such as described in the previously cited OraMetrix PCT application. Tab 454 is a tab by which the user accesses the digital 3D impression of the teeth, obtained from the scanning of the patient. Tab 456 is a case management tab and includes a number of specific available screen displays and menus which are shown in the menu 460 in the lower left of the Figure. The case management tab, and its various features, is described at length in the following discussion. Additionally, there is a digital treatment planning tab 458 which provides further menus, tools and displays by which the practitioner may further move teeth and design the shape and configuration of a customized orthodontic appliance. An example of the types of menus and tools that are available in the tab 458 is the OraMetrix treatment planning software described in application Ser. No. 09/834,412, filed Apr. 13, 2001. However, it is possible to provide, in the workstation, a suite of treatment planning software from different appliance manufacturers in which case the user could access the treatment planning software for whatever appliance manufacturer the practitioner wished to use for treatment of the patient. In this situation, it may be necessary to format the tooth data in a format compatible with the appliance design and treatment planning software so as to ensure compatibility between the various systems that may be installed on the workstation.

In FIG. 21, the user has selected a "treatment strategy" icon 461, which causes the display 462 to appear. In this display, there is a field 464 for the user to enter high level diagnosis and problem classification information, for example in the form of text. A field 466 is provided which provides a matrix format by which the conditions relevant to the patient's soft tissue, skeletal, and dental anatomy are entered, each with respect to vertical, sagittal, and transverse positions, again in text form. The display also includes a treatment strategy field 468 where the user will indicate the general, high level approach to treatment, such as any proposed extractions, appliance type, stages of treatment, etc. These fields 464, 466 and 468, along with displayed image data for the patient, assist the practitioner in identifying the constraints pertinent to the treatment planning.

Figure 21A:
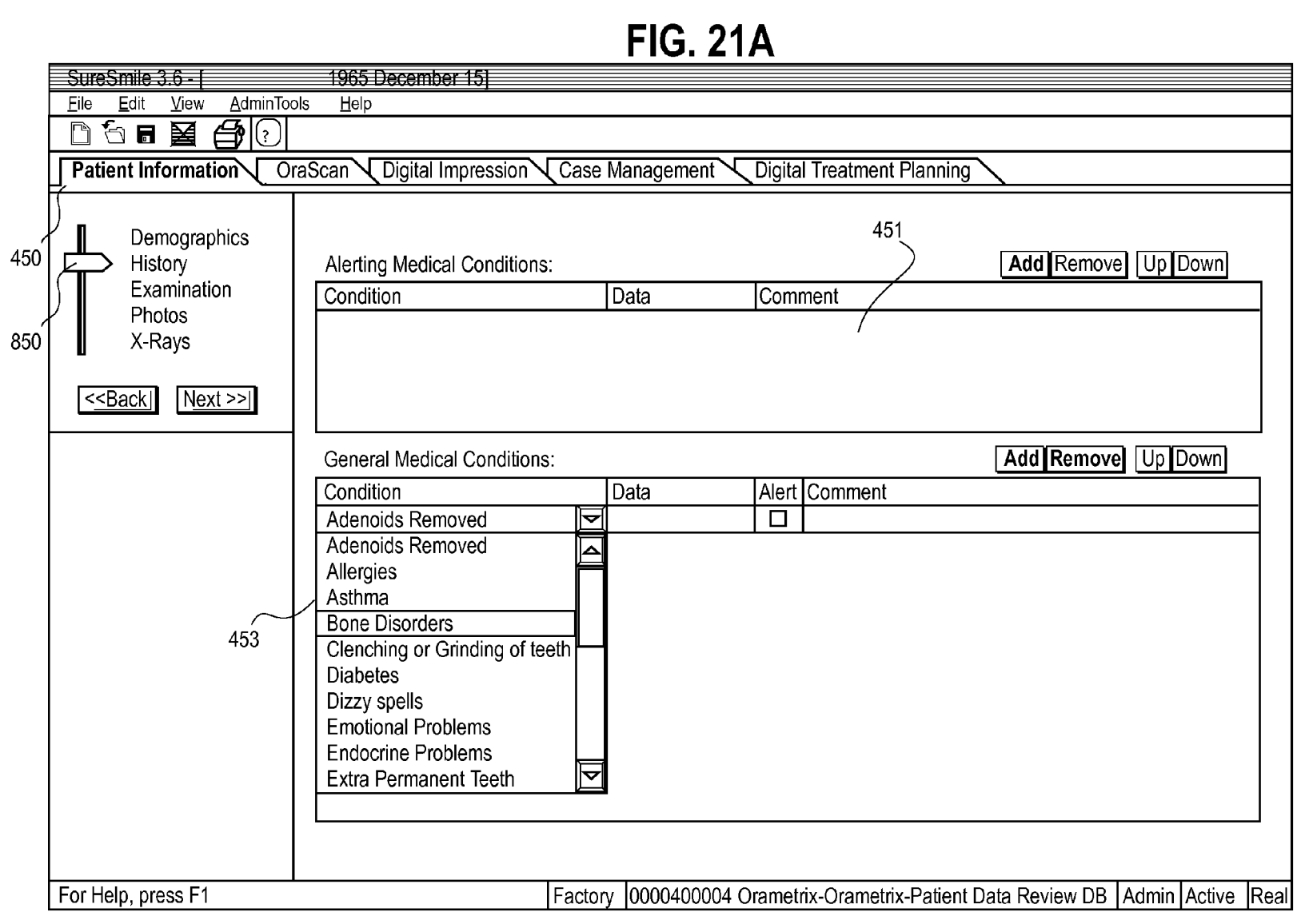

FIG. 21A shows the patient information tab 450, with the slide bar 850 moved next to "history". The screen display shown in FIG. 21A appears, with a field 451 for which the user can enter alerting medical conditions, such as AIDS or HIV infection, epilepsy, allergy conditions, tuberculosis, etc., along with any explanatory data or comment. In field 453, the user is provided with tools to enter general medical condition regarding the patient by clicking on the drop-down menu as shown, and entering any appropriate data or commentary, as shown.

Figure 21B:
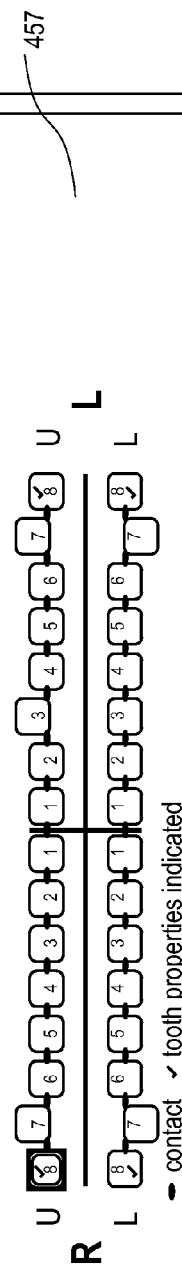

In FIG. 21B, the user has moved the slide bar 850 to the "Examination" icon, which causes the display shown in FIG. 21B to appear. This screen allows the user to enter dental examination data in field 455, a tooth chart 457 where the user clicks on a particular tooth and enters tooth data in fields 459, 461 and 463 as indicated.

After the user has entered the information into the fields 464, 466, 488 shown in FIG. 21, the user clicks on one of the other icons in the field 460 to continue the process of case management and initial treatment planning. At this point the information entered into the fields of FIG. 21 is stored in the computer memory of the workstation.

Figure 22:
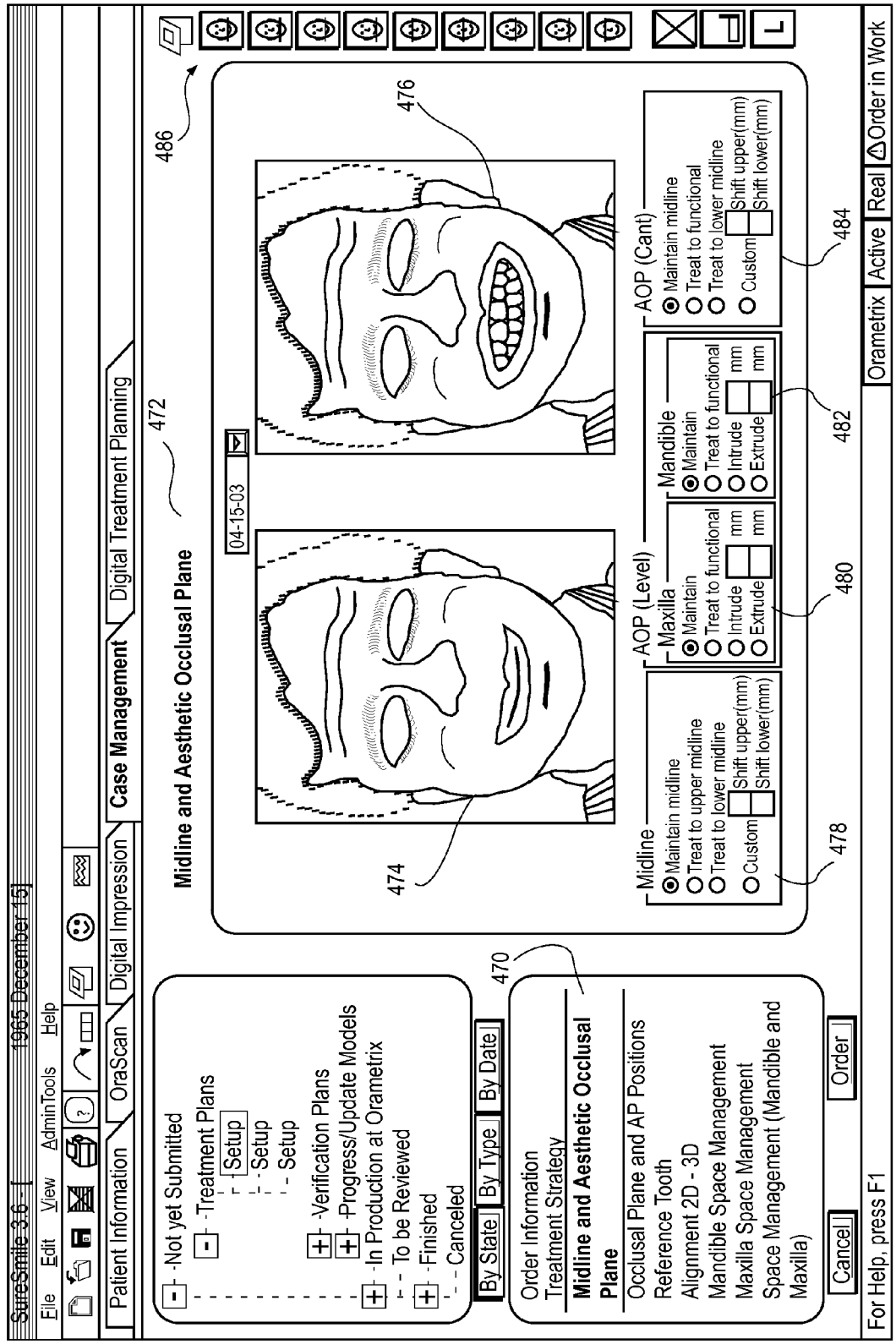

In FIG. 22, the user has now selected a "Midline and Aesthetic Occlusal Plane" icon 470, which causes the screen display 472 to appear. The user uses this screen to evaluate and define both vertical and horizontal lines of references such as soft tissue midline, interpupilliary line, etc and also define the dental midlines for the upper and lower dentition and the aesthetic occlusal planes for both the upper and lower arches and cant of the occlusal planes These midlines and occlusal planes are designed relative to the face, which here is a global reference. These lines are useful references for where you want the patient's teeth to move.

When screen display 472 is activated, the workstation displays a pair of two dimensional color photographs of the patient, shown as a photo 474 with the patient's mouth closed, and a photo 476 with the patient smiling. The display includes a field 478 where the patient can maintain the midline that the user marks on the images, as described below, or activate one of the other tabs indicating treat to upper midline, treat to lower midline, or provide a custom midline. The midline is entered using the tools 486 on the right hand side of the screen A region 480 is provided for the Aesthetic Occlusal Plane (occlusal plane for the front teeth), which the user can indicate or mark on the images of the patient using the tools 486 on the right hand side of the screen. The user marks an Aesthetic Occlusal Plane (AOP) for both the maxilla and mandible dentition, and the user is provided with fields 480 and 482 for customization of these planes (technically, lines in two dimensions). A tab 484 is provided to create a customized canted AOP with various tabs as shown. Thus, the tools provide the user to mark, among other things, a midline and maxilla and mandible levels and cant of an aesthetic occlusal plane.

The display of FIG. 22 includes a set of tools 486 in the form of icons which, when selected, allow the user to mark on the images various vertical and horizontal lines. For example, the user can mark an upper occlusal plane on the photographs of the upper arch of the patient, a lower occlusal plane (line) in the lower arch of the patient, and marking various positions in the upper and lower occlusal planes, e.g., marking a posterior position of the upper or lower occlusal plane (line in 2D); marking a functional position of the upper or lower occlusal plane; and marking an aesthetic position of the upper or lower occlusal plane.

Figure 23:
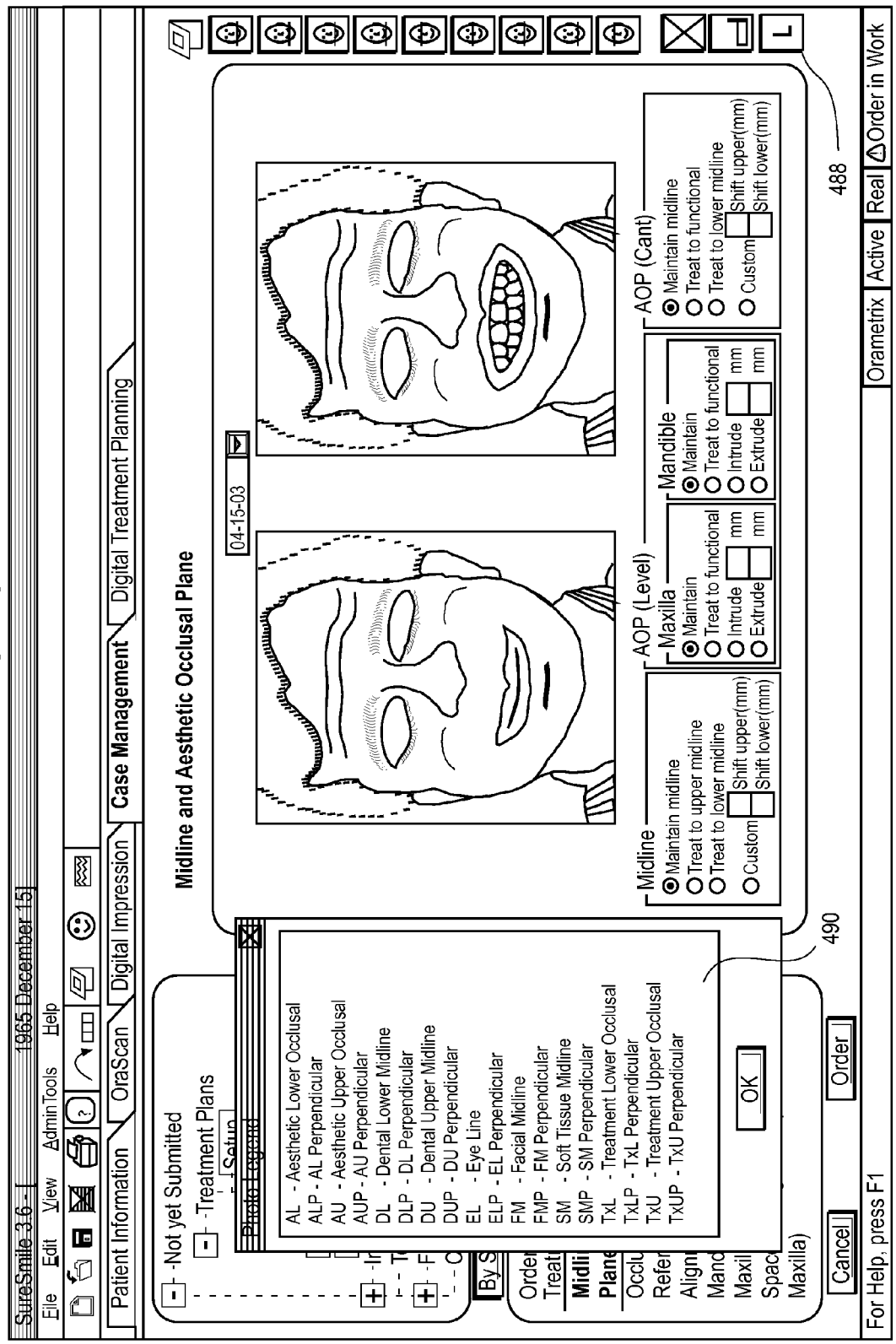

As shown in FIG. 23, when the user activates the legend "L" icon 488, a window 490 pops up and a legend appears that explains the acronyms for various lines and midlines that the user may mark on the images.

Figure 24:
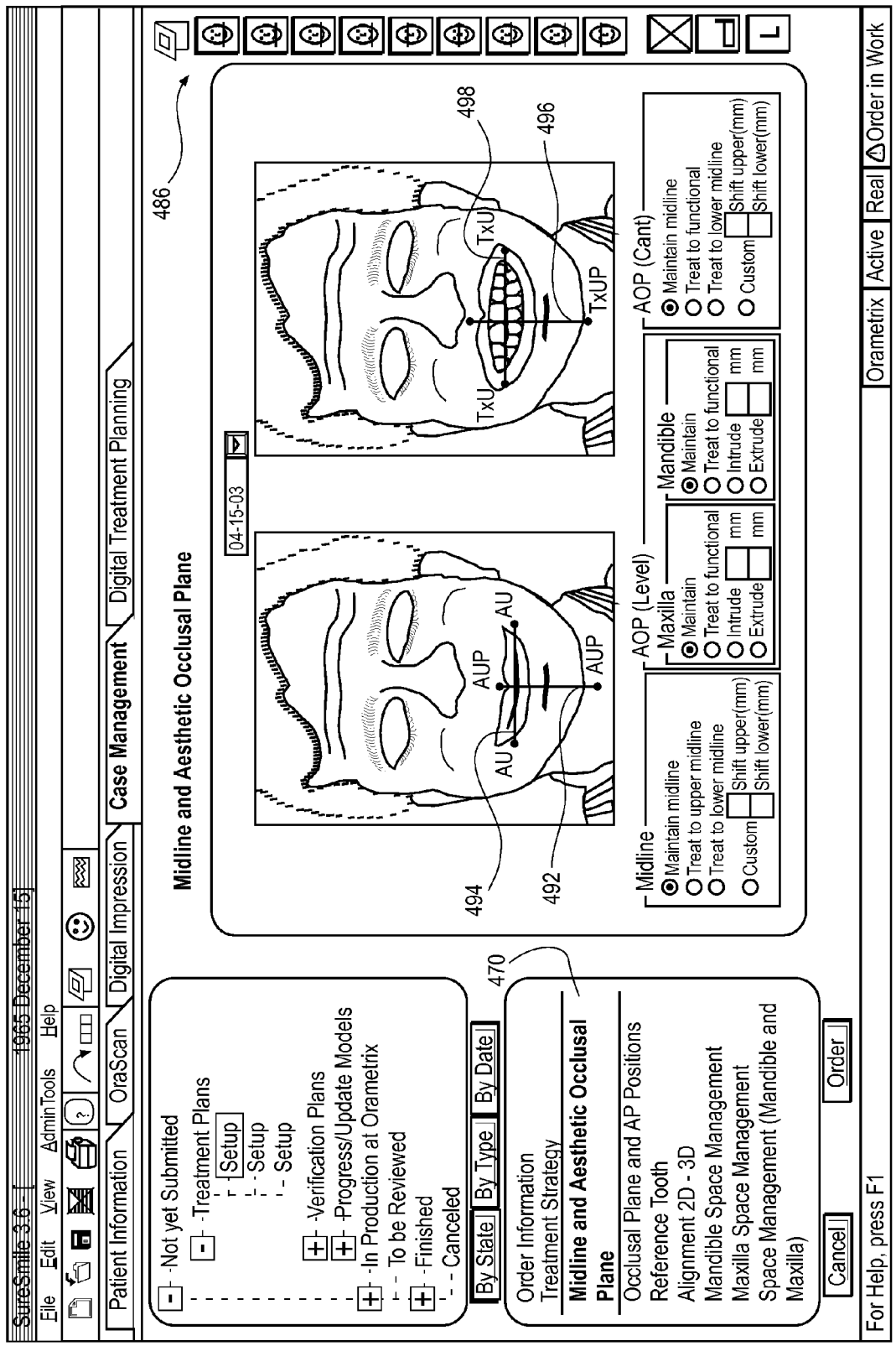

As shown in FIG. 24, the user has activated various icons 486 and has drawn on the virtual model of the patient an aesthetic upper occlusal plane ("AU") 494 and a aesthetic upper perpendicular line ("AUP") 492 in the left-hand image, and a treatment upper occlusal plane ("TxU") 498 and a treatment upper perpendicular line ("TxUP") 496. The lines 492, 494, 496 and 498 are all user specified in terms of their location. The location is selected by using the workstation mouse, moving the cursor to the location where the user wishes to draw the midlines and occlusal planes, and clicking the mouse.

Figure 25:
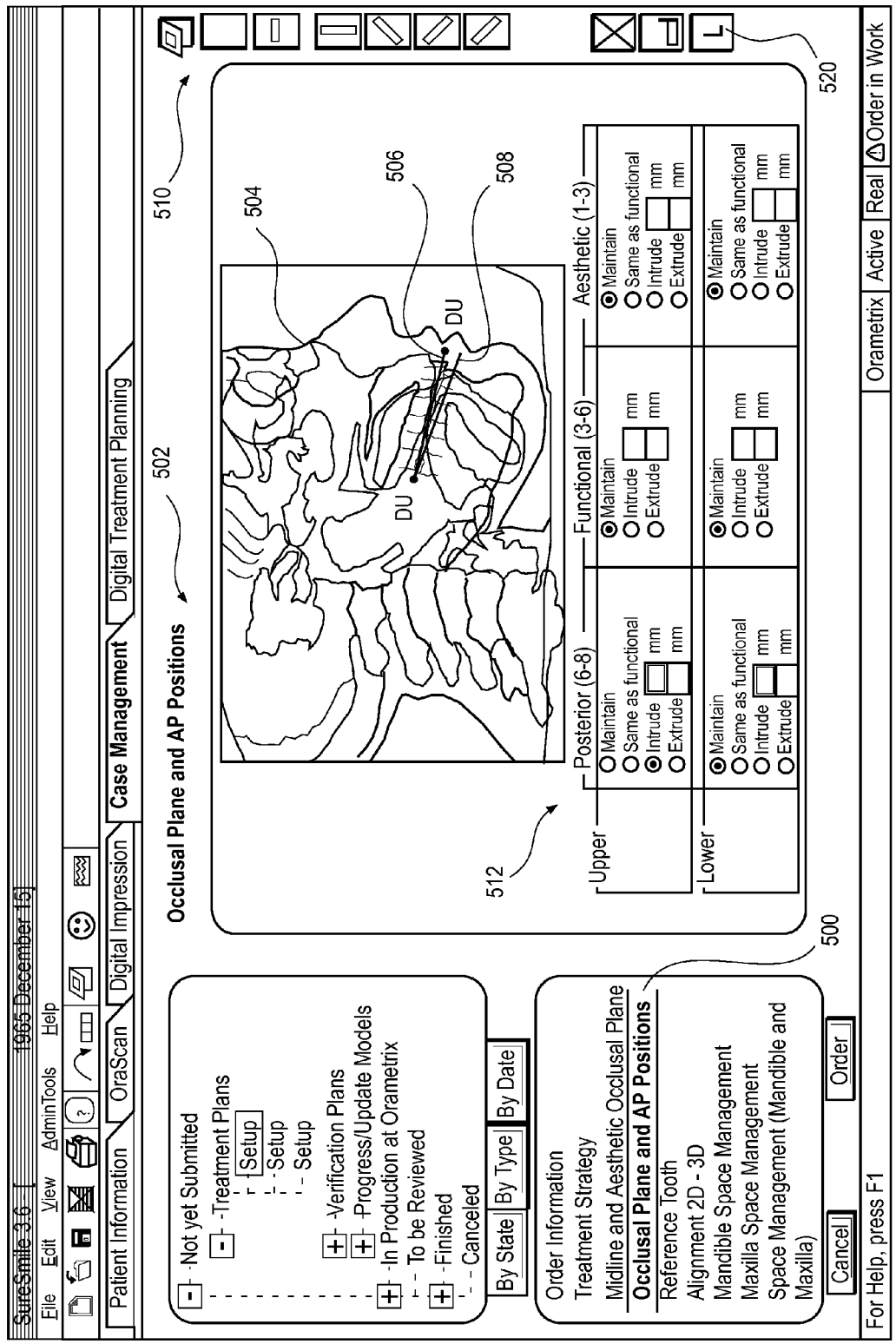
Figure 56:
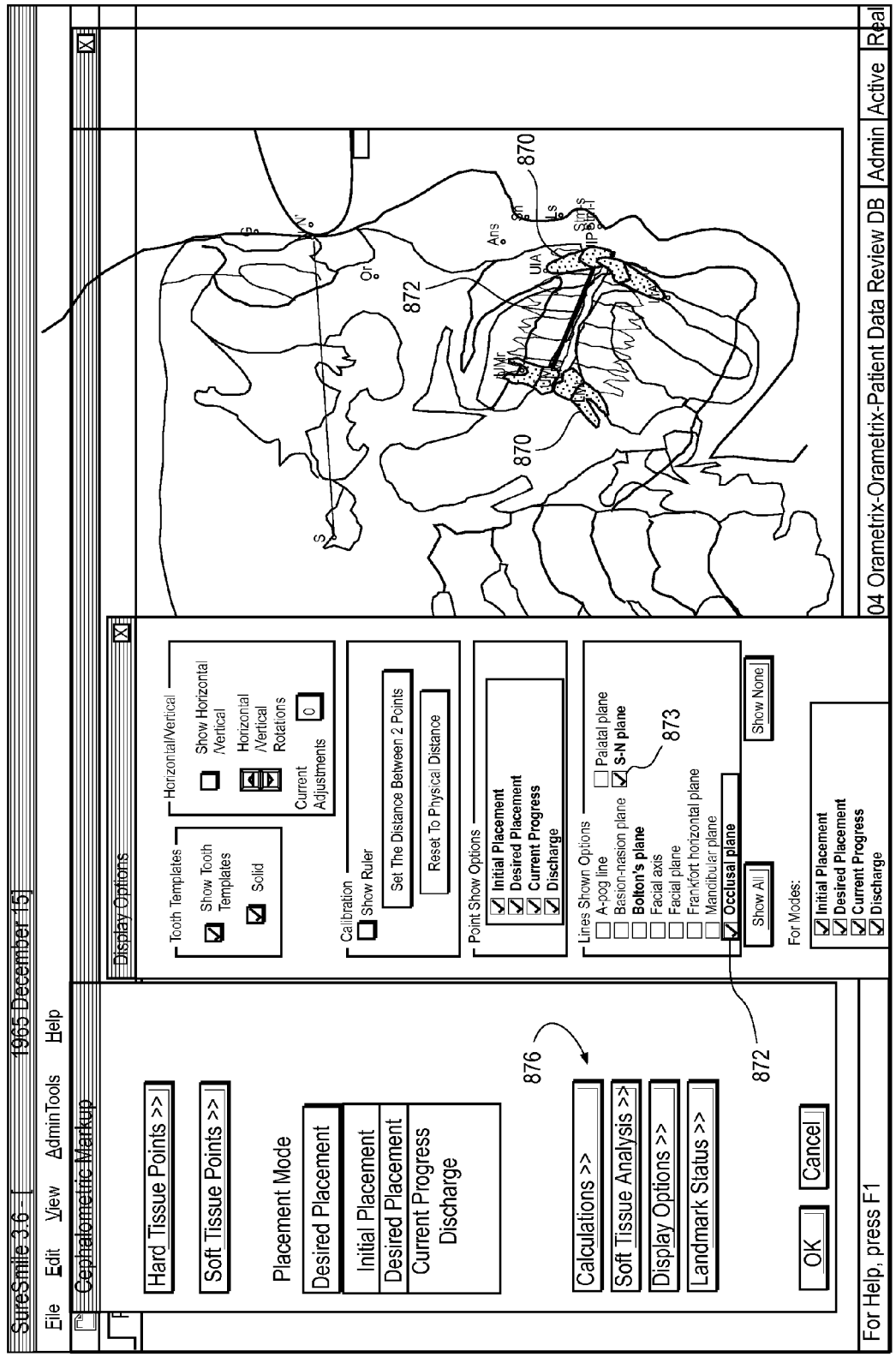
Figure 57:
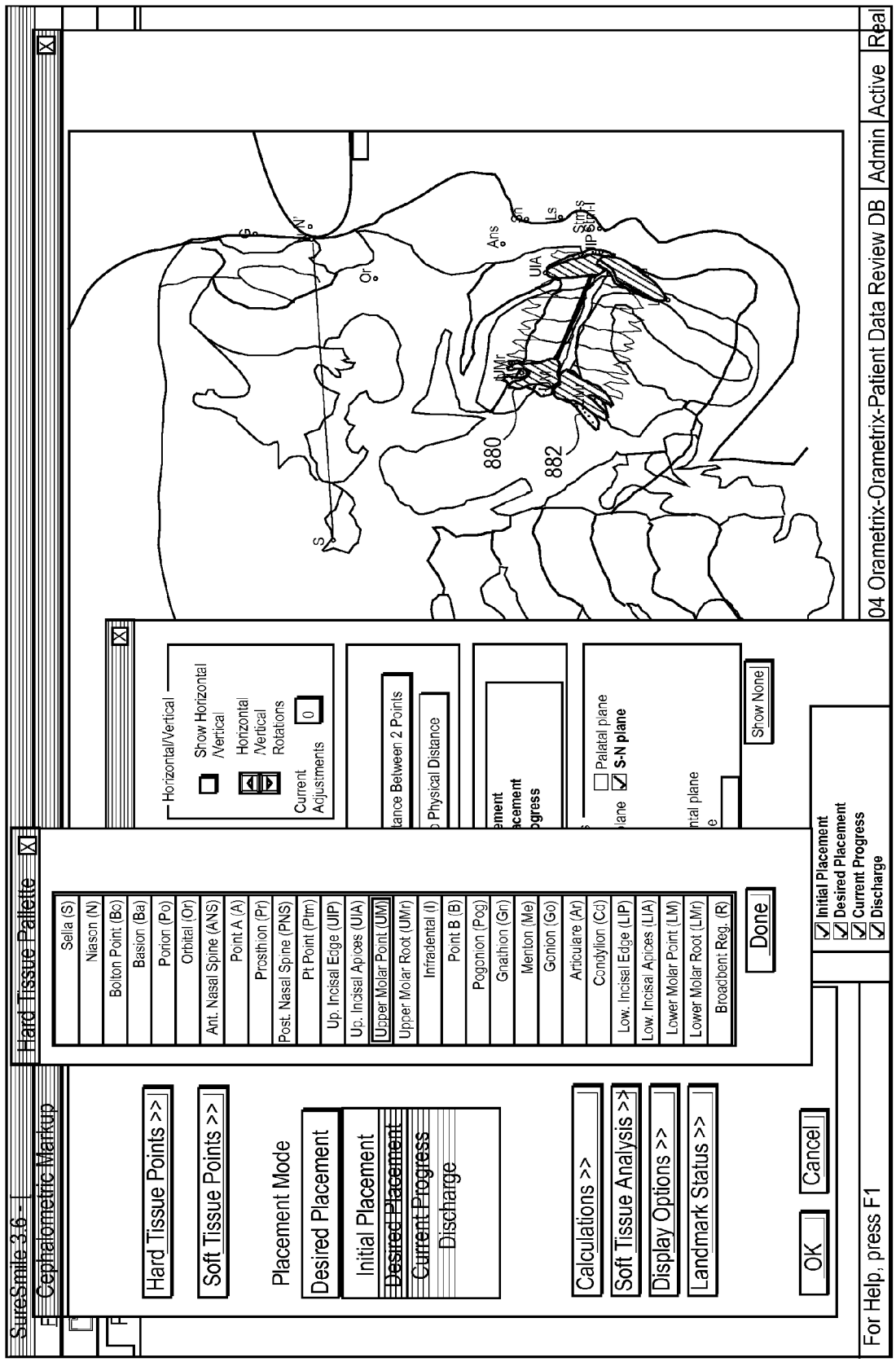

Referring now to FIG. 25, after the user has proceeded to mark the location of midlines and occlusal planes, the user clicks on the icon 500, at which point the "Occlusal Plane and AP [Anterior, Posterior] Positions" screen display 502 appears. The display 504 shows other aspects of the patient virtual model, here a two-dimensional lateral x-ray view of the face, including teeth and jaws. Shown on the display 504 are two of the occlusal planes (line in 2 dimensions) the user has previously entered from the screen display of FIG. 24: a normal occlusal plane ("NO") 506, and a Treatment Occlusal Plane Upper (TxOU) 508, indicating the occlusal plane to which the teeth are designed to be aligned with as a result of treatment of the patient. These lines can be segmented into three separate lines, one for the posterior, functional and aesthetic. The screen display includes a set of icons 510 providing tools for the user to mark various occlusal planes and locations thereof in two dimensions, as well as a Legend icon 520. The display also includes a region 512 whereby the user can modify the location of the aesthetic occlusal plane (front teeth, teeth 1-3), a functional occlusal plane (teeth 3-6), and a posterior occlusal plane (rear teeth, teeth 6-8), for both the upper and lower jaws. The axis of cant of the occlusal plane can be changed by rotating around a predetermined center or fulcrum of rotation. Also, the A/P position and inclinations and the vertical relations of the incisors with respect to the occlusal plane can be represented by animating teeth as shown in FIGS. 56, 57. The desired position of the incisors can be planned. The position of the incisors also drives the change in the position of the soft tissue, e.g. lips. Any changes can be compared against a normative database of positions of various craniofacial structures. A complete 2D cephalometric analysis is thus possible.

Figure 26:
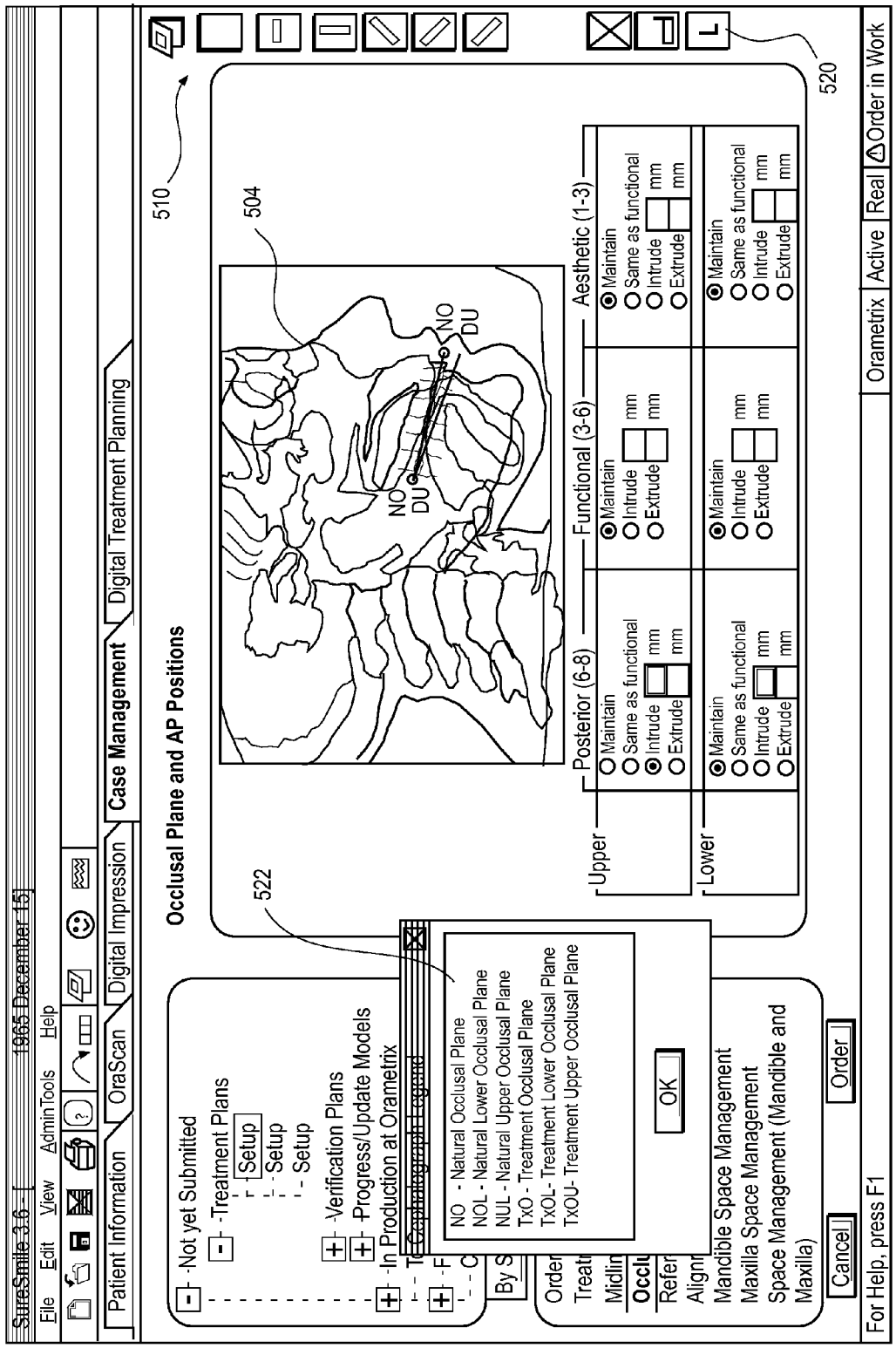

As shown in FIG. 26, when the activates the legend icon 520, the window 522 pops up and provides a legend for the acronyms which accompany the occlusal planes that are shown on the x-ray image 504. The various occlusal planes 522 are accessed by activating the icons 510 at the right hand side of the screen display, and using the mouse to indicate their location on the image 504.

Figure 27:
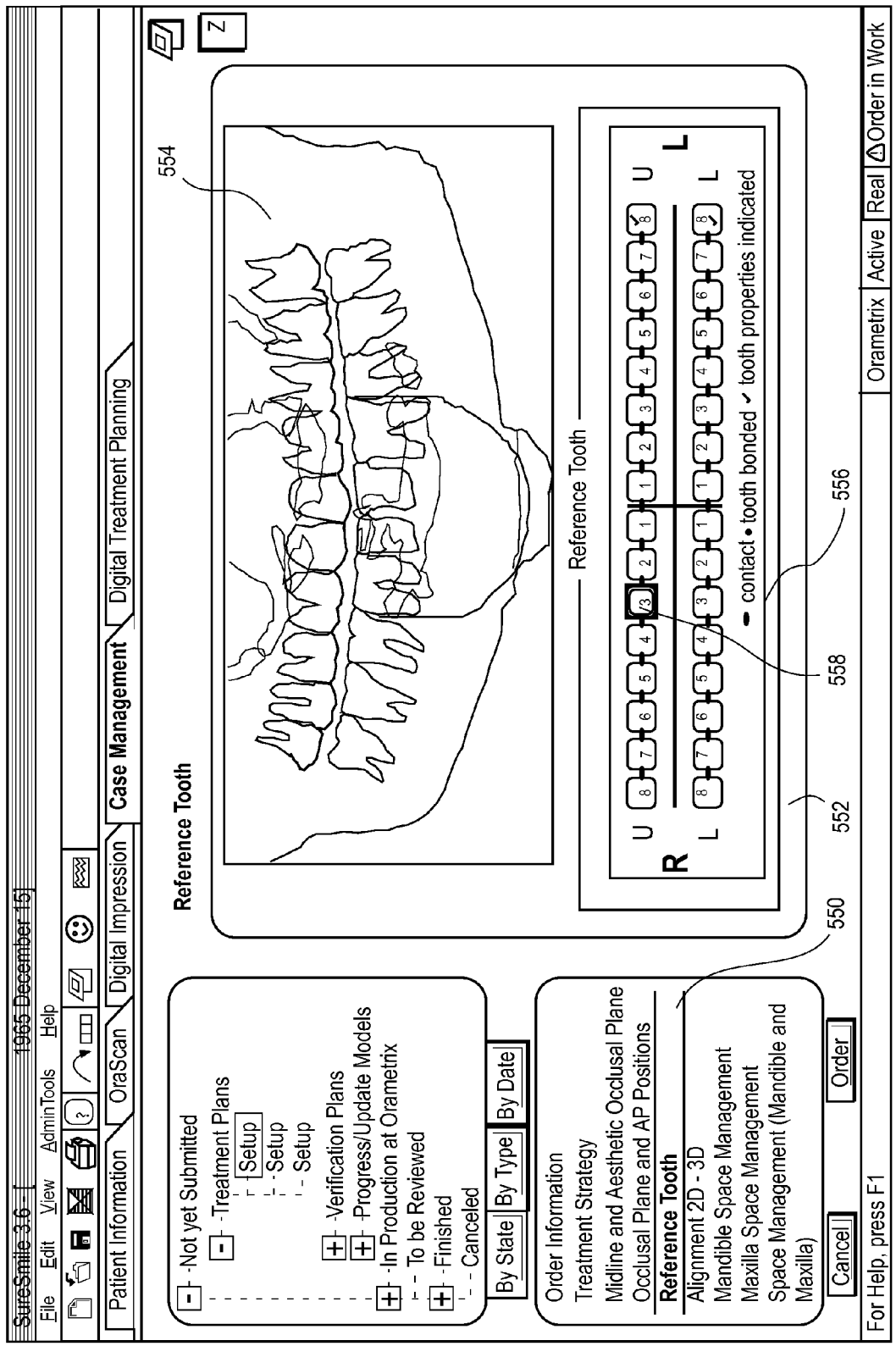

Referring to FIG. 27, the user has finished marking the midline, the occlusal plane(s) and making any anterior/posterior adjustments, and proceeded activate the "Reference Tooth" icon 550. This action causes the display 552 to appear. The display 552 includes a reference tooth selection field 556. The display also changes to show a panoramic X-ray 554 to appear, showing all of the patient's teeth to appear in a line, along with associated soft tissue and surrounding bone structures. The user makes a judgment decision as to which tooth or teeth should be moved the least (or not at all), and selects this tooth (or teeth) to be the reference tooth or teeth. This action is completed by the user moving the mouse cursor to the tooth or teeth in the field 556 and clicking the tooth they wish to select as the reference tooth. Here, the user has selected tooth 3 on the upper right hand side as the reference tooth, as indicated at 558. Any changes in crown position in two dimensions or root positions are seen and transferred into the three-dimensional data sets.

Figure 27A:
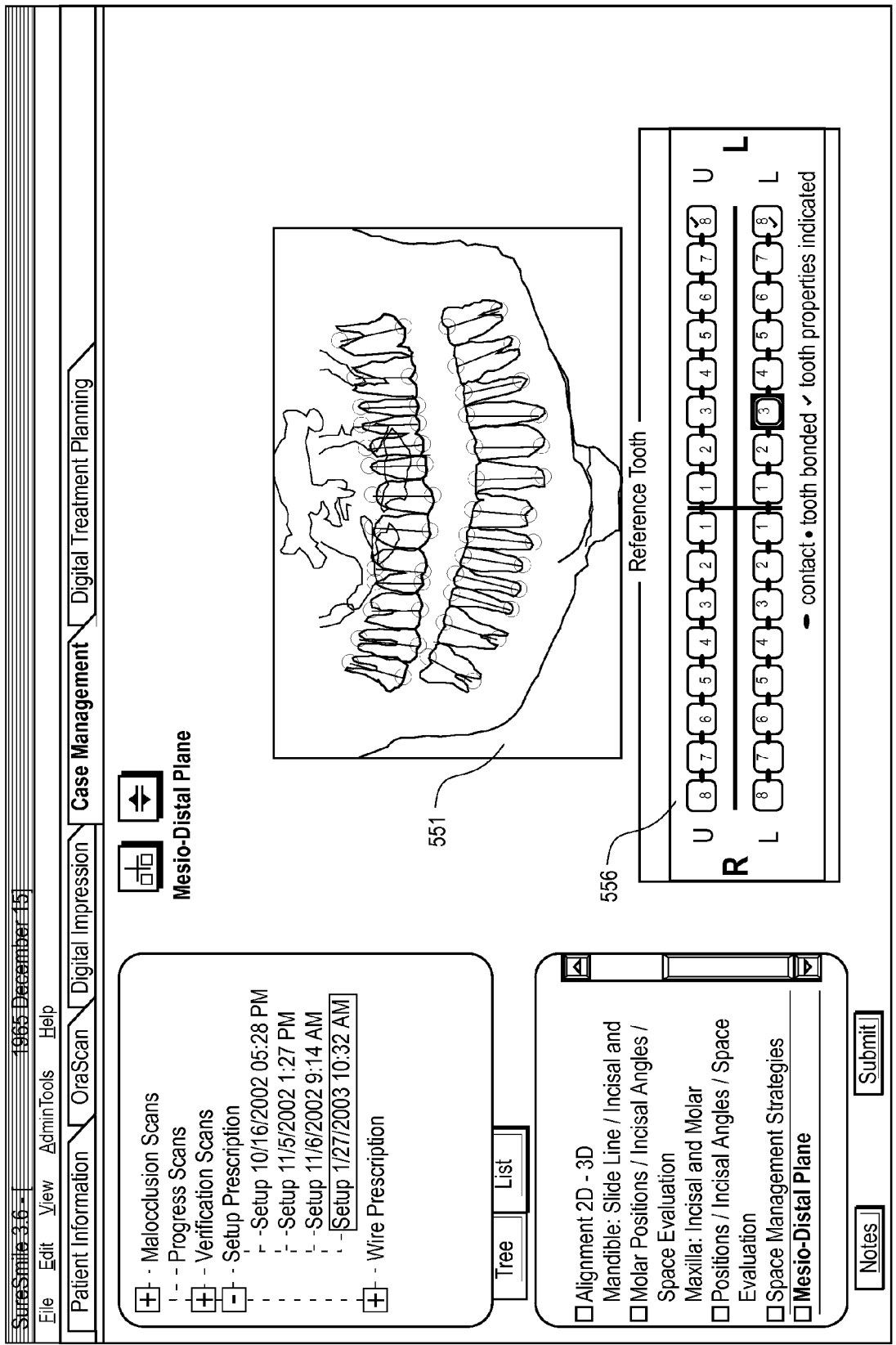

FIG. 27A shows a screen display with the display showing a flattened 3D x-ray of the teeth flattened such that all the teeth lie in a two dimensional line, with each tooth having a tooth axis indicated by a line segment having one end terminating at the cusp or tip of the tooth and the other end of the line segment terminating at the end of the tooth root. This screen is displayed simultaneously with the field 556 showing the reference tooth selected. The user, having inspected the axes of the teeth and their relationship to other teeth via the X-ray, may select a different reference tooth by simply clicking on a different tooth in the field 556. Typically, the user will select a reference tooth in which the axis of the tooth does not move during the course of treatment, and the displays of FIG. 27 and FIG. 27A facilitates that selection. The screen display of FIG. 27A facilitates the measurement of the tooth axes to make the reference tooth selection.

Figure 28:
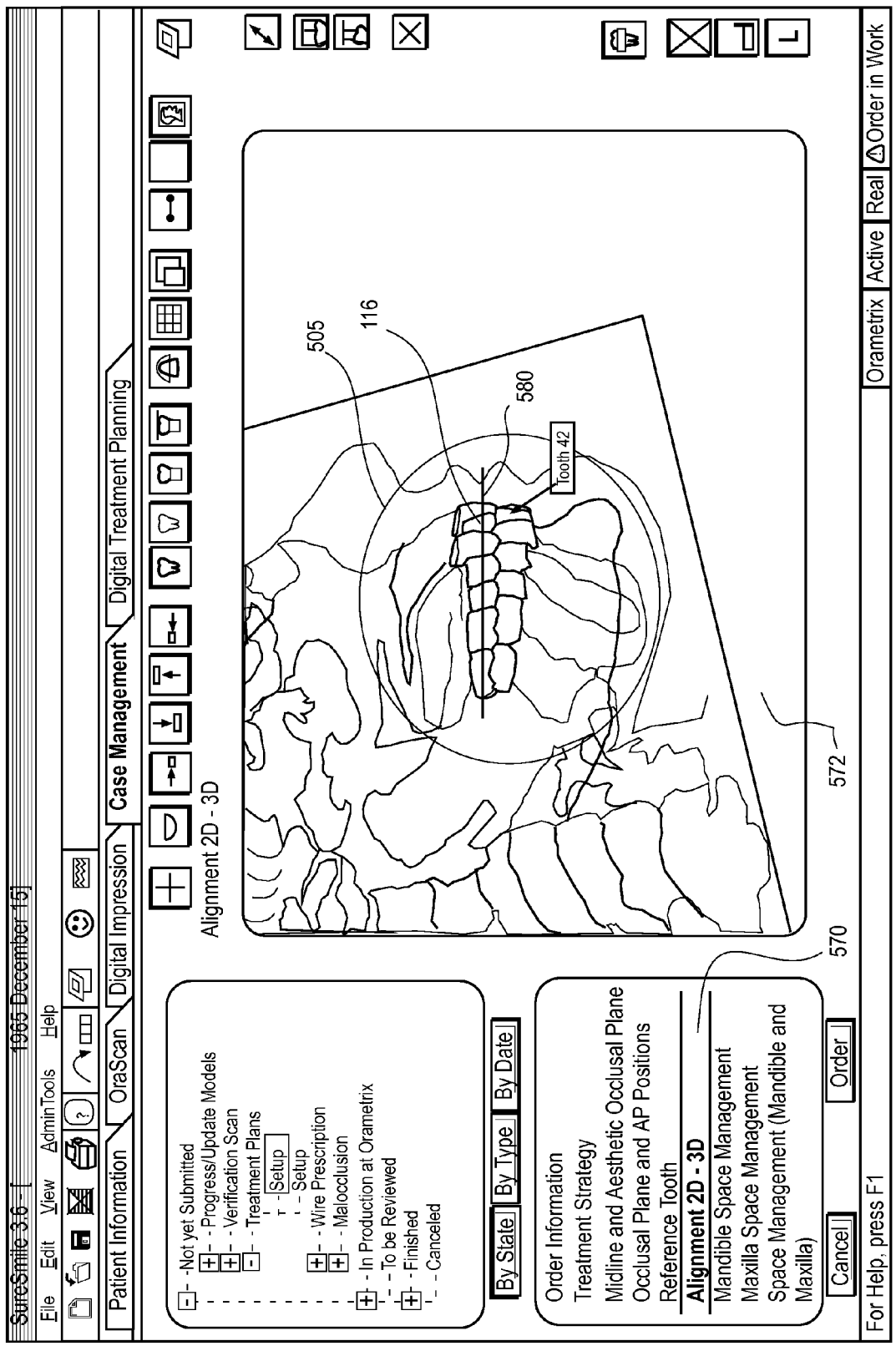

The treatment planning process continues by using the graphical user interface to align two dimensional images of the patient, e.g. x-rays, with three-dimensional virtual teeth models. In this manner, the user progresses from two-dimensional treatment planning to three-dimensional treatment planning. One possible embodiment is shown in FIGS. 28-31. In FIG. 28, the user has selected the "Alignment 2D-3D" icon 570, which causes the screen display 572 to appear. In this display, a 3D virtual model of the teeth 116 appears on the display, superimposed over a two dimensional X-ray photograph 505. The 3D model of teeth 116 is created by suitable scanning techniques, such as in-vivo scan of the dentition or a scan of a model of the dentition, as described previously. After the scan is obtained, the teeth are separated from surrounding structures and represented in the computer as individual, individually moveable, virtual tooth objects. The display includes navigation and other icons by which the user can rotate the model 116 in any desired orientation, show only one or both arches, select or deselect for display gingival tissue, occlusal planes, etc. The 3D tooth models are scaled so that they coincide in size with the size of the teeth in the 2D image. The superposition shown in FIG. 28 could be either performed manually, or possibly automatically with suitable pattern matching algorithms to identify tooth objects in the 2D image and align the 3D tooth objects with the teeth in the 2D image.

In FIG. 28, the functional occlusal plane 508 is displayed together with the teeth and the x-ray. Whereas in FIG. 24, the upper occlusal plane was shown as merely a line, in FIG. 28 the occlusal plane 508 is represented in two dimensions but it actually is also represented in three dimensions in FIG. 43. Thus, the original 2D representation is transferred to a surface in three dimensions. The user is able to view the arrangement of the teeth relative to the bone in any orientation, such as front perspective or side perspective.

The arrangement in FIG. 28 facilitates the user understanding the relationship of the 3D teeth with respect to the soft tissues as well as bone. The 3D plan of the teeth can be oriented relative to the occlusal plane 580 that the user has defined.

Figure 28A:
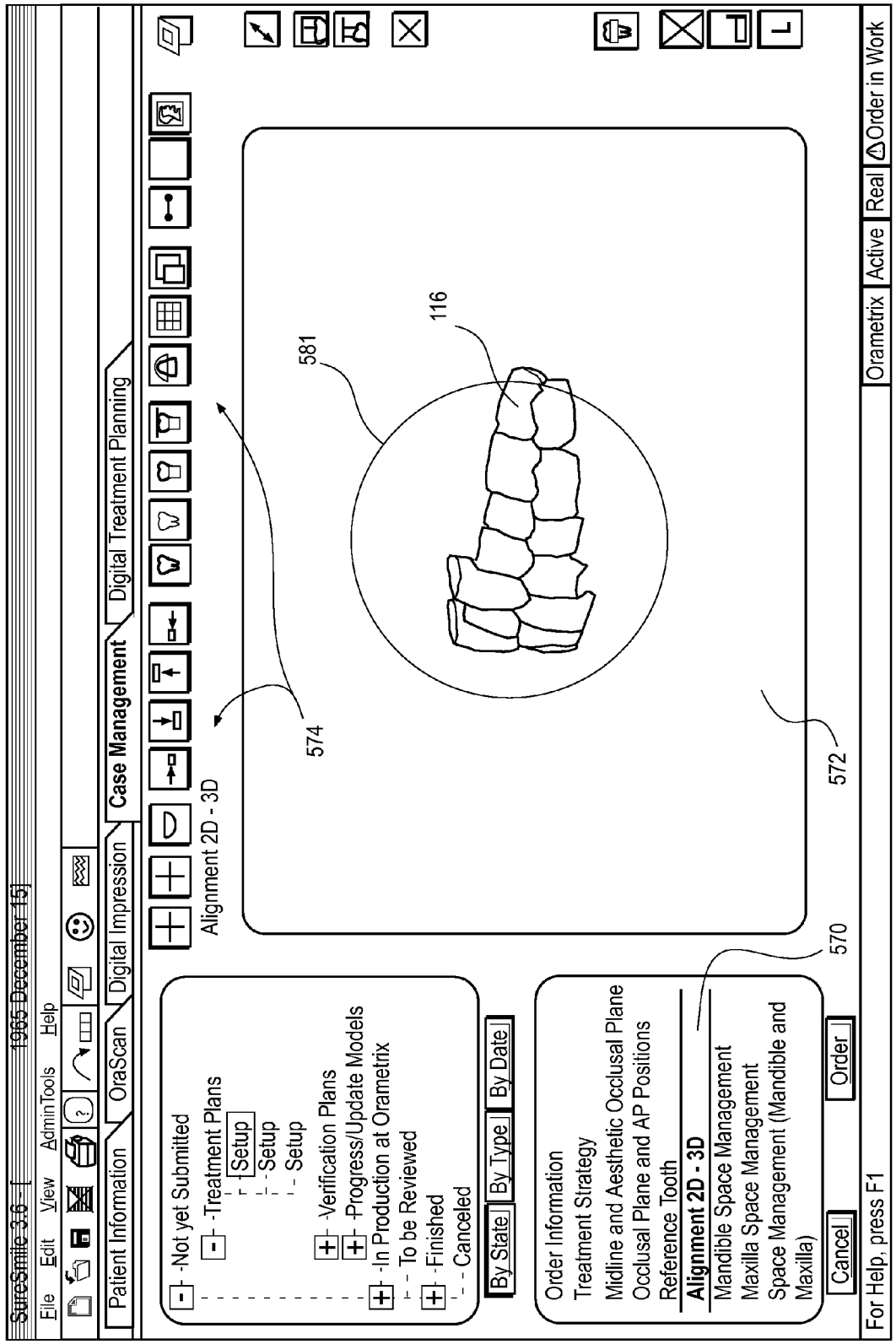

In FIG. 28A, the user has activated icons 574 for display of both arches and a midline plane 581.

Figure 29:
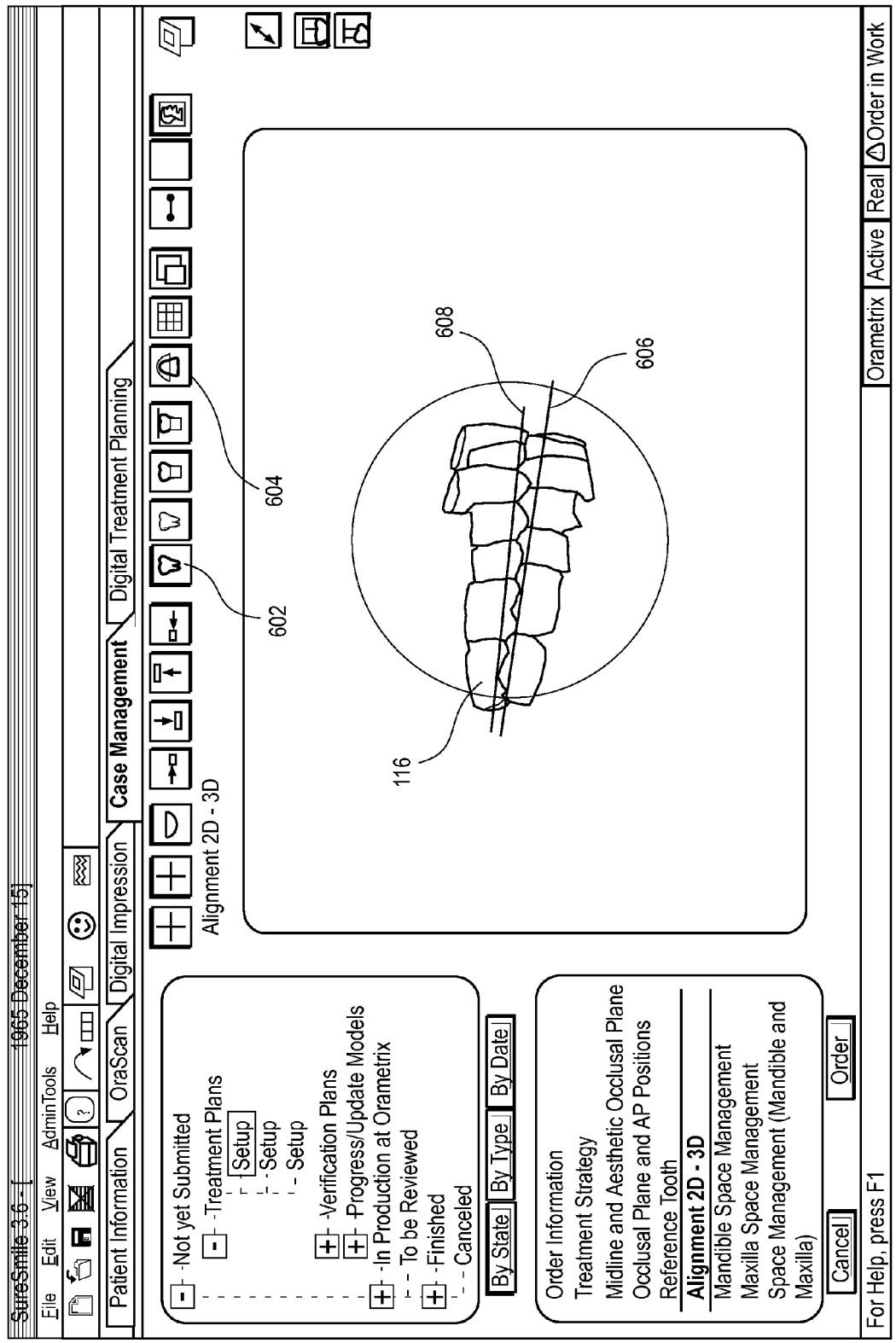

In FIG. 29, the user has selected for display both the upper and lower arches by activation of icon 602, and treatment occlusal planes 606 and 608 for the upper and lower arches. The occlusal planes 606 and 608 are activated by selecting the icon 604. Note that in FIG. 29, the occlusal planes are rendered and displayed in three dimensions as a three-dimensional surface, whereas, initially in FIG. 24, the midline and occlusal planes were rendered in two dimensions. The three dimensionality of the planes 606 and 608 is hard to see in FIG. 29, but becomes more apparent when the model of the teeth is rotated or viewed from an orientation that is not so closely in line with the planes 606 and 608.

Figure 30:
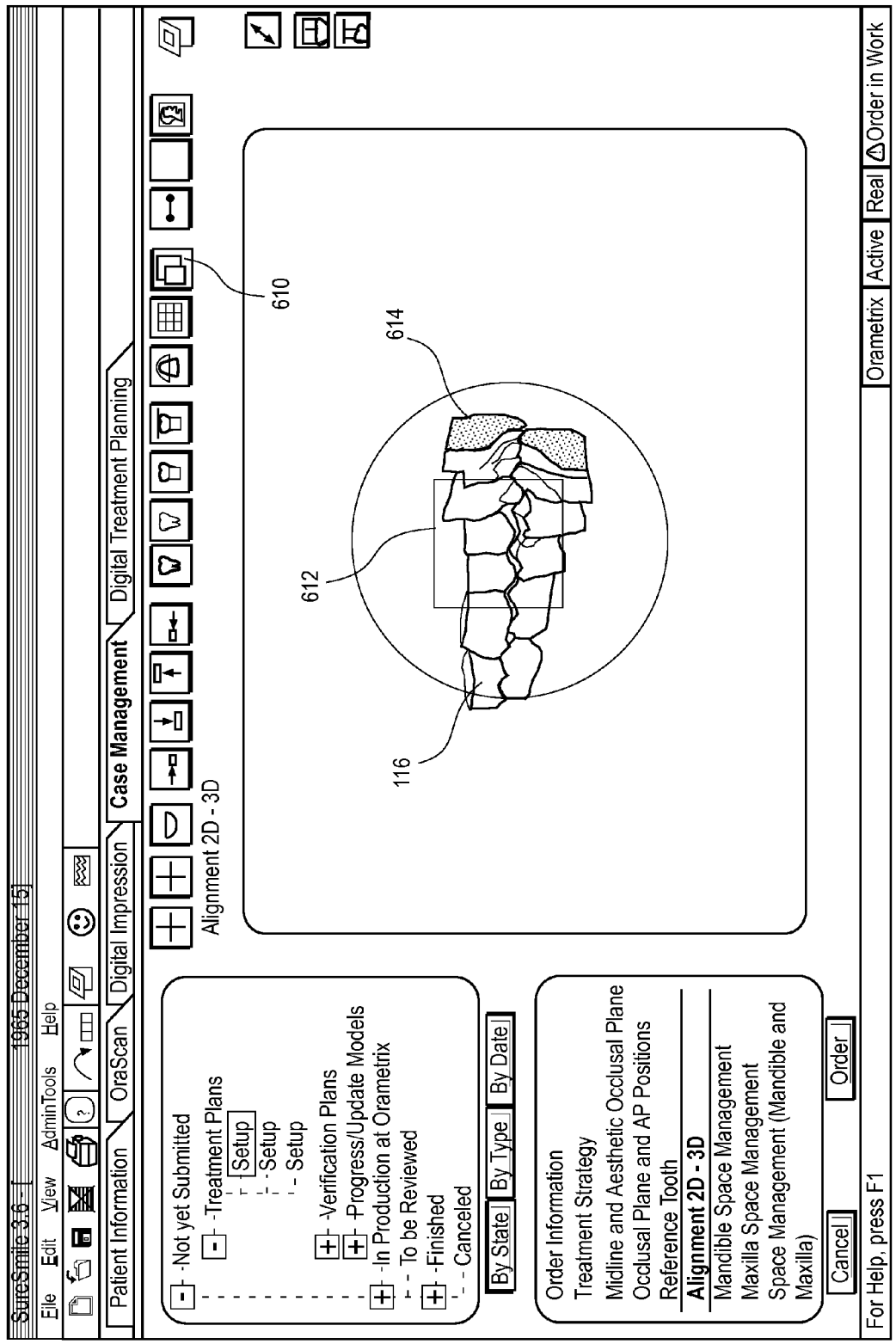

In FIG. 30, the user has activated icon 610 which causes a mid-sagittal clipping plane 612 to appear. The location where the clipping plane 612 intersects the front teeth in the upper and lower arches is shown by the shaded areas 614. The clipping plane can be moved over the arch to view the teeth in any cross-sectional view, using navigation icons. The view shown in FIG. 30 allows the user to judge subjectively the relationship between the upper and lower incisors, and compare that with the 2D views, for example, from a 2D X-ray.

Figure 31:
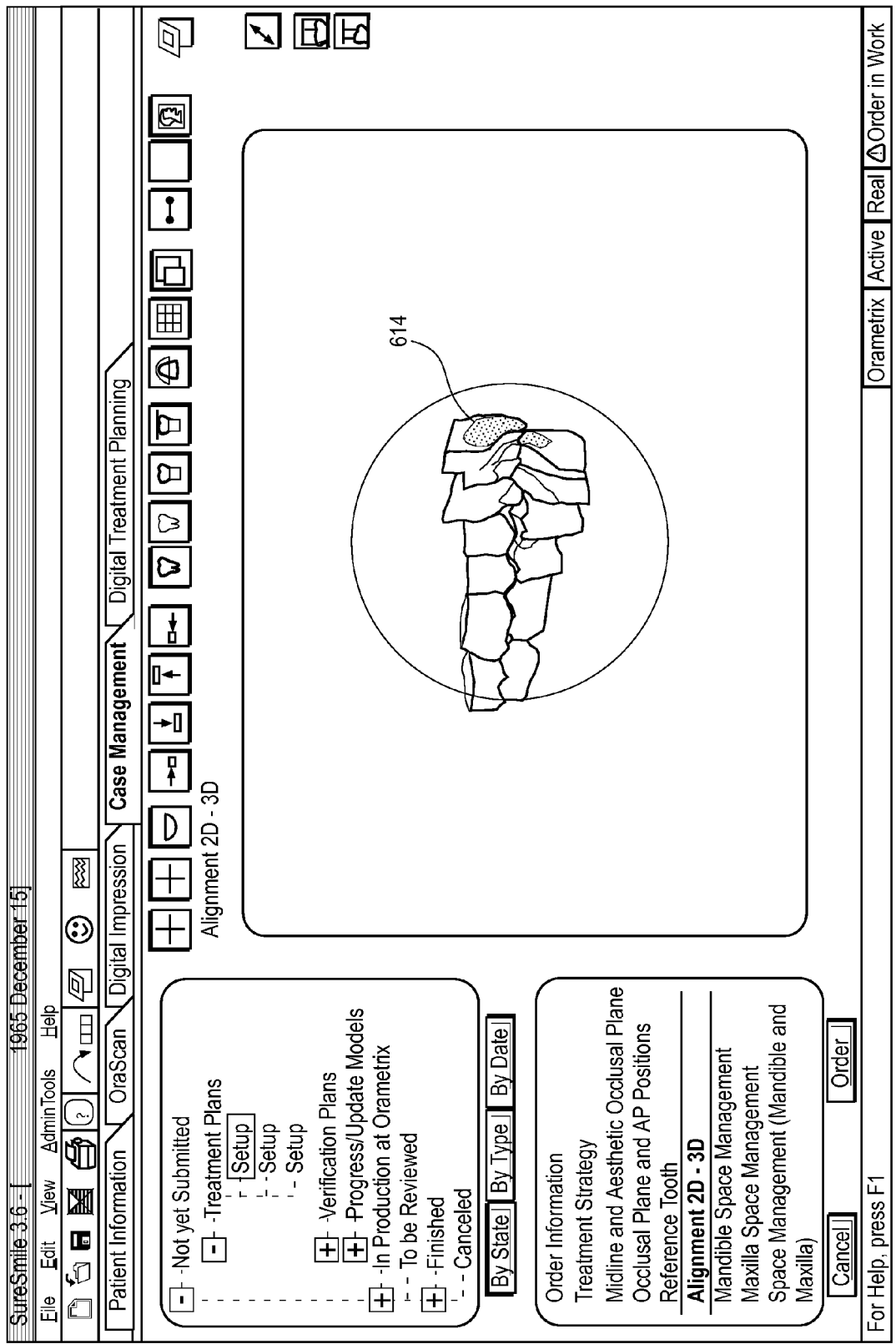
Figure 32:
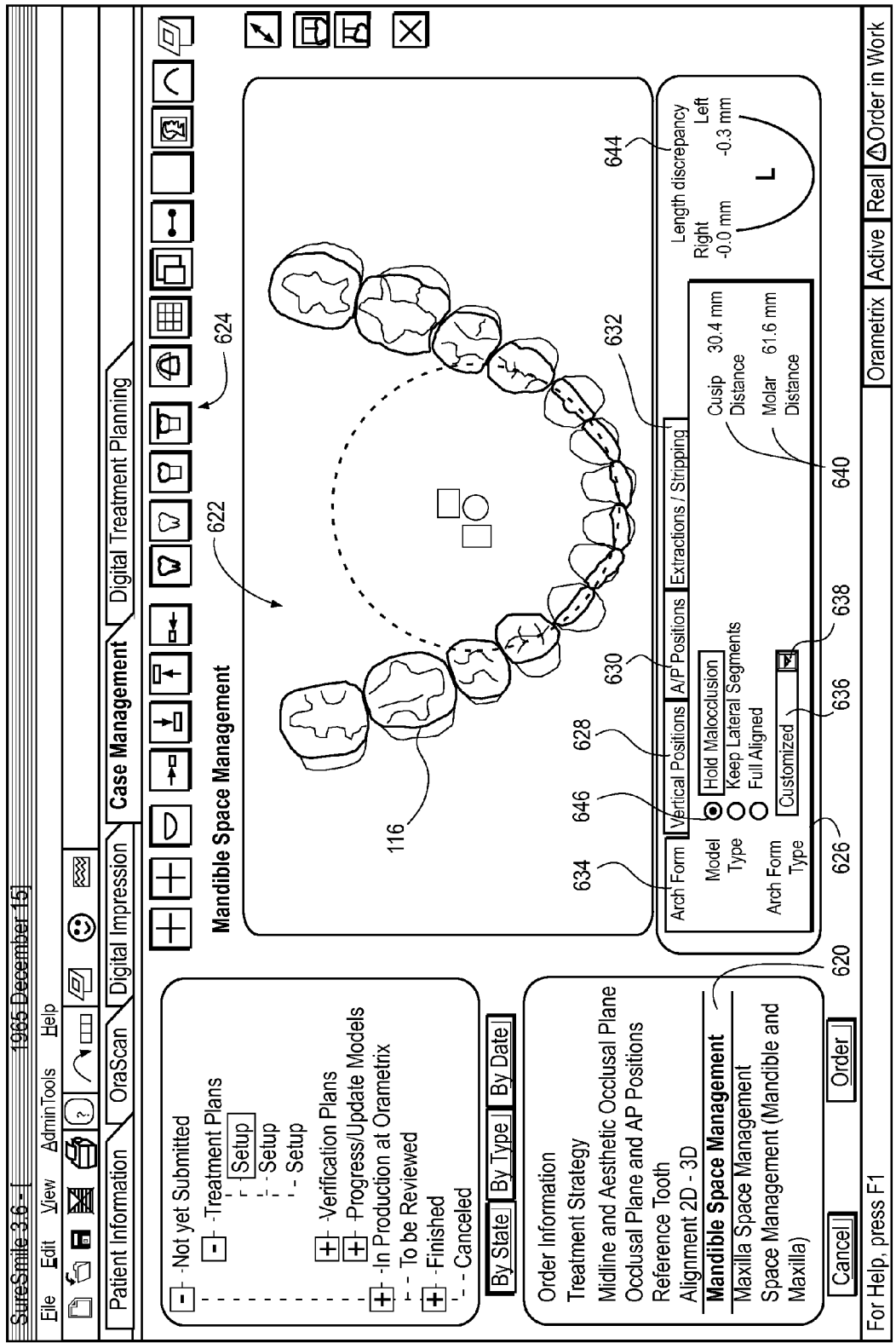

As shown in FIG. 31, the user can adjust the position of the clipping plane and thereby change the location at which the plane intersects the upper and lower arches, as will be appreciated from a comparison of the shaded areas 614 in FIG. 31 with the areas 614 in FIG. 30. The user adjusts the position of the upper and lower incisors in the clipping plane illustration to match the position that was determined in the 2D lateral view in FIG. 57. When the user is satisfied with the 2D-3D aligning step, the user proceeds to additional tasks, including space evaluation, and space management tasks by which the user first evaluates how much space is needed to align the teeth and then how he wishes to manage the space. The user further proceeds with the design of an desired arch form. This is done for both arches, typically the mandible first and then the maxilla. However, at any time the user can view both arches together by activating a hide/display icon. To proceed to these tasks, in the illustrated embodiment, the user selects a mandible space management icon 620, as shown in FIG. 32, which causes the screen display 622 to appear. The screen display 622 includes a plurality of icons 624 which are used for hiding and displaying various aspects of the virtual patient model, soft tissue, occlusal planes, and other features of the software. The central region of the display 622 is used to display the 3D virtual teeth 116. The display 622 also includes a lower region 626, where the user can activate an Arch Form tab 636, as shown, or other tabs, including a Vertical Positions tab 628, a A/P positions tab 630, and an Extractions and Stripping tab 632. The arch form tab 634 includes an area indicating that the user has selected a customized arch form. However, by activating the drop down icon 638, the user can scroll through and select pre-defined arch form types that are stored in the workstation, and adapt tooth position to standard arch forms. At all times, the user is able to interactively move any tooth or teeth on the graphical user interface relative to the desired arch form, by clicking the tooth to select the tooth and then dragging the tooth with the mouse to a new position.

Space analysis can be dynamically evaluated by affecting the following parameters: midline, arch form, A/P position, tooth position, the reference tooth, tooth size, spatial distribution of the teeth in the arch and by appliance prescription, either selectively or in tandem. Furthermore, space management can be effectuated by simulation of interproximal reduction, buildup of the tooth, extraction, distal and mesial tooth movement, expansion of the jaw, axial inclination angle change, rotation change, overject and overbite change, appliance choice, adjustment of inter-arch relationship, or selectively maintaining crowding.

The tab 634 further includes measurement tools 640 which provide cuspid distance measurements and inter-molar distance measurements for the current tooth positions displayed on the screen. The user can also set points anywhere on the virtual model and activate an icon to get a distance measurement, or invoke a graph tool as described elsewhere. FIG. 32 also shows a display 644 that provides an arch length discrepancy measurement (in terms of mm) which indicates, given the current virtual tooth positions, whether there is sufficient length in the arch (positive values) or whether some interproximal reduction, tooth rotation, extraction, distal movement of the molars, uprighting of the molars, changing of the torque of the teeth, changing the A/P position of the incisors, expanding the arch form, maintaining selective crowding, adjusting the level of the occlusal plane or the midline, axial inclination of teeth, overjet or overbite or other action is required to fit the teeth in the arch (negative values). The left-right balance in the arch length discrepancy can be changed by interactively selecting the midline and moving the midline either to the right or left.

Figure 33:
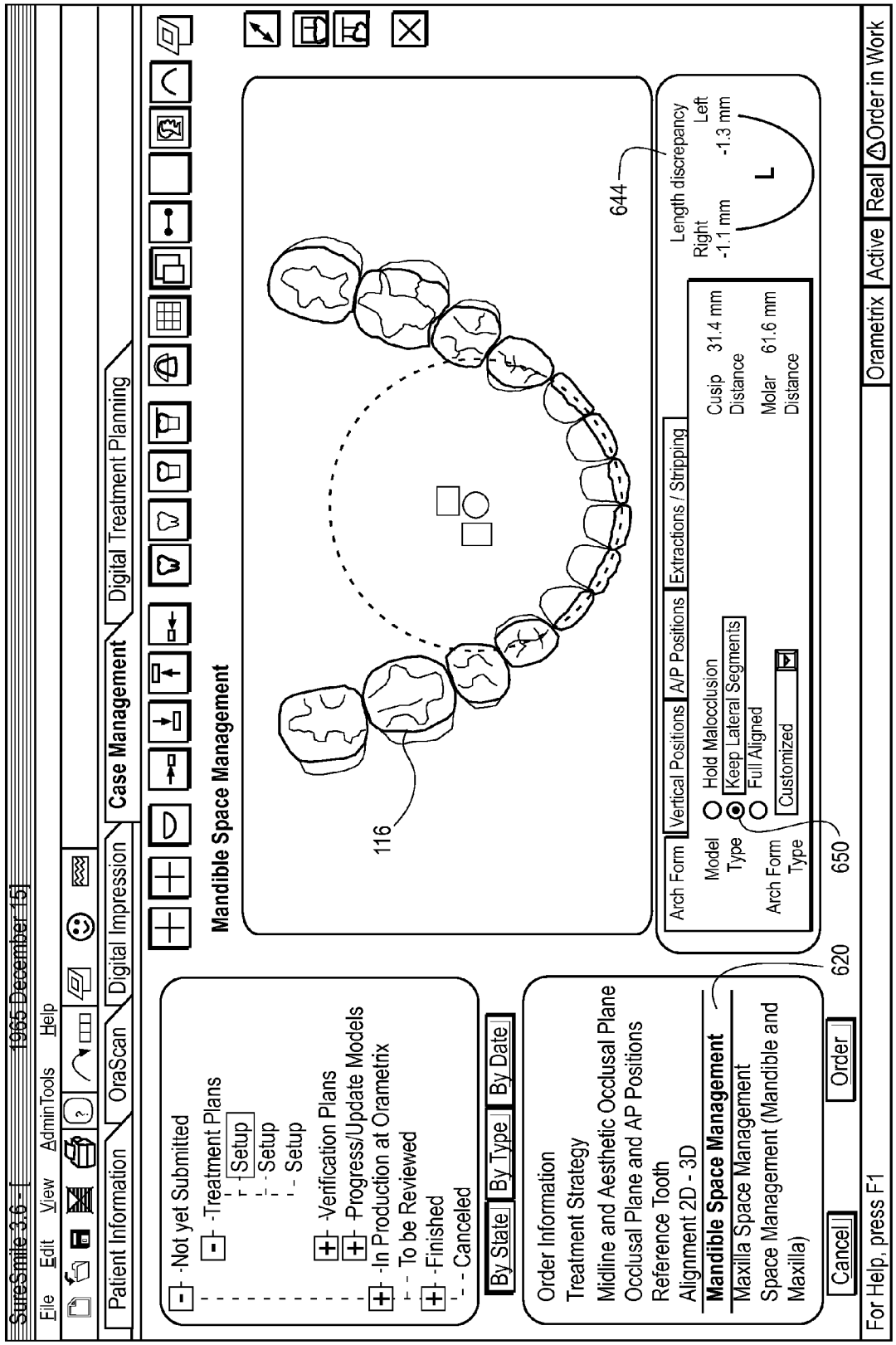

In FIG. 32, the presenting malocclusion is seen. The user has indicated that they wish to hold the malocclusion as indicated at 646. In FIG. 33, the keep lateral segments tab 650 has been activated. This feature immobilizes the lateral segments (premolars and molars) and allows for the alignment to occur only through the change in the arch form anteriorly. The user can define the incisor position based on the lower incisor based on where it was initially. The user can hold the buccal segment (basically holding the lateral segments) then impose no movement and you allow for full alignment of the anterior teeth. What this has done is tell the practitioner how much space is needed in the arch length and at the same time the display provides the inter-molar and inter-cuspid width based upon holding the posterior teeth fixed. In other words, as the user changes the constraints in terms of tooth mobility, the user is provided instantaneous measurements in terms of arch length and the new positions of the teeth that are allowed to move. The user can selectively immobilize teeth or allow their free movement in three planes of space, either individually or in groups.

The teeth are moved to a more ideal position. This action changed the cuspid distance from FIG. 32, but did not change the molar distance. The length discrepancy tool 644 indicates that the right and left arch length has increased from the previous values, which would require some interproximal reduction, extraction, or some other action to fit the teeth to the arch length.

Figure 34:
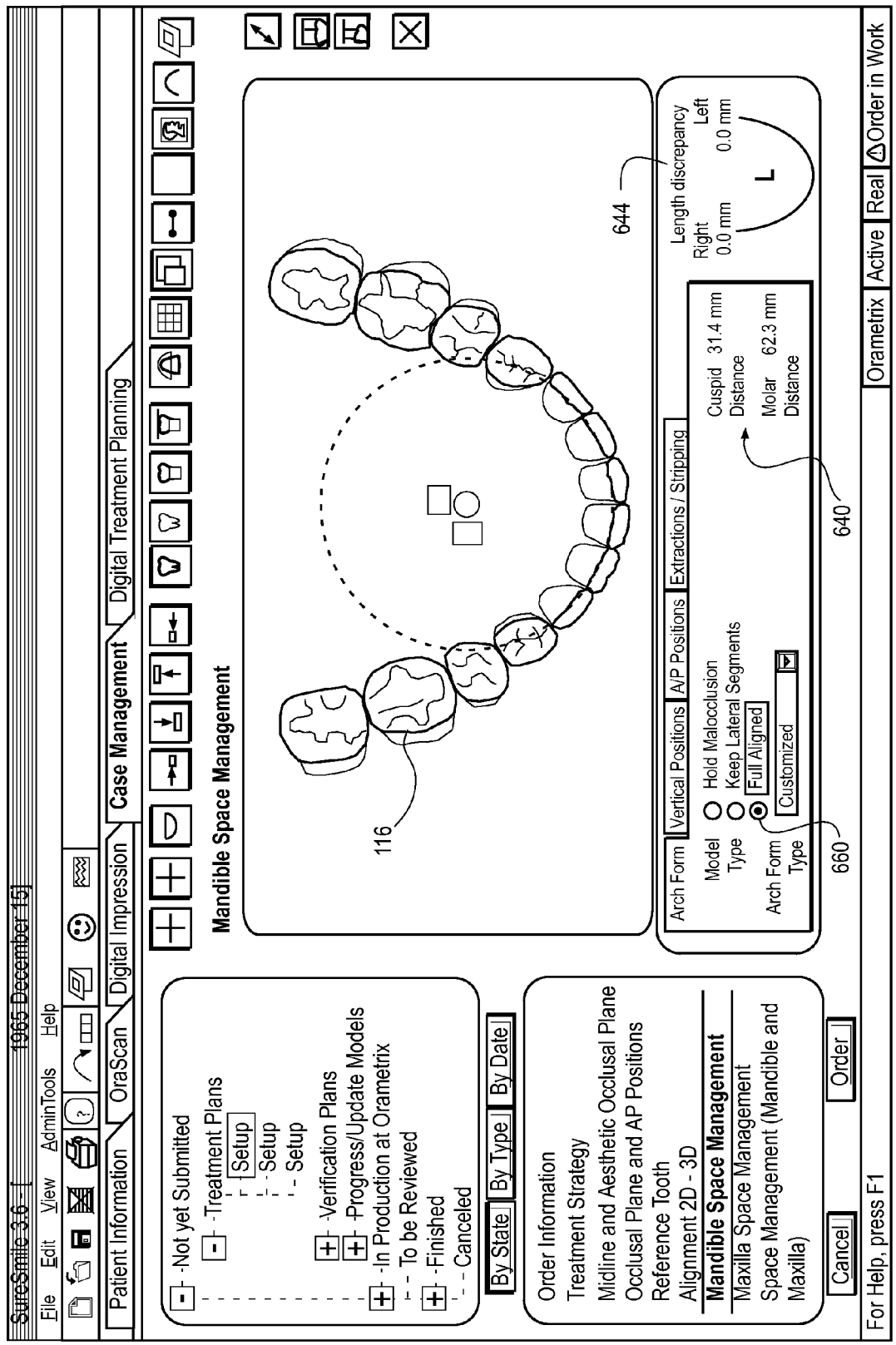

In FIG. 34, the user has selected "full aligned", as indicated at 660. Both the cuspid distance and the molar distance have changed, as indicated by the measurement tools 640. The length discrepancy, as indicated by the display 644, has now returned to zero, indicating that the arch form is "good". "Fully aligned" allows free movement of all the teeth along the pre-selected arch form. If some arch length discrepancy remained, the user could simulate a change in arch form, midline, occlusal plane, rotation of teeth about their axis, extraction etc. to rectify the situation. If the user wants to customize the shape of the arch form they activate the slide line tab, discussed later.

Figure 35:
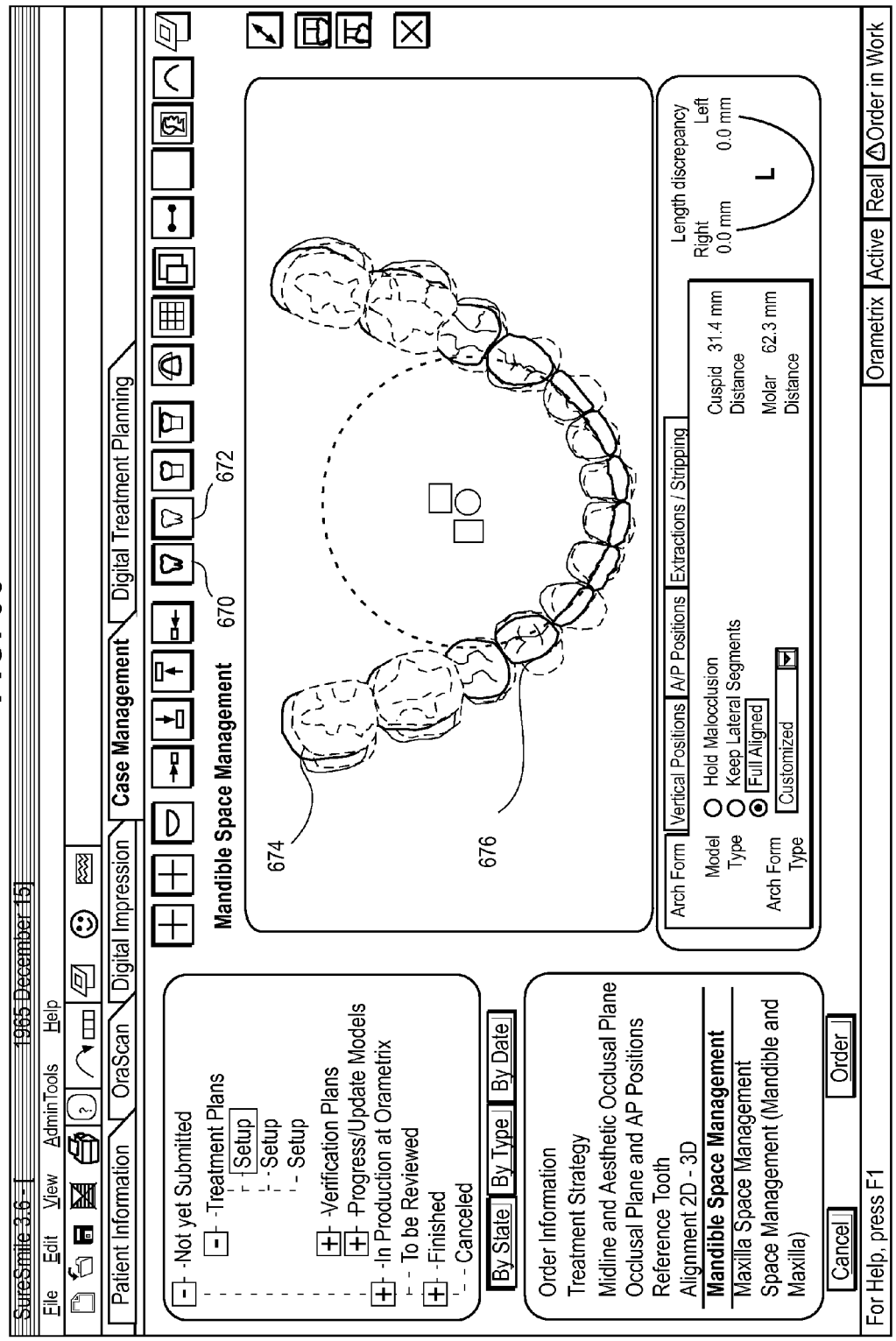

In FIG. 35, the user has activated icons 670 and 672, which causes the display to show both the original position of the teeth (areas with dark shading indicated at 674) and the new position as a result of the mandible space management exercise (white areas, indicated at 676. This color coding helps the user visualize the tooth movement that will occur in accordance with the proposed treatment plan. This feature of reference back to the original malocclusion is available at any time and in any plane, both in 3D or 2D images or combination.

Figure 36:
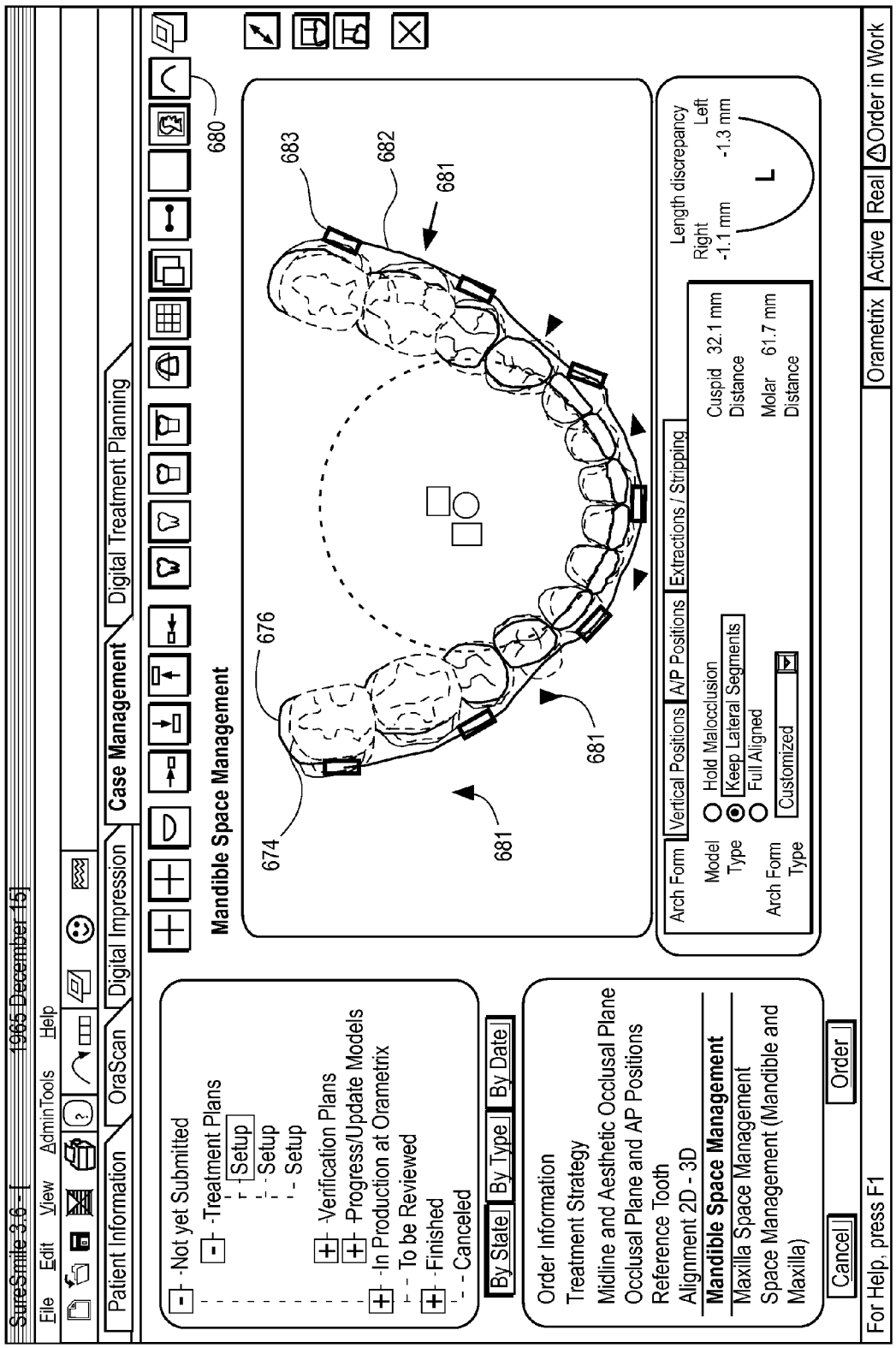

In FIG. 36, the user has activated icon 680 which causes a slide line 682 to appear. The slide line can positioned at different levels, such as the bracket level, the level of the cusp tips, or the level of the interproximal contact points.

Arch length discrepancy can be defined at various levels, including contact points, cusp tips and at the level of brackets, based upon the location of the slide line that is chosen.

Then, the effect of bracket prescription on the dentition is also modeled in defining the position of the teeth in the arch, thus providing the clinician with a method of understanding the effects of his appliances on arch length inadequacy.

The slide line 682 is a tool that assists the user in changing the shape of the arch form. The slide line 680 includes anchor points 683 spaced along the length of the slide line 682, which are affixed to labial surfaces of the teeth in the positions shown, The slide line 682 also includes points 681 equidistantly spaced from the anchor points, which the user manipulates to cause the slide line to bow out or in relative to the teeth, and thereby change the shape of the arch form. For example the user would click on one of the points 681 and drag the point 681 out away from the slide line, which would cause the slide line to bow outwardly towards the point 681. The clamping or anchor points can be moved by the user anywhere along the slide line. The slide line (as was the case with the midline) allows for designing asymmetric arch forms. Whenever the user wishes to compare the proposed arch form with the original tooth position, they activate an icon at the top of the screen and the original tooth position is also shown, with the difference in position shown in a contrasting color.

Figure 36A:
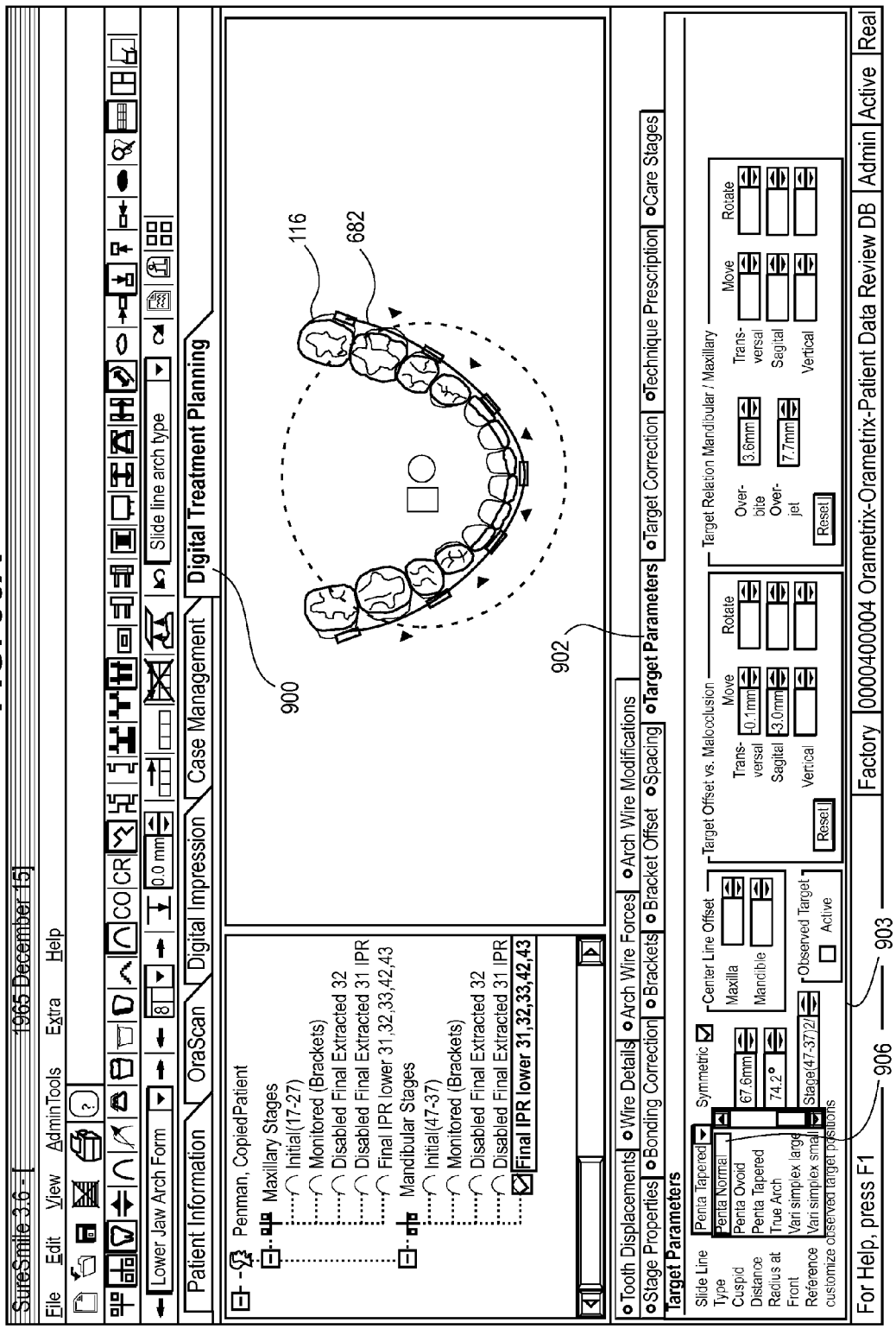

FIG. 36A shows a screen display when the treatment planning icon 900 is actuated. This icon takes the user to addition treatment planning software which enables a user to further define the shape of the arch form, move teeth relative to each other, and design customized appliances. Many of the features shown in the display of FIG. 36 A are described in the published PCT application WO 01/8076, and therefore will not be repeated here. The user has highlighted the "TARGET PARAMETER" icon 902, which allows the user to customize the configuration of the desired target arch form. Here, in area 906, the user can scroll through a series of available general arch form types. In field 903, the user is provided with various tools to make the arch form symmetric (or not symmetric), enter in values for transverse, sagittal or vertical movement, or change the relation of the overbite or overjet. As shown in FIG. 36A, the slide line feature 682 is also displayed, which the user can use as described previously to change the shape of the arch using the slide line features.

In FIG. 37, the user has activated an icon to show a midline plane 690 to appear. By interactively moving the midline (using click and drag technique), the user can change the orientation of the midline relative to the teeth in the arch and thereby change the right/left values shown in the length discrepancy icon 644. The midline is shifted slightly to the patient's right. The lateral segments are held fixed while the midline shift is only carried out by the anterior teeth. If "full aligned" had been checked the all the teeth would move along the slide line to accommodate the new position of the midline. Note also in this Figure that the new position of the teeth can be measured against the original as indicated by the lightly speckled pattern of the posterior teeth, which indicates little movement of the lateral teeth from the malocclusion position (the difference in position indicated by the dark or shaded spots on the teeth).

Figure 37A:
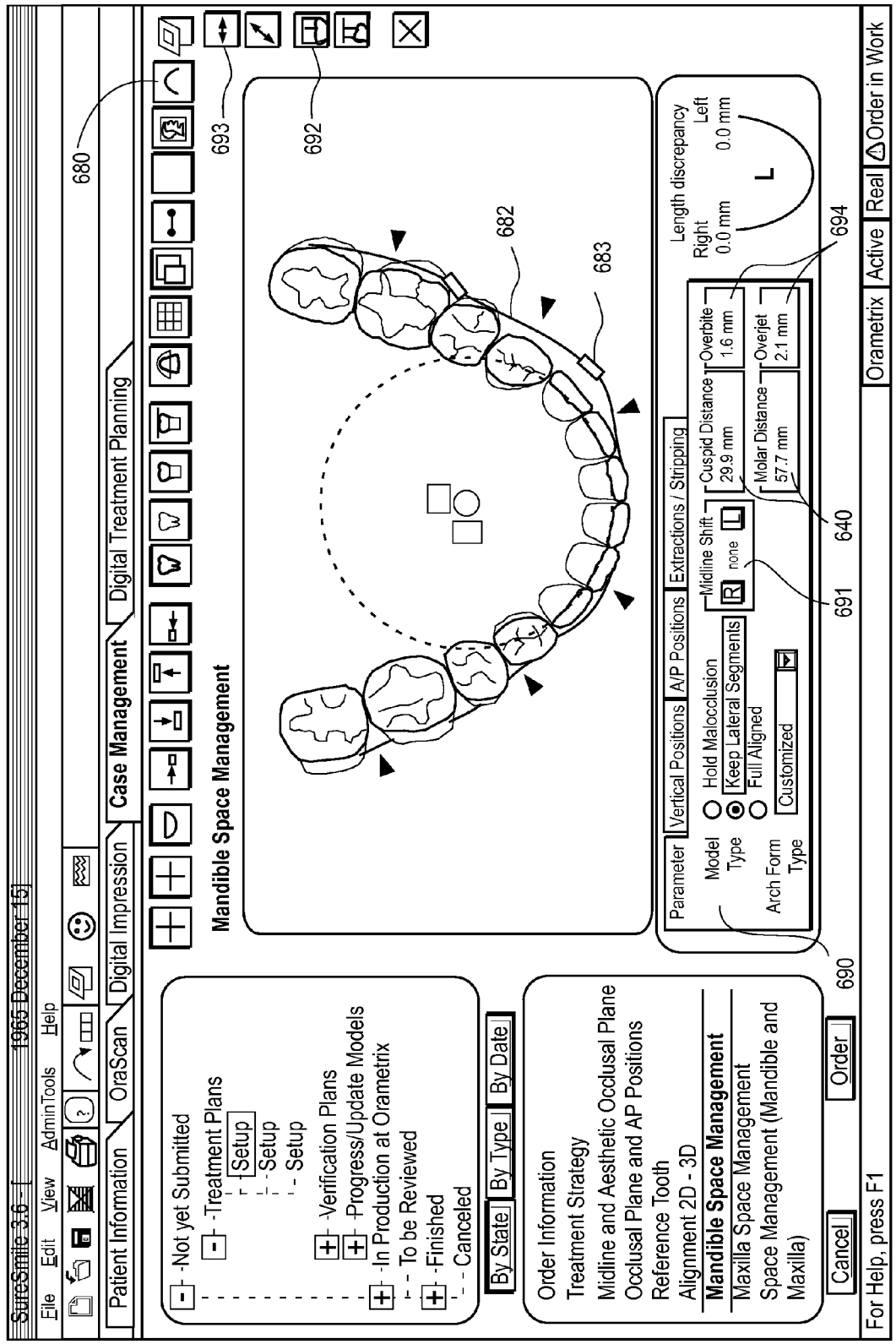

In FIG. 37A, the user has selected a parameter tab 690, which includes icons 691 for midline shift (left or right), the measurement tools providing cuspid and intermolar distance, and a tool 694 indicating the amount of over bite and overjet, given the current configuration. This data is obtainable since the position of the upper arch relative to the lower arch is known in the in the computer, and the position of the incisors in both arches is known in three-dimensional space. Thus, the display allows the user to interactively move the teeth and immediately realize the effect of tooth movement on overbite and overjet. You can also adjust overjet and overbite parameters to see their effect on the arch length inadequacy.

By activating icon 692, the user can manage the spacing between teeth by having all spacing between teeth to be equal. By activating icon 693, the user invokes a collision detection algorithm that prevents the user from moving teeth in a manner such that a tooth collides with another tooth, either in the same arch or in the opposing arch. The software allows for interproximal reduction by morphing the tooth shape to match the available space, using a simple morphing algorithm that shrinks the tooth in two or three dimensions.

Figure 38:
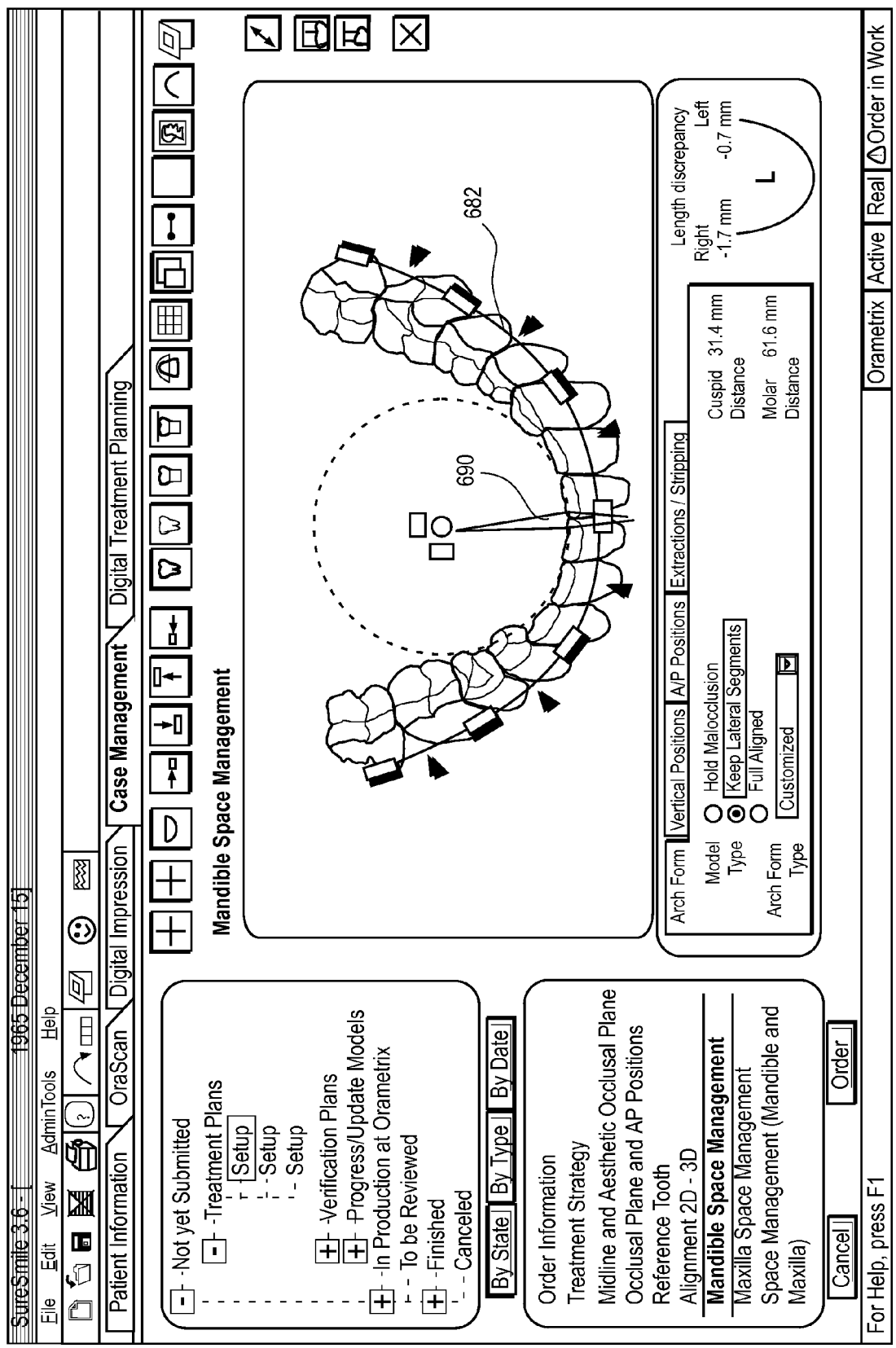

In FIG. 38 the user has invoked the simulation of the midline plane 690. By movement of the midline plane left or right they can correct the length discrepancy (left or right) for the arch.

Figure 39:
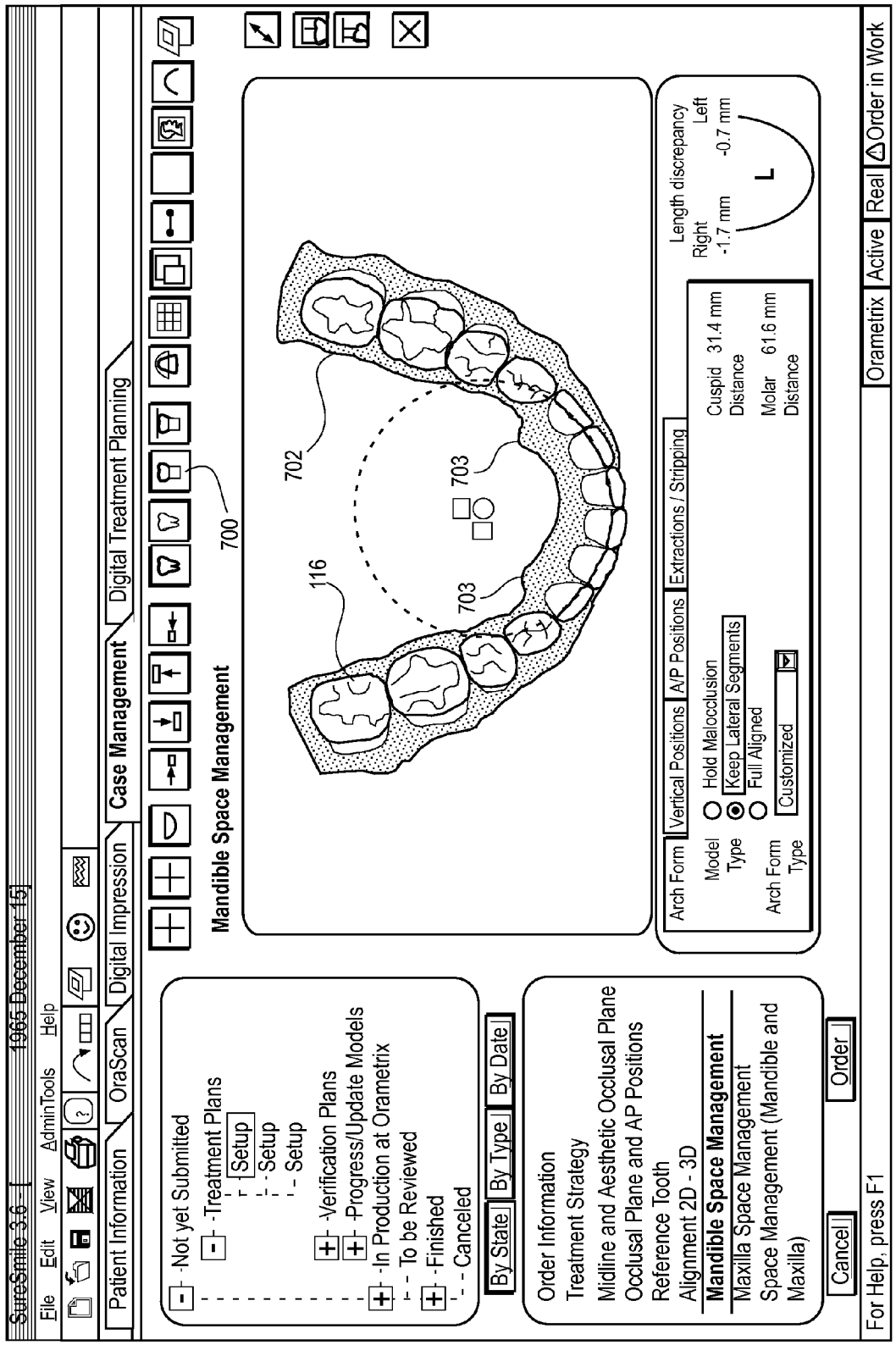
Figure 39A:
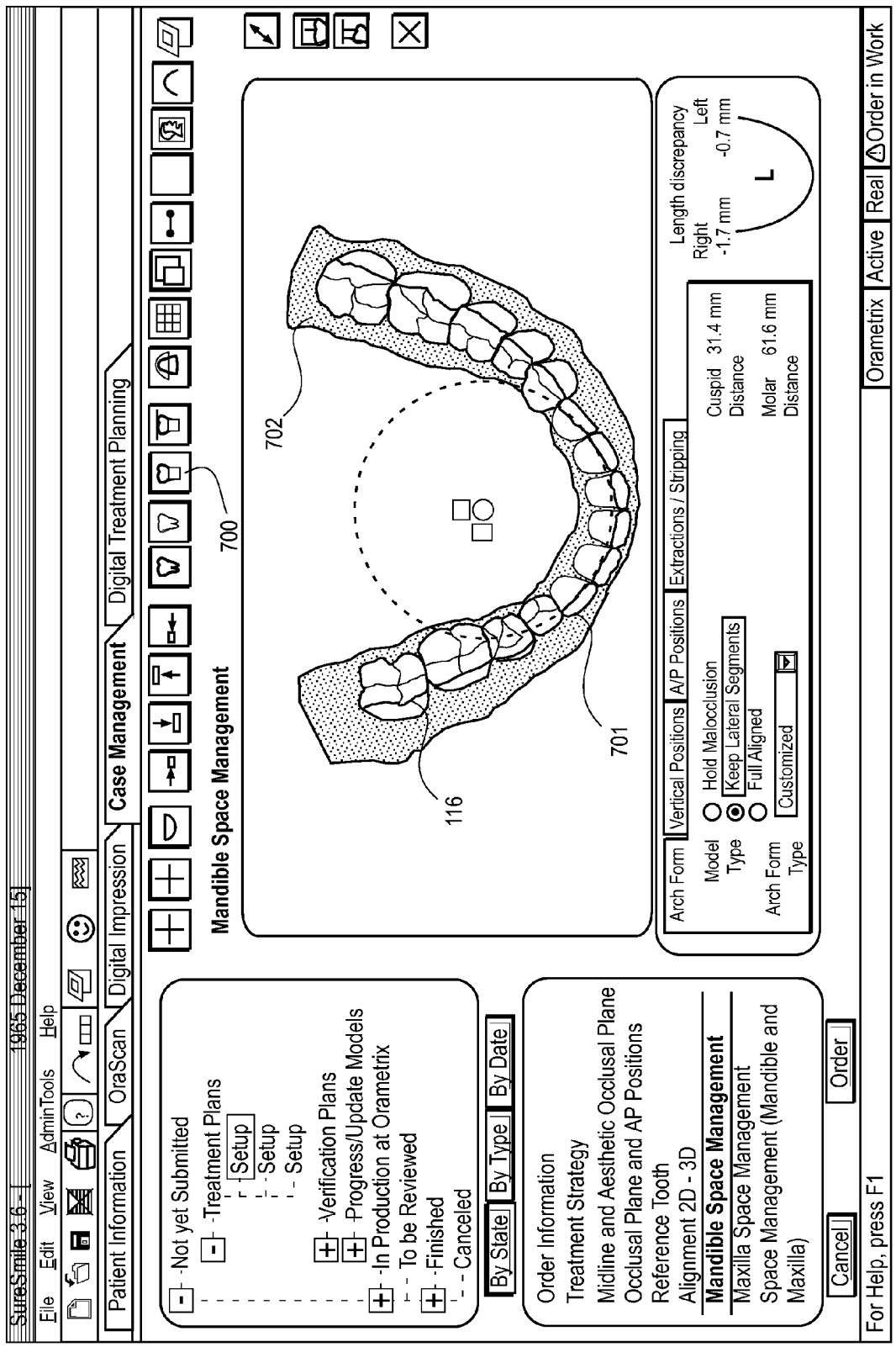

In FIGS. 39 and 39A, the user has activated a gingival display icon 700 which causes the display to show both the 3D virtual teeth 116 and a 3D model of the gingival tissue 702. This icon can be activated at any time in the space planning screen. The model 702 of the gingival tissue can be obtained from a scan of the patient's mouth with an intra-oral 3D scanner as described previously, or it could be obtained from a scan of a physical model of the patient. The gingival tissue 702 is separated from the scan data of the teeth 116 so that the two types of objects can be modeled as separate 3D objects and thus displayed either alone or together. In FIG. 38, the proposed treatment indicates substantial bumps 703 on the lingual side of the teeth. The gingival tissue is morphed to show the effect of tooth movement to this position on the gingival tissue. Since gingival tissue closely follows the underlying bone, the bumps 703 may indicate that the proposed tooth movement is incompatible with the patients mandible bone structure. This could be confirmed for example by zooming in on the location of the bumps 703, invoking the display of underlying bone structure from an X-ray or CT scan stored in the workstation, and examining the superposition of the virtual tooth over the underlying bone. In FIG. 39A, the user has moved tooth 701 slightly and the gingival tissue 702 "morphs" to follow the position of the tooth.

Figure 40:
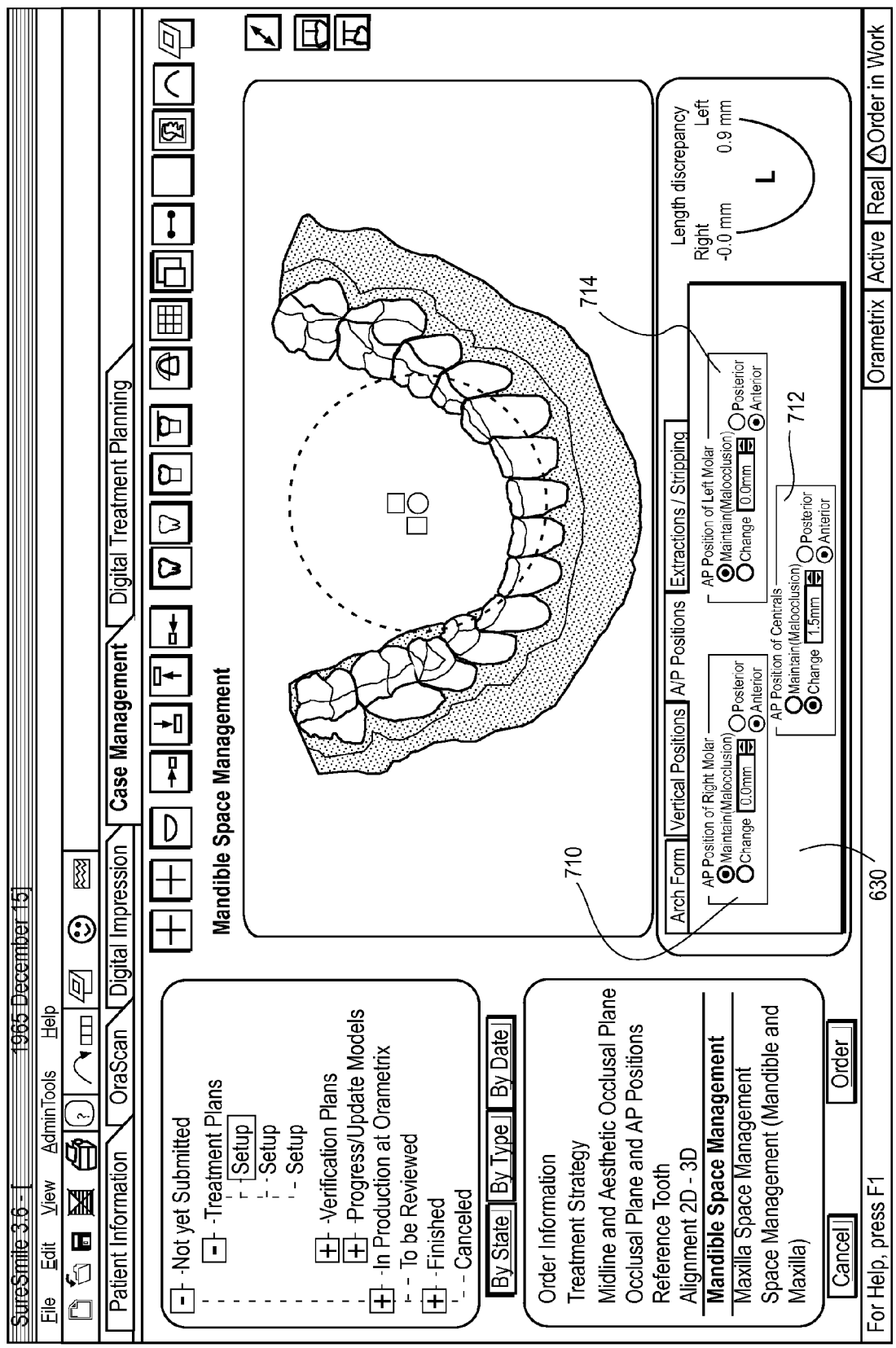

In FIG. 40, the user has activated navigation icons on the display to rotate the model of teeth+gingival tissue to a new orientation. The user has also activated the A/P positions tab 630, which allows the user to constrain either a singular movement of teeth or a group movement of teeth in the A/P direction. The display shows a field 710 which allows the user to either maintain or interactively change the A/P position of the right molar, a field 712 that allows the user to interactively change the A/P position of the central incisors, and a field 714 that allows the user to interactively change or maintain the A/P position of the left molar. As shown in FIG. 40, the user has interactively changed the anterior position of the central teeth by an amount of 1.5 mm, and the change is simulated by moving the central teeth anterior wise by 1.5 mm and keeping the back teeth fixed and showing the new position on the screen display. The 1.5 mm movement may not be sufficient given the 0.9 mm arch length inadequacy remaining.

Figure 41:
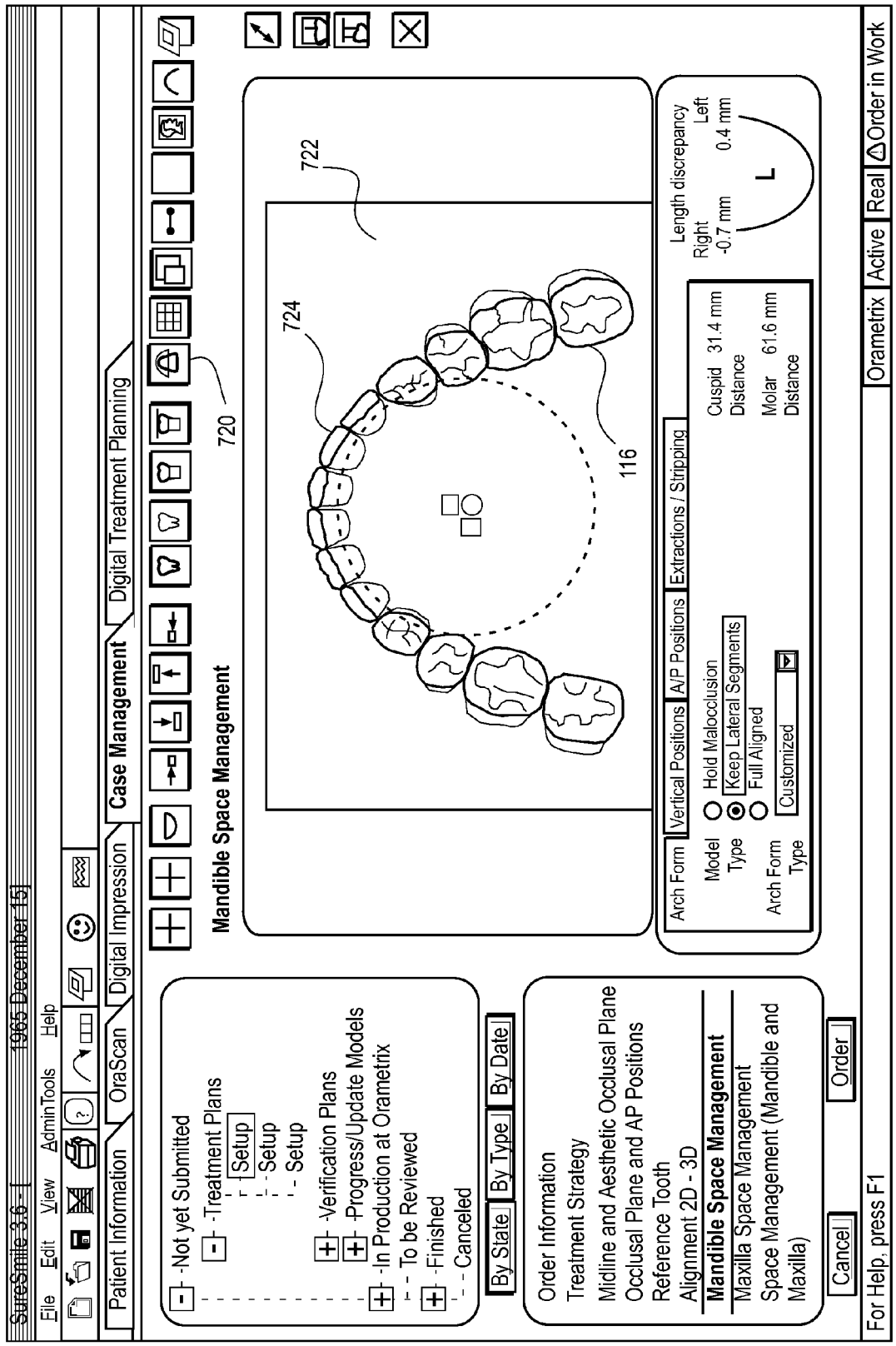

In FIG. 41, the user has selected an icon 720 that causes the display to show an occlusal plane 722, along with the position of the teeth 116 in a proposed arrangement. The areas where the occlusal plane intersects the teeth 116 is shown as white areas 724 of the teeth.

Figure 42:
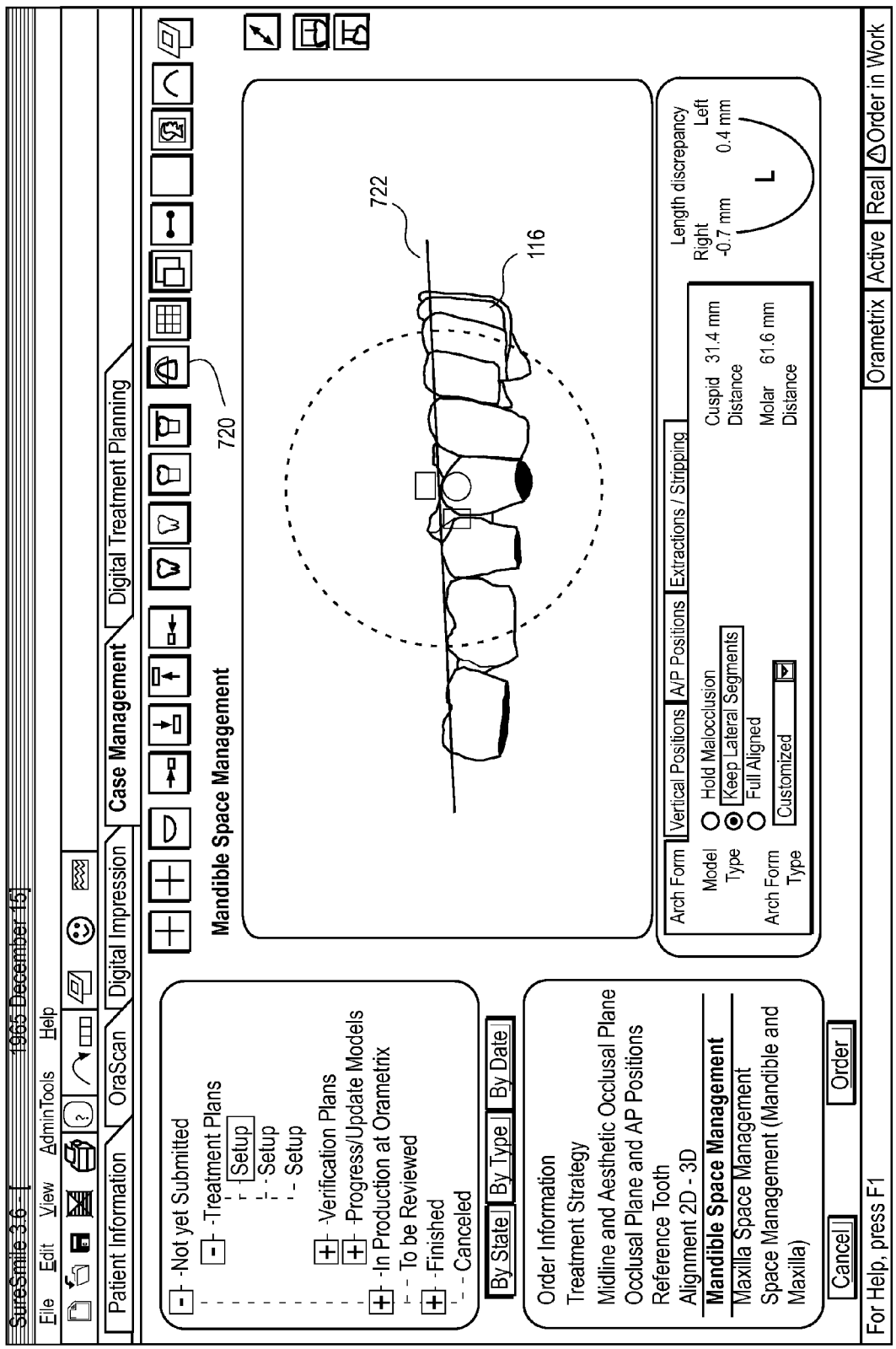

As shown in FIG. 42, the user has re-oriented the teeth to a side view and activated the icons to show both the teeth 116 and the treatment occlusal plane 722. This view gives the user a better view of the points of intersection of the occlusal plane with the teeth.

Figure 43:
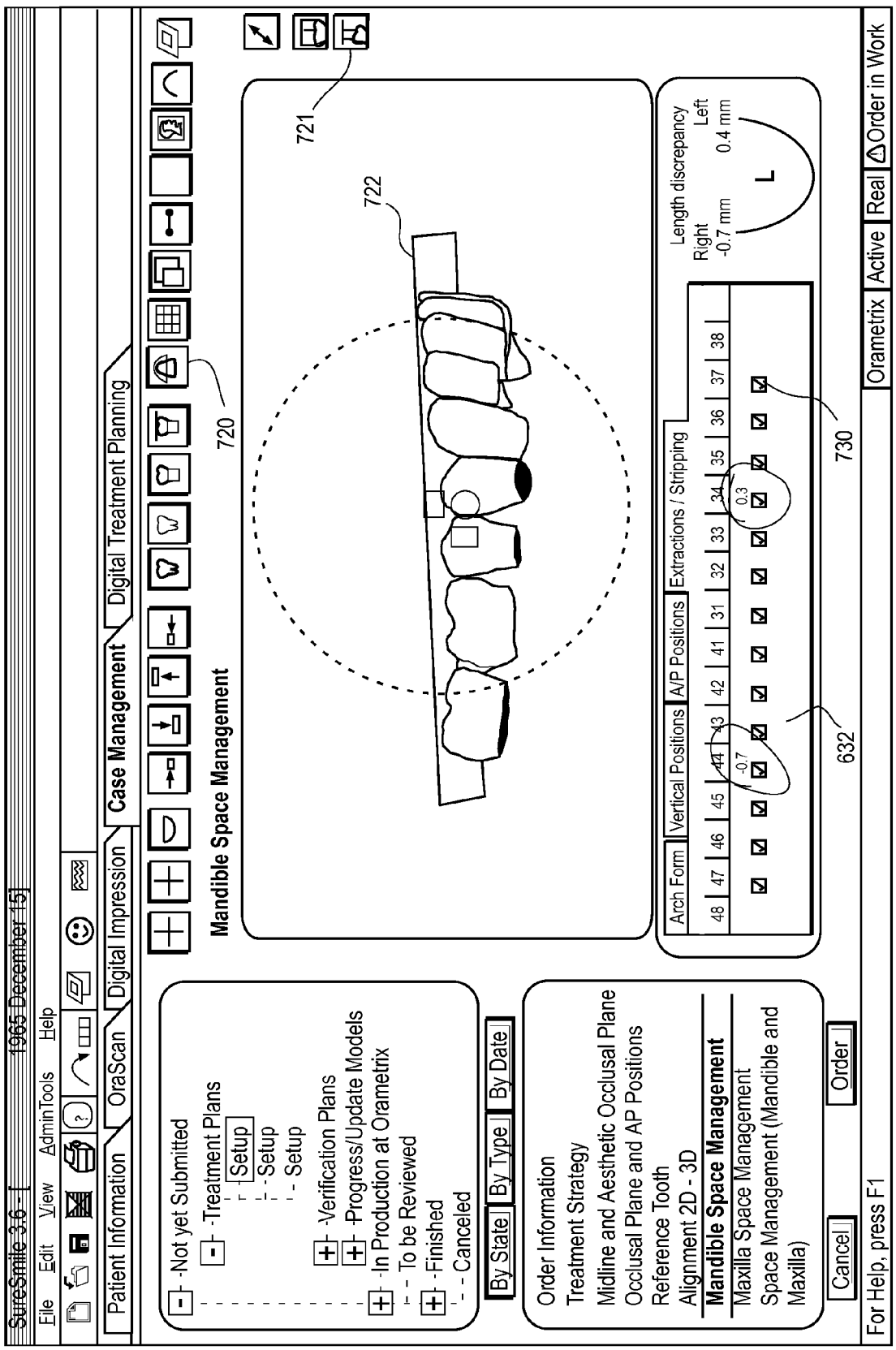

In FIG. 43, the user has activated the extractions/stripping tab 632. This causes the display to show the teeth of the lower arch, and a row of numbers corresponding to each tooth in the lower arch. The display also includes a check box 730 below each number. If the user un-checks the box 730, the corresponding tooth disappears to simulate an extraction. The numbers above the check boxes indicate the spacing needed in each half of the arch to meet the arch length requirements and reduce the arch length discrepancy to zero.

The display also includes an icon 721, which, when activated, all the teeth in the arch are moved in three dimensions such that they just touch the occlusal plane. This is an automatic function, since the location of the teeth and teeth cusps are known in three dimensions, and the treatment occlusal plane is also known in three dimensions.

Figure 44:
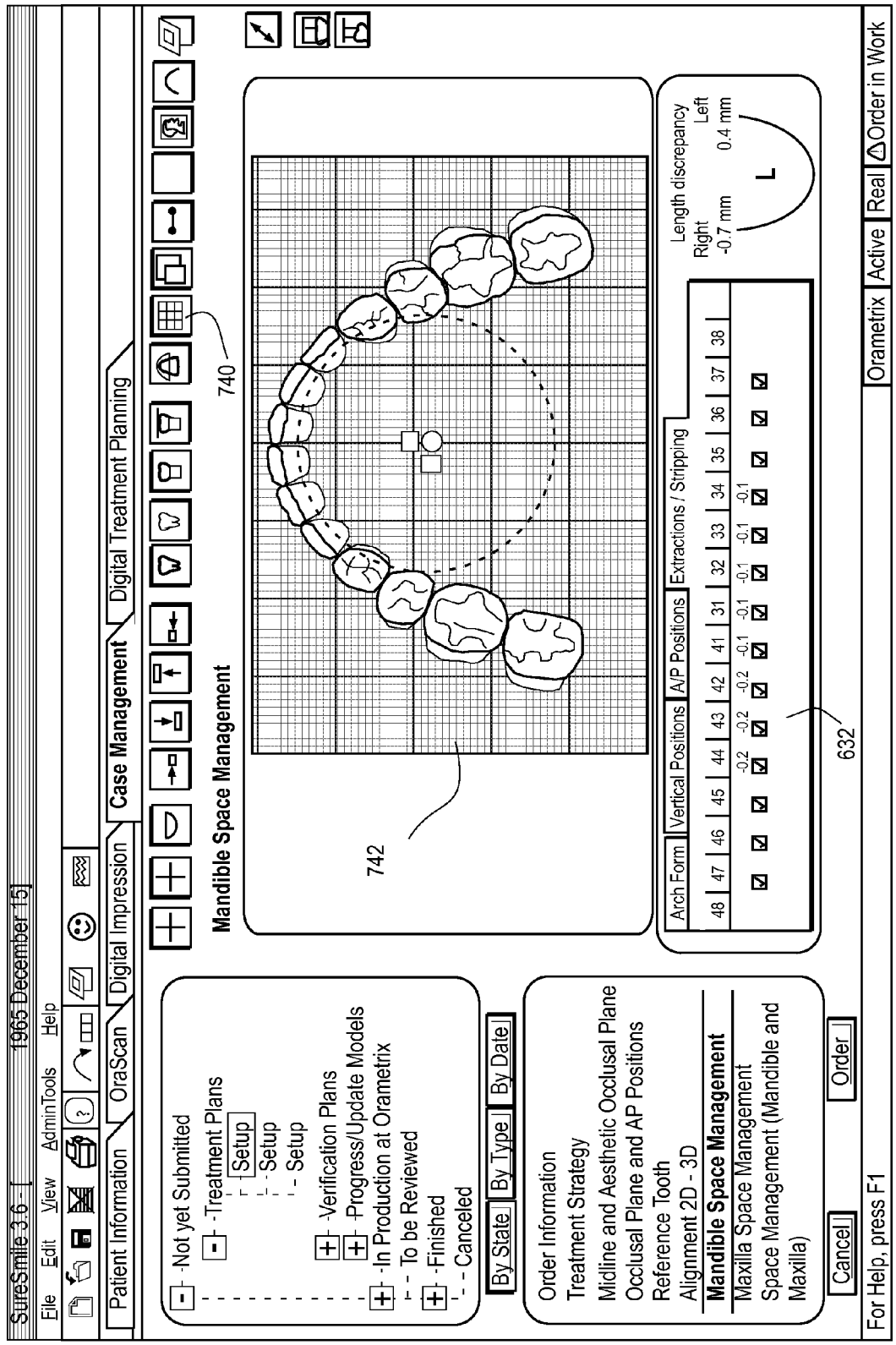
Figure 44A:
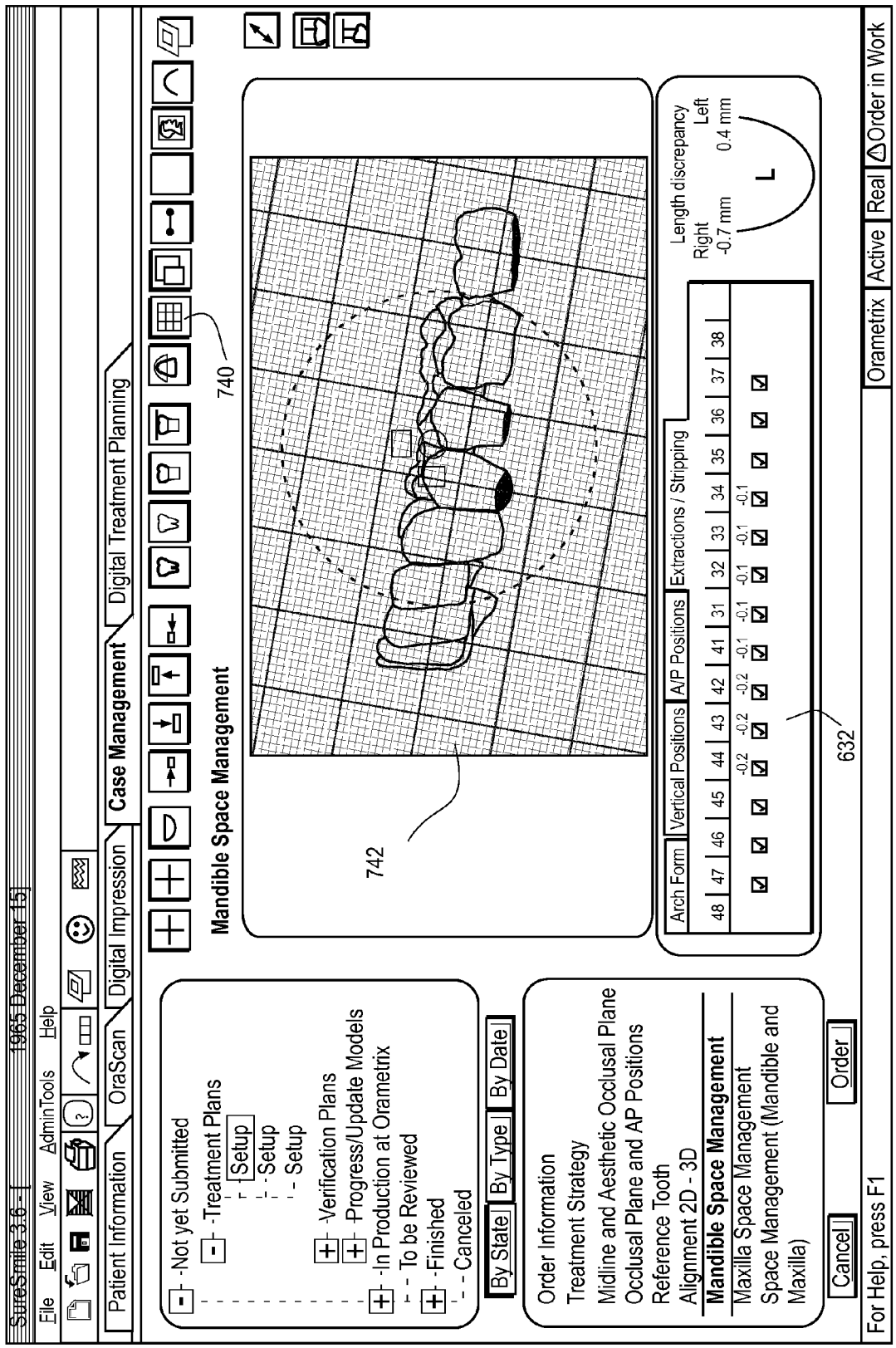

FIGS. 44 and 44A show the user activating a grid icon 740, which causes the display to show a grid 742. The grid, which is in units of millimeters, gives the user an additional tool to gauge distances between teeth (e.g., inter-molar width, inter-canine width, etc.). In FIG. 44, the numbers in the field 632 above the check boxes are essentially evenly distributed among the teeth in the left hand side of the arch, and in the right hand side of the arch, indicating that the interproximal reduction is symmetrically and evenly distributed between the teeth. The teeth can be morphed accordingly to simulate the change in shape either through reduction in size or buildup in size as necessitated by the treatment. By un-checking any of the boxes in field 632, the user can simulate a tooth extraction and move teeth to manage the gap in space on a tooth by tooth basis, or have the space distributed evenly between the teeth, etc. Once the user is satisfied, they can go to the screen of FIG. 28 and see where the teeth are relevant to the bone.

Figure 45:
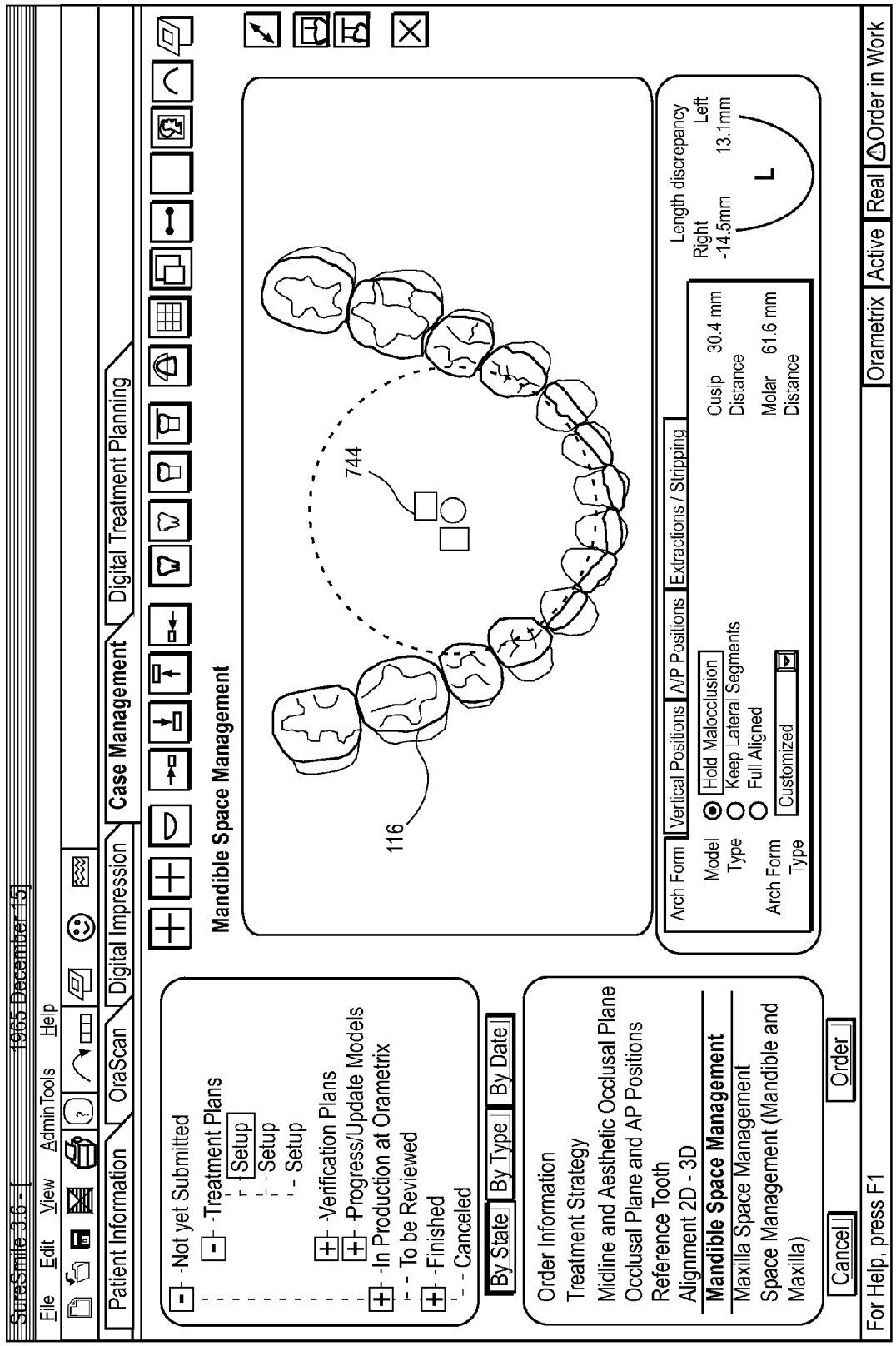

FIG. 45 shows the virtual model of the teeth of the lower jaw. Because the teeth are shown in a plan view it may be difficult for the user to see the texture and surface characteristics of the teeth. Thus, the user interface preferably includes an icon 744, which when activated allows the user to change the simulated illumination of the teeth, i.e., become brighter, or come from a different place, in order to more clearly show the surface characteristics of the teeth.

Figure 46:
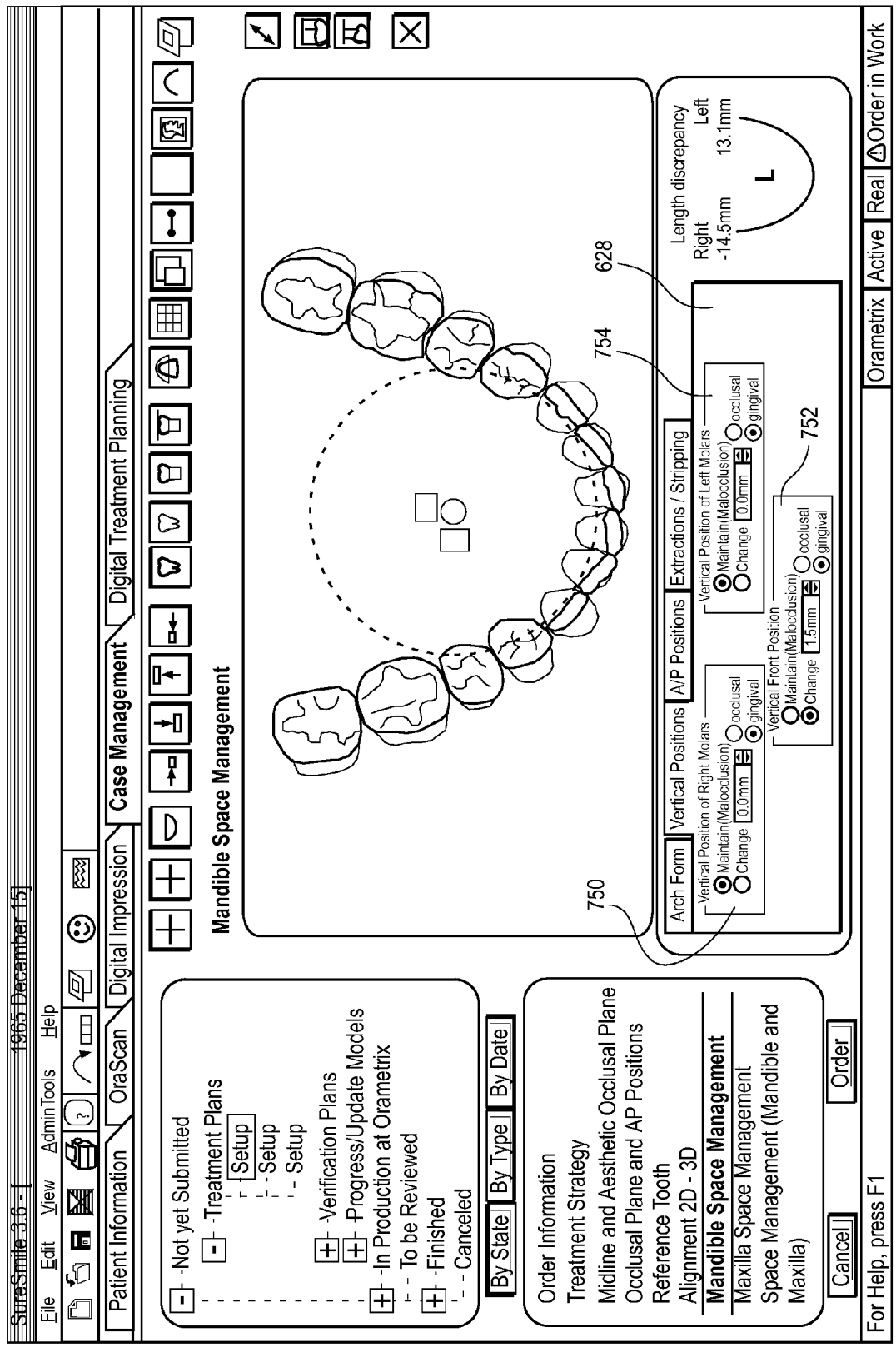

FIG. 46 shows the user activating the vertical position tab 628. This tab includes a field 750 in which the user can either maintain the malocclusion vertical position of the right molars, or change the position by any user specified amount either towards or away from the occlusal plane. Similarly, the tab includes a field 752 where the user can either maintain or change the vertical position of the front teeth. A field 754 allows the user to maintain or change the vertical position of the left molars.

Figure 47A:
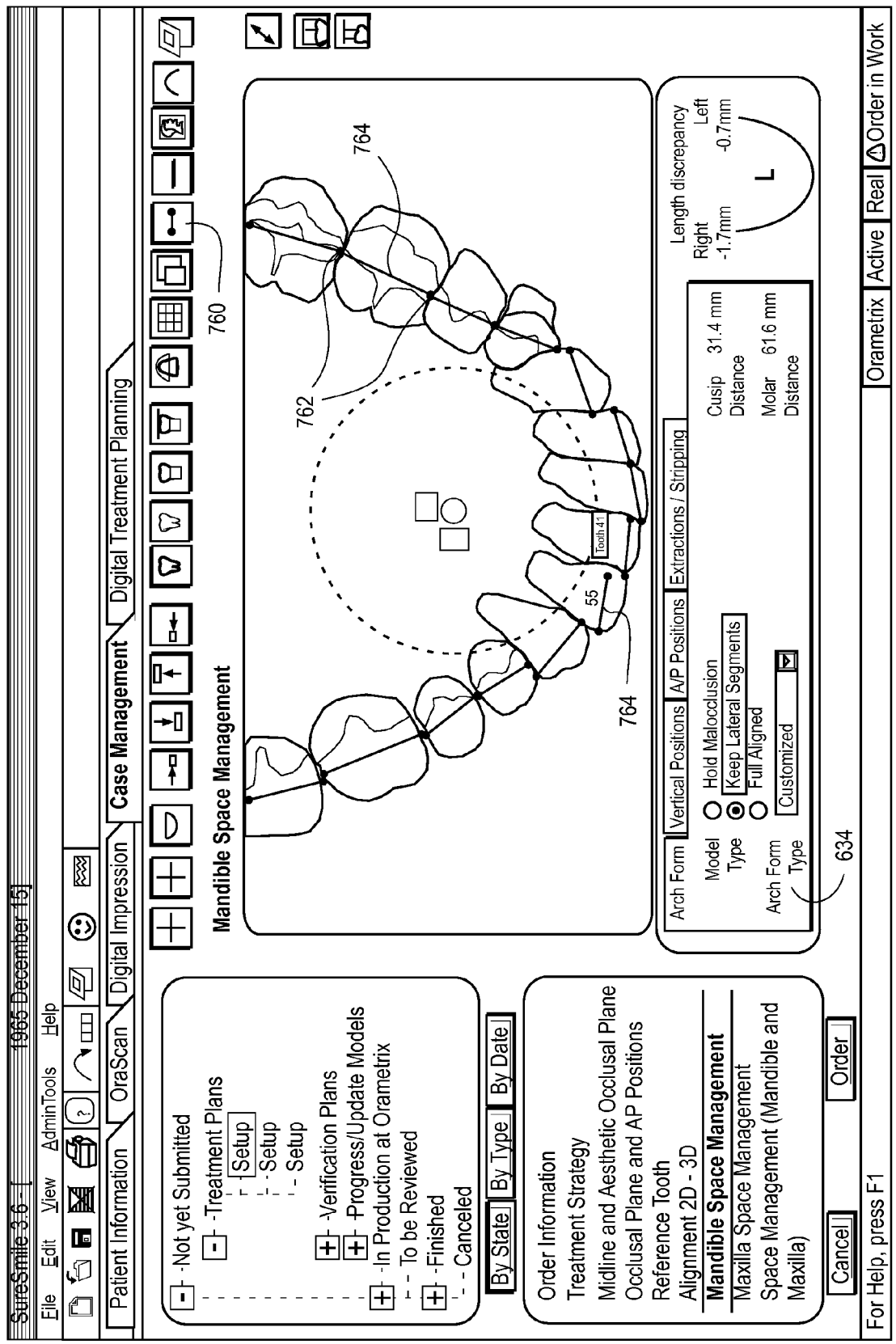

FIG. 47A shows a contact points feature that provides the user of a graphical display of the contact points between teeth. The user has activated the arch form tab 634, but the contact point function can be invoked at any time while the user is in the "Mandible Space Management" routine. The user has activated icon 760, which signifies that the user wishes to inspect and measure and the contact points between the teeth. When icon 760 is clicked, points 762 appear on the teeth which indicate the points of contact between the teeth. The points 762 are joined by straight lines 764, which indicate the shortest distance between the points. By placing the cursor on a particular tooth, the display shows the tooth number and distance along the line in millimeters. This gives us the true measure of the widest points in the teeth. These contact points are automatically identified and the measurements are also automatic. The user can also change the location of the points to make additional measurements of the teeth. For example, for tooth 41, the distance is 5.5 mm.

Figure 47B:
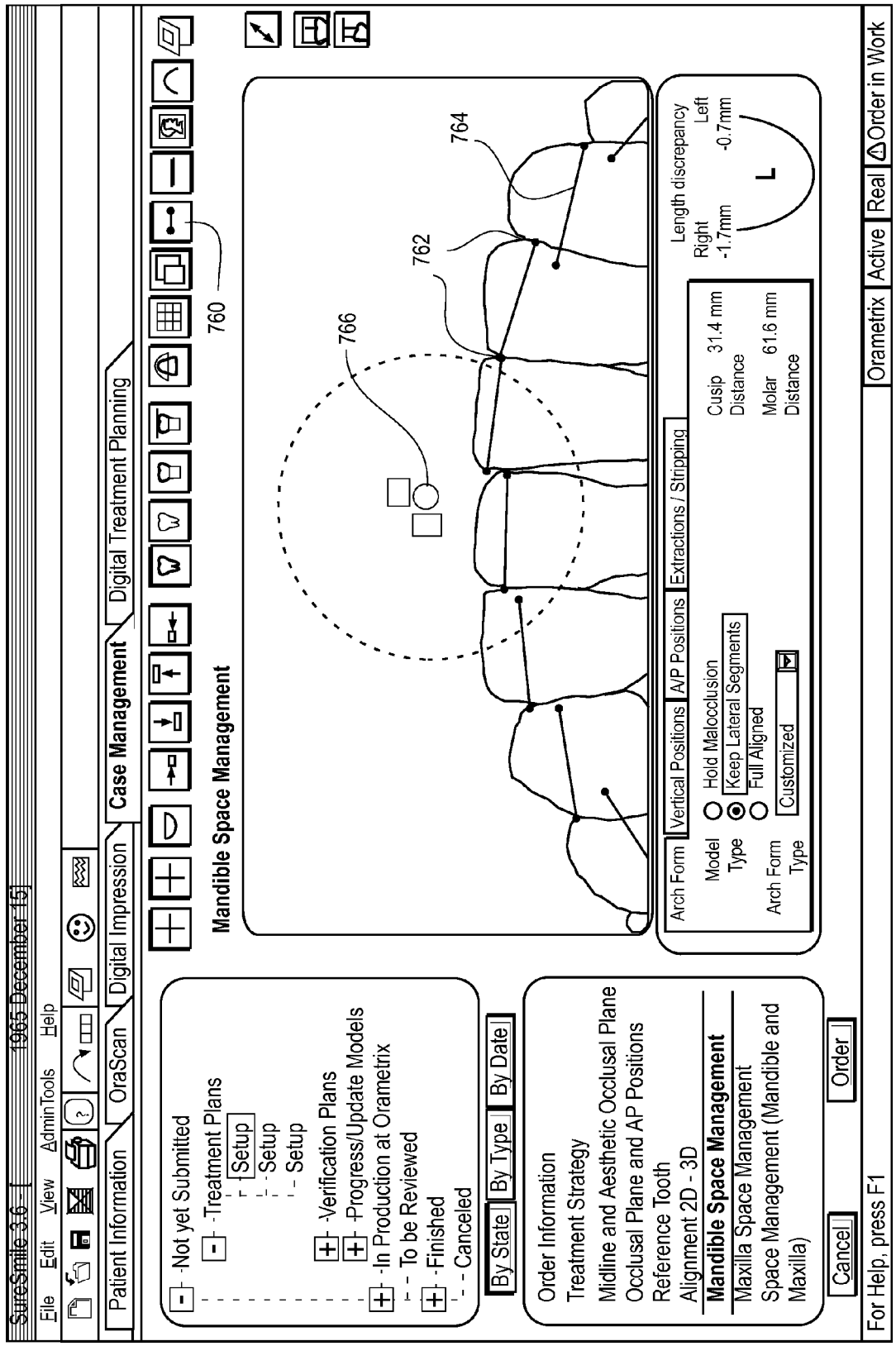

FIG. 47B shows the teeth of FIG. 47A rotated and displayed in a new orientation. By using the camera navigation icons 766, the user can zoom in or rotate the teeth to have a new viewpoint as desired. This enables the user to see more readily, in three dimensions, how the teeth are oriented.

Figure 47C:
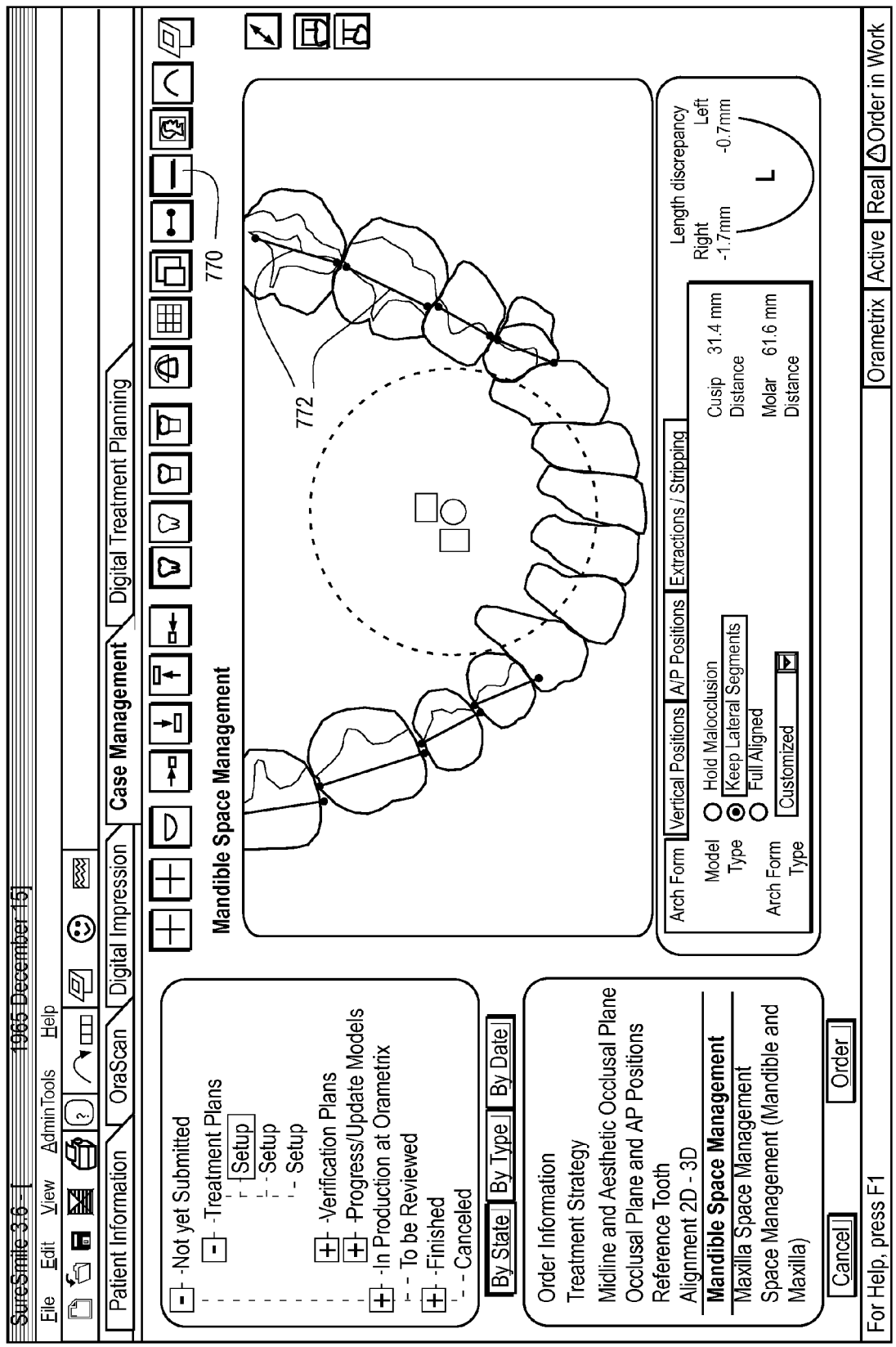
Figure 47D:
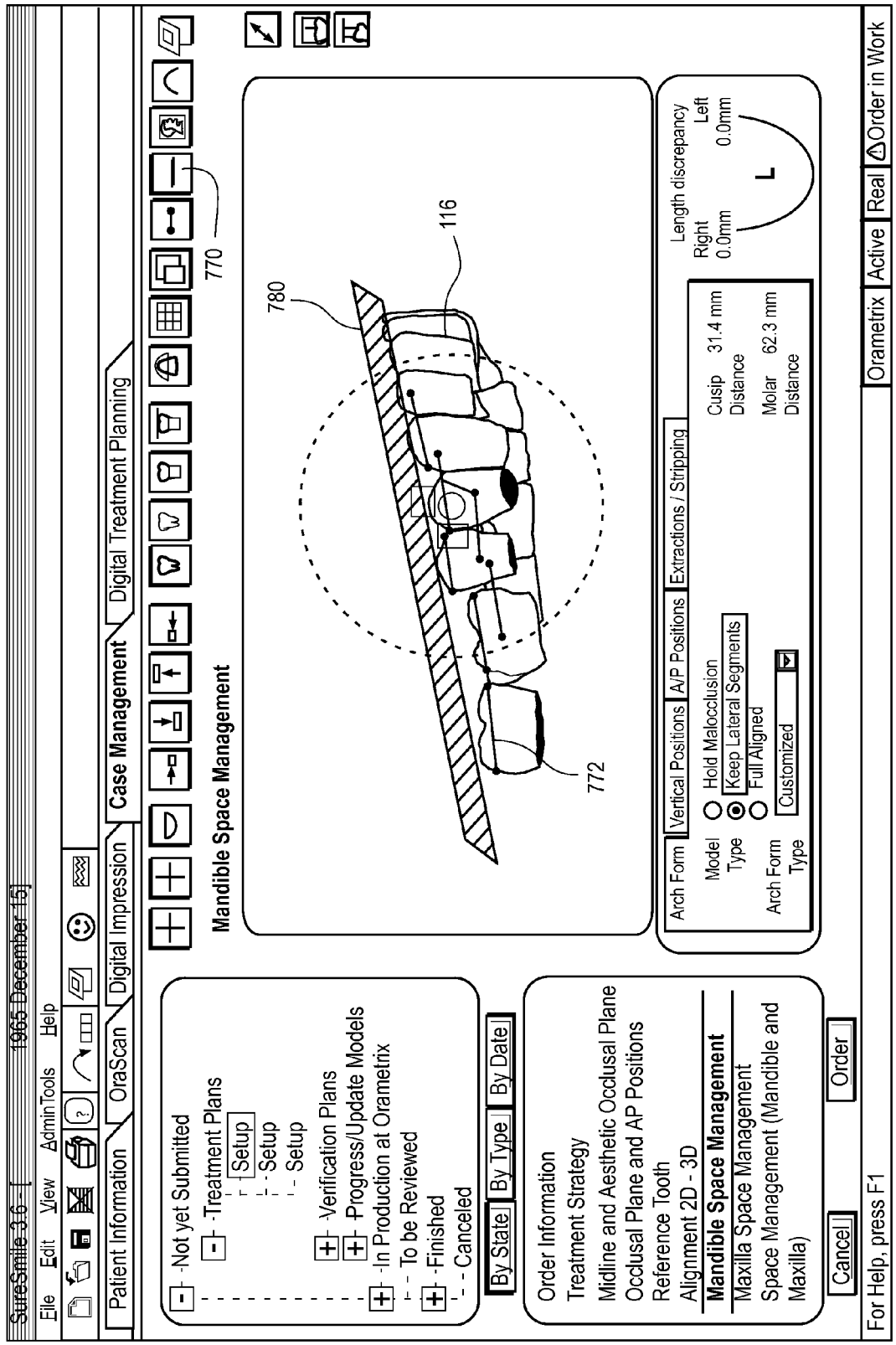
Figure 47E:
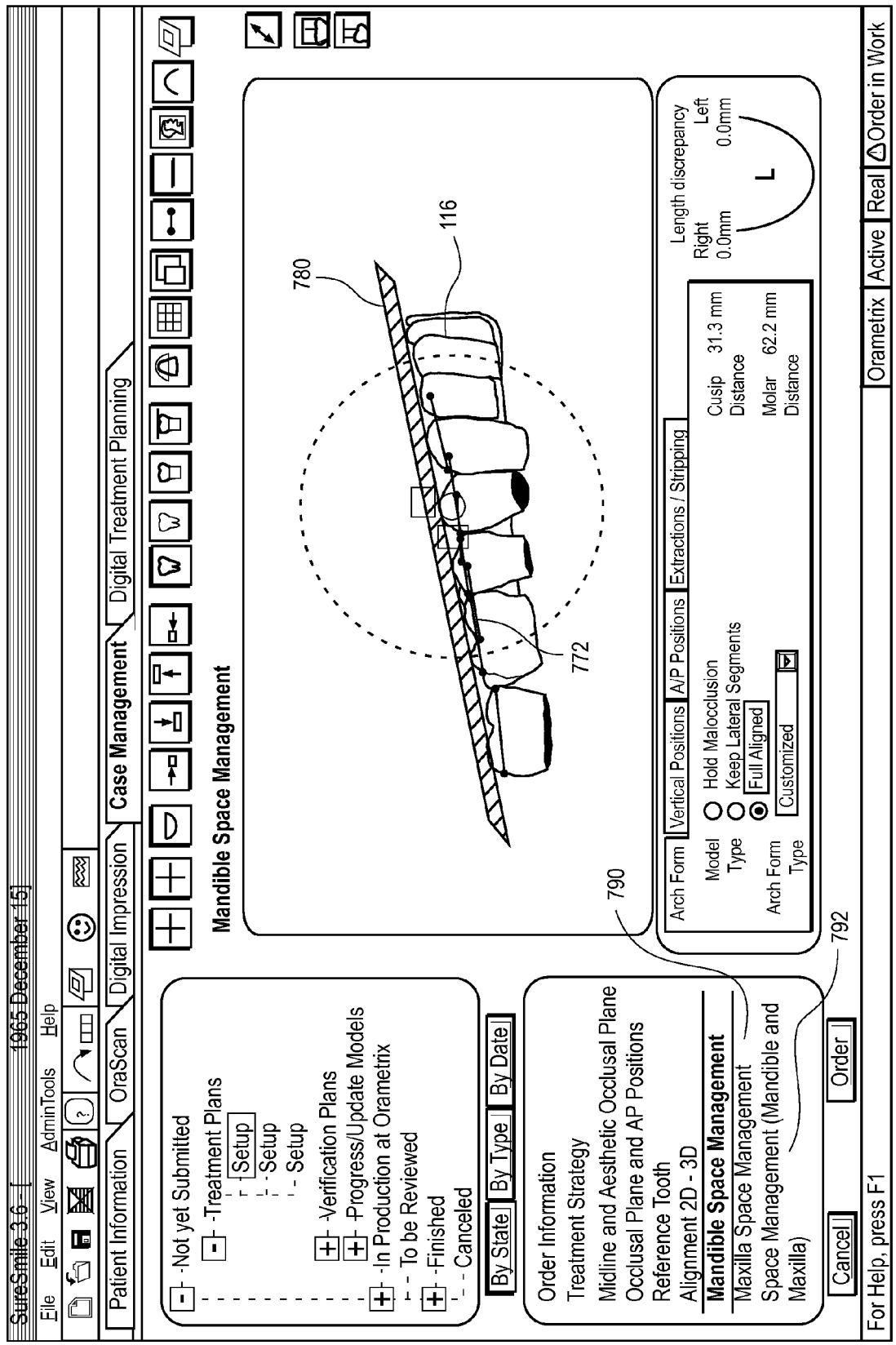

FIG. 47C shows the user activating an icon 770 which uses a feature extraction algorithm to highlight for the user the marginal ridges and indicate the distance along the marginal ridges. The marginal ridges and associated lines connecting them across the teeth are shown in FIG. 47 C as lines 772. Other feature extraction tools are possible, including icons for showing cusp tips and cusp fossa.

Usage of the contact points feature of FIGS. 47A and 47 B is shown in FIGS. 47 C and 47C. In FIG. 47D, the user has displayed the malocclusion teeth model 116 along with the lines 772 indicating the marginal ridges, together with the occlusal plane 780. Note that the lines 772 have a pronounced step relationship. In FIG. 47E, the user has interactively moved the teeth in the model 116 so that the teeth just touch the occlusal plane 780. Note that the step relationship in the lines 772 has essentially disappeared. The user can either move a tooth individually or select a group of teeth and move them as a group. Once the molars have been moved as shown in FIG. 47D the user will typically proceed to setting up the incisor position. To do this, the user may wish to invoke the clipping plane feature discussed elsewhere in this document to cut through the teeth and define the upper and lower incisor relationship in two dimensions, and then in three dimensions.

After the user has completed space management for the mandible using the tools in the previous figures, the user proceeds to maxilla space management using the tab 790. Similar screen displays as shown in the previous "Mandible Space Management" figures are provided to the user and thy perform space management tasks for the upper arch.

Figure 48:
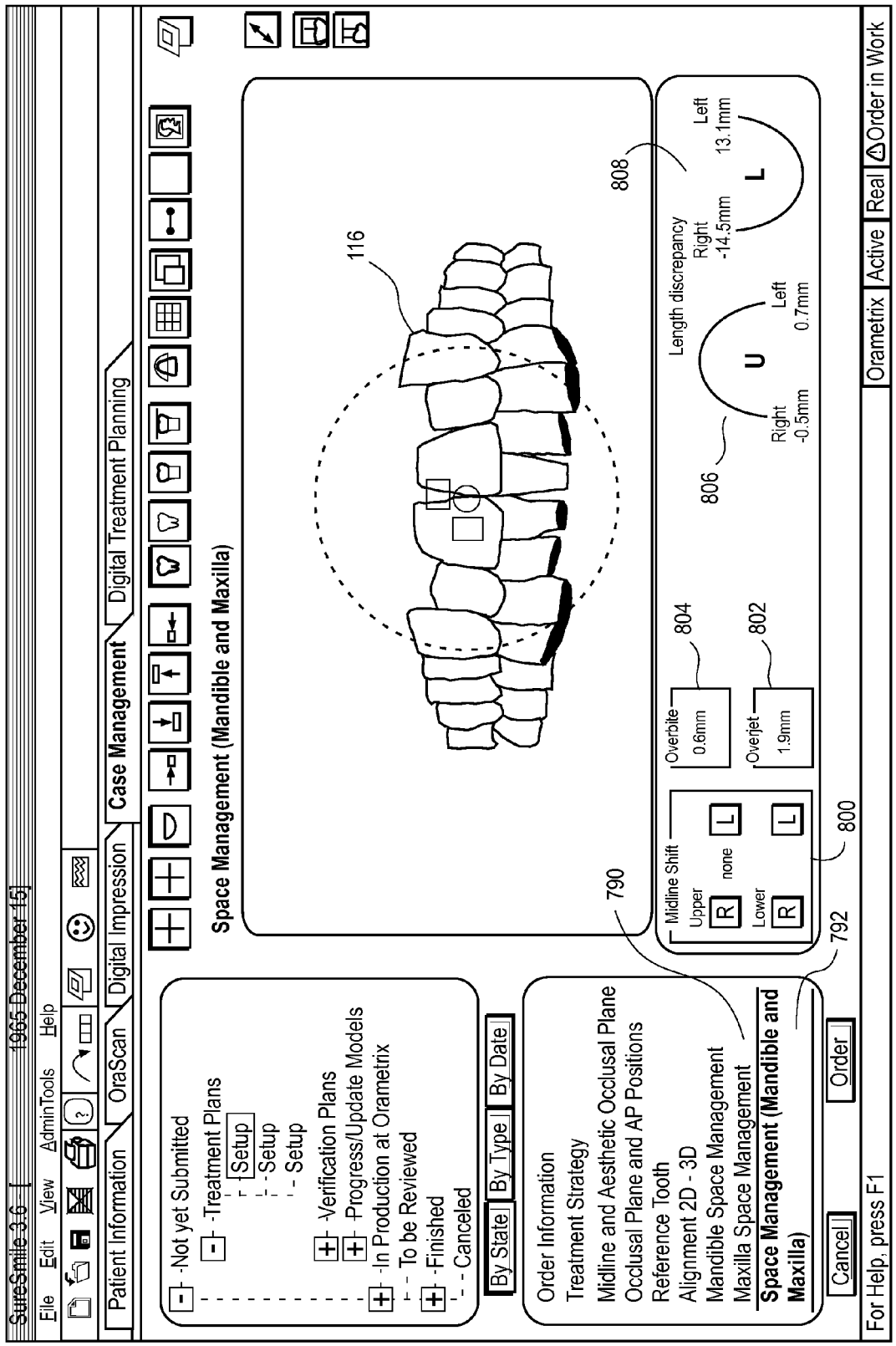
Figure 48A:
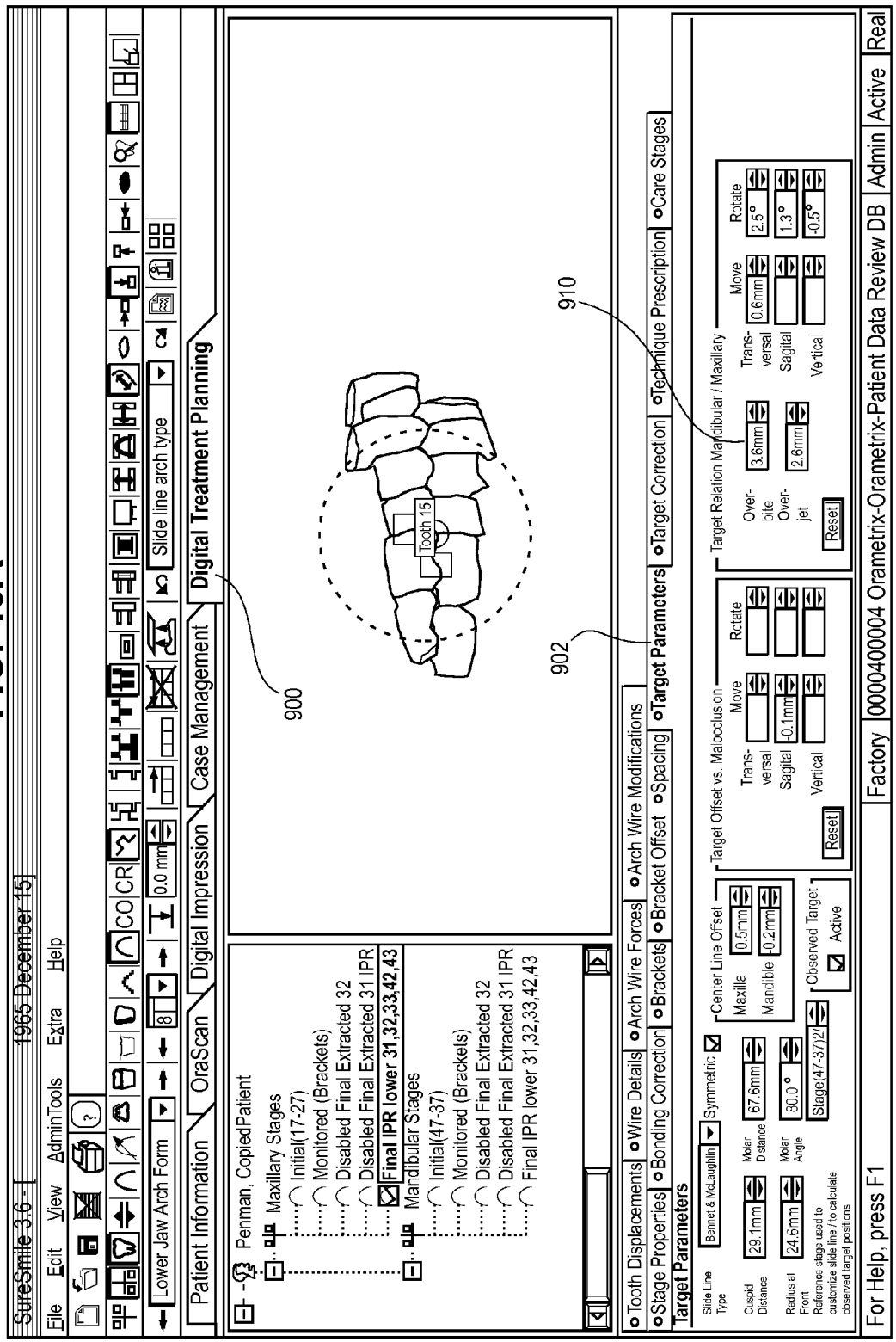
Figure 48B:
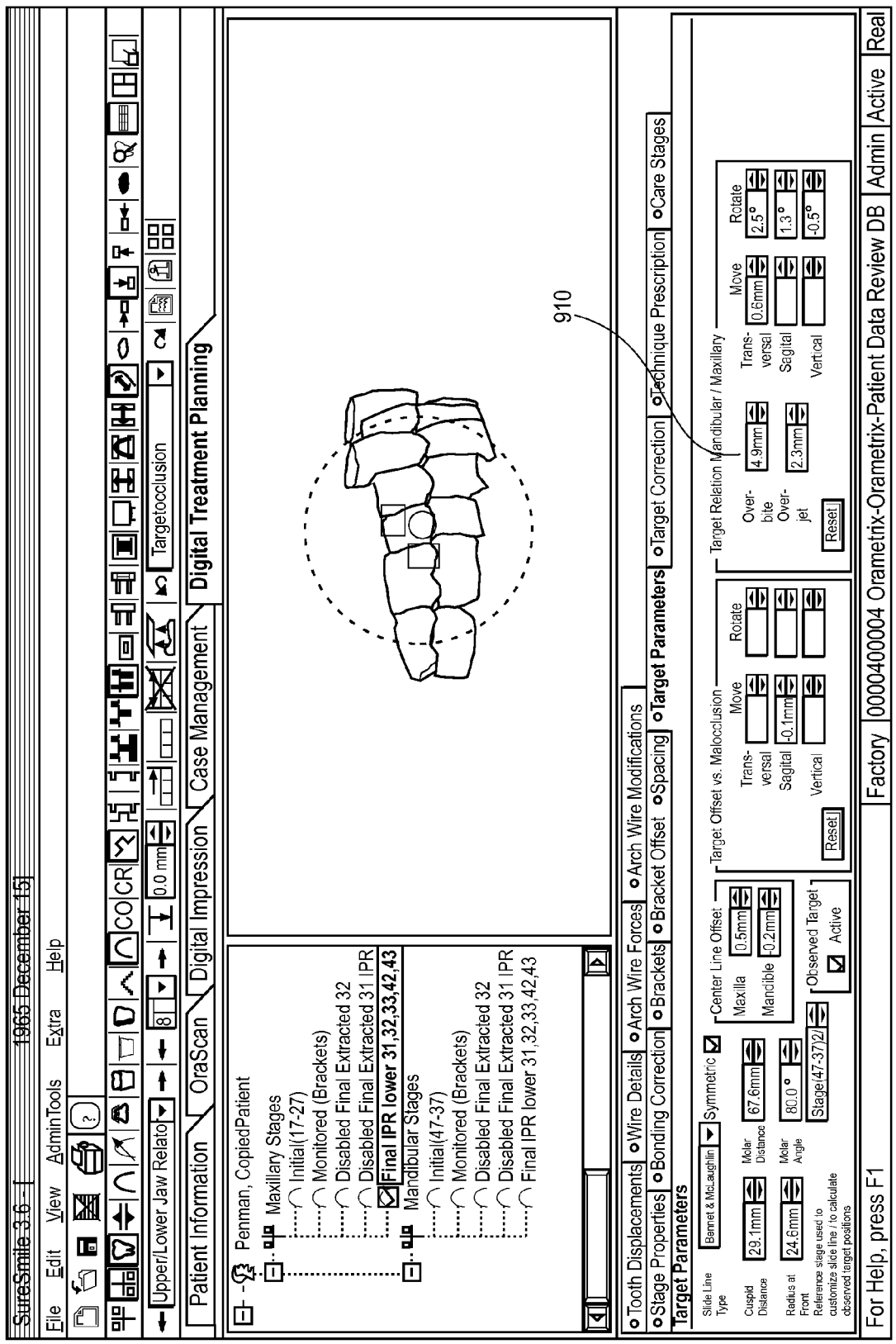

After completion of maxilla space management, the user proceeds to click on a "Space Management (Mandible and Maxilla)" icon 792, and the screen display of FIG. 48 appears. In this display, the user is provided with the same set of icons across the top of the display, allowing the user to hide or show the upper or lower arches, gingival structure, occlusal planes, contact points, X-ray or other image data, etc. Here, the user has selected for display both arches in the occludes condition and the tooth model 116 is displayed. This display includes a field 800 whereby the user can shift the midline of both the upper and lower arches right or left by pressing the R and L buttons with the mouse. The midline then shifts, with the amount of the shift indicated in numerical value. The display includes an overbite icon 804, which indicates the amount of over bite in mm. The user can user the icon to change interactively the amount of the overbite. Similarly, using icon 802 the user can change the amount of the overjet. The tools 806 and 808 provide the length discrepancy for both arches. FIGS. 48A and 48B shows similar functionality being available during activation of the "Digital Treatment Planning Icon 900 and its associated displays; in these figures the Target Parameter tab 902 is selected and the user is changing values for overbite and overjet via the numerical value entry fields 910 and the results are immediately visible on the display.

Figure 49:
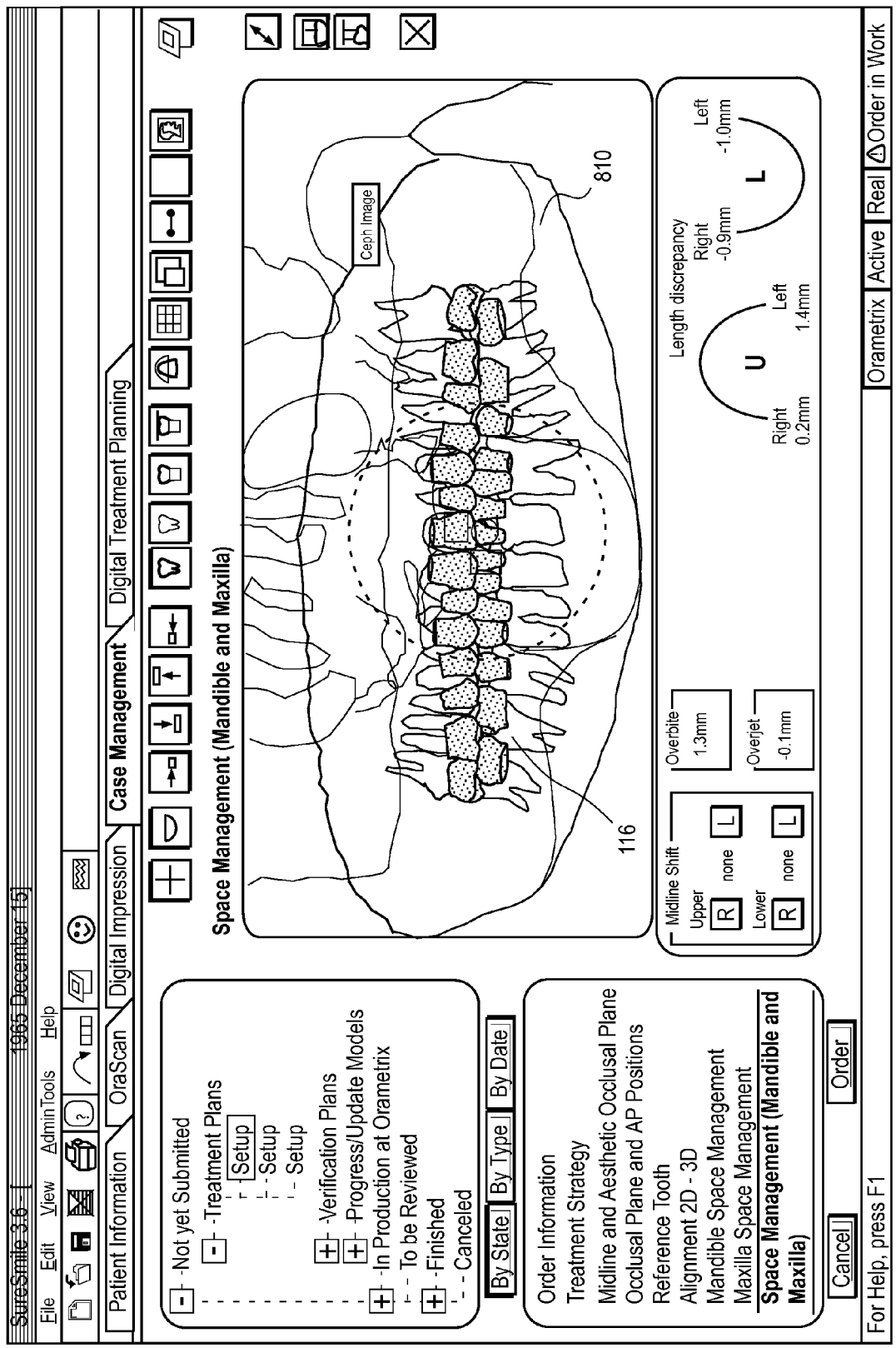
Figure 49A:
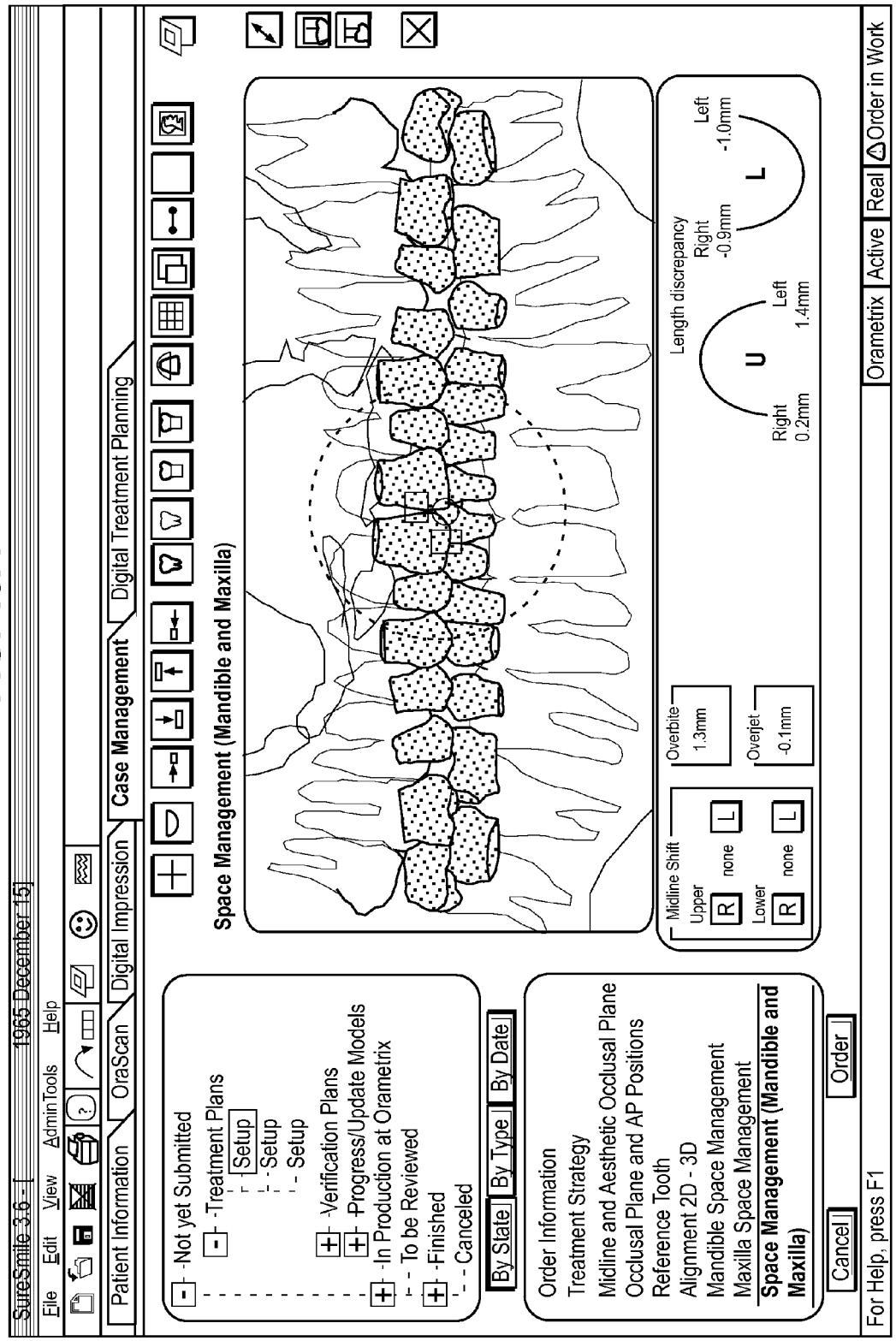
Figure 49B:
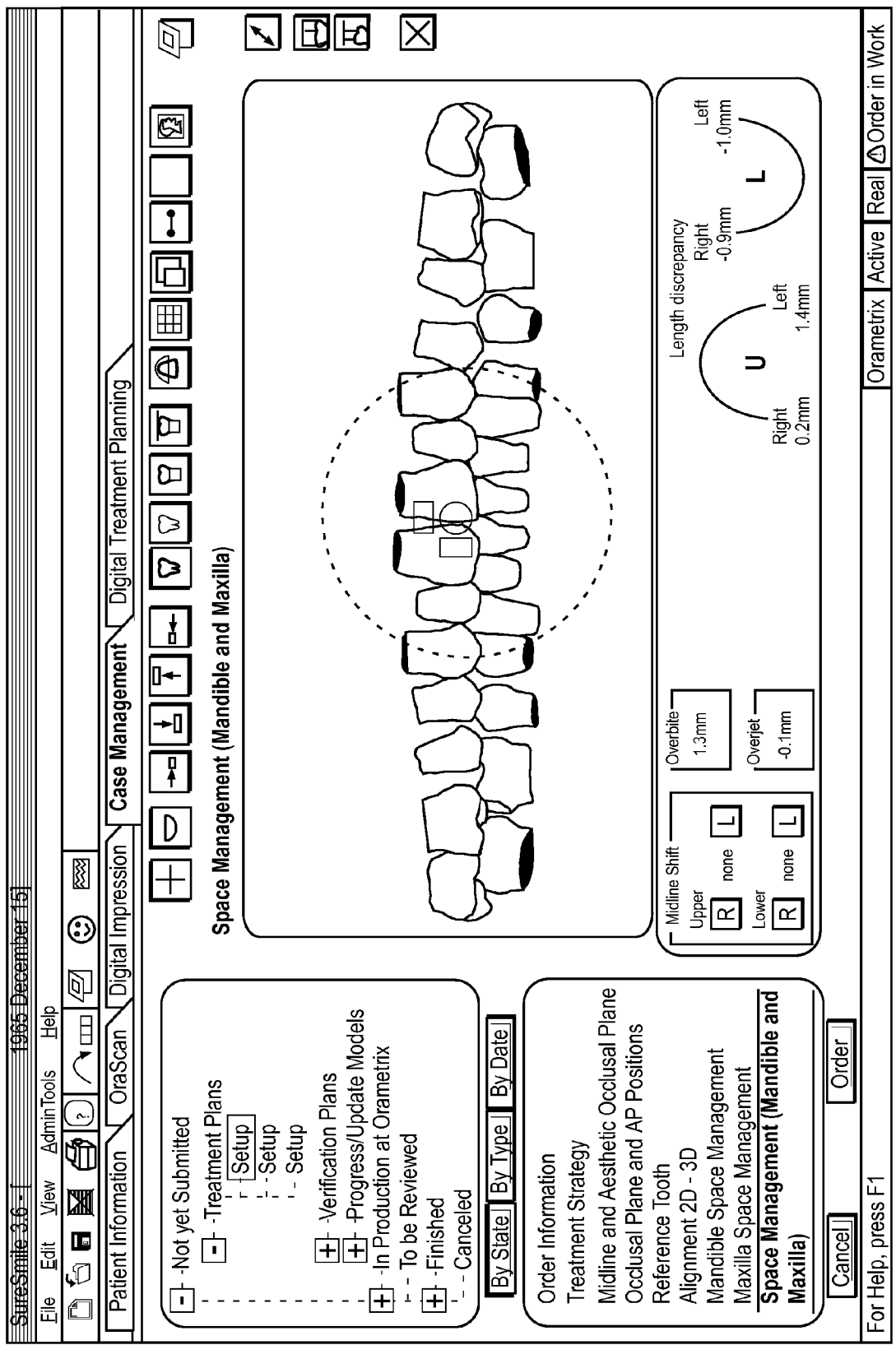

In FIGS. 49 and 49A, the user has activated the icons across the top of the display to simultaneously display both a 2D panoramic X-ray 810 of the teeth and jaw as well as the 3D model of the teeth, but with the teeth 116 spread out and represented in two dimensions in registry with the 2D panorama X-ray. The teeth models that are shown in FIG. 49 represent the tooth positions in a proposed treatment. In FIG. 49B, the user has unchecked the X-ray icon and only the teeth are displayed. In FIGS. 49, 49A and 49B, the user activates the icons to superimpose the 3D model in registry with the 2D x-ray. The user thus is able to figure out the axis inclinations of the teeth and can revisit the selection of a reference tooth (see FIG. 27) if appropriate. Any changes in tooth position and its effect on root position can be evaluated in the 2D/3D model of the panorex radiograph, CT scan, etc. plus super-imposed crowns, as in FIGS. 49A and 49B. From these views, the user can quickly arrive at a proposed setup by aligning (interactively moving) the 3D teeth up and down to find the ideal position, selecting or designing an arch form and midline, and then wrapping the teeth around the desired arch form in three dimensions. When viewing the resulting proposed set up, e.g., in FIGS. 48 and 48A, the user is again given arch length inadequacy from a three dimensionsal model and proceed to modify the set up to eliminate the arch length inadequacy using the techniques described previously. As proposed modifications are made, the user is instantly provided with new values for arch length inadequacy, and can immediately determine whether the proposed modifications are sufficient to remove remaining arch length inadequacy.

Figure 50:
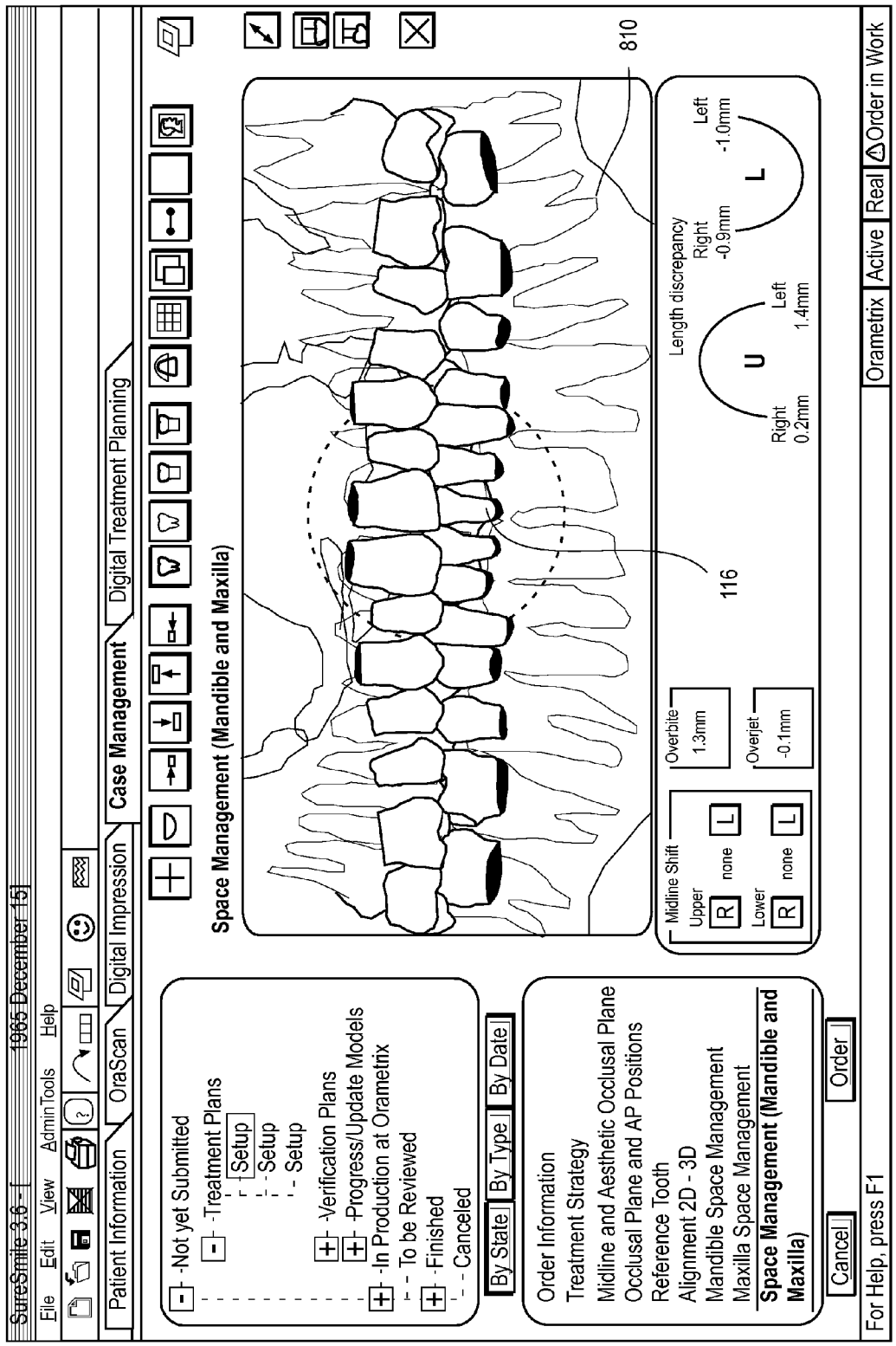

In FIG. 50 the teeth 116 that are shown are the malocclusion or original arrangement of the teeth. Thus, FIGS. 49 and 50 show that the user can toggle back and forth between initial tooth configuration and proposed treatments for the patient. Any changes in any one environment changes the values in the other environments.

Figure 51:
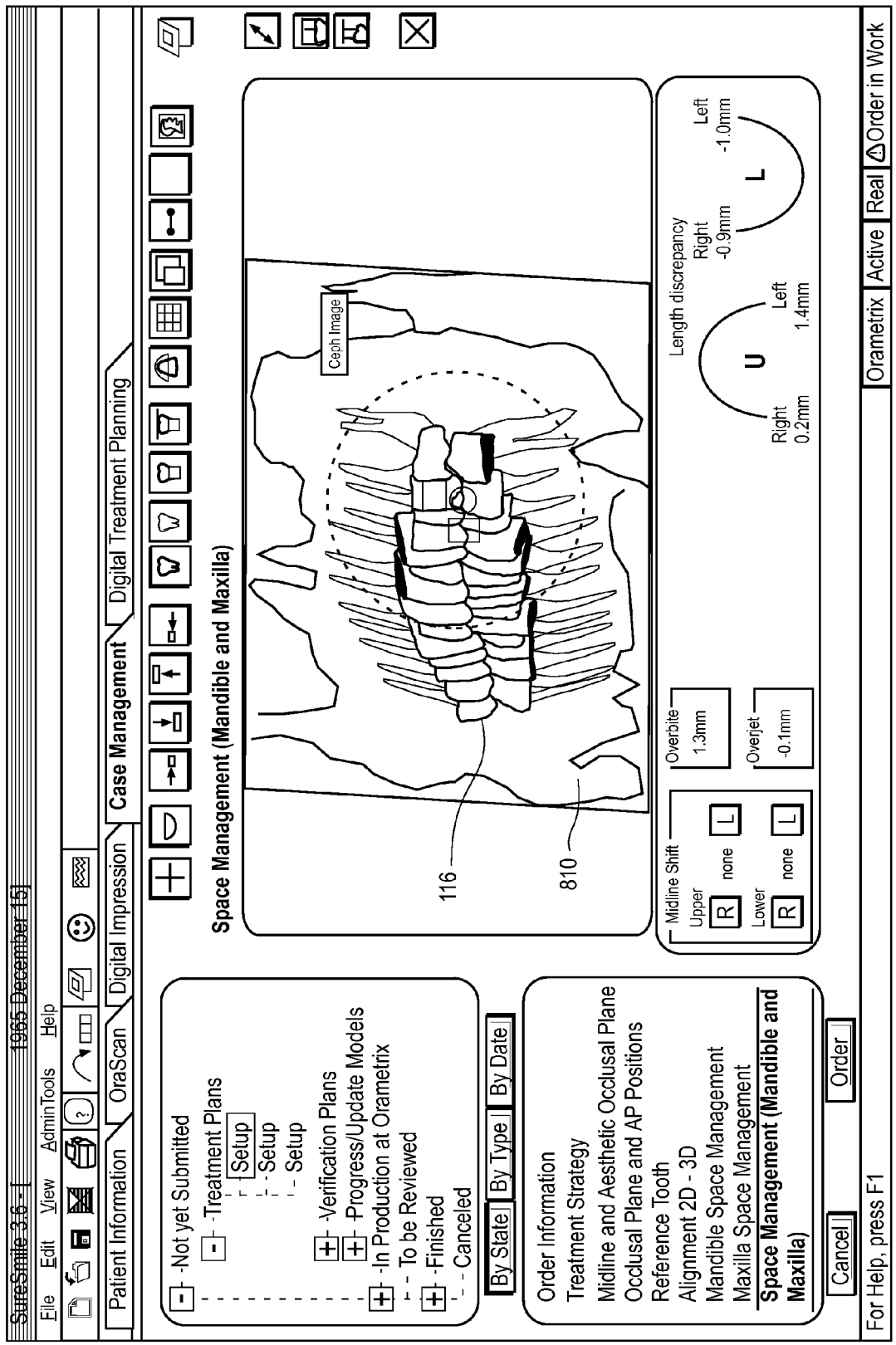
Figure 51A:
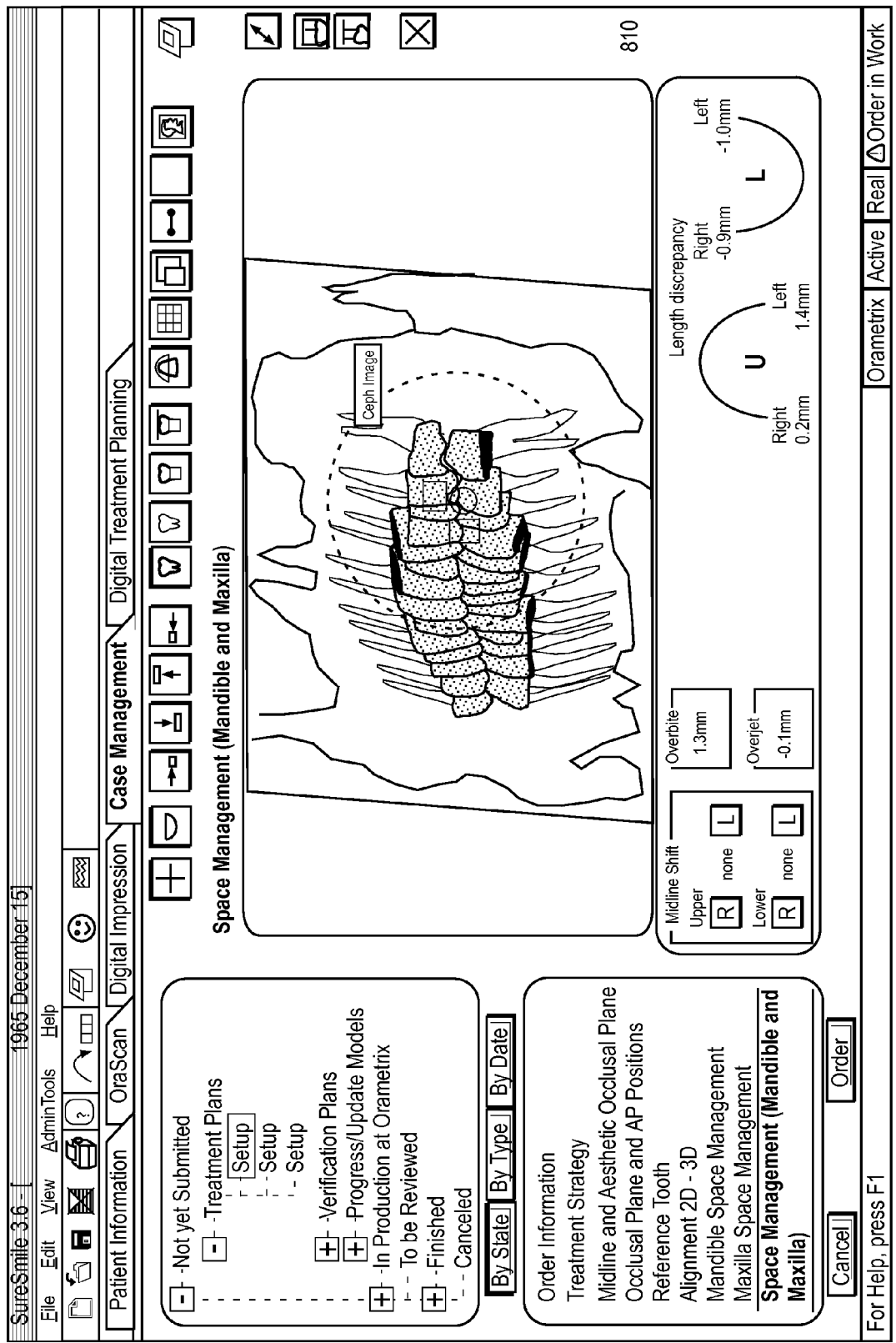

In FIG. 51 and FIG. 51A, the user has used the navigation icons to rotate the view shown in FIG. 50. The user is provided with excellent visual aids to view how the teeth line up with the tooth roots.

Figure 52:
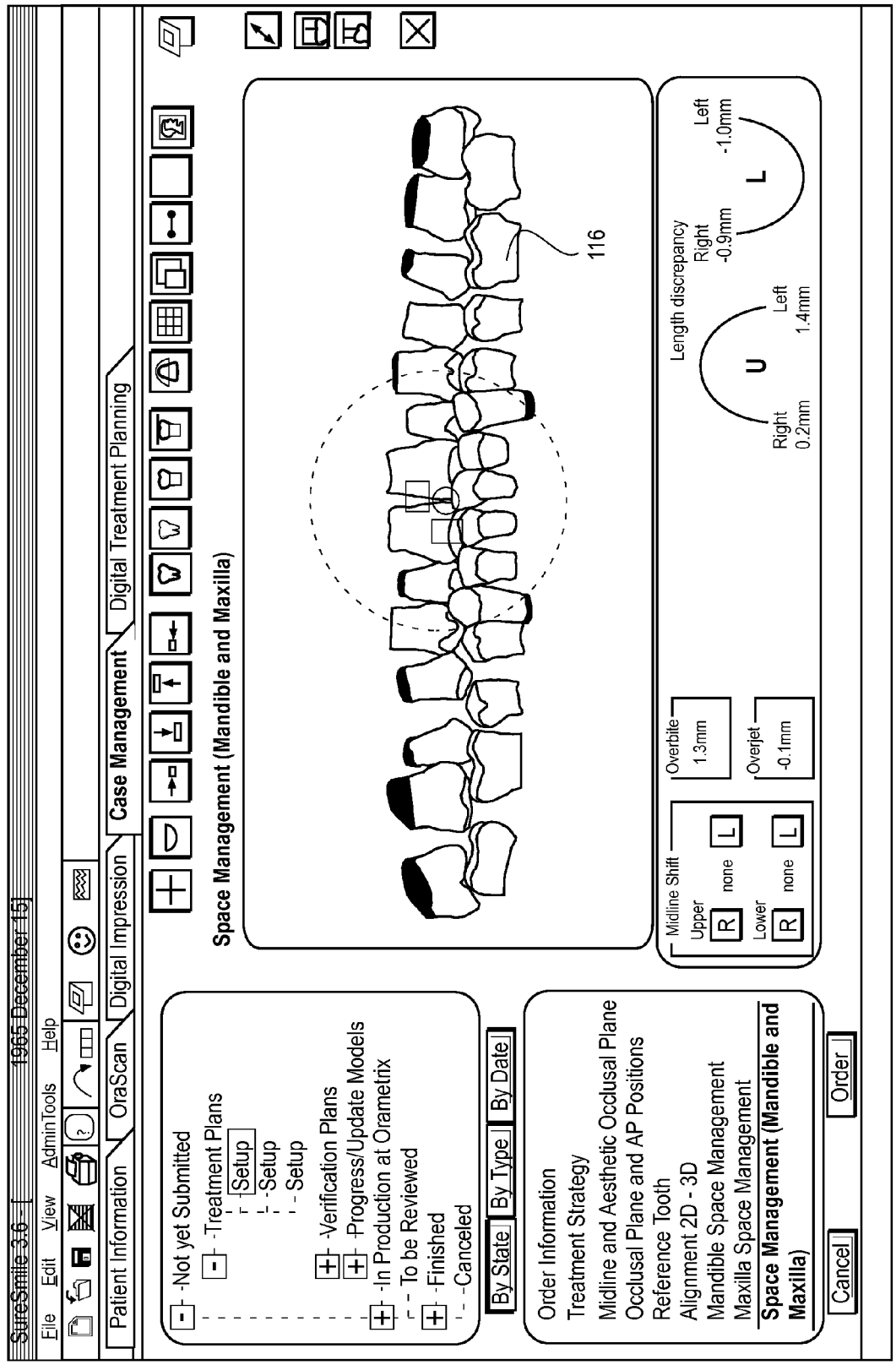
Figure 53:
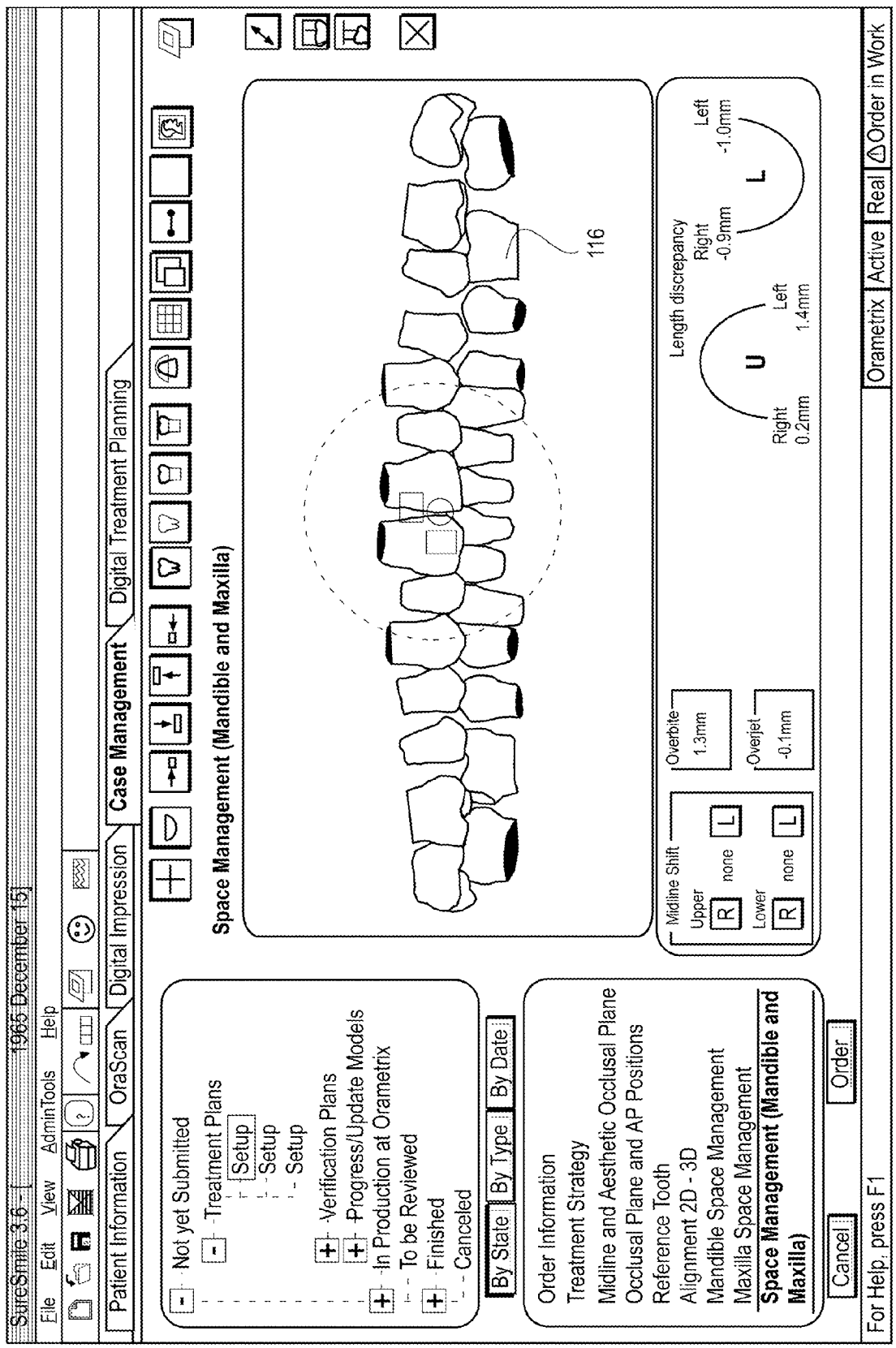

FIG. 52 illustrates that the user can unclick the icon causing the X-ray to appear on the screen and simply perform space management for both the upper and lower arches using the virtual teeth models. As shown in FIG. 52, the teeth 116 are arranged in a line and seen from an anterior view. FIG. 53 shows the view of the teeth 113 from the opposite direction. After the user has completed the task of managing space between the virtual teeth in the proposed arrangement; the user is able to cycle back and repeat any of the previous steps by activating the icons on the lower left portion of the display and entering into the appropriate displays and making further adjustments in the proposed arrangement.

The user can then access the rest of the treatment planning software, such as the software indicated by tab 458 (FIG. 21) and proceed with additional treatment planning procedures. Finally, when they are finished, the user selects a finalized proposed treatment plan for treating the patient. This updates the patient's prescription and is stored in the workstation. The display of FIG. 48 shows how the patient's teeth will look at the end of treatment. Adjustments in inter-arch relationships, as shown in FIGS. 28 and 29, either as a result change in overjet or overbite, or change in relationship of the jaws, are either tooth driven or jaw driven. These actions change arch length inadequacy values. These can all be simulated on the user interface.

Figure 54:
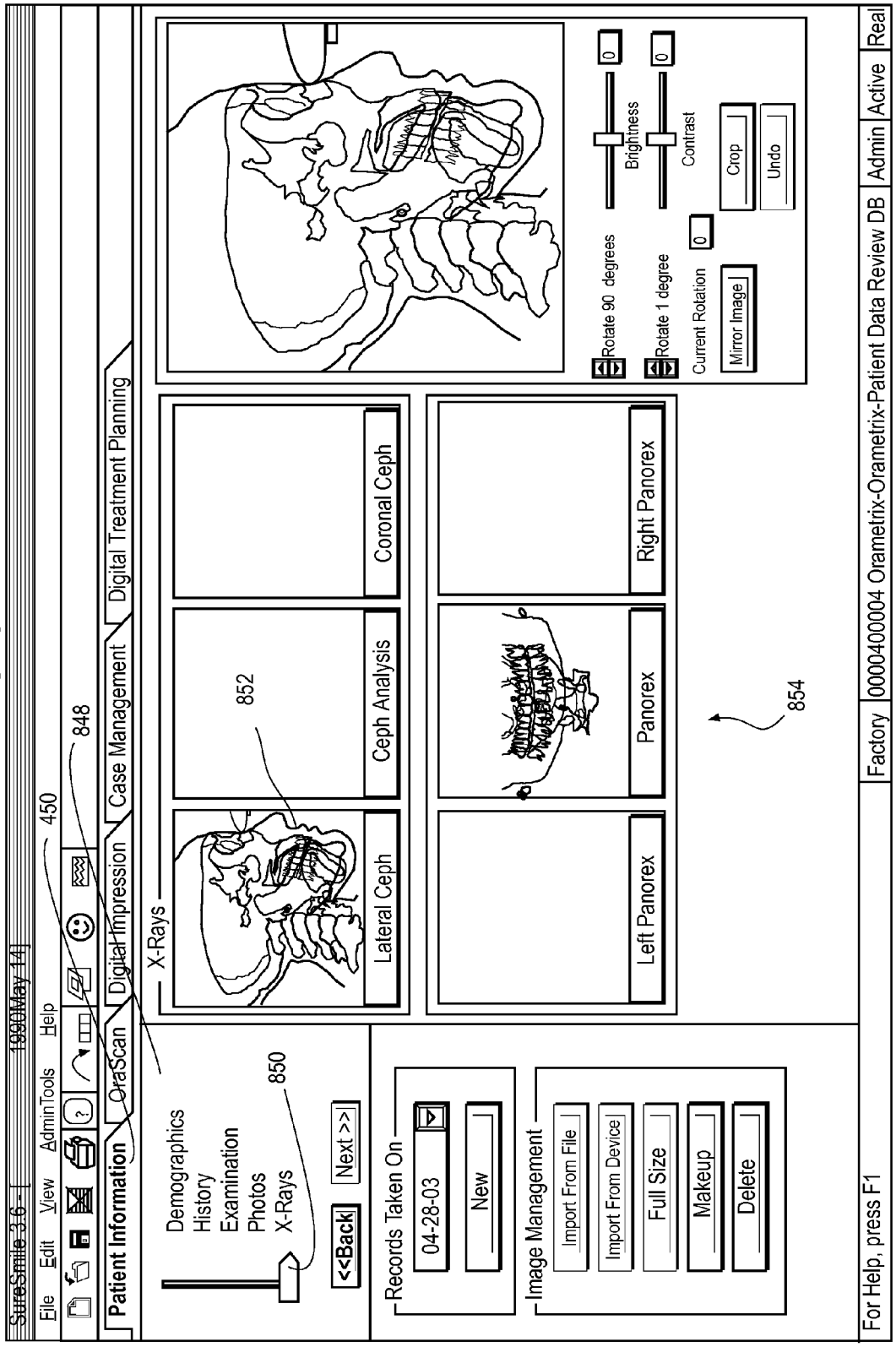

FIG. 54 shows the user entering the patient information tab 450, where the patient has access to dental clinical examinations and dental radiographic examination. The upper left hand portion 848 includes a slide bar 850 that allows the user to access various fields, including demographics, patient history, examination (notes), photographs, and X-rays. Additional fields are made available by activating the "Next" icon. The user has moved the slide bar to X-rays. In the display 854, the user is provided with the X-rays that are currently stored for the patient, which include a later X-ray of the face ("Lateral Ceph). The portion 856 of the display shows the X-ray and icons for rotation of the X-ray, changing the brightness and contrast, and displaying a mirror image of the X-ray. The user can point and click in any region of interest to access dental history or access photo image databases, radiographic images, and so forth. The navigation icons allow the user to rotate, pan, zoom all the X-rays to see them appropriately to check for pathology, etc. Also, the user can mark up the X-rays for making measurements in two dimensions, measuring angles, and entering that information into the patient database.

Figure 55:
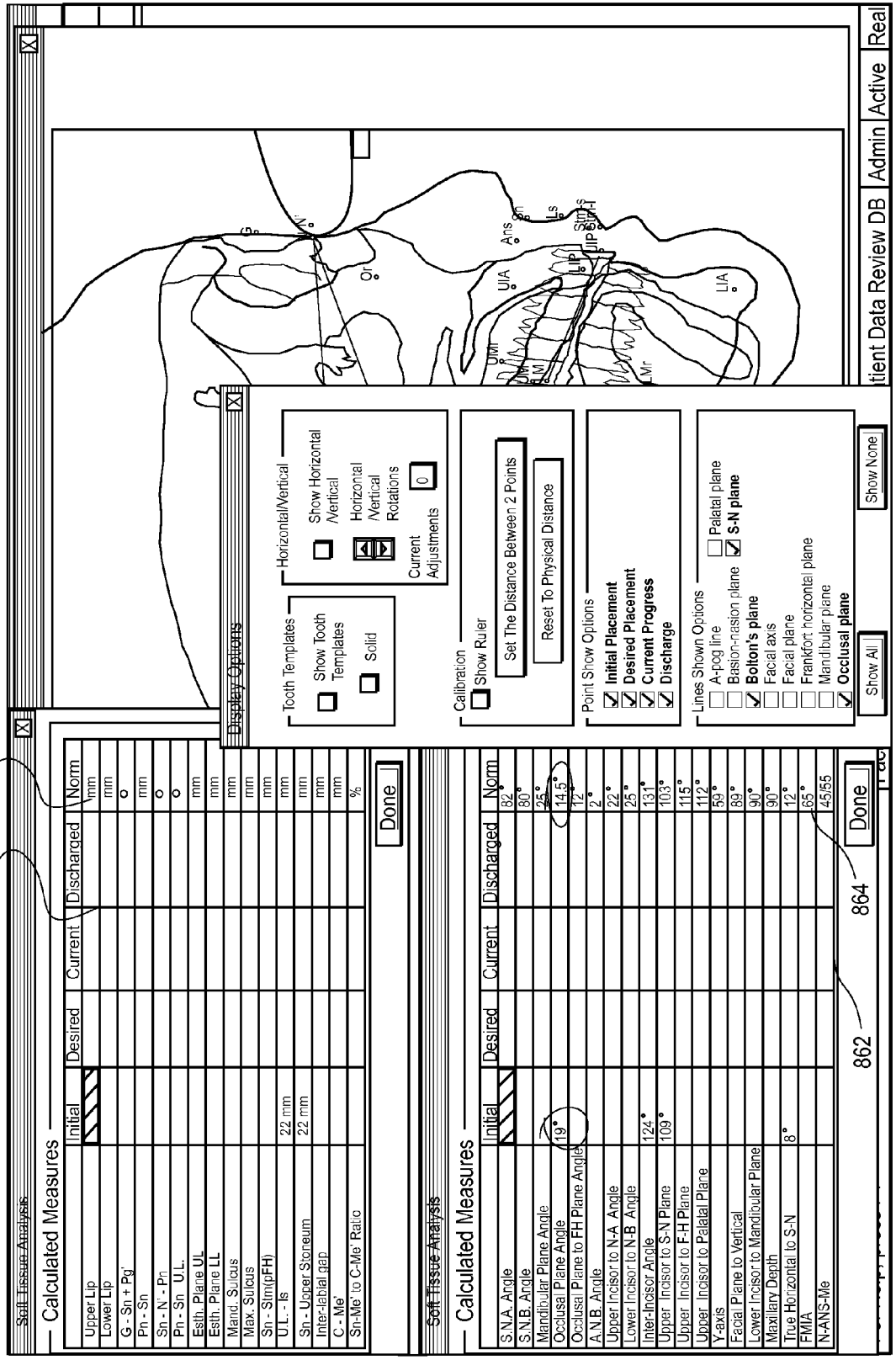

In FIG. 55, the user has navigated to a soft tissue analysis screen from the patient information window. Here, the user is allowed to enter into the workstation via field 860 specific, numerical values for initial measurements of soft tissue, desired values for these soft tissue parameters. In the field 862, the user is able to measure or calculate angles, e.g., between various teeth and various planes, angles of canting of planes that the user has specified, etc. Again, these angles are calculated by means of display on the workstation of patient's X-rays or other image data (including possibly scan data).

The workstation includes a database of "normal" or normative measurements for patients of different ages, races, and sexes, for both soft tissue measurements as well as all of the angles shown in FIG. 55. The comparison thus leads the practitioner to identify deviations from normative measurements. The display shows the normal values in the right hand column 864 of the displays 860 and 862. Thus, as the user is designing treatment and entering proposed or "desired" values for any of these biological parameter, the screen display simultaneously displays the "normal" values for a patient having the same (or approximately the same) characteristics as that of the patient.

Additional feature extraction algorithms that the workstation preferably provides besides the marginal ridge and contact points features described previously, include algorithms for identifying tooth cusps and fossa of the teeth. Such measurement tools are useful in automatically performing the Bolton tooth discrepancy level and Angel classification methods.

One of the unique features of the software is that the measurement features described herein allow the practitioner to determine the Bolton tooth size discrepancy.

Bolton Analysis

A method developed by W. Bolton (1958) for the evaluation of mesiodistal tooth size discrepancies between sets of corresponding maxillary and mandibular teeth. The analysis distinguishes between the "overall ratio," which involves all permanent teeth except the second and third molars, and the "anterior ratio," which encompasses only the six anterior teeth of each jaw. For this analysis it is assumed that the relatively smaller tooth material is the correct one. A table of standard values lists the tooth width value in the opposing arch that is ideally related to this given correct value. The difference between the ideal and actual dental width in the arch with the excess value gives an estimate in millimeters of the severity of tooth size discrepancy between the arches.

Tooth Size Discrepancy (Bolton Discrepancy)

Incongruity between the sums of the mesiodistal tooth sizes of sets of corresponding maxillary and mandibular teeth, is determined by the Bolton analysis. A discrepancy could involve the "overall ratio" (which encompasses all permanent teeth except the second and third molars) or the "anterior ratio" (which includes the six anterior teeth of each jaw) and is identified as a maxillary or mandibular excess or deficiency. Only deviations that are larger than two standard deviations are considered to be of potential clinical significance.

A tooth size discrepancy may cause difficulties in achieving an ideal overjet and to overbit or arriving at a good intercuspation during the final stages of orthodontic treatment. Different ways to address such a problem include extraction of teeth in the arch with the excess tooth material (usually one mandibular incisor), interproximal stripping, compromising the angulation of some teeth so they can occupy a larger or a smaller space in the arch, or increasing the mesiodistal tooth size in the arch with the deficiency in tooth material (build-ups).

The present software provides measuring tools for measuring these parameters and conducting this analysis h (using the contact points algorithm described and illustrated previously). Moreover, the workstation includes a database of normative or normal ratios for patients. The user compares the ratio for the patient, obtained directly using the measuring tools, and compares the result with the normative values from the database in the workstation. The difference is displayed for the user. The result is the Bolton tooth size discrepancy and is useful in treatment planning and allows the user to measure the total form or shape of the teeth.

Another feature provided herein is the so-called "Angle classification", which is a measure of how closely the upper and lower arches fit in an occluded condition. The classification system is as follows.

Class I Malocclusion (Neutroclusion)

A malocclusion in which the buccal groove of the mandibular first permanent molar occludes with the mesiobuccal cusp of the maxillary first permanent molar. The term "Class I" is sometimes used incorrectly as a synonym for normal occlusion, although in reality, it only signifies a normal relationship of maxillary and mandibular first molars in the sagittal plane.

Class II Malocclusion (Distoclusion, Postnormal Occlusion)

A malocclusion in which the buccal groove of the mandibular first permanent molar occludes posterior (distal) to the mesiobuccal cusp of the maxillary first permanent molar. The severity of the deviation from the Class I molar relationship usually is indicated in fractions (or multiples) of the mesiodistal width of a premolar crown ("cusp" or "unit")

Class II Malocclusion, Division 1

A Class II malocclusion with proclined maxillary incisors, resulting in an increased overjet Class III Malocclusion (Mesioclusion, Prenormal Occlusion)

A malocclusion in which the buccal groove of the mandibular first permanent molar occludes anterior (mesial) to the mesiobuccal cusp of the maxillary first permanent molar. The same conventions as described above are used to indicate the severity of deviation from a Class I molar relationship.

Angle Classification

"Subdivisions" (left or right) are used in asymmetric situations to indicate the side that deviates from a Class I molar relationship.

The workstation software features measurement tools to directly make these measurements (by measuring the distance between cusps and fossa of opposing teeth). The results can be quantified and displayed to a user, and compared to normative values in a database. Additionally, the values can be classified in accordance with the Angle classification system, e.g., Class I, Class II or Class III. The resulting display of classification is useful for interdigitation or changing the spacing between the opposing teeth.

Another feature of the software is that it allows the teeth in either or both arches to be displayed as semi-transparent objects, which allows the user to view through the teeth to see opposing teeth or adjacent teeth. Several possible method of providing semi-transparent teeth is to show fewer of the points in a point cloud of teeth or fewer triangles in a mesh or triangle surface representation of the teeth.

FIG. 56 illustrate the patient has navigated to a cephalometric marking screen in the patient information tab, where the user has chosen for display a lateral ceph X-ray of the head. The user has also retracted two dimensional template teeth 870 from a library of template teeth and superimposed the template teeth over the X-ray. The user has also activated the icon s 872 and 873 which causes an occlusal plane 874 to appear on the display. By activating the icons 876 in the left hand side of the display, the use can navigate to calculations screens and associated tools, which provide the user with the ability to calculate various parameters, a soft tissue analysis screen, landmark status, display options and other tools. The user can move the teeth in two dimensions, both the upper and lower teeth. The user marks the occlusal plane, and that the user is able to move the teeth relative to the occlusal plane.

In FIG. 57, the user has navigated to a hard tissue analysis screen, wherein the user is provided with tools to mark various hard tissue anatomical locations on the X-ray image. Here, the user has activated icons to compare initial and desired tooth positions using template teeth to simulate a proposed treatment of the patient. The dark teeth 880 represent a proposed tooth position whereas the light teeth 882 represent initial tooth positions. The user can change the proposed tooth position by moving the dark teeth using the mouse by clicking and dragging.

In FIG. 58, the user has navigated to a screen display showing both the hard and soft tissue, with the display 884 proving the user the tools to mark specific soft tissue locations on the virtual patient model, including Glabella, soft tissue Naison, subnasele, mentolabial sucus, etc. By closing out of window 884, the user accesses the window 886 where the user is able to enter hard tissue points in a similar fashion on the display. The user is again able to make measurements between any points that are marked on the screen and measure corresponding angles.

The treatment planning described in FIGS. 22-26 and 54-60 is essentially done in two dimensions. After these initial steps are taken, the software allows the user to undergo more specific treatment planning operations in three dimensions using the virtual 3D model of the teeth, as described in conjunction with FIGS. 27-53. All changes to dental position or bone changes can be translated into changes in soft tissue appearance using morphing algorithms. The icons also allow for standardized views: side, planar, etc., After the user has completed the task of managing space between the virtual teeth in the proposed arrangement, designing the desired arch form, and arriving at a proposed tooth arrangement or treatment plan, the user is able to cycle back and repeat any of the previous steps by activating the icons on the lower left portion of the display and entering into the appropriate displays and making further adjustments in the proposed arrangement.

The user can then access the rest of the treatment planning software, such as the software indicated by tab 458 (FIG. 21) and proceed with additional treatment planning procedures. Finally, when they are finished, the user selects or saves the treatment plan. The process can be repeated as often as desired and the screen displays are structured so that the user can navigate anywhere in the displays at any time, and therefore repeat, as necessary, the aligning steps, the design of the arch, enter additional patient information, access the appliance design features and change the appliance design, etc. Moreover, as the design of tooth finish position dictates or drives the prescription of the appliance, the present treatment planning techniques lead directly to appliance design parameters (bracket and wire position, or other treatment design, such as staged shell configuration) for treatment of the patient.

It will be appreciated that the comprehensive functionality provided by software described herein is fully applicable to a full range of craniofacial disorders, and while the preferred embodiment is in an orthodontic context, the invention is certainly not so limited.

It will further be noted that there may be some interdependencies between the constraints, in other words, if the user changes one constraint, e.g., occlusal plane, other constraints may also be affected (in 2 and 3 dimensions). Examples of such constraints include A/P positions of the incisors and molars, intermolar width, intercanine width, amount of overjet, amount of overbite, sagittal relation of the teeth, and lip protrusion. Most of the user interface tools described herein can be used to evaluate the quality of a set-up, using a series of logical steps. Basically, the set-up is the proposed tooth position or prescription for treating a patient. The setup evaluation may be performed by the practitioner that prepared the set up, or it may be performed by a third party. The purpose of the evaluation is several fold:

a) Determine how close the set up is to the objectives identified for treatment of the patient;

b) Determine how close the setup is to established clinical standards of care;

c) Provide a means by which the proposed set up can be evaluated in a multipractitioner environment, for example in a situation where all practitioners in the group have to agree on the set-up. Obviously, the proposed set up is transportable over a communications network in the form of a file or else accessible on a central server where others can access it.

d) The evaluation can also serve as a guide by evaluating the course of treatment and the eventual outcome of treatment and providing a means to measure the difference between the actual outcome and the expected outcome. To realize this aspect, the practitioner would need to periodically obtain updated scans of the patient during the course of treatment and compare the current (or final) tooth position with the expected position and use measuring tools or other graphical devices (shading on tooth models) to quantify the amount of variance between the actual and expected position. Obtaining tooth position data during the course of treatment can be obtained by using the in-vivo scanner described in the published PCT application of OraMetrix, cited previously.

e) Provide a check on the choice and design of therapeutic devices. Unless the setup is evaluated correctly any therapeutic device design (e.g., bracket placement location or archwire shape) may be wrong. The evaluation provides for dynamic change of the setup, and resulting appliance design, before the initiation of treatment.

The treatment planning system described herein provides an ideal basis for performing these evaluations. More particularly, it provides a complete and integrated workstation environment and all the necessary processes and software tools to perform the evaluation. Image data and actual measurements quantifying the relationship between the patient's teeth and associated bone and facial anatomy is literally at the practitioner's fingertips. The workstation provides ways to systematically look at the set-up, including providing standardized views (plan, side, anterior, posterior, etc.). The workstation provides both measurement tools and a full suite of visualization tools to both measure the proposed setup as well as model interactively proposed changes in the set up. Complete user interaction with the virtual patient and the proposed set up is possible, both in a single site (on one workstation) and also in a multiple site situation where the model is shared with different practitioners (e.g., surgeons, orthodontists, prosthodontists, etc. all treating the same patient).

While various possible approaches to set up evaluation may be taken, the following is one presently preferred approach.

In the evaluation process, the evaluator checks for the compliance of the proposed set up with practitioner developed boundary conditions: the midline, the occlusal plane(s), the arch form, and any other reference points such as the patient's face or smile, soft tissue, skeletal tissue, dental tissue, functional movement of the jaw, or other boundary condition. These references could be either boundary conditions or used as a starting point. The tools used here are the radiographic examination records (X-rays), two-dimensional photographs, and initial model of the teeth, and the various icons and user interface features that allow the user to access these data points and interactively view them and change their position. A key feature here is the ability to superimpose the virtual 3D teeth or 2D or 3D image data showing bone and root structures of the teeth, and provide the user to freely navigate through the models and images, view them from any orientation, and zoom in or out, etc.

Moreover, the proposed set-up and its relationship to boundary conditions can be observed in various combinations of hard and soft tissue, such as teeth and gingival, teeth and lip or cheek, teeth and bone, or teeth, bone and soft tissue.

The setup evaluation further includes features to evaluate the inter-arch relationship, as described herein. The Angle classification of the occlusion can be determined, as described above. The degree of overjet and overbite in the proposed arrangement can be both visually observed and quantified numerically. Clipping plane features allow for viewing the cross-section of the teeth. The analysis of the inter-arch relationship can proceed by an evaluation of teeth on a tooth by tooth basis, by comparison of a slide line for the upper arch with the slide line of the lower arch, evaluation of the position and axis of inclination of a reference tooth, display of gingival tissue, or hiding gingival tissue, and evaluation of the contact points between teeth in the same arch, the marginal ridges, cusp tips and fossa.

While the evaluation may proceed in any manner, one possible checklist, and order of evaluation of the proposed set-up, is as follows 1. Were the boundary conditions met? In other words, conduct a check that the boundary conditions in the set up have been delivered in accordance with the proposed prescription. This would involve evaluation of the midline (viewing frontal photographs and panorex images), the tooth models and checking the upper and lower midlines. Next, the occlusal planes are checked. Then the axis of the reference tooth or teeth are checked. Then a check of any fixed teeth is made—confirm A/P position of the teeth is fixed, the vertical position is held fixed, and the torques are held fixed.

2. Is the set up ideal? This includes a check of the aesthetic appearance of the teeth in the proposed arrangement, in various perspectives. The set up evaluation includes evaluation or confirmation of the following a) the inter-arch relationships: occlusion class for both right and left sides, overjet, overbite, as well as b) tooth-to-tooth relationships: front intra-arch incisor alignment for uppers and lowers (axial alignment, embrasures, contact points), canine tooth intra-arch tooth alignment, lateral intra-arch buccal segment tooth alignment, and tooth positions and rotations (in/out relationships, first order rotation alignment, contact points for both upper and lower arches. The evaluation proceeds to checking the marginal ridges, third order torque for the buccal segments and front segments (including left/right torque symmetry).

The user then performs a final check of the setup by comparing the frontal photographs to the malocclusion and then the setup. After concluding the evaluation, the user indicates their decision by selected Accept, Modify or Reject. If the user seeks to modify the set up, they check Modify and then go back and use any of the tools described herein to make appropriate changes, and then go through the evaluation checklist again. When they are finally finished, they check "ACCEPT" and the proposed setup is saved as such in memory for the workstation along with the date the set-up was accepted.

Figure 59A:
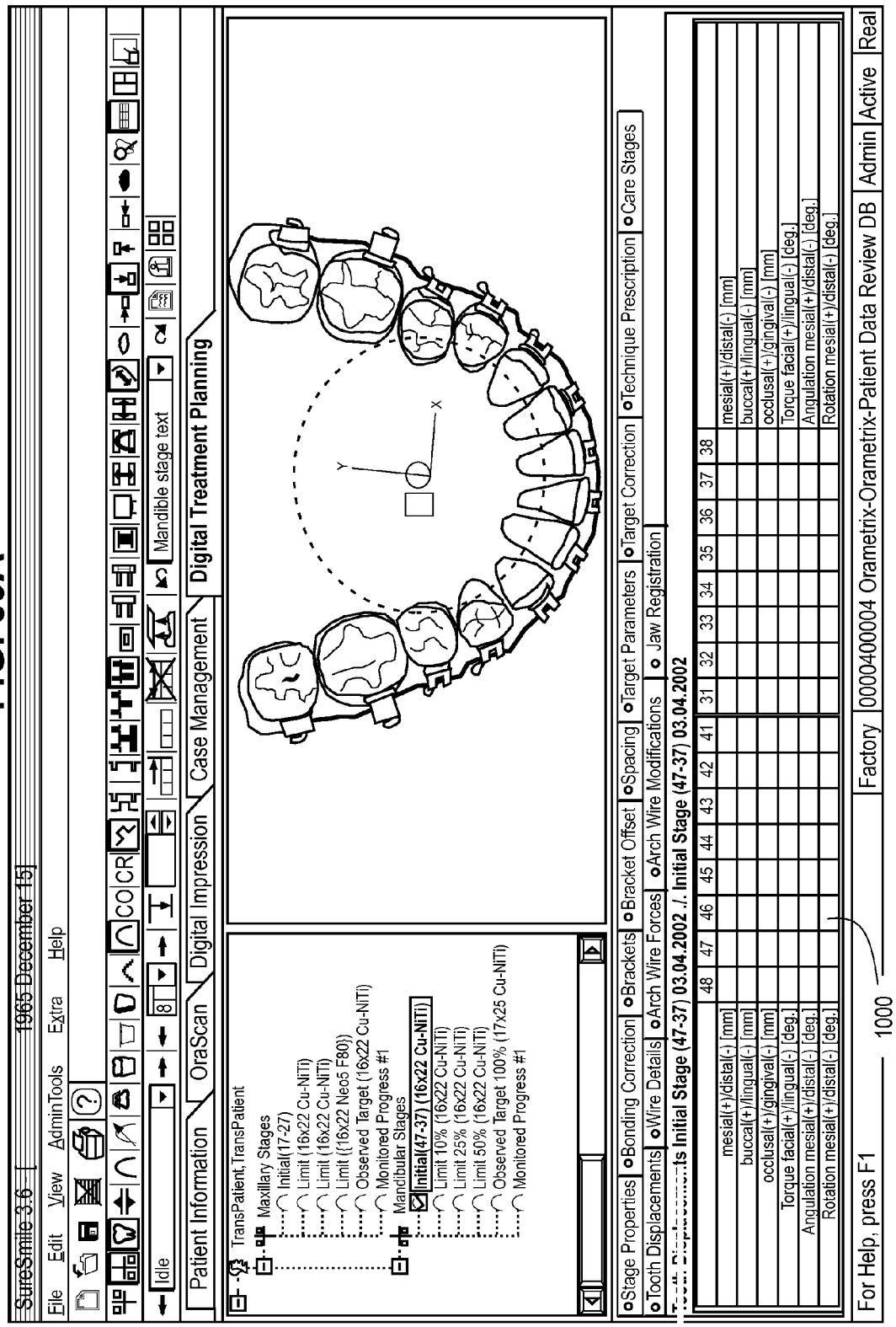
Figure 59B:
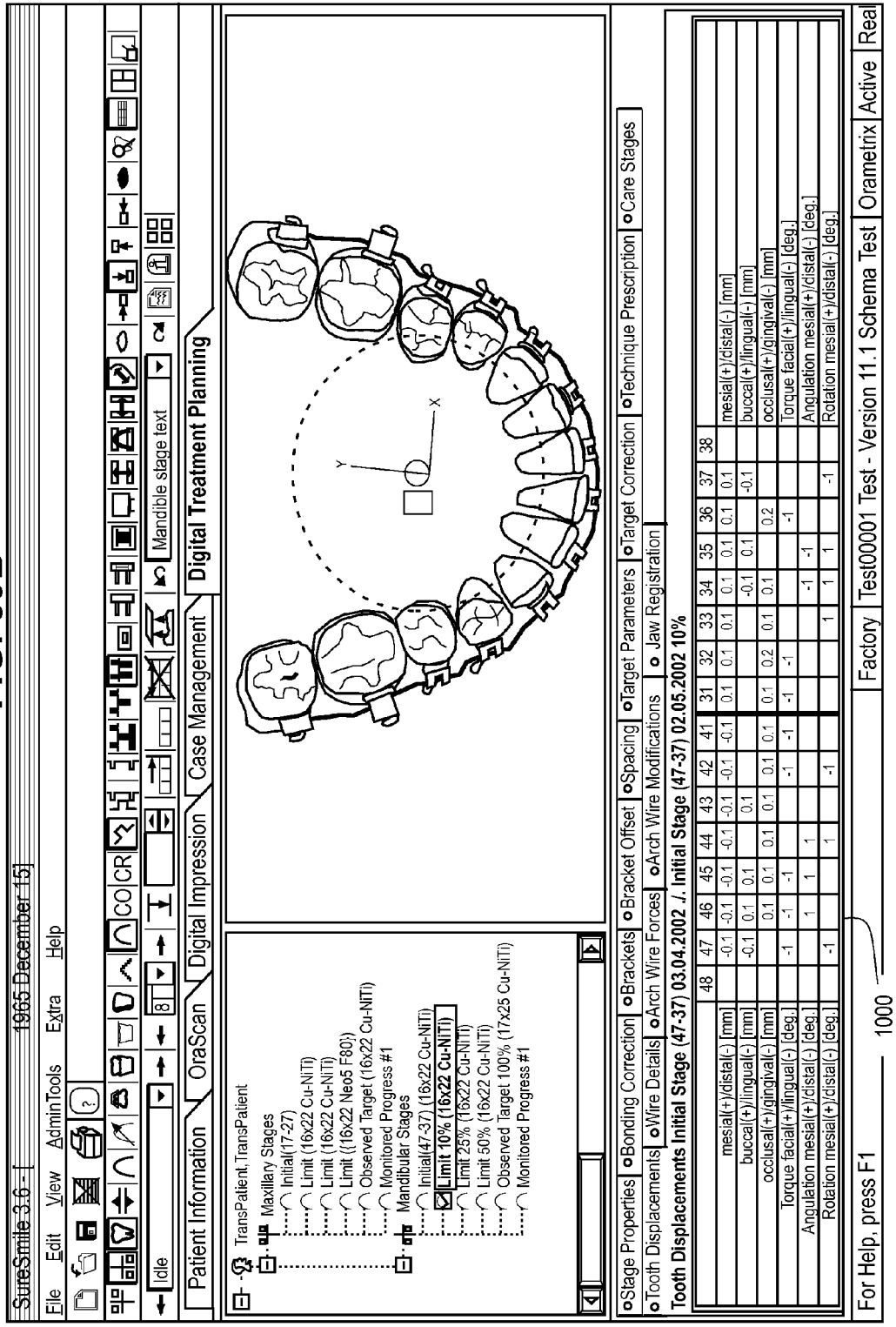

An example of the user staging treatment in stages is set forth in FIGS. 59A-59-I. FIG. 59A shows a virtual model of the teeth in a malocclusion with virtual brackets and wires in a configuration designed to move the teeth to a desired position. The placement of the brackets and wires is provided via the digital treatment planning procedures available in the software. The field 1000 indicates actual tooth movement during the stages of treatment; in FIG. 59A, the fields are blank since the teeth are in the original position. In FIG. 59B, the user simulated a 10 percent stage of treatment, that is, 10% of the movement of the teeth is simulated. Such simulations are possible since the workstation knows both the initial position of each tooth and the final position of each tooth in three dimensions. The values in the field 1000 show that some tooth movement has occurred. During treatment, when the practitioner expects that roughly 10 percent of tooth movement should have occurred, the user scans the patient, stored the virtual model of the teeth in the workstation, and compares actual tooth position with the planned tooth position by hiding or showing the relevant tooth models and or superimposing them and using color codeing or shading to indicate deviation between actual and expected positions.

Figure 59C:
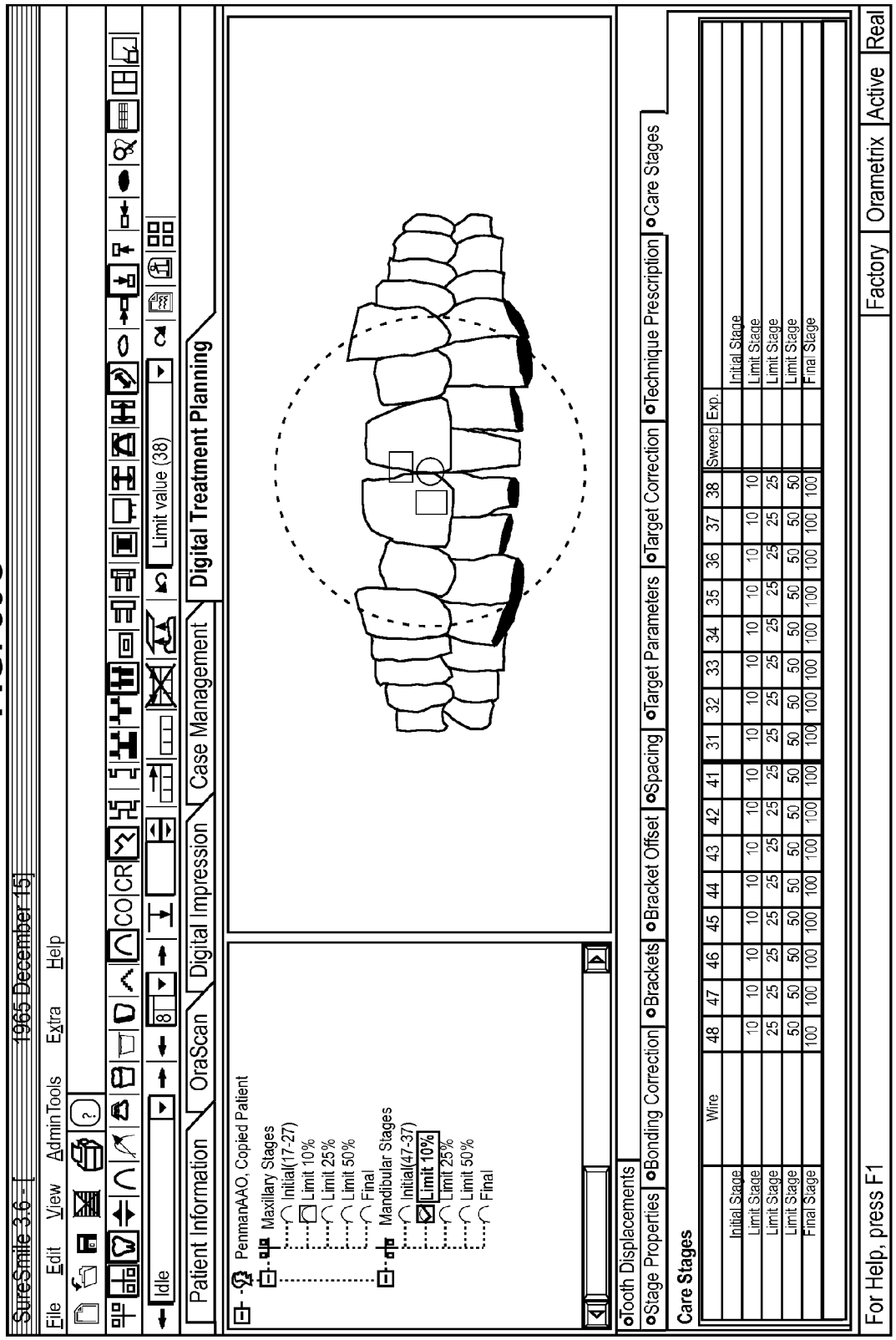

FIG. 59C shows the model 116 of the teeth in the 10 percent stage, with the brackets and wires hidden.

Figure 59D:
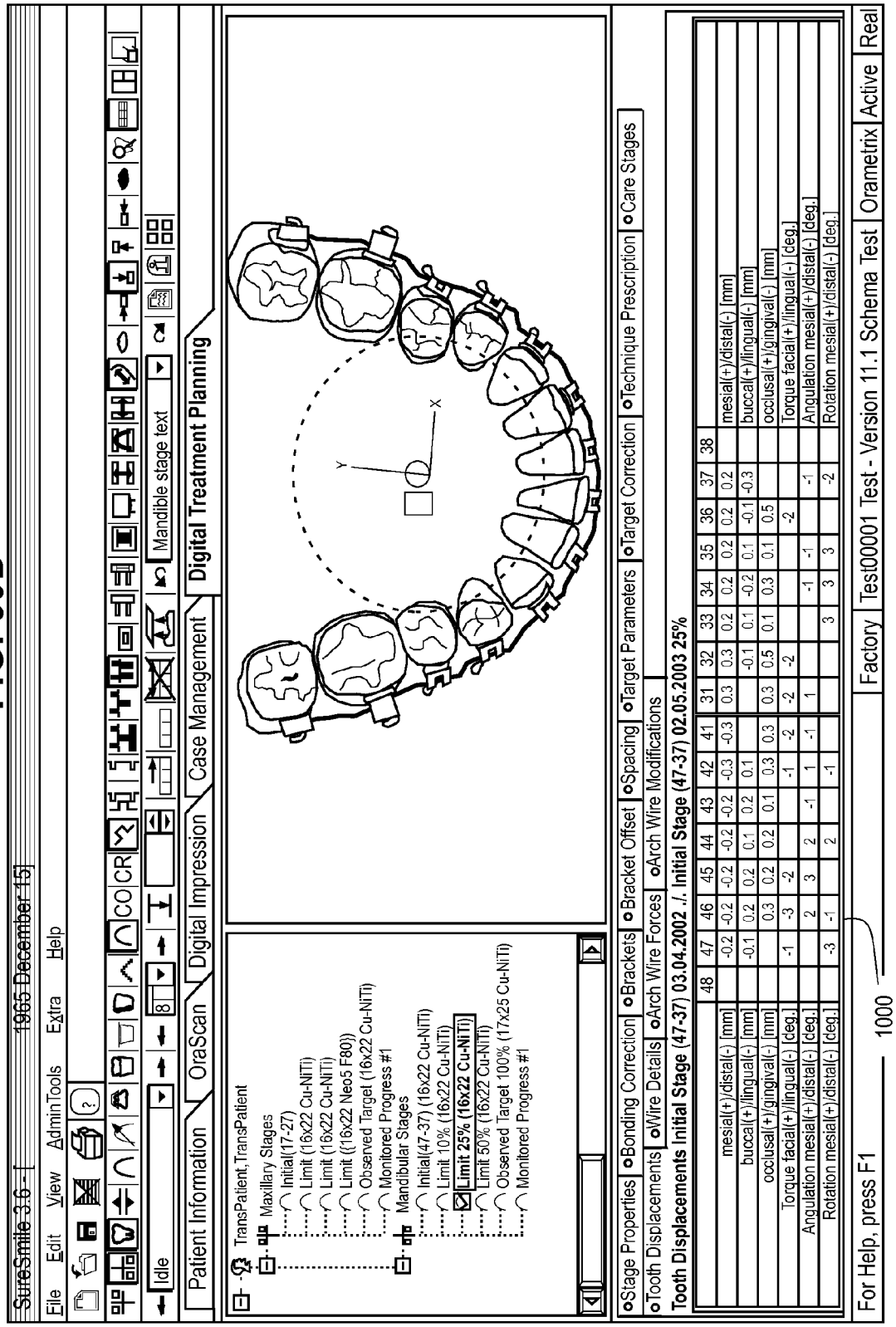

FIG. 59D shows the shows the expected tooth position in the mandibular arch at a 25 percent stage in a plan view.

Figure 59E:
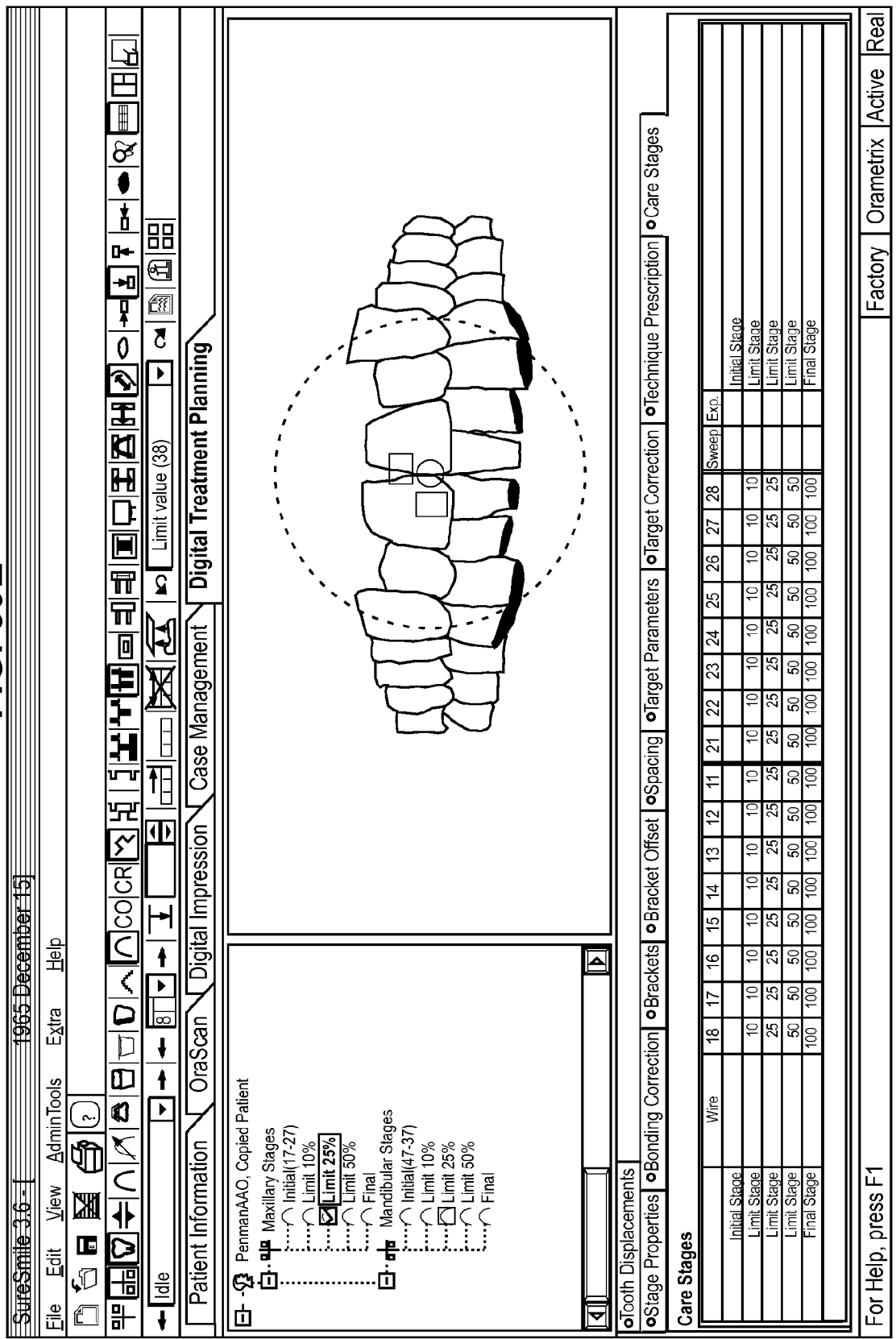

FIG. 59E. shows both arches at the 25 percent stage.

Figure 59F:
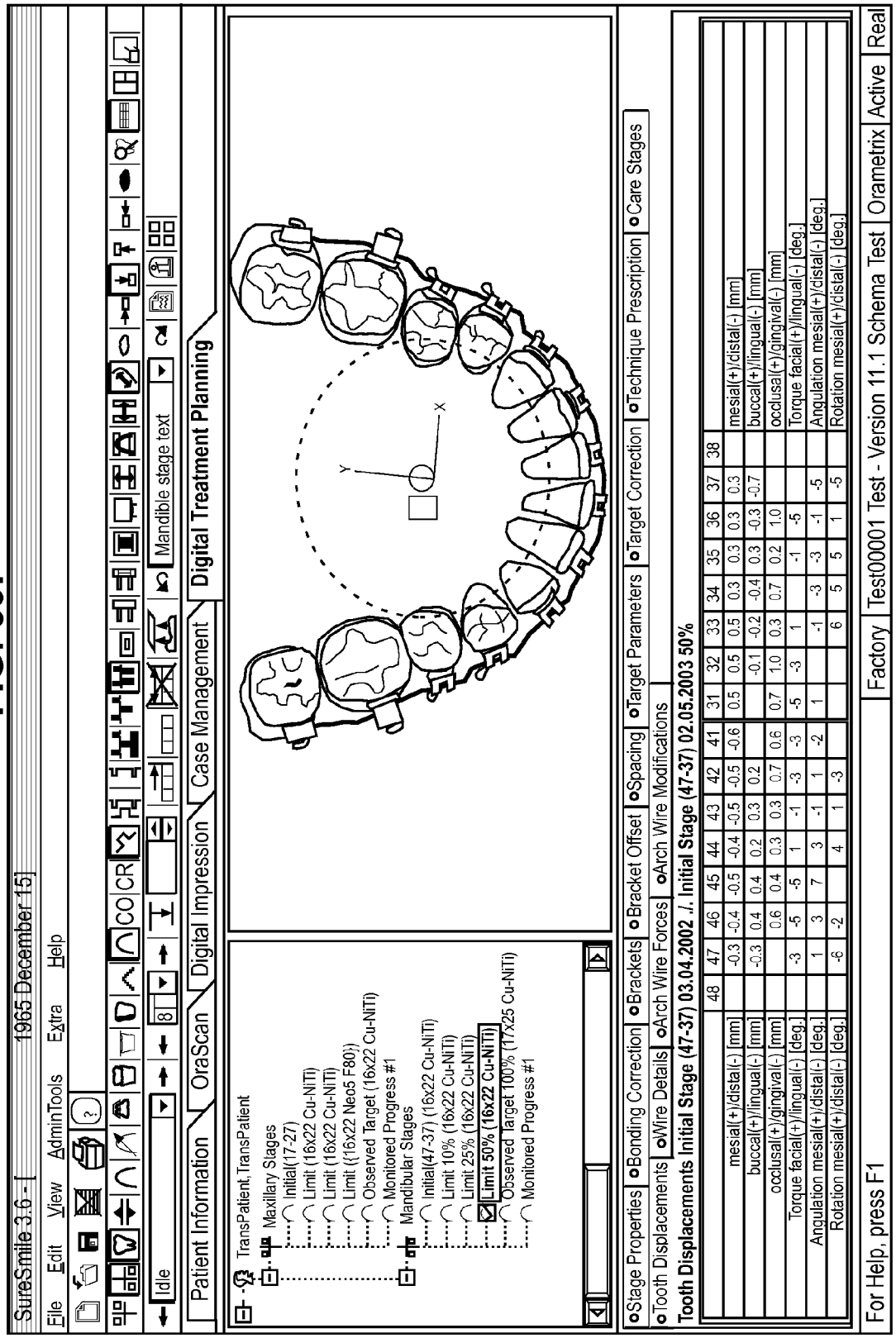

FIG. 59F shows the expected tooth position at the 50 percent stage.

Figure 59G:
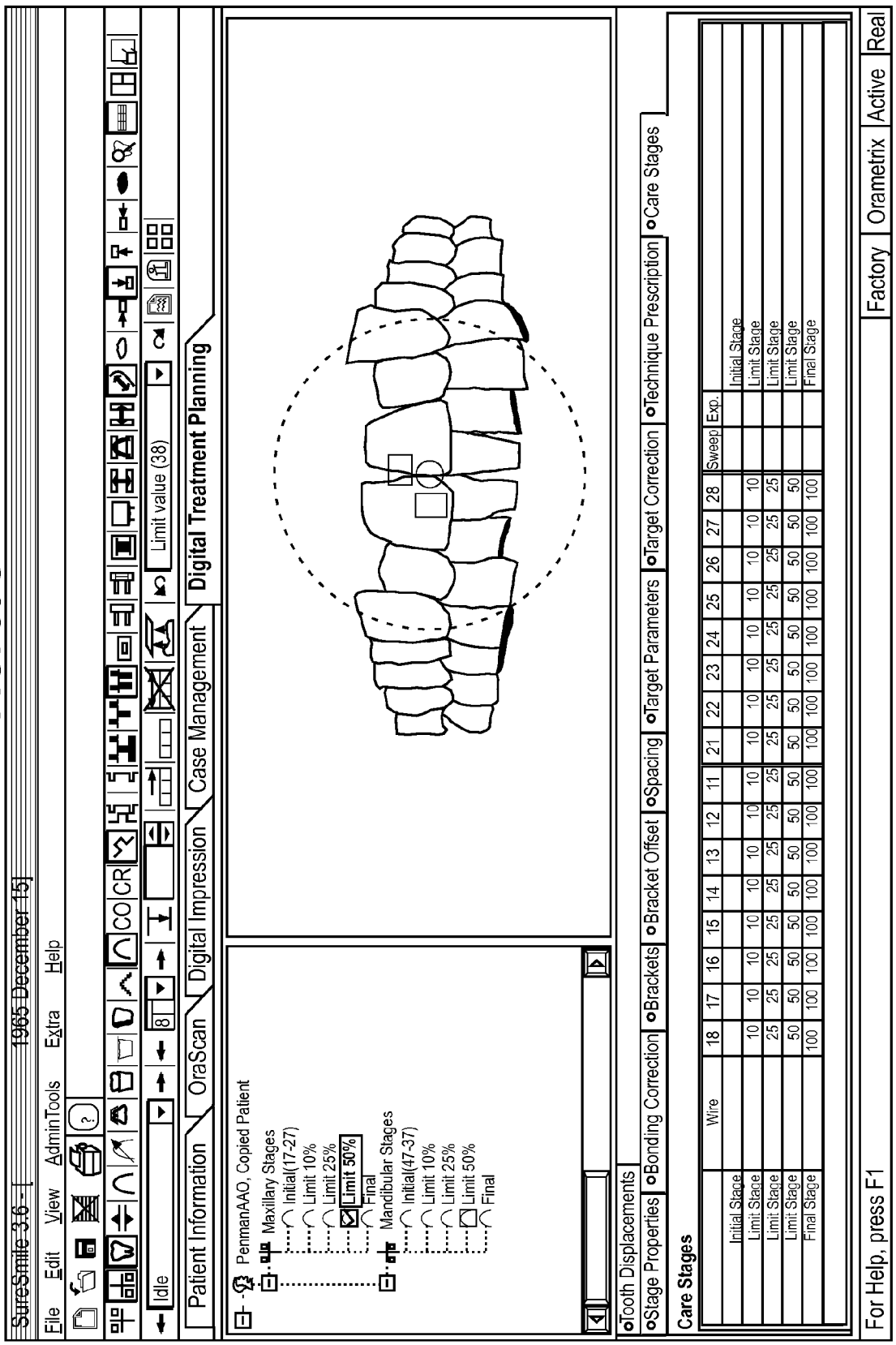

FIG. 59G shows the position of both arches at the 50 percent stage.

Figure 59H:
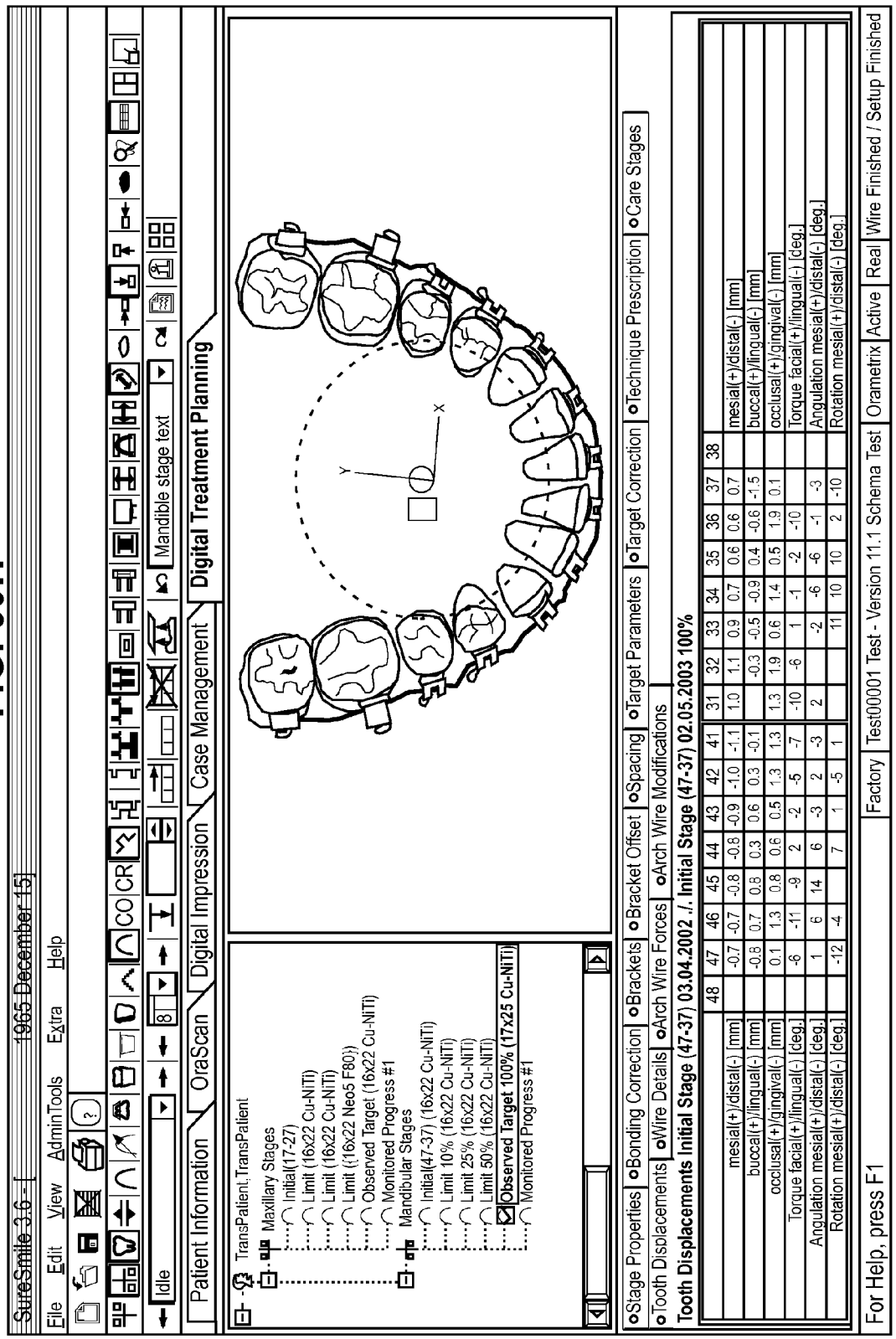

FIG. 59H shows the position of expected position of the teeth at the target position (100 percent).

Figure 59I:
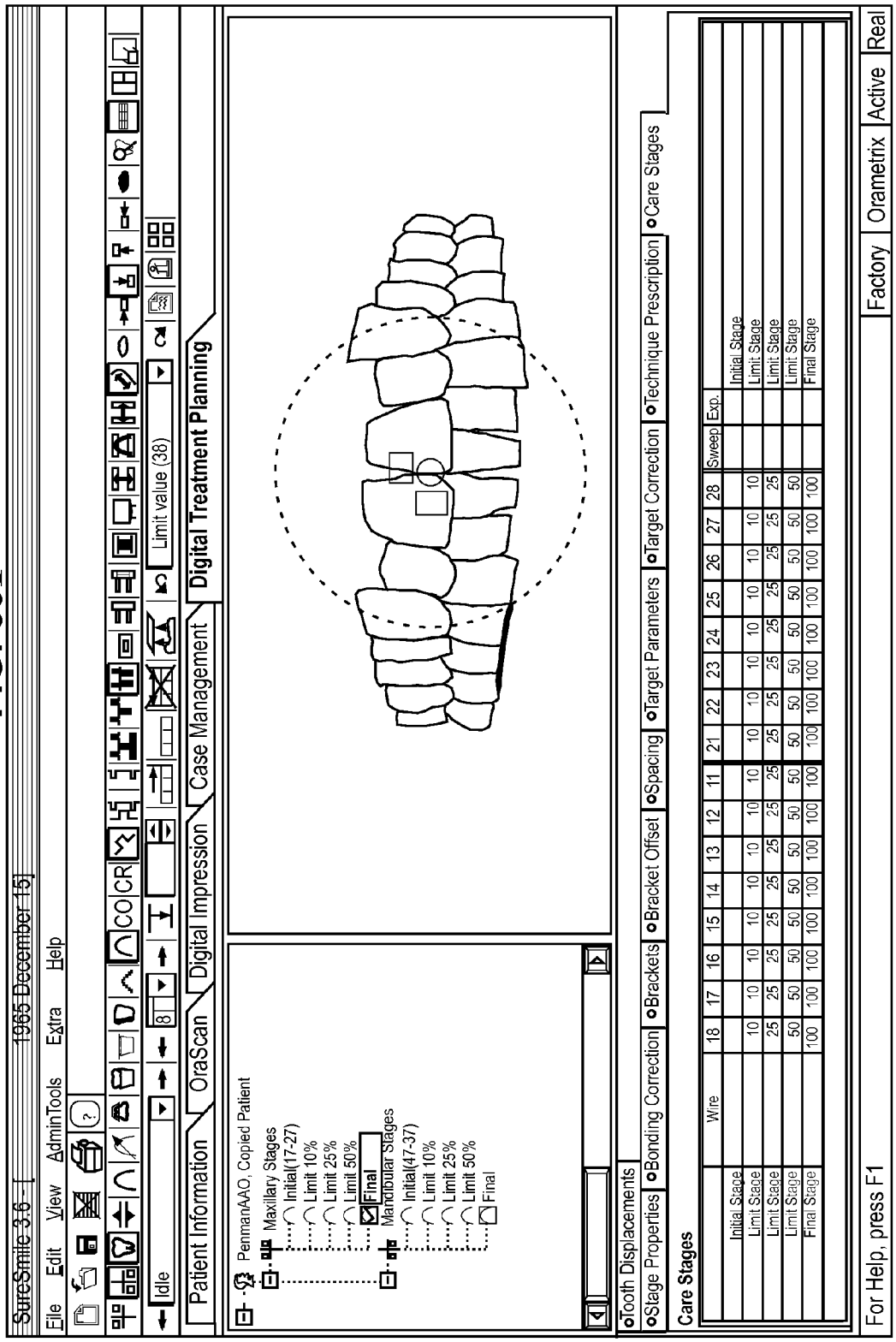

FIG. 59I shows the position of both arches at the 100 percent (final tooth position).

Figure 60:
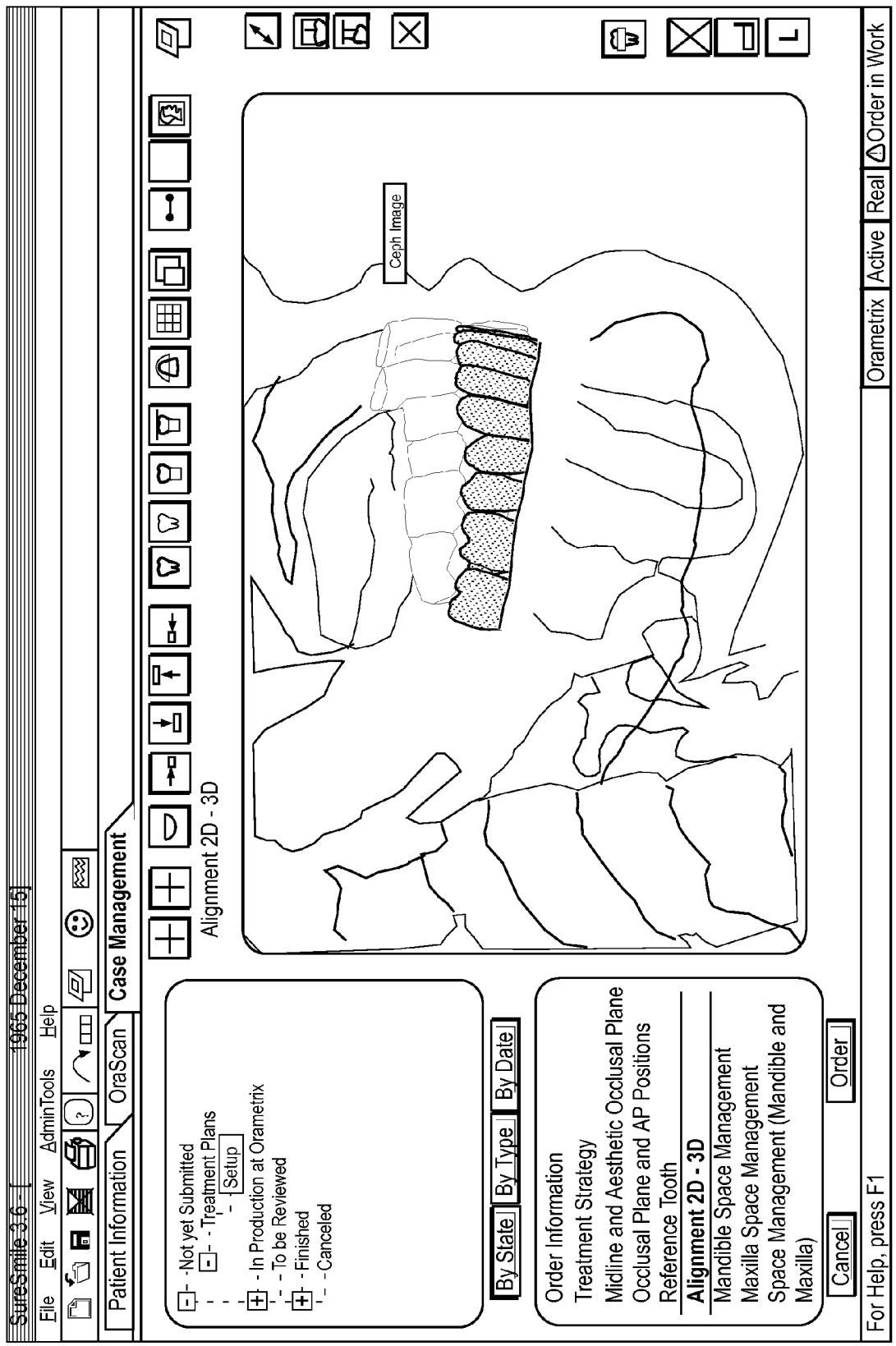

FIG. 60 shows a representation of the tooth models using a "transparent" function in which the tooth is rendered in a semi-transparent manner, instead of being a solid object.

Presently preferred and alternative embodiments of the invention have been set forth. Variation from the preferred and alternative embodiments may be made without departure from the scope and spirit of this invention. Furthermore, the reference in the claims to an optical scanner for scanning the dentition of the patient is intended to encompass both an in-vivo scanner scanning the teeth of the patient directly or the use of an optical, laser, destructive, or other type of scanner scanning a physical model of the teeth of the patient or an impression thereof.

We claim:

1. A method for orthodontic treatment planning of a patient with a workstation comprising a computing platform having a graphical user interface, a processor and a computer storage medium containing digitized records pertaining to a patient, said digitized records including image data, and a set of software instructions providing graphical user interface tools for access to said digitized records, the method comprising the steps of:

designing a treatment plan for a patient with the aid of the workstation;

identifying one or more constraints by way of placing markings on a first virtual model of the patient, whereby said software instructions in said workstation automatically enable showing said markings on a second virtual model of the patient; wherein either (a) said first virtual model is a two-dimensional virtual model and said second virtual model is a three-dimensional virtual model, or (b) said first virtual model is a three-dimensional virtual model and said second virtual model is a two-dimensional virtual model of the patient;

simulating the movement of the teeth in accordance with the treatment plan as a series of two or more incremental tooth movement steps between an initial position and an ideal tooth finish position; and providing the user with the ability to interactively vary the tooth incremental steps and view on the workstation graphical user interface the associated impact on tooth position and space between teeth;

whereby the user is able to interactively evaluate several alternative treatment scenarios by the variance in said incremental tooth movements steps.

2. The method of claim 1, wherein said treatment plan comprises a hybrid treatment plan comprising, for the patient, both a) fixed appliances; and b) removable appliances.

3. The method of claim 1, wherein the incremental steps are compared to treatment responses of the patient so as to measure the patient's response to treatment.

4. A workstation for orthodontic treatment planning of a patient comprising;

a computing platform having a graphical user interface, a processor and a computer storage medium containing digitized records pertaining to the patient, said digitized records including image data, and a set of software instructions providing graphical user interface tools for access to said digitized records;

said workstation further comprising software instructions for:

(a) enabling a user to design a treatment plan for the patient;

(b) identifying one or more constraints by way of placing markings on a first virtual model of the patient, whereby said software instructions in said workstation automatically enable showing said markings on a second virtual model of the patient; wherein either (i) said first virtual model is a two-dimensional virtual model and said second virtual model is a three-dimensional virtual model, or (ii) said first virtual model is a three-dimensional virtual model and said second virtual model is a two-dimensional virtual model of the patient;

(c) simulating movement of the patient's teeth in accordance with the treatment plan as a series of two or more incremental tooth movement steps between an initial position and an ideal tooth finish position; and (d) providing the user with the ability to interactively vary the tooth incremental steps and viewing on the workstation graphical user interface associated impact on tooth position and space between teeth;

whereby the user is able to interactively evaluate several alternative treatment scenarios by the variance in said incremental tooth movements steps.

5. The workstation of claim 4, wherein said treatment plan comprises a hybrid treatment plan comprising, for the patient, both a) fixed appliances; and b) removable appliances.

* * * * *